US012600746B2

(12) United States Patent
Payne et al.

(10) Patent No.: US 12,600,746 B2
(45) Date of Patent: Apr. 14, 2026

(54) SYNTHETIC METHODS USING NATIVE CHEMICAL LIGATION IN FLOW

(71) Applicant: The University of Sydney, New South Wales (AU)

(72) Inventors: Richard J. Payne, New South Wales (AU); Tim Chisholm, New South Wales (AU)

(73) Assignee: The University of Sydney, New South Wales (AU)

( * ) Notice: Subject to any disclaimer, the term of this patent is extended or adjusted under 35 U.S.C. 154(b) by 1072 days.

(21) Appl. No.: 17/057,069

(22) PCT Filed: May 22, 2019

(86) PCT No.: PCT/AU2019/050502
§ 371 (c)(1),
(2) Date: Nov. 19, 2020

(87) PCT Pub. No.: WO2019/222805
PCT Pub. Date: Nov. 28, 2019

(65) Prior Publication Data
US 2023/0133885 A1 May 4, 2023

(30) Foreign Application Priority Data
May 22, 2018 (AU) ................................ 2018901799

(51) Int. Cl.
*C07K 1/107* (2006.01)
*C07K 7/06* (2006.01)

(52) U.S. Cl.
CPC .............. *C07K 1/1075* (2013.01); *C07K 7/06* (2013.01)

(58) Field of Classification Search
CPC ........ C07K 1/1075; C07K 7/06; C07K 1/026; C07K 1/107; C07K 14/001; C07K 1/08; C07C 323/36; C07C 323/25; C07C 327/22; C07C 391/02
See application file for complete search history.

(56) References Cited

U.S. PATENT DOCUMENTS

2015/0023988 A1    1/2015  Murray et al.

FOREIGN PATENT DOCUMENTS

WO    WO 2013/177221 A1    11/2013
WO    WO 2014/194361 A1    12/2014
WO    WO 2016/138563 A1     9/2016

OTHER PUBLICATIONS

Hartman, et al, Deciding whether to go with the flow: evaluating the merits of flow reactors for synthesis, Angew. Chem Int. Ed. 2011, 50, 7502-7519 (Year: 2011).*

Dang et al.; "Native Chemical Ligation at Asx-Cys, Glx-Cys: Chemical Synthesis and High-Resolution X-ray Structure of ShK Toxin by Racemic Protein Crystallography"; Journal of American Chemical Society; vol. 135; 2013; Supporting Information; p. S1-S11.
Watson et al.; "Mosquito-Derived Anophelin Sulfoproteins Are Potent Antithrombotics"; ACS Central Science; vol. 4; 2018; Supporting Information; p. S1-S31.
Sun; "Preparation of solid surfaces for native chemical ligation in the quartz crystal microbalance"; Surface and Interface Analysis; vol. 45; 2013; p. 1799-1804.
Simon et al.; "Rapid Flow-Based Peptide Synthesis"; Chembiochem; vol. 15(5); Mar. 2014; p. 713-720.
Simon et al.; "Rapid Flow-Based Peptide Synthesis"; Chembiochem; vol. 15(5); Mar. 2014; Supporting Information; 47 pages.
Malins et al.; "Peptide ligation chemistry at selenol amino acids"; Journal of Peptide Science; vol. 20; 2014; p. 64-77.
Metanis et al.; "Traceless Ligation of Cysteine Peptides Using Selective Deselenization"; Angewandte Chemie; vol. 122; 2010; p. 7203-7207.
Baumann et al.; "A Continuous-Flow Method for the Desulfurization of Substituted Thioimidazoles Applied to the Synthesis of Etomidate Derivatives"; European Journal of Organic Chemistry; 2017; p. 6518-6524.
Cuesta et al.; "Photochemical desulfurization of thiols and disulfides"; Tetrahedron Asymmetry; vol. 10; 1999; p. 2643-2646.
Watson et al.; "Mosquito-Derived Anophelin Sulfoproteins Are Potent Antithrombotics"; ACS Central Science; vol. 4; 2018; p. 468-476.
Malins et al.; "Synthetic Amino Acids for Applications in Peptide Ligation-Desulfurization Chemistry"; Aust. J. Chem.; vol. 68; 2015; p. 521-537.
Dang et al.; "Native Chemical Ligation at Asx-Cys, Glx-Cys: Chemical Synthesis and High-Resolution X-ray Structure of ShK Toxin by Racemic Protein Crystallography"; Journal of American Chemical Society; vol. 135; 2013; p. 11911-11919.
Monbaliu et al.; "Recent trends in Cys- and Ser/Thr-based synthetic strategies for the elaboration of peptide constructs"; Chemical Communications; vol. 48; 2012; p. 11601-11622.
International Patent Application No. PCT/AU2019/050502; Int'l Written Opinion and Search Report; dated Aug. 12, 2019; 12 pages.
Bondalapati et al.; "Expanding the chemical toolbox for the synthesis of large and uniquely modified proteins"; Nature Chemistry; vol. 8; May 2016; p. 407-418.
Dawson; "Native Chemical Ligation Combined with Desulfurization and Deselenization: A General Strategy for Chemical Protein Synthesis"; Isr. J. Chemical; vol. 51; 2011; p. 862-837.
Dawson et al.; "Synthesis of Proteins by Native Chemical Ligation"; Science; vol. 266; Nov. 1994; p. 776-779.
Fosgerau et al.; "Peptide therapeutics: current status and future directions"; Drug Discovery Today; vol. 20; Jan. 2015; p. 122-128.

(Continued)

*Primary Examiner* — Sudhakar Katakam
(74) *Attorney, Agent, or Firm* — BakerHostetler

(57) ABSTRACT

The disclosure relates to the synthesis of amide containing compounds in flow. In particular, the disclosure relates to the synthesis of polypeptides via native chemical ligation in flow. The disclosure also relates to selective desulfurization or deselenization of amide containing compounds comprising a thiol, disulfide, selenol or diselenide functional group respectively, particularly polypeptides.

27 Claims, 115 Drawing Sheets

Specification includes a Sequence Listing.

(56) References Cited

OTHER PUBLICATIONS

Hay et al.; "Clinical development success rates for investigational drugs"; Nature Biotechnology; vol. 32; Jan. 2014; p. 40-51.

Hoffman et al.; "The Desulfurization of Mercaptans with Trialkyl Phosphites"; J. Am. Chem. Soc.; vol. 78; 1956; p. 6414.

Huang et al.; "Synthesis of L- and D-Ubiquitin by One-Pot Ligation and Metal-Free Desulfurization"; Chemistry A European Journal; vol. 22; 2016; p. 7623-7628.

Jin et al.; "P-B Desulfurization: An Enabling Method for Protein Chemical Synthesis and—Site-Specific Deuteration"; Agew. Chem. Int.; vol. 56; 2017; p. 14607-14611.

Johnson et al.; "Insights into the Mechanism and Catalysis of Native Chemical Ligation Reaction"; J. Am. Chem. Soc.; vol. 128; 2006; p. 6640-6646.

Kent; "Chemical Synthesis of Peptides and Proteins"; Annual Reviews Biochemical; vol. 57; 1988; p. 957-989.

Kent; "Total chemical synthesis of proteins"; Chem. Soc. Rev.; vol. 38; 2009; p. 338-351.

Kulkarni et al.; "Rapid and efficient protein synthesis through expansion of the native chemical ligation concept"; Nature Reviews; vol. 2; 2018; 17 pages.

Malins et al.; "Recent extensions to native chemical ligation for the chemical synthesis of peptides and proteins"; Current Opinion in Chemical Biology; 2014; 17 pages.

Malins et al.; "Modern Extensions of Native Chemical Ligation for Chemical Protein Synthesis"; Topics in Current Chemistry; vol. 362; Springer Int'l Publishing; 2015; p. 27-88.

Merrifield; "Solid Phase Peptide Synthesis. I. The Synthesis of a Tetrapeptide"; vol. 85; Jul. 1963; p. 2149-2154.

Sakamoto et al.; "Imidazole-Aided Native Chemical Ligation: Imidazole as a One-Pot Desulfurization-Amenable Non-Thiol-Type Alternative to 4-Mercaptophenylacetic Acid"; Chem. Eur. Journal; vol. 22; 2016; p. 17940-17944.

Sayers et al.; "Thiazolidine-Protected B-thiol Asparagine: Applications in One-Pot Ligation-Desulfurization Chemistry"; Org. Letter; vol. 17; 2015; 4 pages.

Thompson et al.; "Chemoselective Peptide Ligation-Desulfurization at Aspartate"; Agnewandte Chemie; vol. 125; 2013; p. 9905-9909.

Thompson et al.; "Trifluoroethanethiol: An Additive for Efficient One-Pot Peptide Ligation-Desulfurization Chemistry"; Journal of the American Chemical Society; vol. 136; 2014; p. 8161-8164.

Usmani et al.; "THPdb: Database of FDA-approved peptide and protein therapeutics"; PLOS One; Jul. 2017; 12 pages.

Wan et al.; "Free-Radical-Based, Specific Desulfurization of Cysteine: A Powerful Advance in the Synthesis of Polypeptides and Glycopolypeptides"; Angew. Chem.; vol. 119; 2007; p. 9408-9412.

Yan et al.; "Synthesis of Peptides and Proteins without Cysteine Residues by Native Chemical Ligation Combined with Desulfurization"; J. Am. Chem. Soc.; vol. 123; 2001; p. 526-533.

Zheng et al.; "Chemical synthesis of proteins using peptide hydrazides as thioester surrogates"; Nature Protocols; vol. 8; 2013; p. 2483-2495.

Gerardy et al.; "Continuous Flow Organic Chemistry: Successes and Pitfalls at the Interface with Current Societal Challenges"; European Journal of Organic Chemistry; 2018; p. 2301-2351.

Kambanis et al. "Expressed Protein Ligation in Flow"; Journal of the American Chemical Society; 2024; 9 pages.

* cited by examiner

6 M Gdn·HCl, 0.1 M HEPES
200 mM TCEP
20 mM VA-044, 40 mM GSH
pH = 7.4 – 7.5, 37 °C

1: R = H
6: R = Ac-LYRANA
7: R = Ac-LYRANV

8: R = H
9: R = Ac-LYRANA
10: R = Ac-LYRANV

Figure 9

6 M Gdn•HCl, 0.1 M HEPES
200 mM TCEP, 40 mM GSH
1.25 M 2-MIM, pH = 7.3 - 7.4, rt
λ = 254 nm/302 nm/365 nm, 35 W

1: R = H
6: R = Ac-LYRANA
7: R = Ac-LYRANV

8: R = H
9: R = Ac-LYRANA
10: R = Ac-LYRANV

6 M Gdn•HCl, 0.1 M HEPES
200 mM TCEP, 125 mM GSH
λ = 254 nm, 35 W
rt, pH = 7.4 - 7.5

6 M Gdn·HCl, 0.1 M HEPES
200 mM TCEP, 40 mM GSH
20 mM VA-044
37 °C, pH = 7.4 - 7.5

SYNTHETIC METHODS USING NATIVE CHEMICAL LIGATION IN FLOW

CROSS-REFERENCE TO RELATED APPLICATIONS

This application is a 371 National Stage of international patent application no. PCT/AU2019/050502, filed May 22, 2019, which claims priority to Australia patent application no. 2018901799, filed May 22, 2018, the entire contents of which are incorporated by reference herein.

SEQUENCE LISTING

The instant application contains a Sequence Listing which has been submitted electronically in ASCII format and is hereby incorporated by reference in its entirety. Said ASCII copy, created on Sep. 6, 2024, is named 120755_000001_SL.txt and is 10,679 bytes in size.

FIELD OF THE INVENTION

The disclosure relates to the synthesis of amide containing compounds in flow. In particular, the disclosure relates to the synthesis of polypeptides via native chemical ligation in flow. The disclosure also relates to selective desulfurization or deselenization of amide containing compounds comprising a thiol, disulfide, selenol or diselenide functional group respectively, particularly polypeptides.

BACKGROUND OF THE INVENTION

Peptides and proteins are ubiquitous molecules in living systems and generally exhibit exquisite selectivity for their targets, a property that has led to renewed interest in polypeptides as therapeutics. These so called "biologics" have been reported to have twice the approval rate of small molecule therapeutics (Hay 2014) and currently make up 10% of approved drugs (Fosgerau 2015; Usmani 2017). As a result of this renaissance in polypeptide-based therapeutics, attention has turned to the development of methods to access these biomolecules in an efficient manner.

Solid phase peptide synthesis (SPPS) represents the most efficient avenue for generating peptides via chemical synthesis (Merrifield 1963; Kent 1988). However, there is a significant limitation on the size of targets that can be produced en bloc (typically 40-50 residues). This limitation of SPPS was largely addressed through the development of native chemical ligation (NCL), a transformative technology that enables convergent and chemoselective fusion of unprotected peptide fragments (Dawson 1994; Kent 2009). NCL is performed between a peptide containing an N-terminal cysteine (Cys) residue and a peptide functionalized as a C-terminal thioester, and usually requires the use of a suitable thiol additive to generate a reactive thioester (SR2) that accelerates the rate-limiting trans-thioesterification step (Johnson 2006; Thompson 2014). Mechanistically, the reaction proceeds through an initial trans-thioesterification step followed by a rapid S→N acyl rearrangement to afford a native peptide bond. NCL has dramatically increased the size of target polypeptides that can be assembled by total chemical synthesis.

An important advance to the seminal methodology was the development of metal-based desulfurization (Yan 2001), and later a milder radical-based protocol (Wan 2007; Jin 2017), that facilitate the conversion of the least abundant proteinogenic amino acid Cys to an alanine (Ala) residue at the ligation junction. The subsequent development of thiolated amino acids (as Cys surrogates) has served to expand the number of targets accessible via NCL technology (Dawson 2011; Kulkarni 2018; Malins 2015; Malins 2014; Malins 2015; Bondalapati 2016). A further innovation has been the development of one-pot ligation-desulfurization chemistry using thiol additives (e.g. trifluoro-ethanethiol (TFET)) (Thompson 2014; Huang 2016). These additives serve to enhance the rate of the NCL reaction but, unlike traditionally used aryl thiols, do not interfere with subsequent radical desulfurization chemistry which can therefore be performed without intermediary purification.

Despite the impact that NCL and the associated methodological advances have had on the field of peptide and protein science, the technology has yet to be used for the manufacture of any approved peptide or protein pharmaceuticals. There remains a need for the development of methods that allow for the rapid and facile preparation of native peptides and proteins and furthermore are clean, robust, and scalable.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present disclosure relates to a method of preparing an amide containing compound in flow comprising the step of reacting:

(i) an ester, with (ii) a molecule comprising a terminal amino acid selected from the group consisting of cysteine, cystine, a thiol-derivatized amino acid, a disulfide-derivatized amino acid, selenocysteine, selenocystine, a selenol-derivatized amino acid, and a diselenide-derivatized amino acid;

wherein the ester is a thioester or selenoester.

The amide containing compound is preferably a polypeptide. Preferably, the polypeptide is defined by formula (I):

I $$N_{term} \diagdown {(AA)^n} \diagdown \underset{H}{N} - AA_{lig} \diagdown (AA)^n \diagdown C_{term}$$

the ester is defined by formula (II):

II $$N_{term} \diagdown {(AA)^n} \diagdown DG$$

the molecule comprising a terminal amino acid selected from the group consisting of cysteine, a thiol-derivatized amino acid, selenocysteine, and a selenol-derivatized amino acid is defined by formula (III):

III the molecule comprising a terminal amino acid selected from the group consisting of cystine, a disulfide-derivatized amino acid, selenocystine and a diselenide-derivatized amino acid is defined by formula (IV):

IV wherein:

$N_{term}$ is the N-terminus of the polypeptide;
$C_{term}$ is the C-terminus of the polypeptide;
AA is an amino acid;
n is an integer;
$(AA)_n$ represents a polypeptide comprising n number of amino acid monomers;
DG is a displaceable group selected from a thiolate and a selenoate; and is a thiol, disulfide, selenol or diselenide functionalised amino acid residue at the ligation site selected from the group consisting of cysteine, cystine, a thiol-derivatized amino acid, a disulfide-derivatized amino acid, selenocysteine, selenocystine, a selenol-derivatized amino acid, and a diselenide-derivatized amino acid.

The ester is preferably a "reactive ester". A reactive ester is capable of reacting with the terminal amino acid in the molecule in the absence of a thiol additive or a selenol additive and accelerates the rate-limiting trans-esterification step. Preferably the reactive ester is selected from the group consisting of trifluoroethyl thioester, 4-mercaptophenyl acetic acid thioester, mercaptoethylsulfonate thioester, methylthioglycolate thioester, thiophenyl thioester, benzylmercaptan thioester, phenylselenoester, and 4-selenophenyl acetic acid selenoester. Preferably, when the ester is a reactive ester the reaction is conducted in the absence of a thiol additive or selenol additive.

In another embodiment, the ester may be a less reactive ester. The ester may be transformed into a reactive ester by reacting the ester with a thiol additive or selenol additive. Examples of less reactive esters include: ethyl 3-mercapto-propionate thioester, reduced L-glutathione (GSH) thioester, dithiothreitol (DTT) thioester, mercaptopropionic acid-leucine thioester, tert-butylthiol thioester, mercaptopropanoyl glycine thioester, selenoacetamide selenoester, selenopropionic acid-isoleucine selenoester, and (9-fluorenylmethyl) selenoester. In this embodiment, the reaction is conducted in the presence of a thiol additive or a selenol additive. In one embodiment, the ester is a thioester and the reaction is conducted in the presence of a thiol additive or a selenol additive. Preferably, the thiol additive is selected from the group consisting of trifluoroethanethiol, 4-mercaptophenyl acetic acid, mercaptoethylsulfonate, methylthioglycolate, thiophenol, and benzylmercaptan. Preferably, the selenol additive is an aryl selenol, more preferably phenylselenol or 4-selenophenyl acetic acid.

In another embodiment, the ester is a selenoester and the reaction is conducted in the presence of a selenol additive. Preferably, the selenol additive is an aryl selenol, more preferably phenylselenol or 4-selenophenyl acetic acid.

Preferably, the reaction is conducted in an aqueous solution.

In one embodiment, the reaction is conducted in the presence of a first nucleophilic agent. The first nucleophilic agent may accelerate the rate of the ligation reaction. Preferably, the first nucleophilic agent comprises an imidazole. More preferably, the first nucleophilic agent is selected from the group consisting of 2-methylimidazole, imidazole and combinations thereof.

In one embodiment, a second nucleophilic agent may be used to thiolyze, aminolyze, hydrolyze or hydrazinolyze product ester formed between the amide containing compound and the ester. In a preferred embodiment, the second nucleophilic agent is selected from the group consisting of reduced glutathione (GSH), dithiothreitol (DTT), cysteine, an imidazole, an amine, hydroxide ion, hydrazine, and combinations thereof. Preferably, the second nucleophilic agent is GSH. Preferably, the second nucleophilic agent is added to the ligation reaction mixture after completion of the ligation reaction.

The reaction may be conducted using a concentration of the molecule comprising the terminal amino acid of about 5 mM to about 20 mM. In another embodiment, the reaction may be conducted at high dilution using a concentration of the molecule comprising the terminal amino acid of less than about 1 mM, preferably less than about 500 μM, more preferably less than about 100 μM, more preferably less than about 50 μM. Preferably, the reaction comprises at least about a 1.2 molar equivalent, more preferably about a 2 molar equivalent, of the ester.

In one embodiment, the method additionally comprises the step of desulfurizing or deselenizing the amide containing compound in flow.

In a preferred embodiment, when is a thiol or disulfide functionalised amino acid residue at the ligation site selected from the group consisting of cysteine, cystine, a thiol-derivatized amino acid, and a disulfide-derivatized amino acid, the method additionally comprises the step of desulfurizing the amide containing compound in flow. Preferably, the desulfurization comprises exposing the compound to UV irradiation in the presence of a phosphine source.

5      6

In another preferred embodiment, when is a selenol or diselenide functionalised amino acid residue at the ligation site selected from the group consisting of selenocysteine, selenocystine, a selenol-derivatized amino acid, and a diselenide-derivatized amino acid, the method additionally comprises the step of deselenizing the amide containing compound in flow. Preferably, the deselenization comprises exposing the compound to UV irradiation in the presence of a phosphine source.

In another aspect of the invention, there is provided a method of desulfurizing an amide containing compound comprising a thiol group or disulfide group in flow. Preferably, the amide containing compound is the reaction product of a native chemical ligation reaction. Preferably, the desulfurization comprises exposing the compound to UV irradiation in the presence of a phosphine source.

In yet another aspect of the invention, there is provided a method of deselenizing an amide containing compound comprising a selenol group or diselenide group in flow. Preferably, the amide containing compound is the reaction product of a native chemical ligation reaction. Preferably, the deselenization comprises exposing the compound to UV irradiation in the presence of a phosphine source.

In another aspect of the invention, there is provided a method of desulfurizing an amide containing compound comprising a thiol group or disulfide group, wherein the desulfurization comprises exposing the compound to UV irradiation in the presence of a phosphine source. The method may be performed in batch or in flow.

In yet another aspect of the invention, there is provided a method of deselenizing an amide containing compound comprising a selenol group or diselenide group, wherein the deselenization comprises exposing the compound to UV irradiation in the presence of a phosphine source. The method may be performed in batch or in flow.

The phosphine is preferably water soluble. Preferably, the phosphine source is TCEP.

In another preferred embodiment, the desulfurization or deselenization further comprises a hydrogen atom source. Preferably, the hydrogen atom source is selected from the group consisting of reduced L-glutathione (GSH), dithiothreitol (DTT), tert-butylthiol, cysteine, and combinations thereof. More preferably, the hydrogen atom source is GSH.

In another preferred embodiment, the desulfurization or deselenization is conducted in the absence of a chemical radical initiator.

The invention also relates to amide containing compounds prepared by the methods described herein. The invention also relates to desulfurized or deselenized amide containing compounds prepared by the methods described herein.

In yet another aspect, the invention relates to a method of preparing an amide containing compound in batch comprising the step of reacting:

(i) an ester, with (ii) a molecule comprising a terminal amino acid selected from the group consisting of cysteine, cystine, a thiol-derivatized amino acid, a disulfide-derivatized amino acid, selenocysteine, selenocystine, a selenol-derivatized amino acid, and a diselenide-derivatized amino acid;

in the presence of a reductant, optionally including a radical scavenger;

wherein the ester is a thioester or selenoester; and wherein the concentration of the molecule is less than about 1 mM.

In a preferred form of this embodiment, the concentration of the molecule comprising the terminal amino acid is less than about 500 μM, more preferably less than about 100 μM, more preferably less than about 50 μM. Preferably, the reaction comprises at least about a 1.2 molar equivalent, more preferably about a 2 molar equivalent, of the ester.

In a preferred form of this embodiment, the reductant may be selected from the group comprising: a thiol group containing reductant, a selenol group containing reductant, a phosphine group containing reductant, or a combination thereof. Examples of thiol group containing reductants include but are not limited to, MPAA (4-mercaptophenylacetic acid), thiophenol, TFET (2,2,2-trifluoroethanethiol), methylthioglycolate, benzylmercaptan, and MESNa (sodium 2-mercaptoethanesulfonate). Examples of selenol group containing reductants include but are not limited to, phenyl selenol, 4-selenophenyl acetic acid, and methyl selenol. Examples of phosphine group containing reductants include but are not limited to, TCEP (tris(2-carboxyethyl) phosphine), tributylphosphine and THPP (tris(3-hydroxypropyl)phosphine). In another embodiment, the reductant may be selected from DTT (dithiothreitol), glutathione, $NaBH_4$, $NaHBH_3CN$, and ascorbic acid. In another embodiment, the reductant may be a non-chemical reductant such as an electrochemical reductant.

In one embodiment the radical scavenger may be selected from the group comprising: aryl selenols and diselenides, more particularly phenylselenol, diphenyl diselenide, and 4-selenophenyl acetic acid; aryl thiols, more particularly MPAA and thiophenol; and more broadly ascorbic acid, 2,2,6,6-tetramethylpiperidine, tetrahydroxy-1,4-benzoquinone, phenyl N-t-butylnitrone, 2,2-diphenyl-1-picrylhydrazyl, and naringenin.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE FIGURES

FIG. 1: Native Chemical Ligation-Desulfurization. A) trans-thioesterification with a thiol additive; B) trans-thioesterification between two reacting peptide fragments; C) intramolecular S→N acyl shift of thioester intermediate; D) desulfurization of Cys to Ala at the ligation junction.

FIG. 2: General scheme for native chemical ligation between model peptide 1 and model peptide thioesters 2, 3, 4 and 5.

FIG. 9: General scheme for the desulfurization of Cys-containing peptides 1, 6 and 7.

Percentage desulfurization was calculated through peak integration of analytical UPLC chromatograms at $\lambda$=280 nm.

Figure 16:
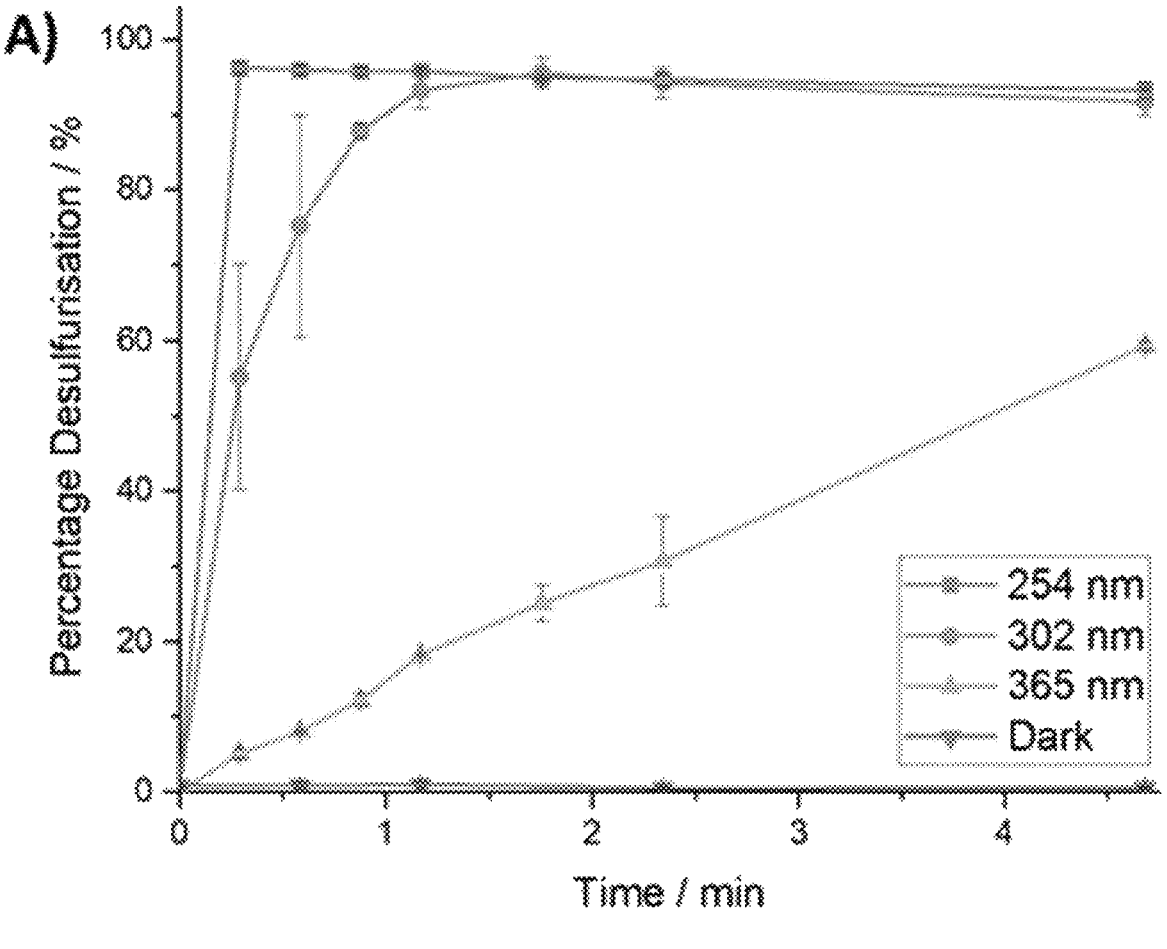
Figure 16:
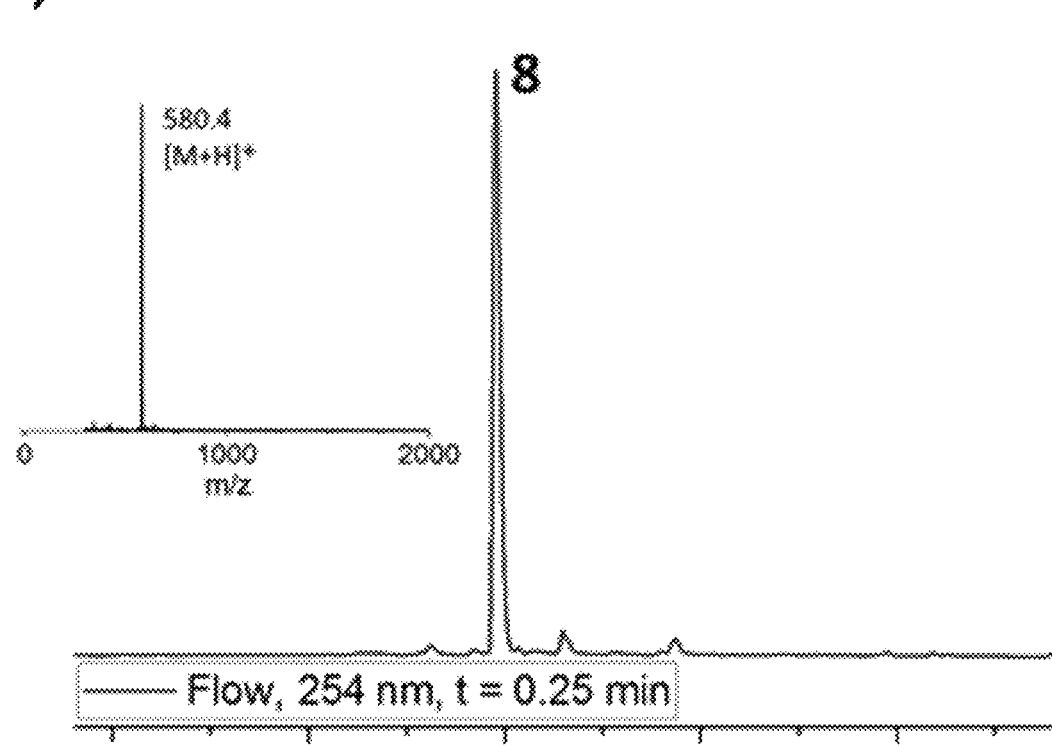
Figure 16:
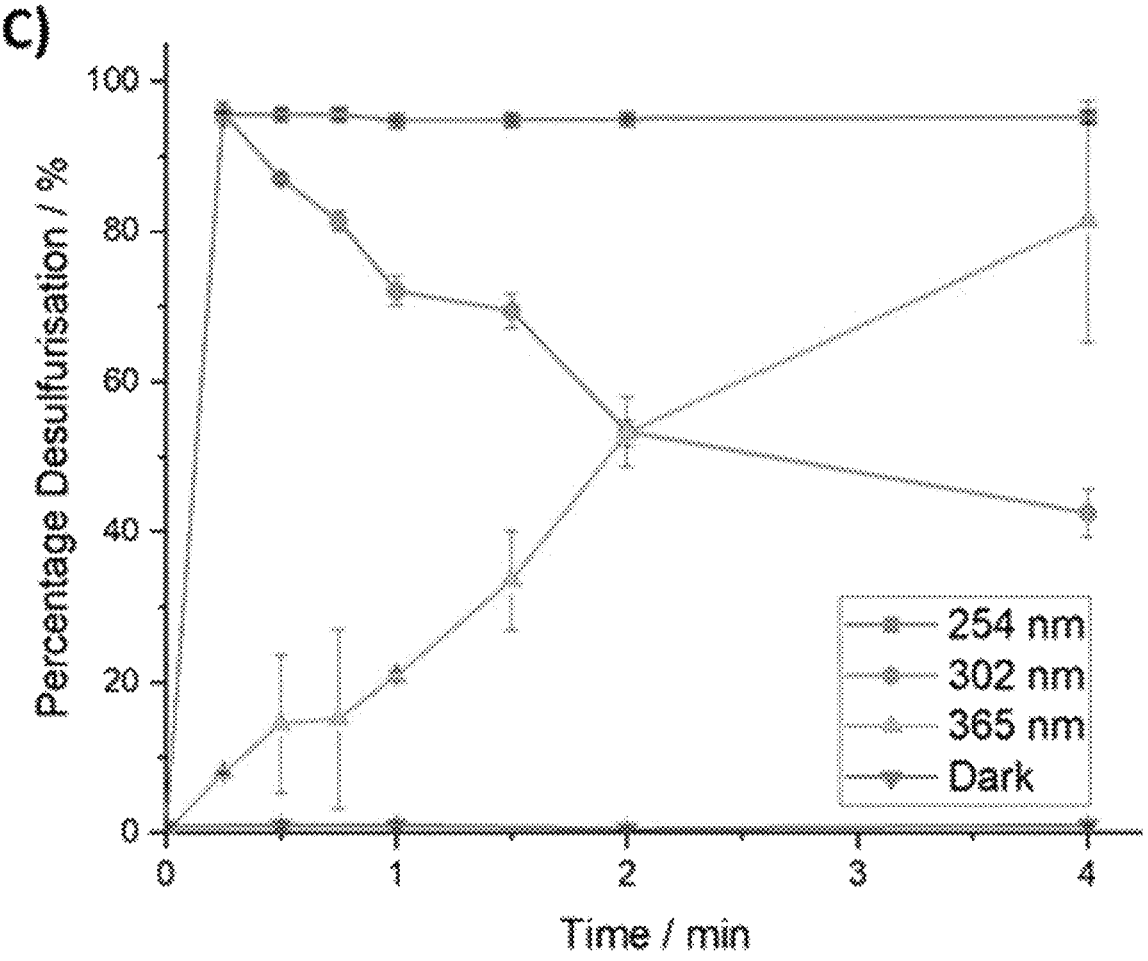
Figure 16:
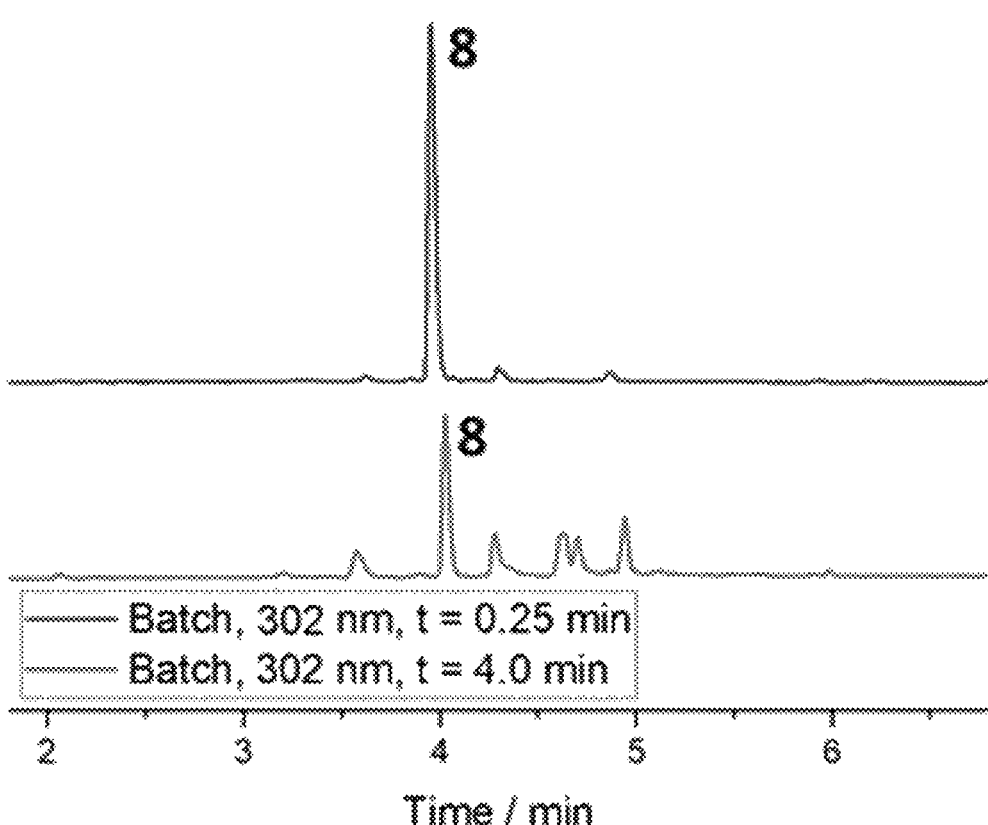

FIG. 16: Desulfurization experiments performed on 1 with 40 mM GSH, 200 mM TCEP in the absence of VA-044 under UV irradiation at $\lambda$=254 nm, 302 nm, and 365 nm (35 W, rt) A) kinetics in the flow system shown in Scheme S7 on a 150 µL scale; B) a crude UPLC chromatogram ($\lambda$=280, 0 to 15% B over 5 min, 0.1% TFA) of the photodesulfurization of H-CSPGYS-NH$_2$ (SEQ ID NO: 1) 1 to H-ASPGYS-NH$_2$ (SEQ ID NO: 8) 8 performed in flow at 254 nm after 0.25 minutes; C) kinetics in batch on a 150 µL scale; D) a crude UPLC chromatogram ($\lambda$=280, 0 to 15% B over 5 min, 0.1% TFA) of the photodesulfurization of H-CSPGYS-NH$_2$ (SEQ ID NO: 1) 1 to H-ASPGYS-NH$_2$ (SEQ ID NO: 8) 8 performed in batch at 302 nm after 0.25 minutes and 4.0 min. After 4.0 min, multiple unidentified peaks were observed alongside the desired product. Percentage desulfurization was calculated from integrating UPLC chromatogram peaks at $\lambda$=280 nm. Error bars represent one standard deviation above and below the mean calculated from three independent experiments. Inset MS data was collected over the entire target peptide UV peak in the UPLC-MS chromatogram.

Figure 17:
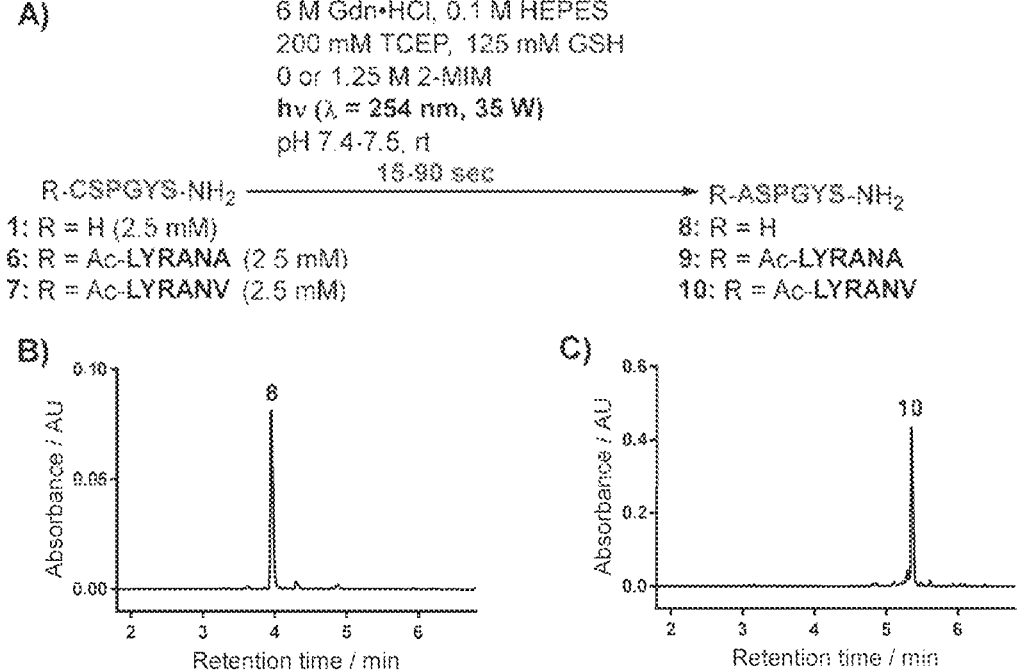

FIG. 17: A) Novel peptide photodesulfurization; UPLC chromatograms for the crude photodesulfurization reaction of B) 1 to 8 (0 to 15% B over 5 min, $\lambda$=214 nm) and C) 7 to 10 (0 to 28% B over 5 min, $\lambda$=214 nm).

Figure 18:
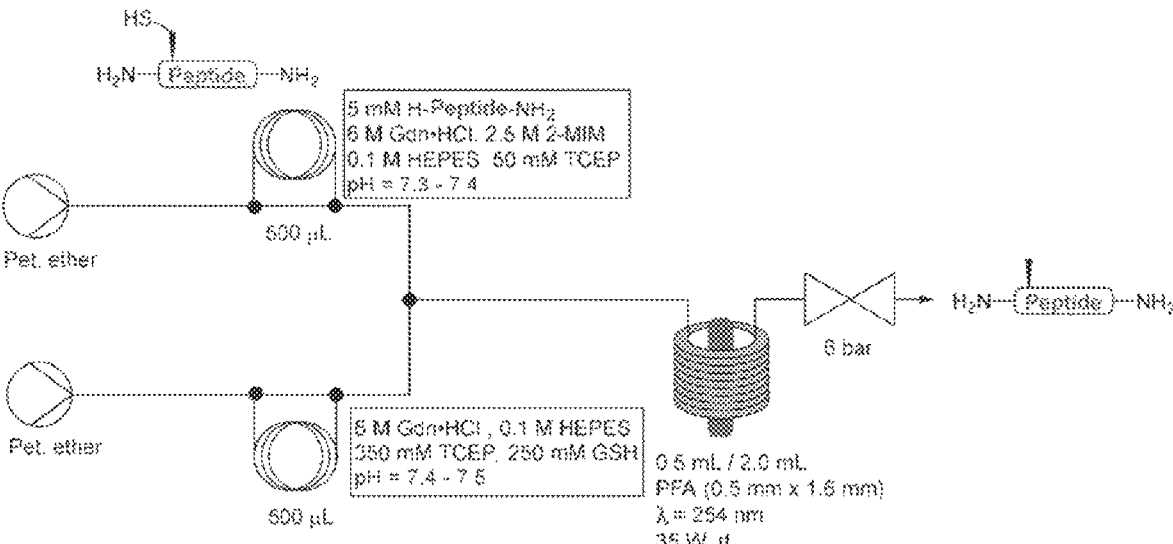

FIG. 18: Generalized photodesulfurization scheme in flow using conditions optimized for thiolysis.

Figure 19:
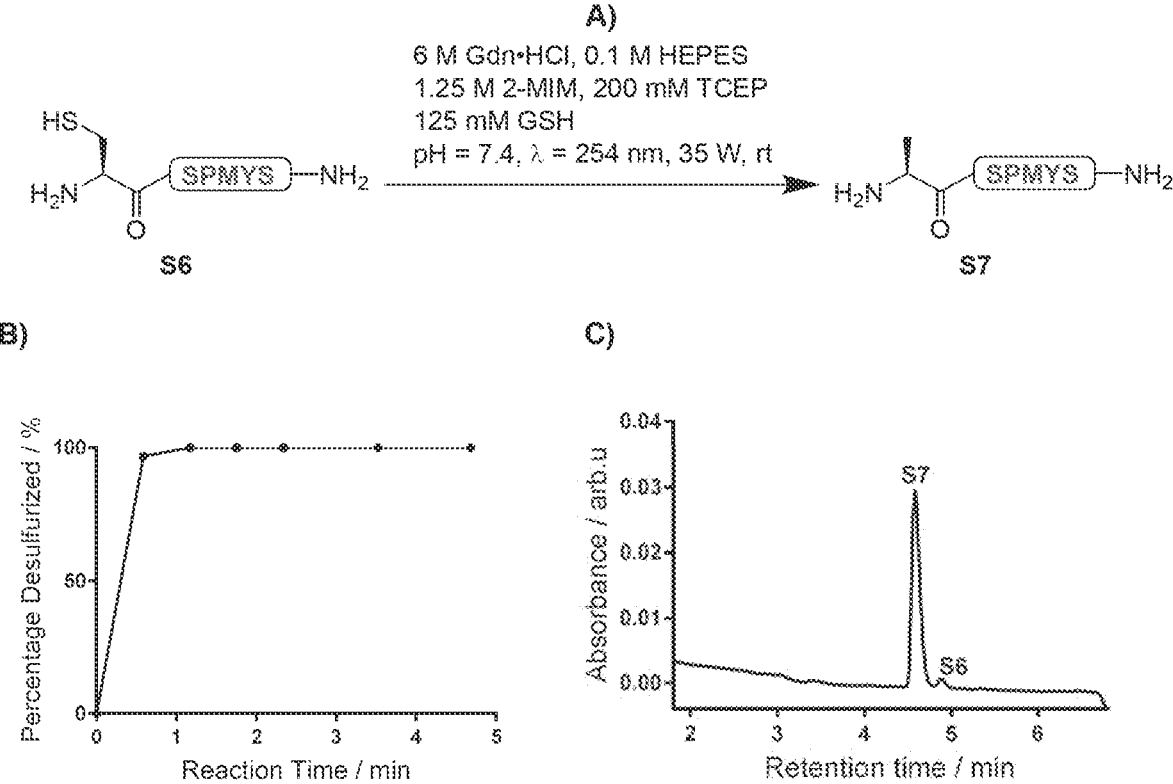

FIG. 19: A) Reaction scheme for the photodesulfurization of H-CSPMYS-NH$_2$ (SEQ ID NO: 18) S6 to H-ASPMYS-NH$_2$ (SEQ ID NO: 19) S7, using the flow system shown in Scheme S12. B) Kinetics of the photodesulfurization reaction. Percentage desulfurization is calculated from integrating UPLC chromatogram peaks at $\lambda$=280 nm. C) Crude UPLC chromatogram of photodesulfurization after 0.5 min ($\lambda$=280 nm, 0 to 15% B over 5 min, 0.1% TFA).

Figure 20:
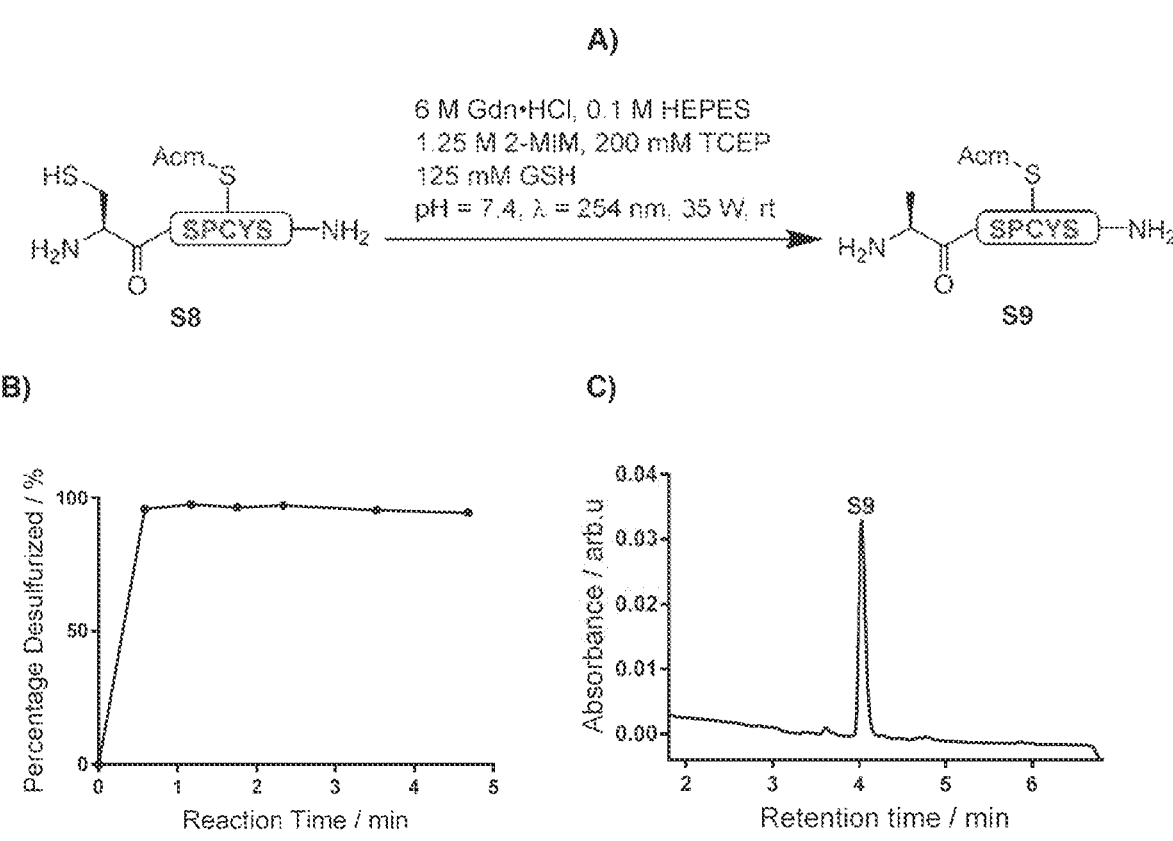

FIG. 20: A) Reaction scheme for the photodesulfurization of H-CSPC(Acm)YS-NH$_2$ (SEQ ID NO: 20) S8 to H-ASPC(Acm)YS-NH$_2$ (SEQ ID NO: 21) S9, using the flow system shown in Scheme S12. B) Kinetics of the photodesulfurization reaction. Percentage desulfurization is calculated from integrating UPLC chromatogram peaks at $\lambda$=280 nm. C) Crude UPLC chromatogram of photodesulfurization after 0.5 min ($\lambda$=280 nm, 0 to 15% B over 5 min, 0.1% TFA).

Figure 21:
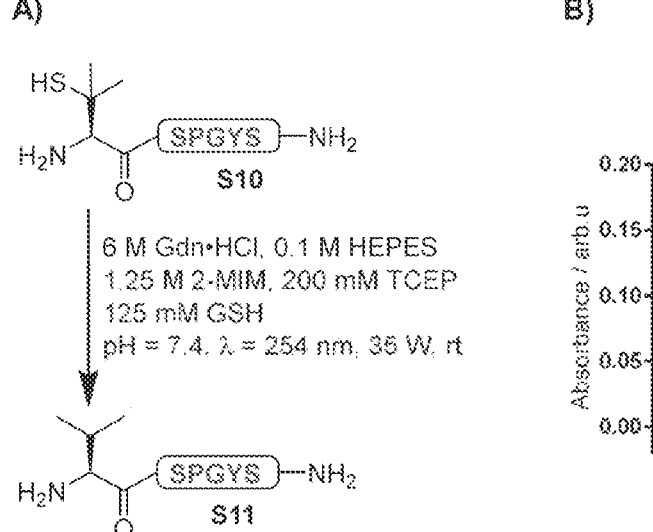
Figure 21:
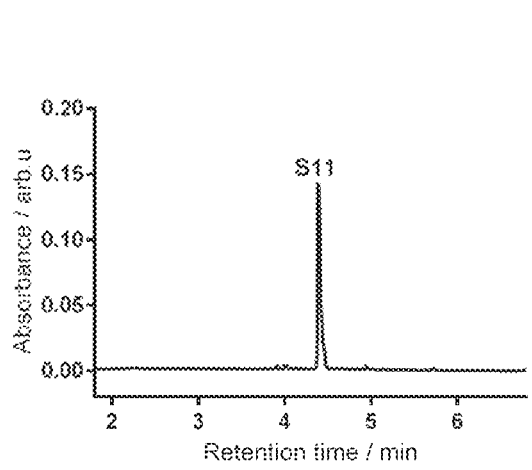

FIG. 21: A) Reaction scheme for the photodesulfurization of H-PenSPGYS-NH$_2$ (SEQ ID NO: 22) S10 to H-VSPGYS-NH$_2$ (SEQ ID NO: 23) S11, using the flow system shown in Scheme S12. B) Crude UPLC chromatogram of photodesulfurization after 1.0 min ($\lambda$=280 nm, 0 to 15% B over 5 min, 0.1% TFA).

Figure 22:
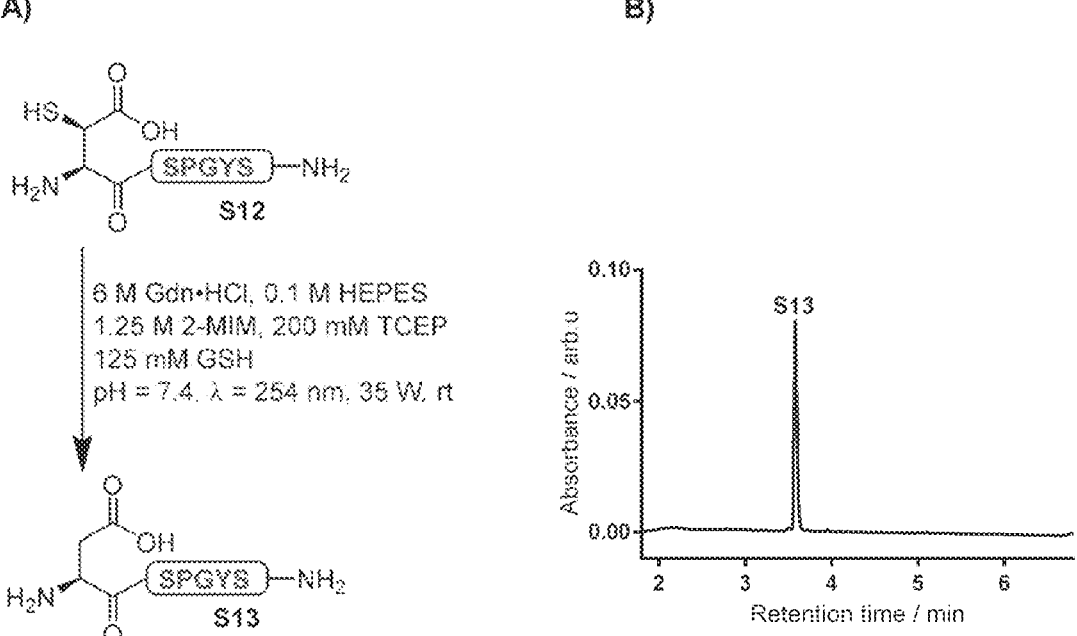

FIG. 22: A) Reaction scheme for the photodesulfurization of H-($\beta$-SH) DSPGYS-NH$_2$ (SEQ ID NO: 24) S12 to H-DSPGYS-NH$_2$ (SEQ ID NO: 25) S13, using the flow system shown in Scheme S12. B) Crude UPLC chromatogram of photodesulfurization after 0.5 min ($\lambda$=280 nm, 0 to 15% B over 5 min, 0.1% TFA).

Figure 23:
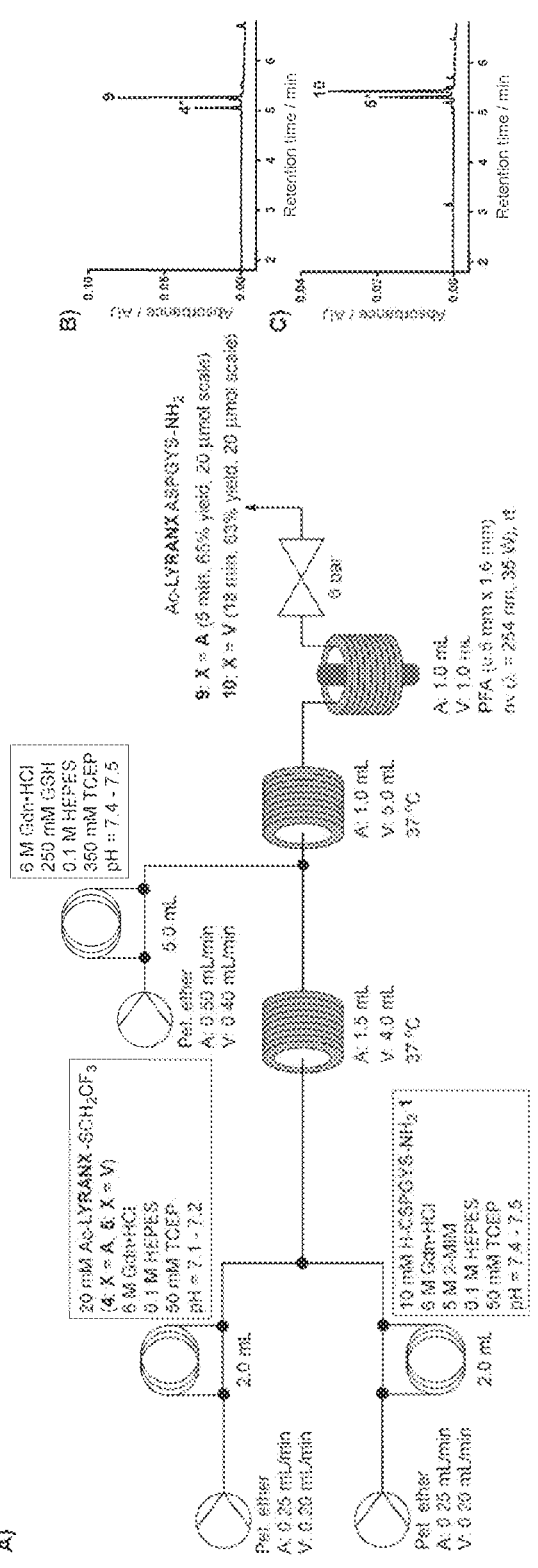

FIG. 23: A) Setup for the ligation-photodesulfurization procedure in flow. Crude UPLC trace (gradient: 0 to 28% B over 5 min, $\lambda$=280 nm) of the ligation-photodesulfurization procedure performed between 1 and B) alanine thioester 4 to generate 9 (total reaction time 5 min) and C) valine thioester 5 to generate 10 (total reaction time 18 min). * peak corresponds to the GSH thioester of 4 and 5.

Figure 24:
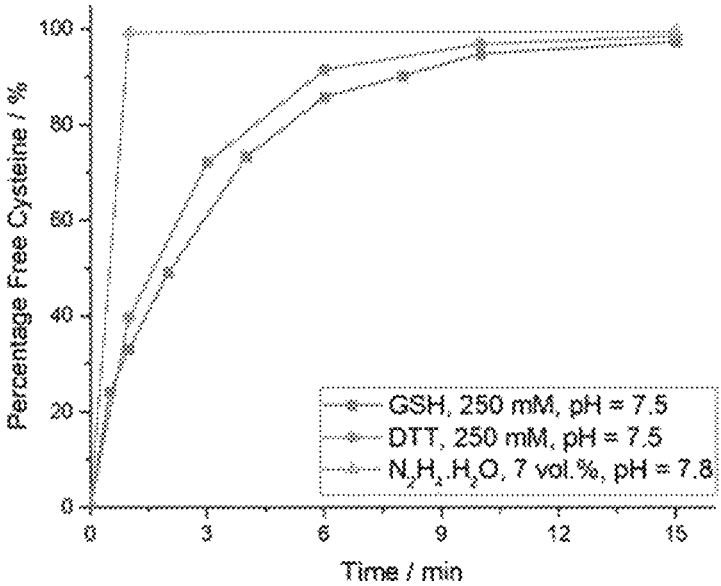

FIG. 24: The rate of thiolysis and hydrazinolysis of the valine product thioester S3 under different additive conditions.

Figure 25:
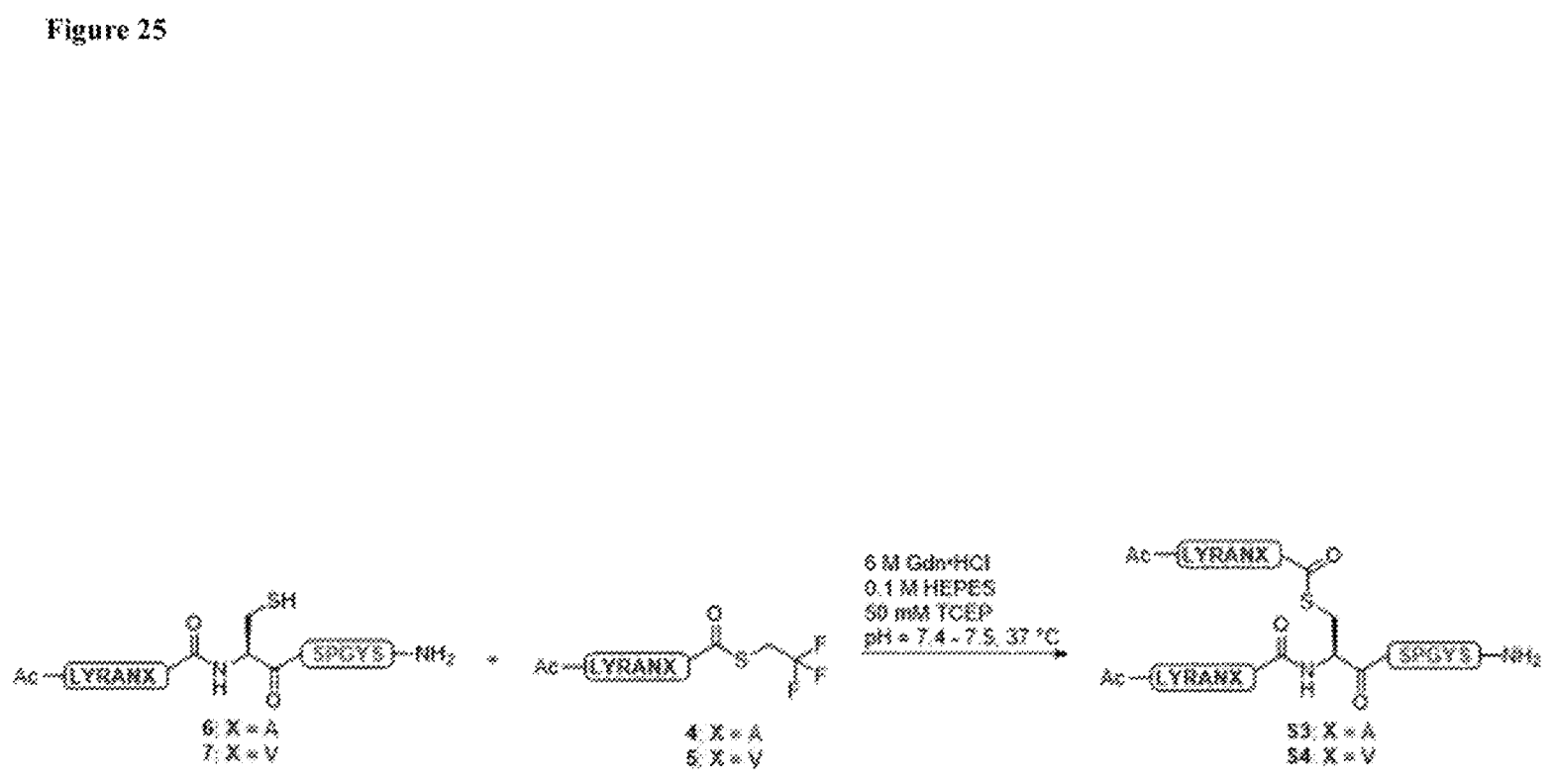

FIG. 25: Formation of product thioester species during ligation.

Figure 26:
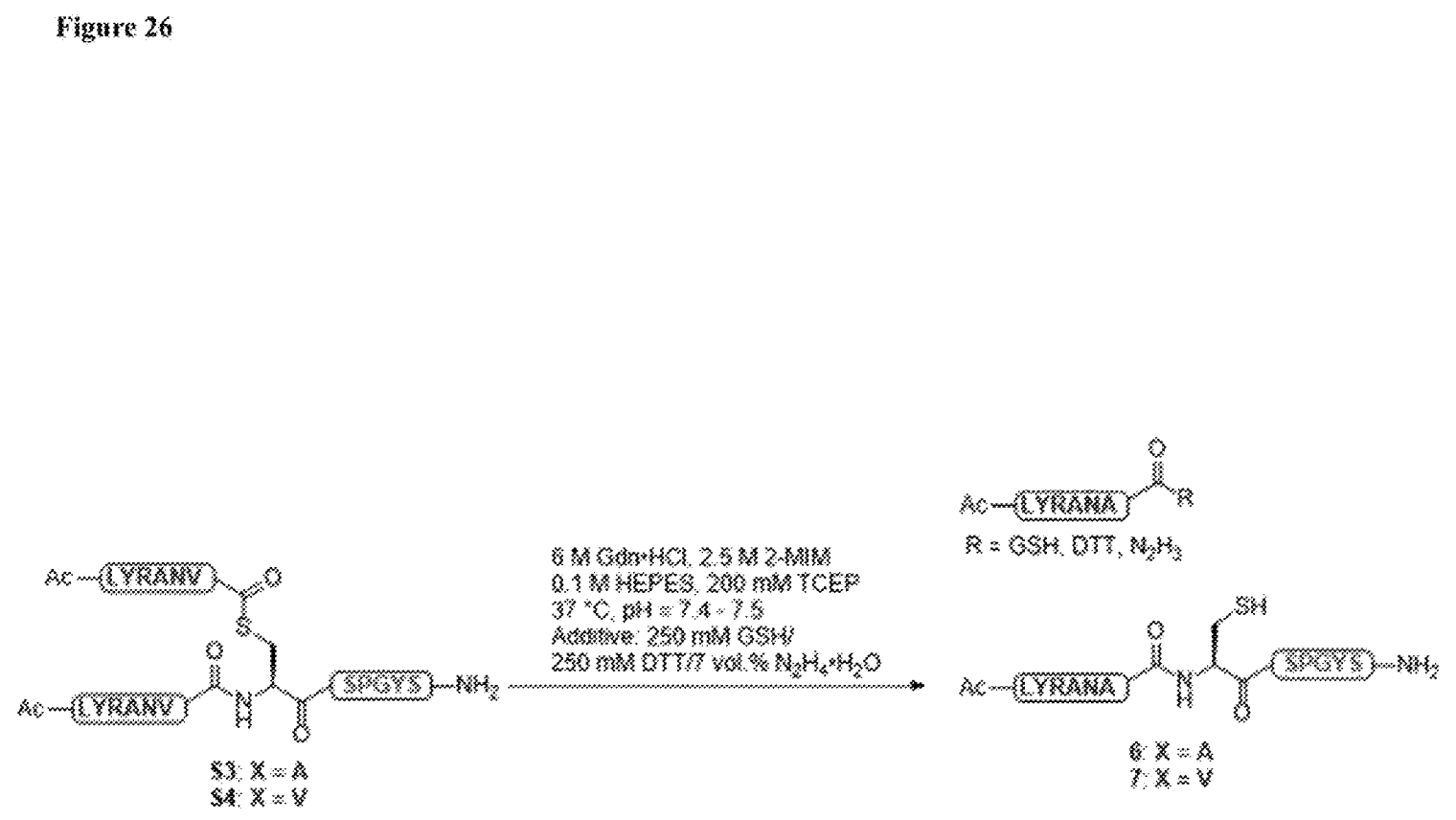

FIG. 26: General scheme for thiolysis and hydrazinolysis of S3 and S4.

Figure 27:
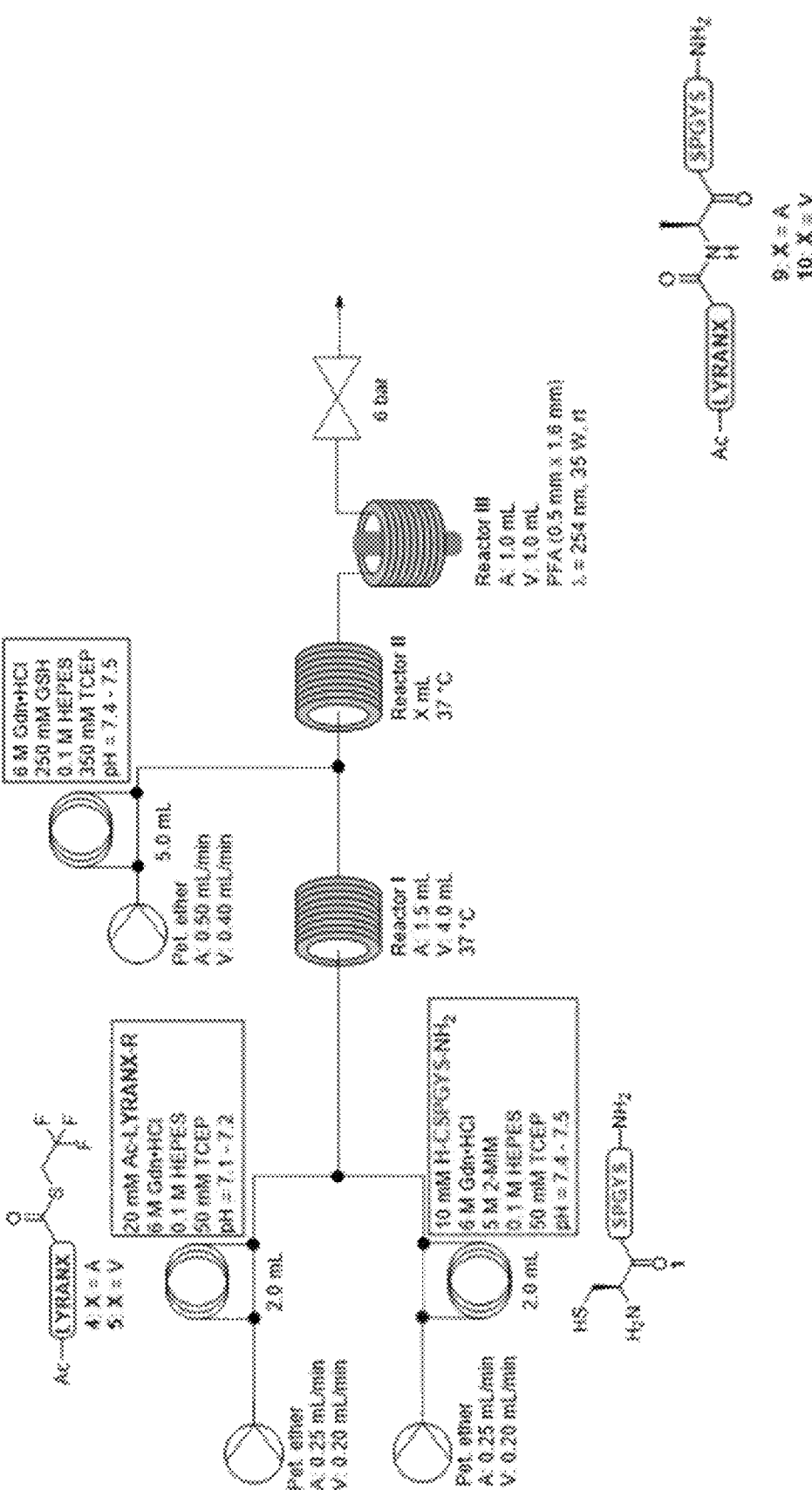

FIG. 27: Flow system used to perform in flow ligation-photodesulfurization in flow to investigate the rate of thiolysis of product thioesters S3 and S4.

Figure 28:
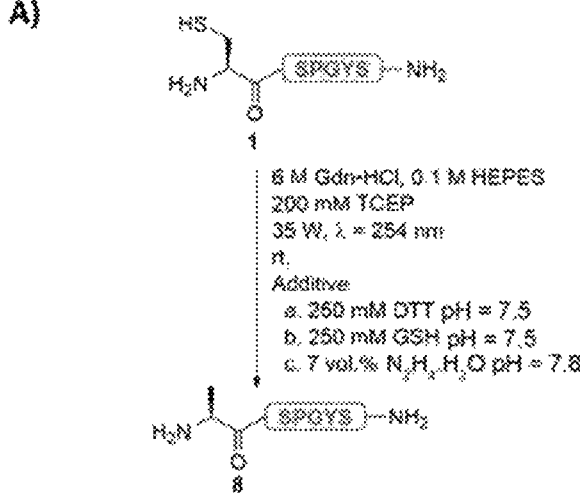
Figure 28:
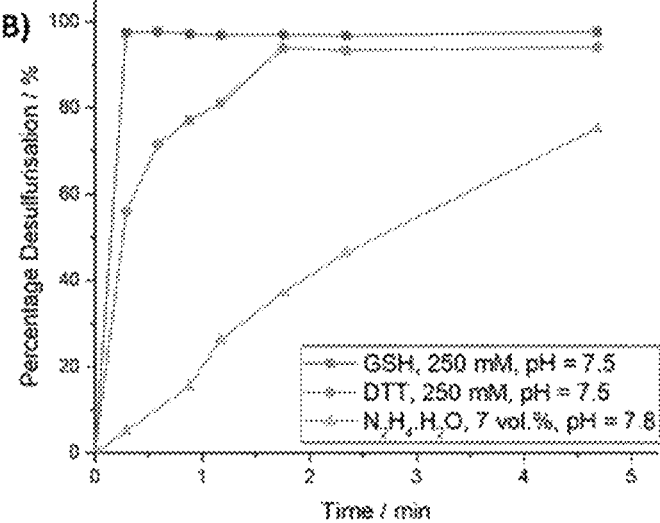

FIG. 28: A) Scheme for the photodesulfurization of 1 under different additive conditions; and B) the rate of photodesulfurization of 1 under different additive conditions (used for the thiolysis of product thioesters). Percentage desulfurization was calculated from integrating UPLC chromatogram peaks at $\lambda$=280 nm.

Figure 29:
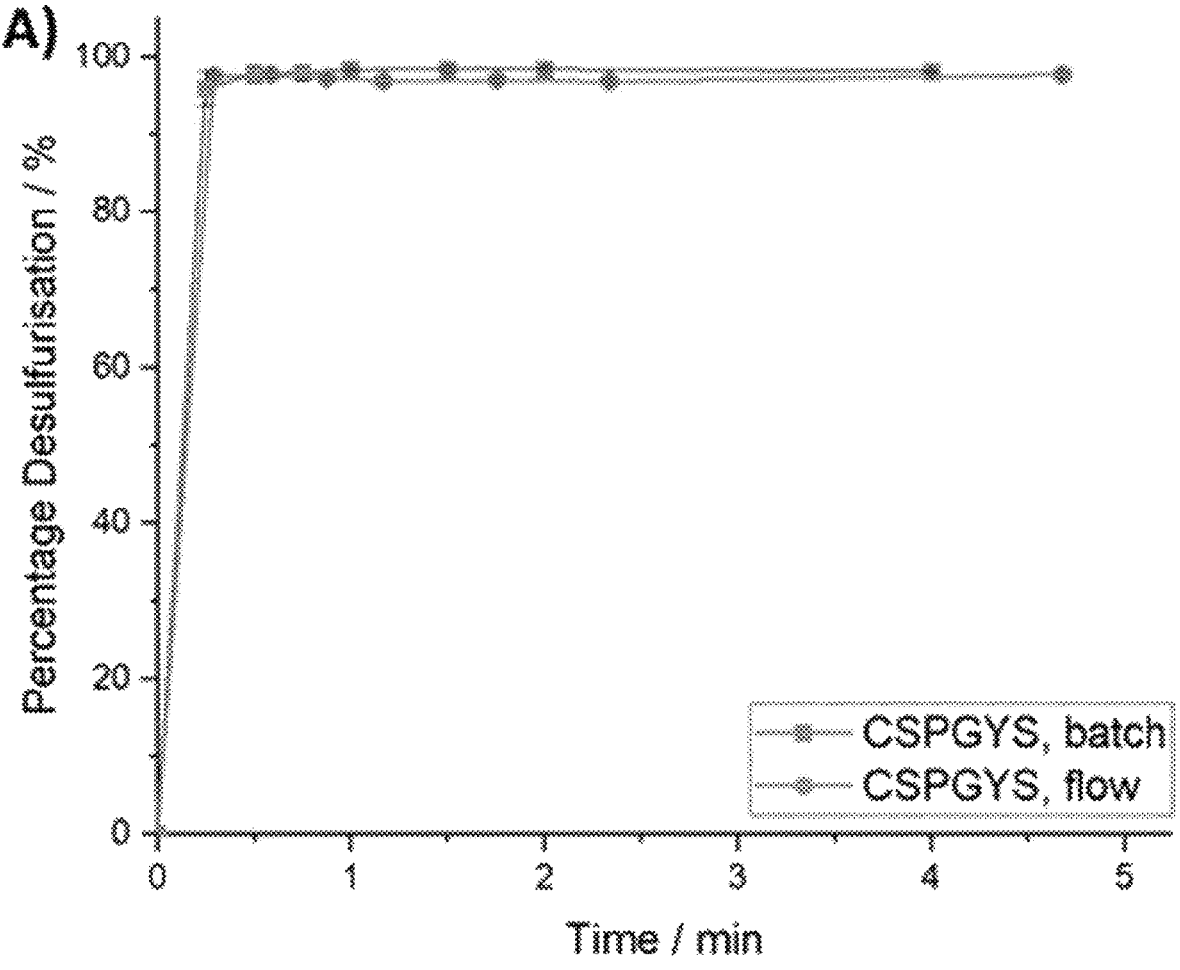
Figure 29:
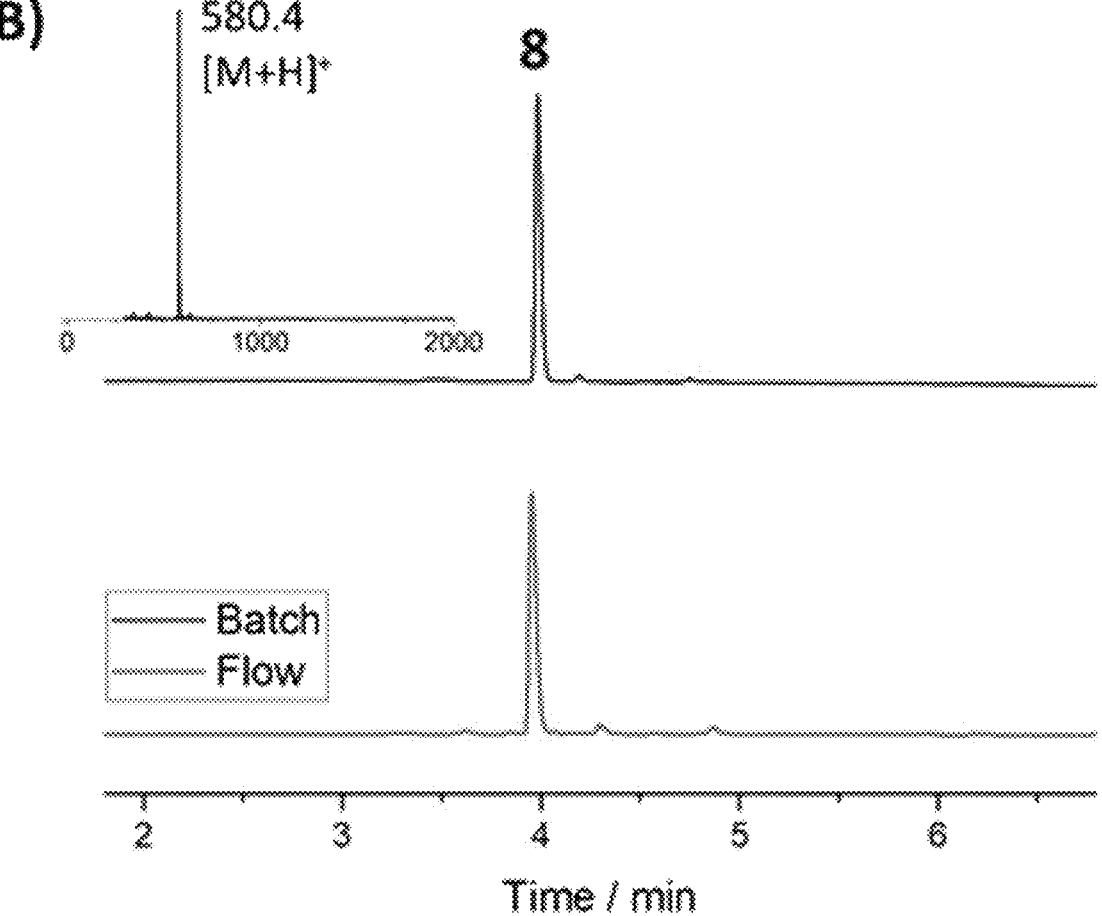
Figure 29:
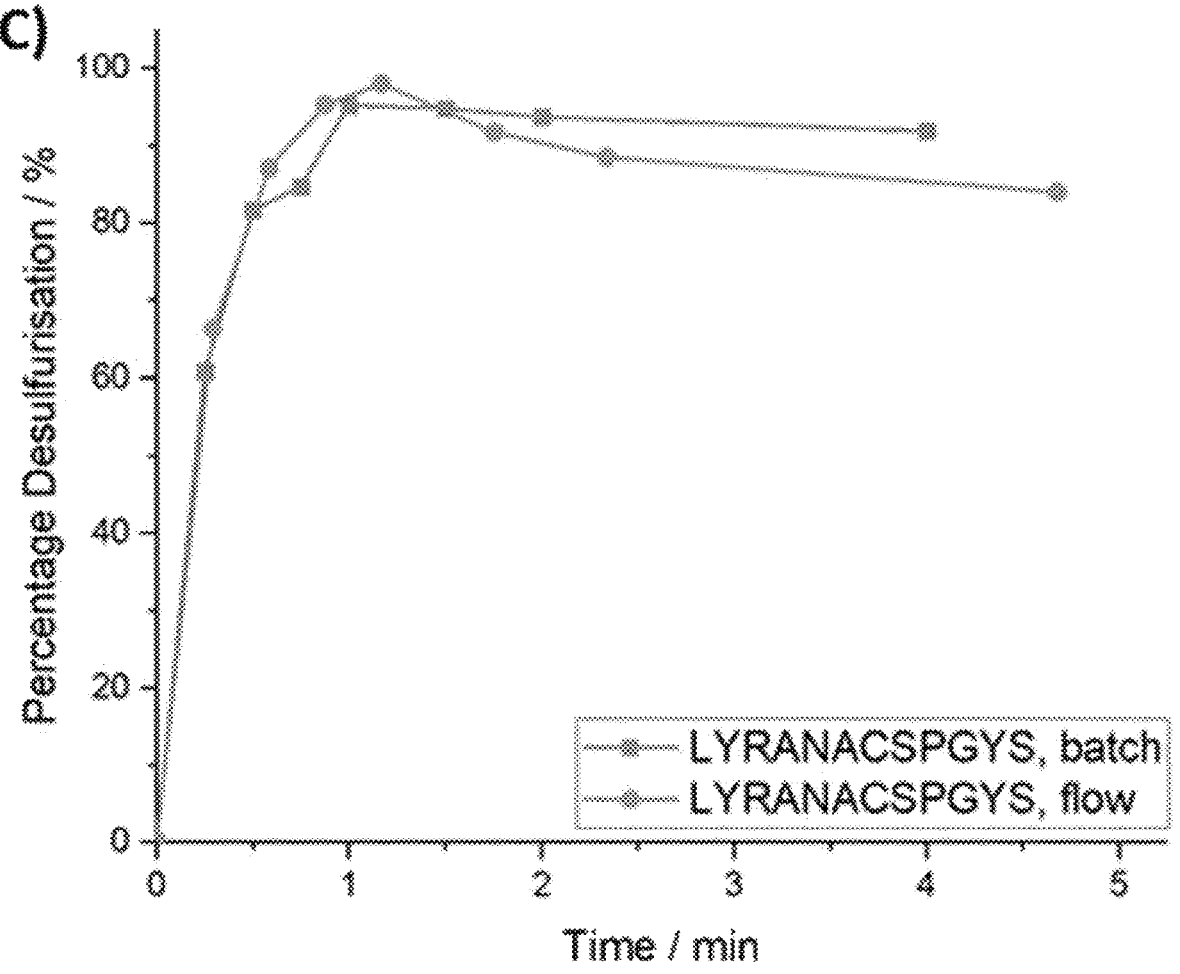
Figure 29:
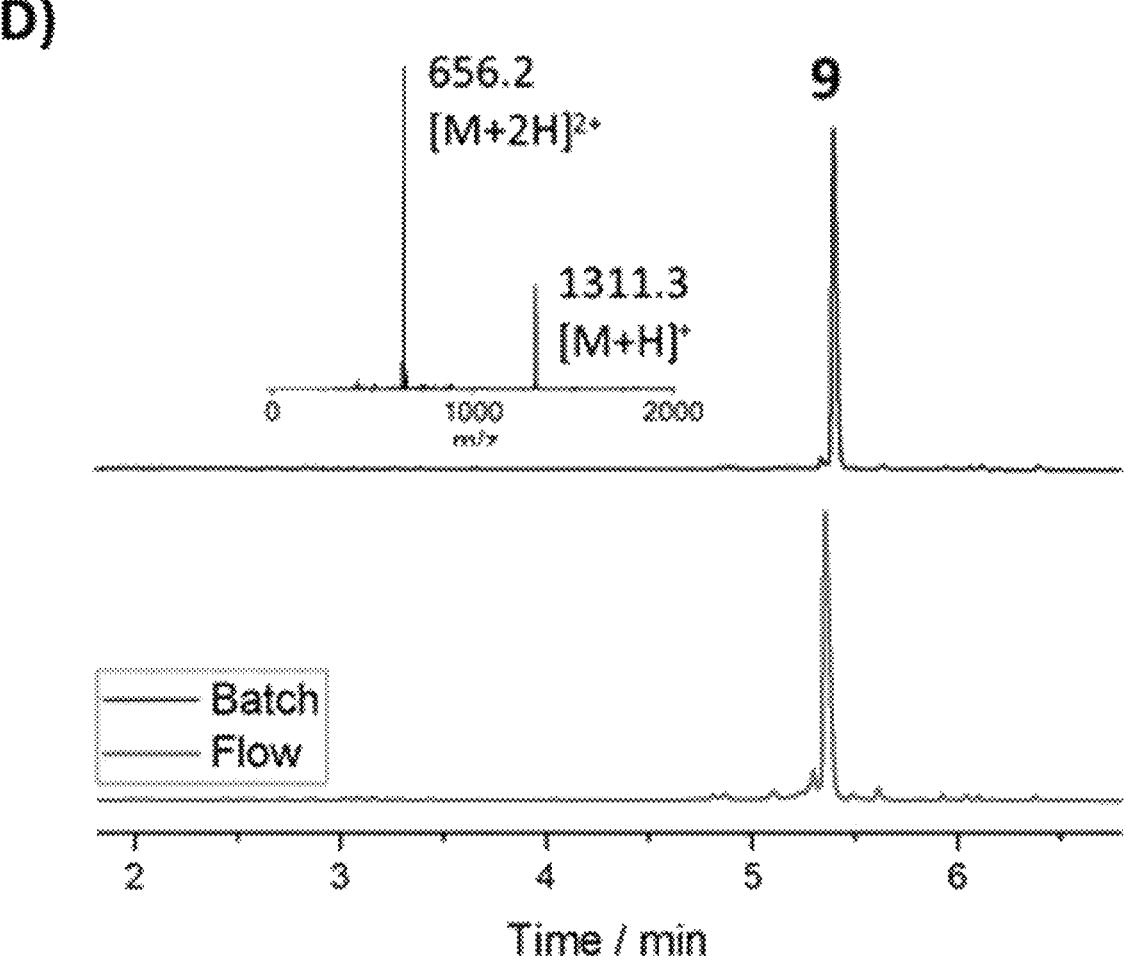
Figure 29:
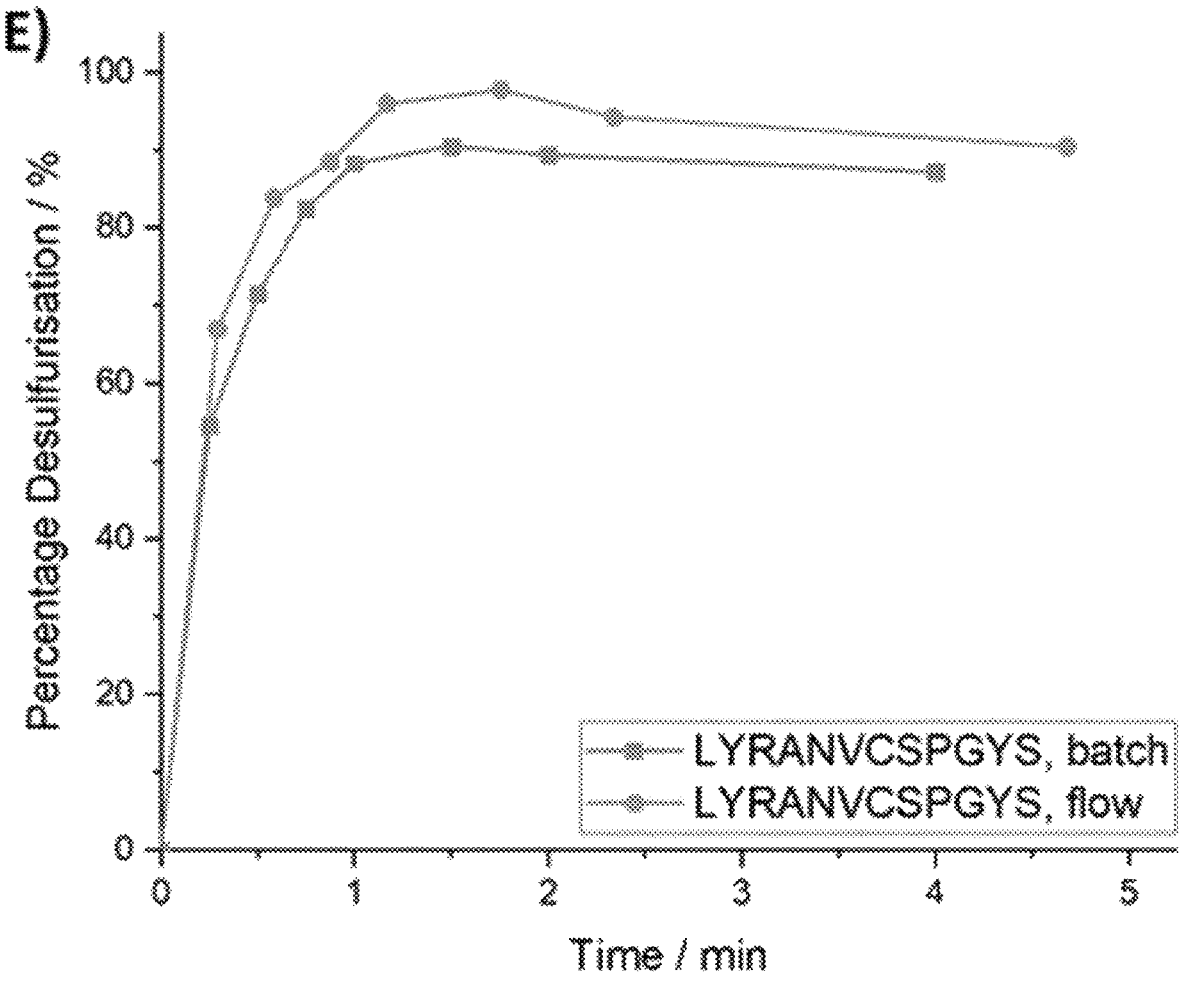
Figure 29:
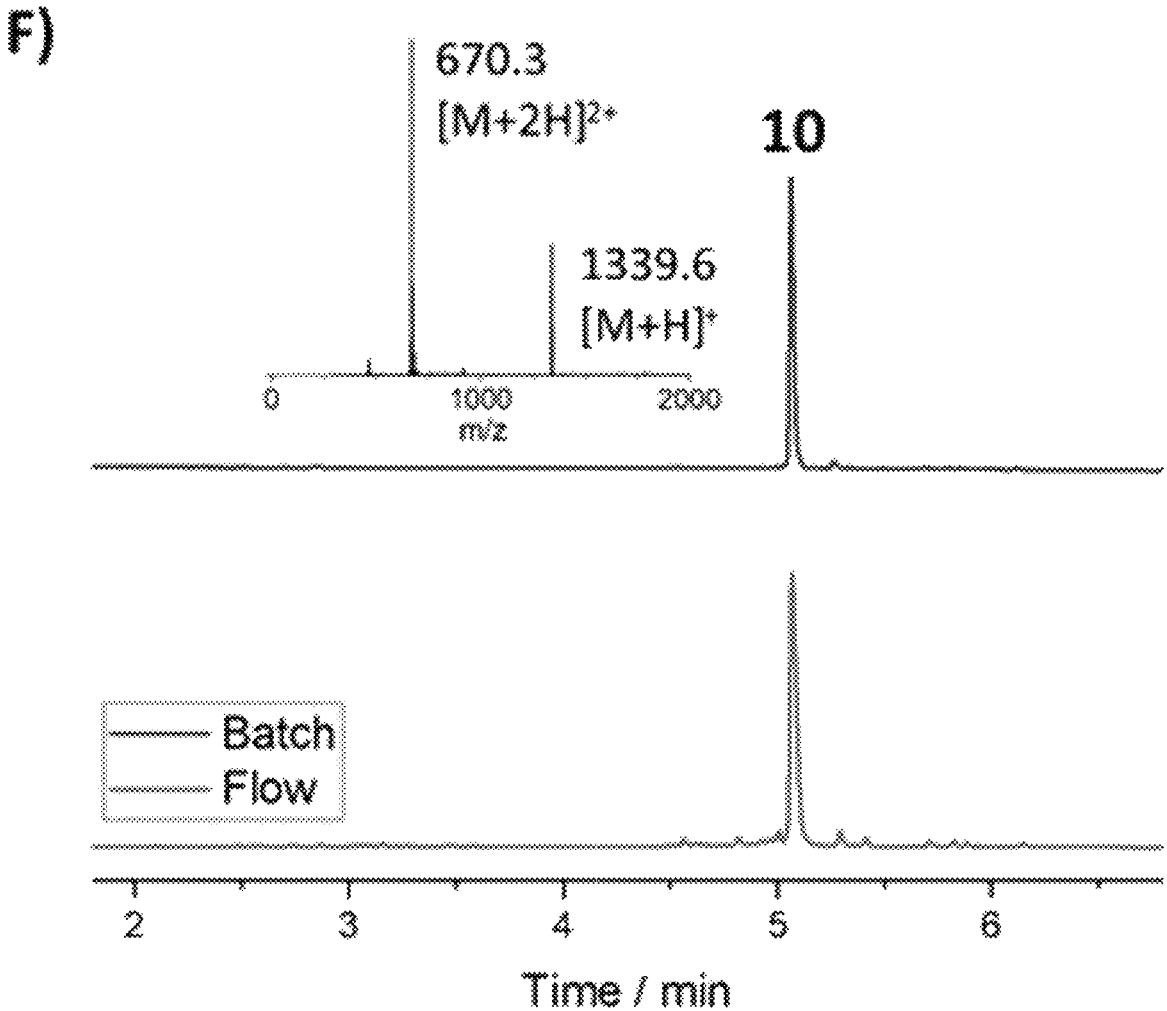

FIG. 29: A) Photodesulfurization kinetics of H-CSPGYS-NH$_2$ (SEQ ID NO: 1) 1 to H-ASPGYS-NH$_2$ (SEQ ID NO: 8) 8; B) associated UPLC chromatogram after 0.25 minutes ($\lambda$=280 nm, 0 to 15% B over 5 min, 0.1% TFA); C) Photodesulfurization kinetics of Ac-LYRANACSPGYS-NH$_2$ (SEQ ID NO: 6) 6 to Ac-LYRANAASPGYS-NH$_2$ (SEQ ID NO: 9) 9; D) associated UPLC chromatogram after 1.5 minutes ($\lambda$=280 nm, 0 to 28% B over 5 min, 0.1% TFA); E) Photodesulfurization kinetics of Ac-LYRANVCSPGYS-NH$_2$ (SEQ ID NO: 7) 7 to Ac-LYRANVASPGYS-NH$_2$ (SEQ ID NO: 10) 10; F) associated UPLC chromatogram after 1.5 minutes ($\lambda$=280 nm, 0 to 28% B over 5 min, 0.1% TFA). Percentage desulfurization is calculated from integrating UPLC chromatogram peaks at $\lambda$=280 nm. Error bars represent a single standard deviation above and below the mean calculated from three independent experiments.

Figure 30:
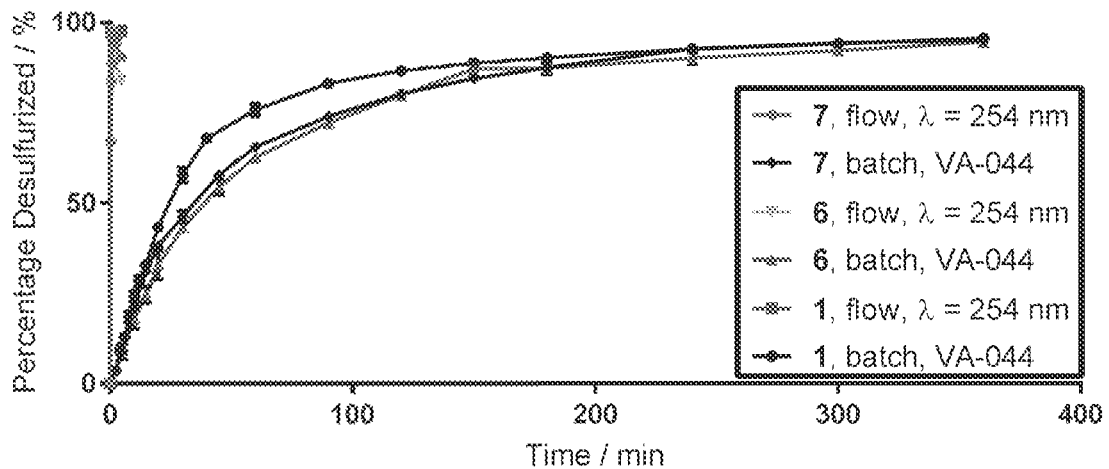

FIG. 30: Photodesulfurization kinetics of H-CSPGYS-NH$_2$ (SEQ ID NO: 1) 1 to H-ASPGYS-NH$_2$ (SEQ ID NO: 8) 8, Ac-LYRANACSPGYS-NH$_2$ (SEQ ID NO: 6) 6 to Ac-LYRANAASPGYS-NH$_2$ (SEQ ID NO: 9) 9, and Ac-LYRANVCSPGYS-NH$_2$ (SEQ ID NO: 7) 7 to Ac-LYRANVASPGYS-NH$_2$ (SEQ ID NO: 10) 10 under either standard VA-044 (20 mM) initiated conditions, or under photoirradiation conditions at $\lambda$=254 nm, 35 W. Percentage desulfurization is calculated from integrating UPLC chromatogram peaks at $\lambda$=280 nm. Error bars represent a single standard deviation above and below the mean calculated from three independent experiments.

Figure 31:
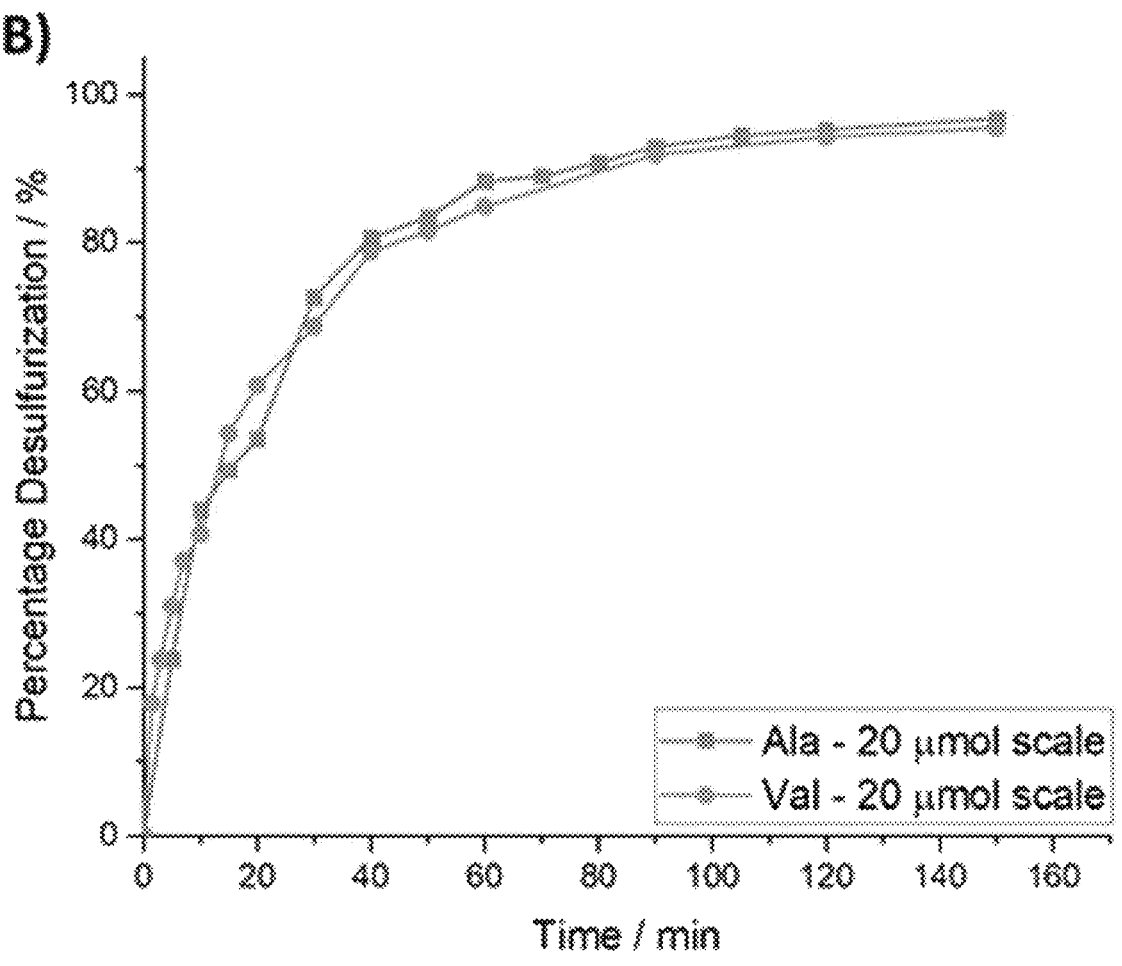
Figure 31:
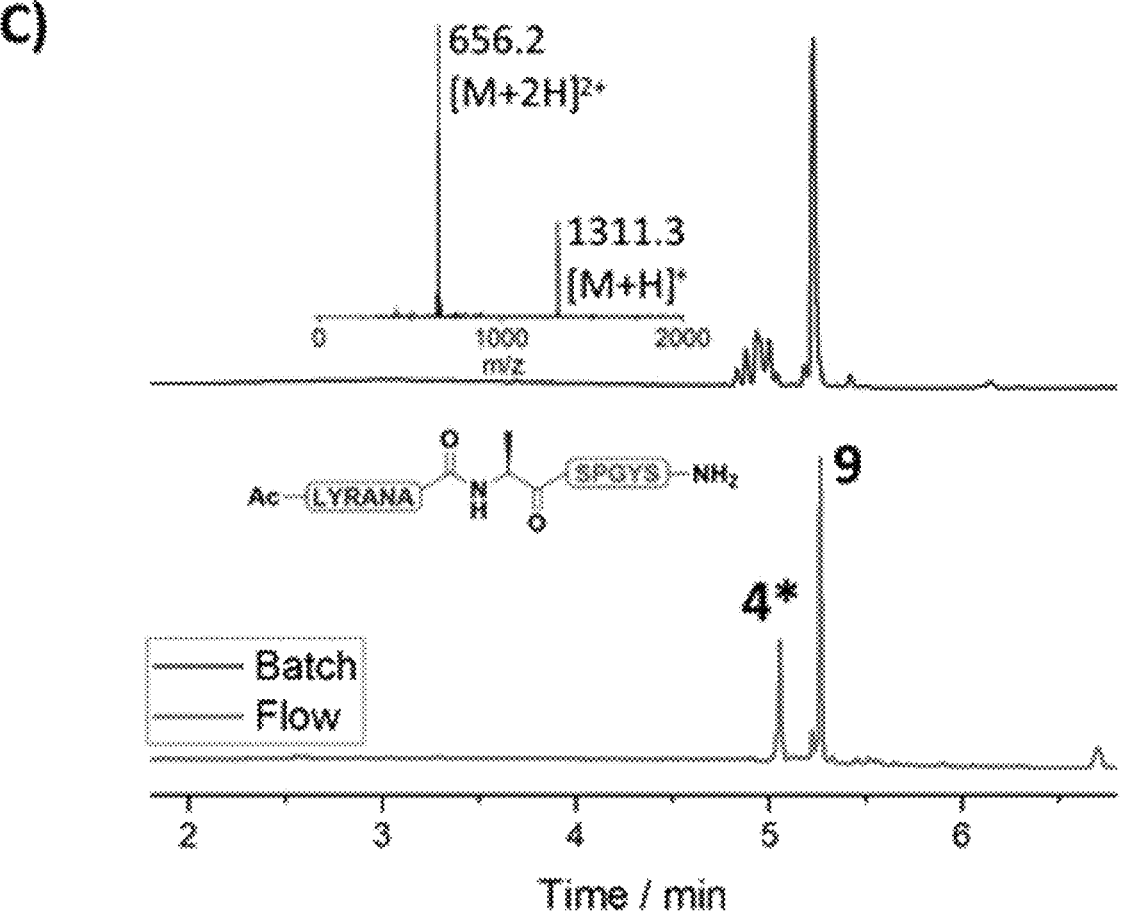
Figure 31:
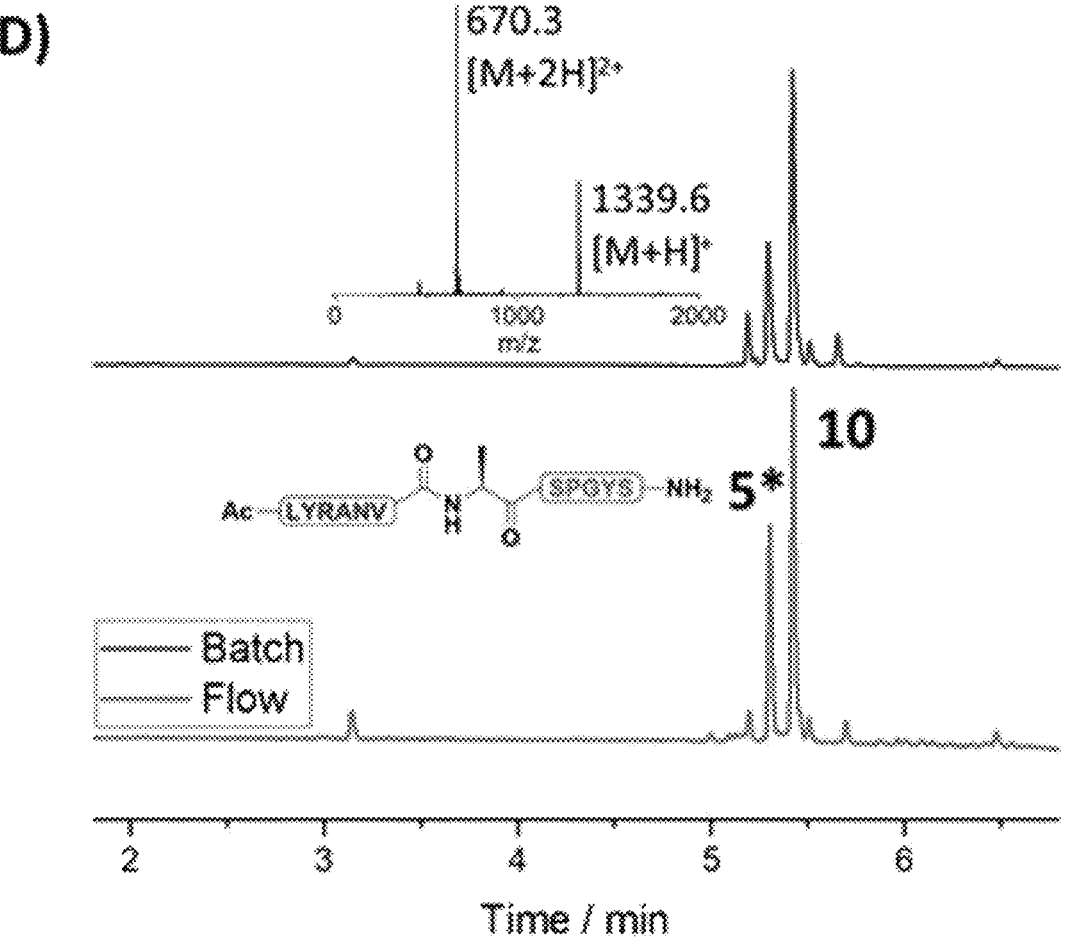

FIG. 31: A) Scheme of the novel photodesulfurization protocol employed; B) kinetics for the photodesulfurization of 6 and 7 on a 20 µmol scale in batch; C) crude UPLC chromatograms ($\lambda$=280 nm, 0 to 28% B over 5 min, 0.1% TFA) for in-line ligation-photodesulfurization in flow at alanine showing the desired product Ac-LYRANAASPGYS-NH$_2$ (SEQ ID NO: 9) 9, and glutathione thioester Ac-LYRANA-GSH (SEQ ID NO: 33) 4* derived from thioester Ac-LYRANA-SCH$_2$CF$_3$ (SEQ ID NO: 4) 4. D) crude UPLC chromatograms ($\lambda$=280 nm, 0 to 28% B over 5 min, 0.1% TFA) for in-line ligation-photodesulfurization in flow at valine showing the desired product AC-LYRANVASPGYS-NH$_2$ (SEQ ID NO: 10) 10 and glutathione thioester Ac-LYRANA-GSH (SEQ ID NO: 33) 5* derived from thioester Ac-LYRANV-SCH$_2$CF$_3$ (SEQ ID NO: 5) 5. Percentage desulfurization is calculated from integrating UPLC chromatogram peaks at $\lambda$=280 nm. Inset MS data was collected over the entire target peptide UV peak in the UPLC-MS chromatogram.

Figure 32:
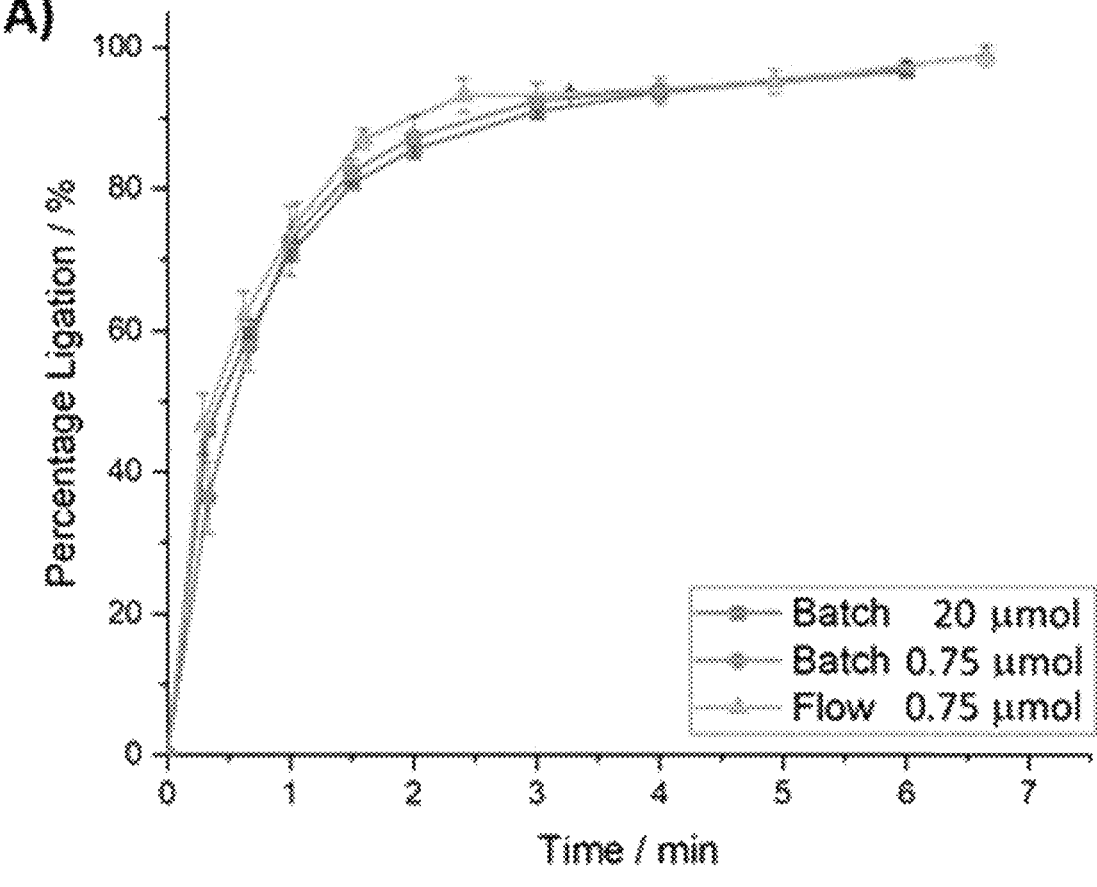
Figure 32:
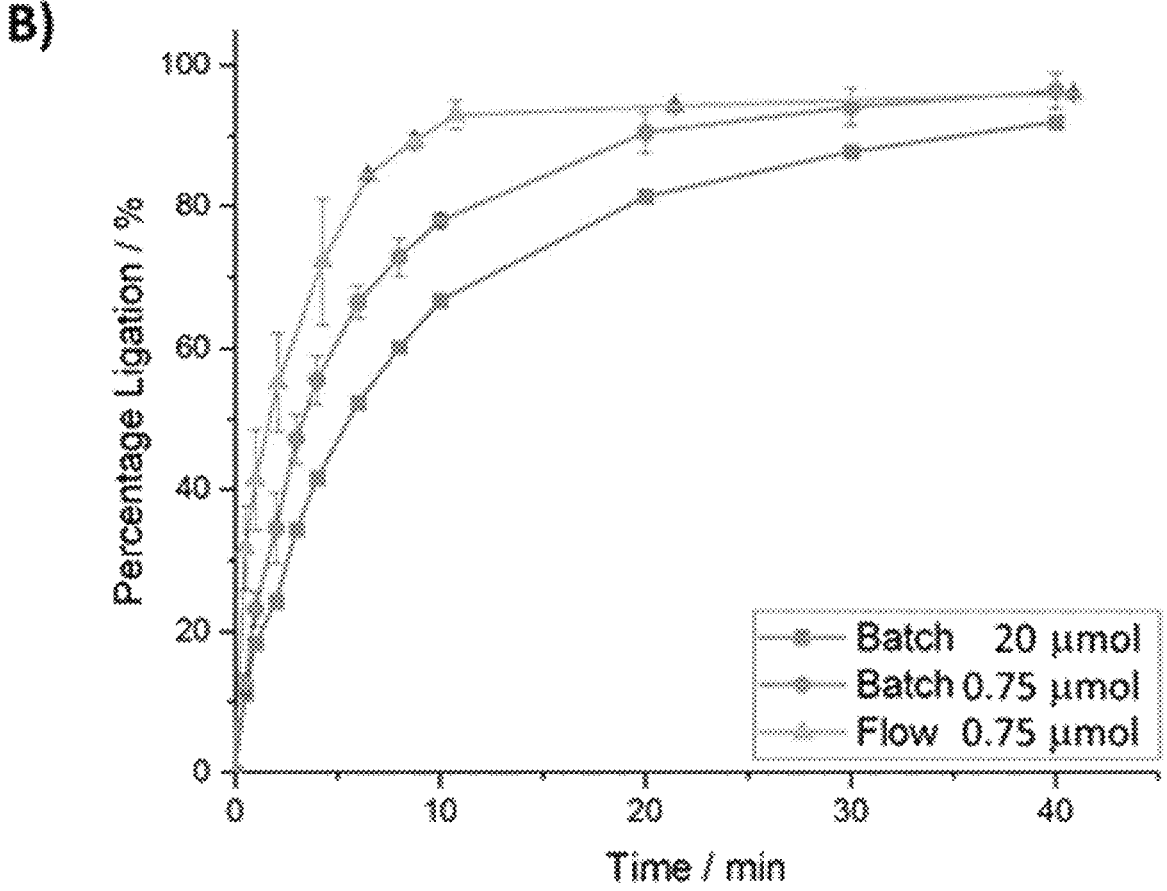
Figure 32:
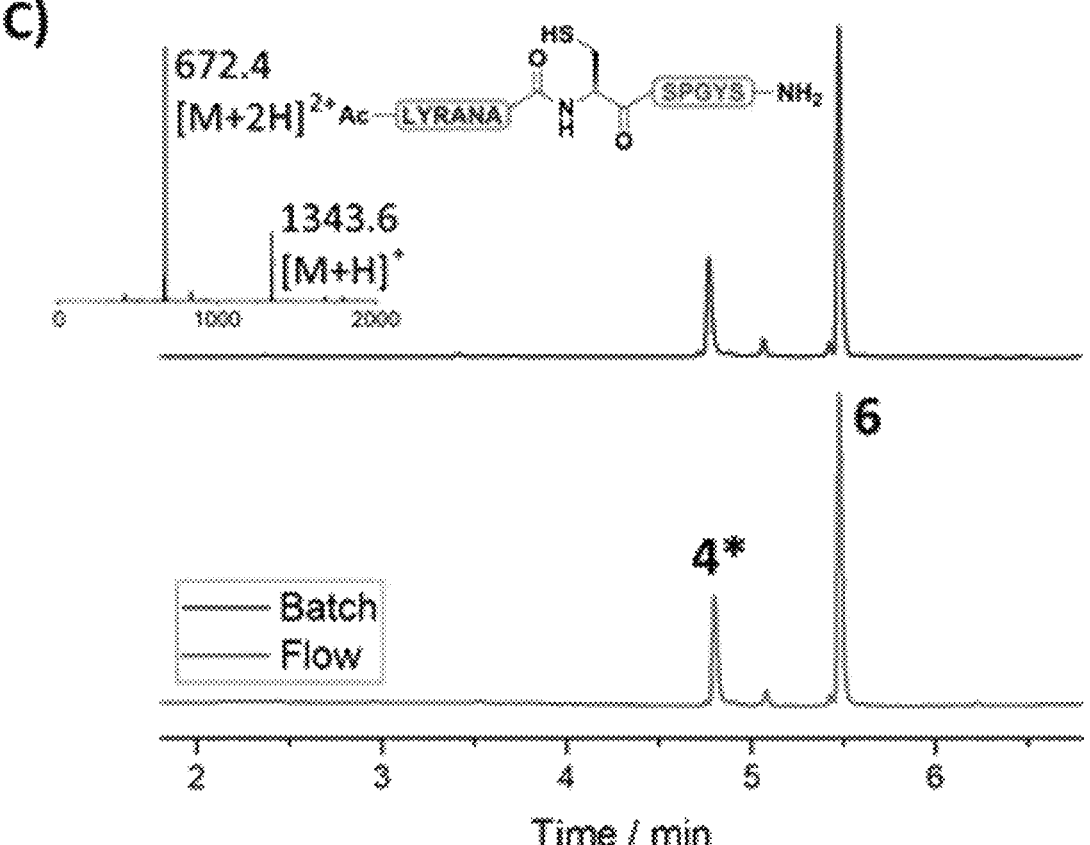
Figure 32:
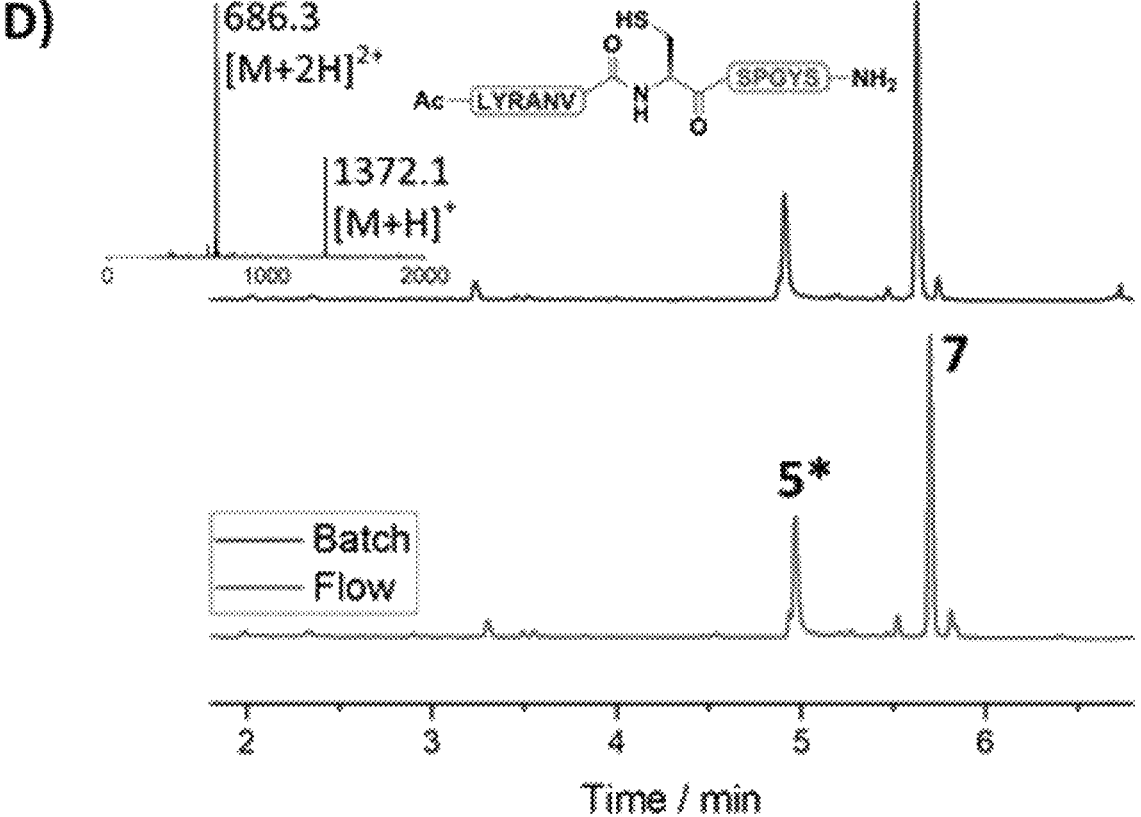

FIG. 32: Native chemical ligation was performed using peptide trifluoroethyl thioesters 4 and 5 and 2.5 M 2-MIM as an additive, in batch and flow, on a 0.75 µmol scale and in batch on a 20 µmol scale. Kinetics were monitored at A)

an alanine junction, and B) a valine junction. C) Crude UPLC chromatogram ($\lambda$=280 nm, 0 to 28% B over 5 min, 0.1% TFA) for ligation at alanine on a 0.75 µmol scale in both batch and flow, showing conversion to the desired product Ac-LYRANACSPGYS-NH$_2$ (SEQ ID NO: 6) 6 as well as the peptide acyl hydrazide Ac-LYRANA-NHNH$_2$ (SEQ ID NO: 34) 4* (formed from Ac-LYRANA-SCH$_2$CF$_3$ (SEQ ID NO: 4) 4 upon the addition of hydrazine hydrate to quench the reaction). D) Crude UPLC chromatogram ($\lambda$=280 nm, 0 to 28% B over 5 min, 0.1% TFA) for ligation at valine on a 0.75 µmol scale in both batch and flow, showing conversion to the desired product Ac-LYRANVCSPGYS-NH$_2$ (SEQ ID NO: 7) 7 as well as the peptide acyl hydrazide Ac-LYRANV-NHNH$_2$ (SEQ ID NO: 35) 5* (formed from Ac-LYRANV-SCH$_2$CF$_3$ (SEQ ID NO: 5) 5 upon the addition of hydrazine hydrate to quench the reaction). Inset MS data was collected over the entire target peptide UV peak in the UPLC-MS chromatogram.

Figure 33:
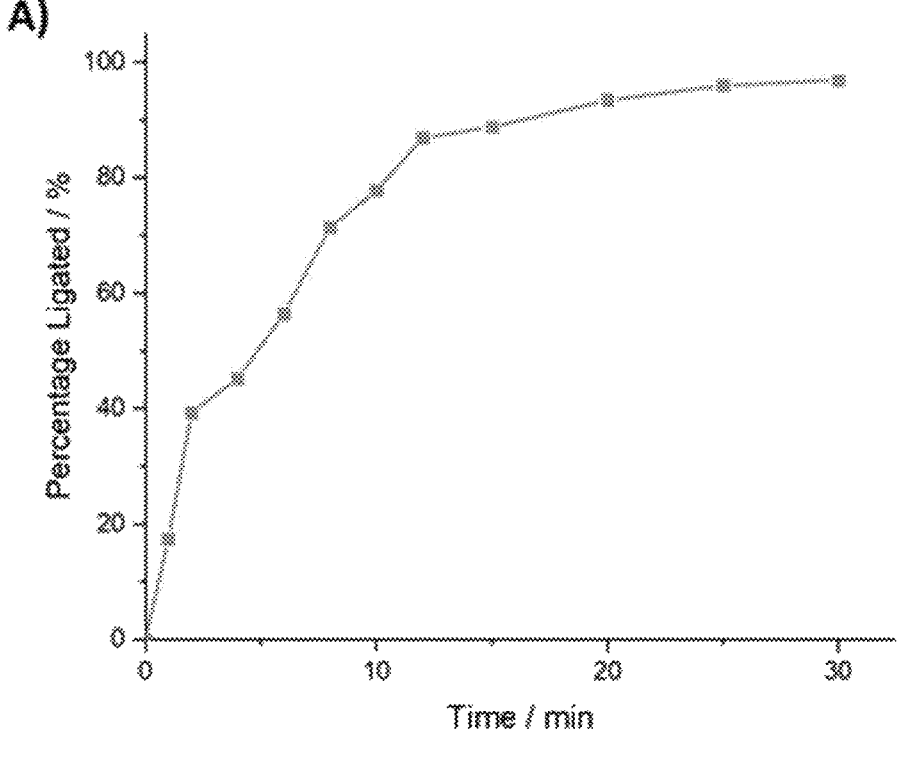
Figure 33:
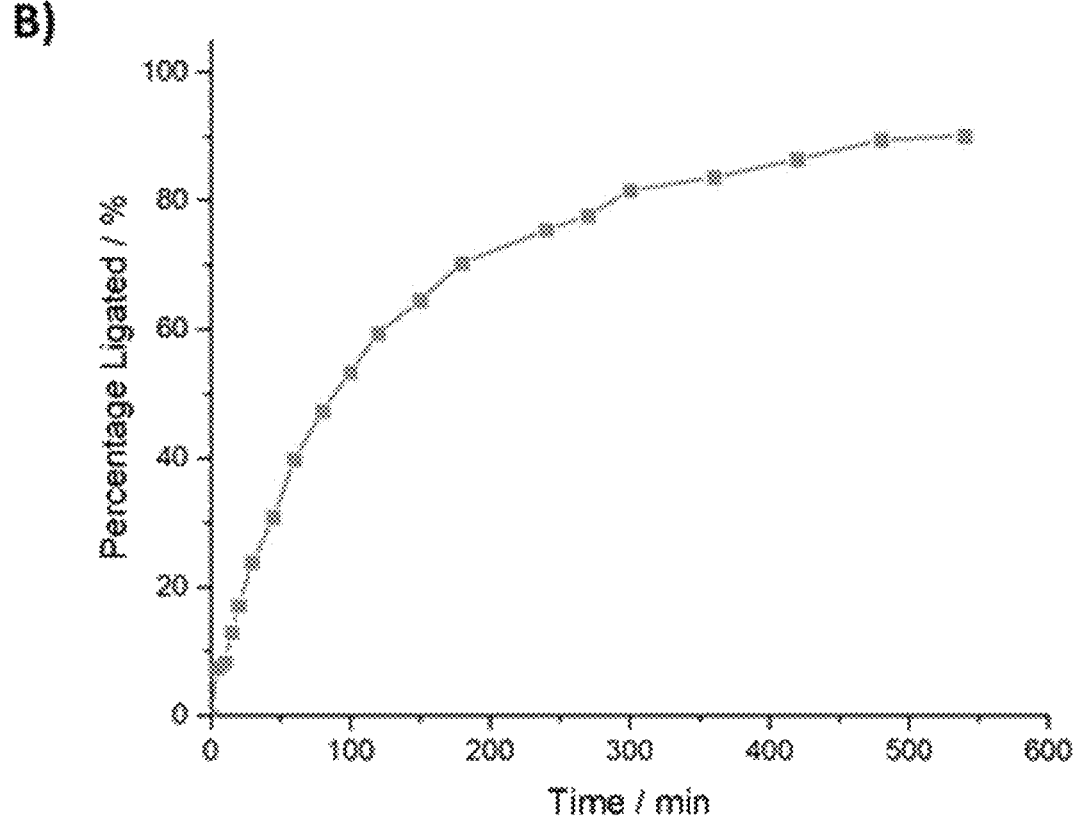
Figure 33:
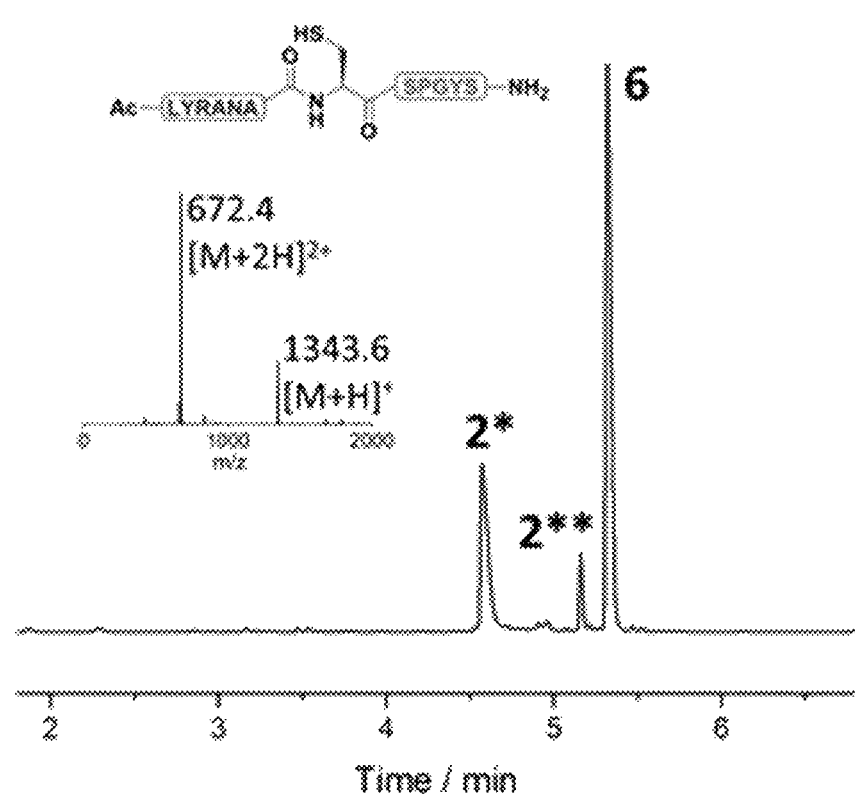
Figure 33:
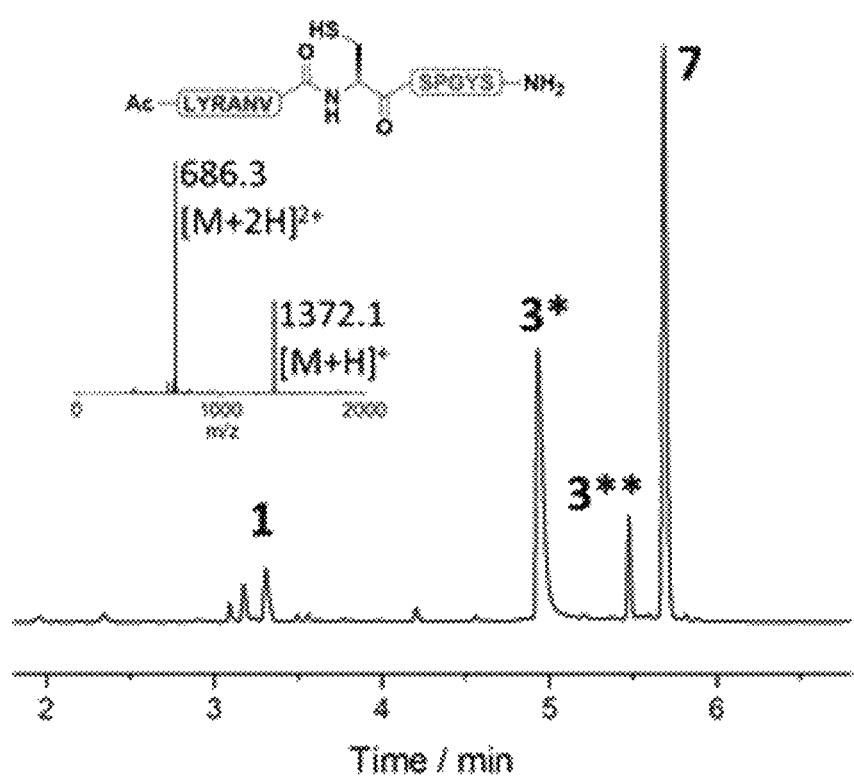

FIG. 33: Kinetics of native chemical ligation using ethyl 3-mercaptopropionate thioesters and TFET as an additive on a 20 µmol scale at A) alanine, and B) valine; C) Crude UPLC chromatogram ($\lambda$=280 nm, 0 to 28% B over 5 min, 0.1% TFA) for ligation at alanine showing the desired ligated product Ac-LYRANACSPGYS-NH$_2$ (SEQ ID NO: 6) 6 alongside the peptide acyl hydrazide Ac-LYRANA-NHNH$_2$ (SEQ ID NO: 34) 2* (formed from Ac-LYRANA-S(CH$_2$)$_2$CO$_2$Et (SEQ ID NO: 2)$_2$ upon the addition of hydrazine hydrate to quench the reaction) and the hydrolysis product Ac-LYRANA-OH (SEQ ID NO: 36) 2**. D) Crude UPLC chromatogram ($\lambda$=280 nm, 0 to 28% B over 5 min, 0.1% TFA) for ligation at valine showing the desired ligated product Ac-LYRANVCSPGYS-NH$_2$ (SEQ ID NO: 7) 7 alongside the peptide acyl hydrazide Ac-LYRANV-NHNH$_2$ (SEQ ID NO: 35) 3* (formed from Ac-LYRANV-S(CH$_2$)$_2$CO$_2$Et (SEQ ID NO: 3) 3 upon the addition of hydrazine hydrate to quench the reaction), the hydrolysis product Ac-LYRANV-OH (SEQ ID NO: 37) 3**, and unreacted H-CSPGYS-NH$_2$ (SEQ ID NO: 1) 1. Inset MS data is collected over the entire target peptide UV peak in the UPLC-MS chromatogram.

Figure 34:
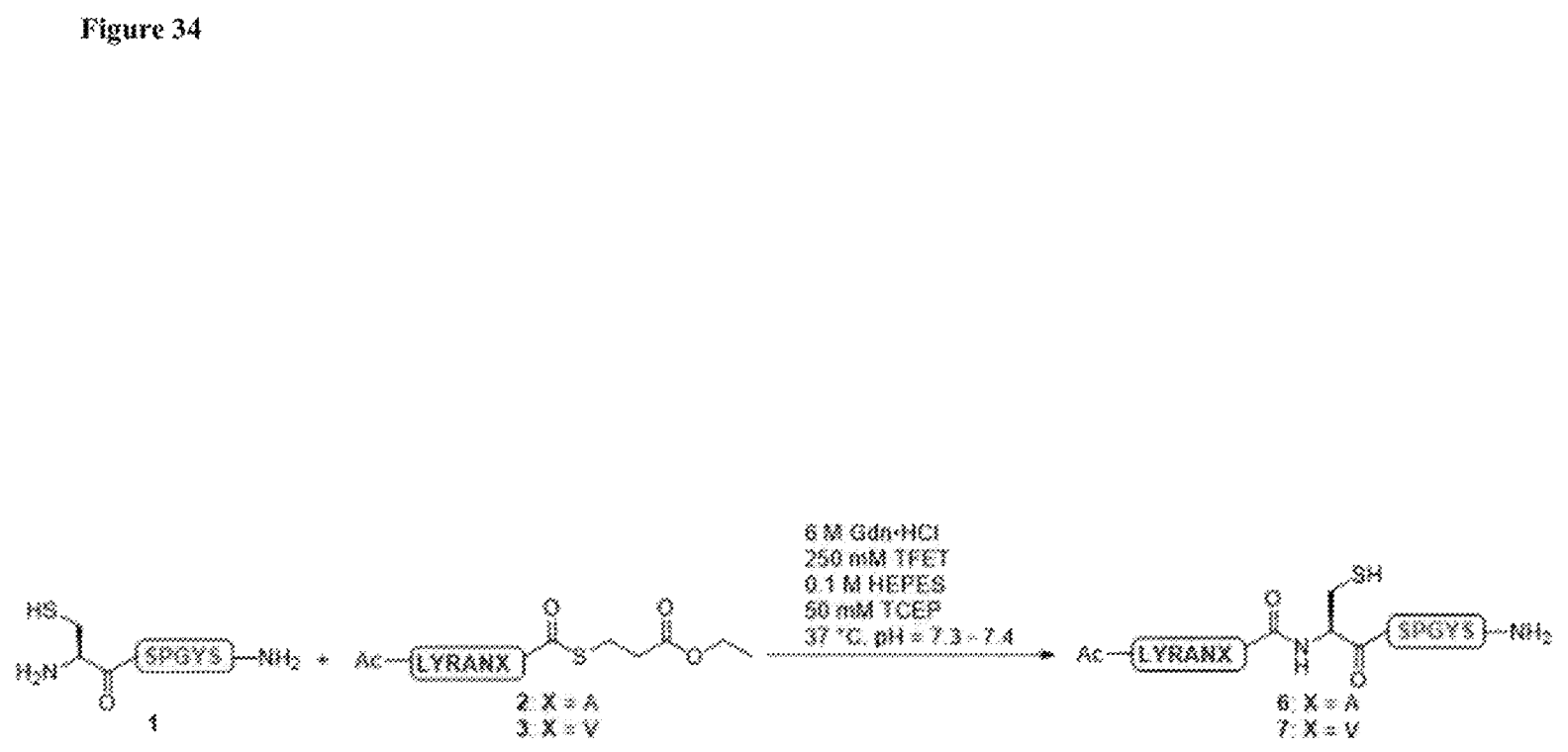

FIG. 34: Reaction scheme for performing NCL using previously reported batch conditions, with an ethyl 3-mercaptopropionate thioester and TFET as an exogenous additive.[6]

Figure 35:
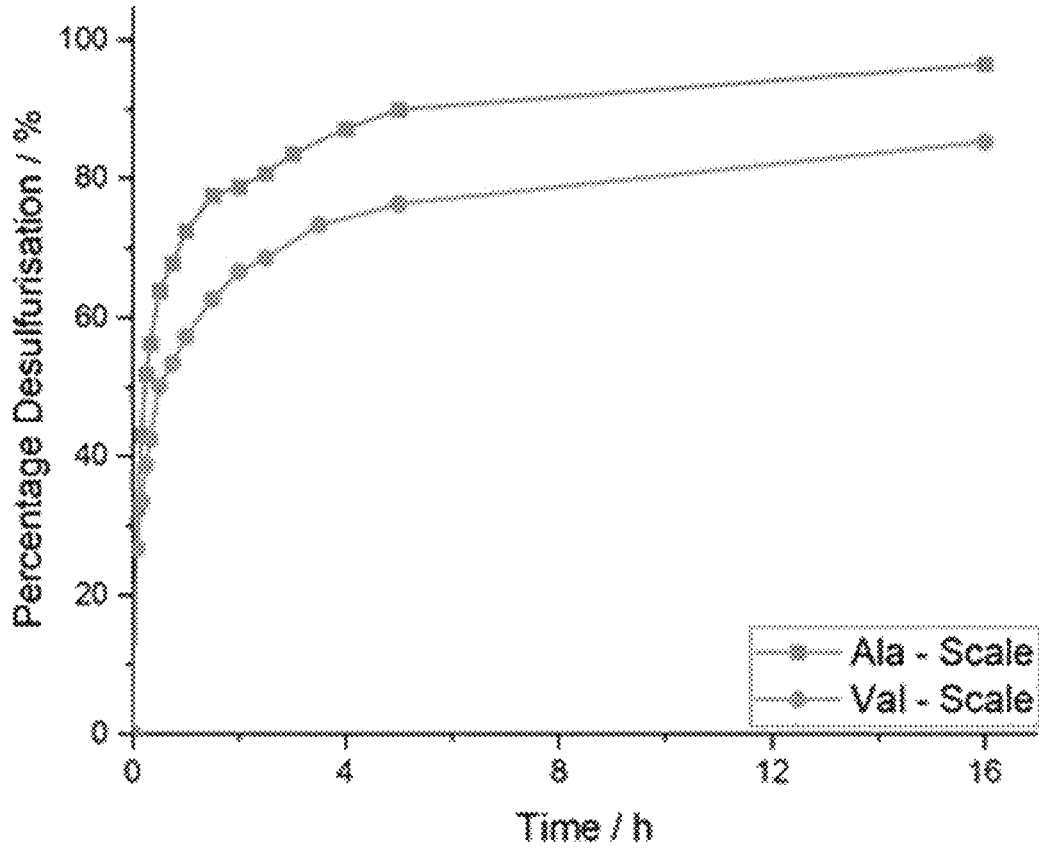
Figure 35:
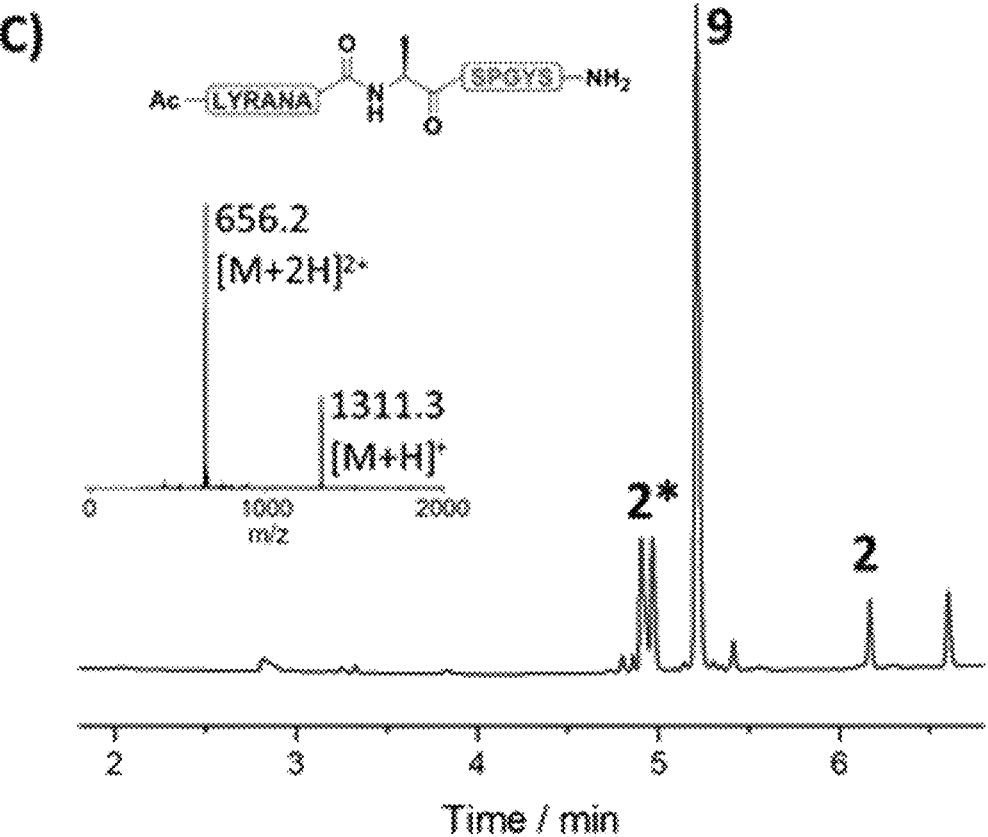
Figure 35:
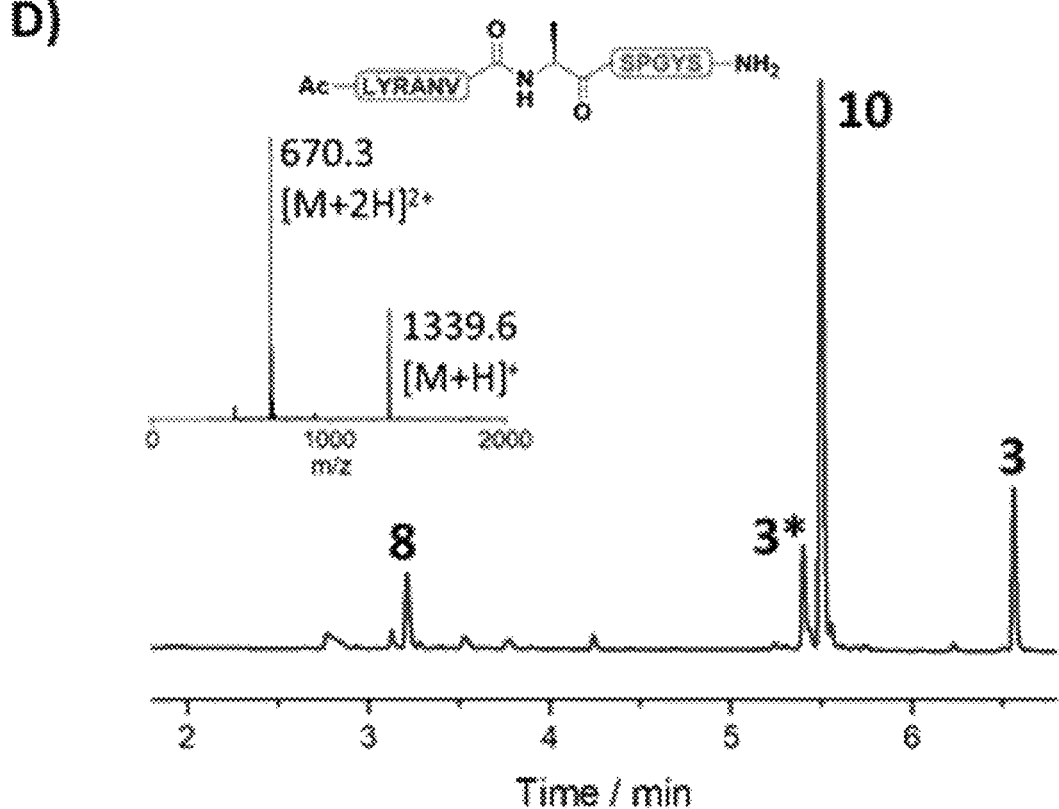

FIG. 35: One-pot desulfurization was performed under standard conditions using VA-044. A) Scheme for the standard desulfurization technique employed; B) The kinetics for desulfurization in batch for alanine and valine; C) Crude UPLC chromatogram ($\lambda$=280 nm, 0 to 28% B over 5 min, 0.1% TFA) for the desulfurization of 6 showing the desired product Ac-LYRANAASPGYS-NH$_2$ (SEQ ID NO: 9) 9 alongside unreacted Ac-LYRANA-S(CH$_2$)$_2$CO$_2$Et (SEQ ID NO: 2)$_2$ and a mixture of the hydrolyzed peptide free acid Ac-LYRANA-OH (SEQ ID NO: 36) and glutathione thioester Ac-LYRANA-GSH (SEQ ID NO: 33) 2*; D) Crude UPLC chromatogram ( )=280 nm, 0 to 28% B over 5 min, 0.1% TFA) for the desulfurization of 7 showing the desired product Ac-LYRANVASPGYS-NH$_2$ (SEQ ID NO: 10) 10 alongside unreacted Ac-LYRANV-S(CH$_2$)$_2$CO$_2$Et (SEQ ID NO: 3) 3, a mixture of the hydrolyzed peptide free acid Ac-LYRANV-OH (SEQ ID NO: 37) and glutathione thioester Ac-LYRANV-GSH (SEQ ID NO: 38) 3*, and H-ASPGYS-NH$_2$ (SEQ ID NO: 8) 8. Inset MS data was collected over the entire target peptide UV peak in the UPLC-MS chromatogram.

Figure 36:
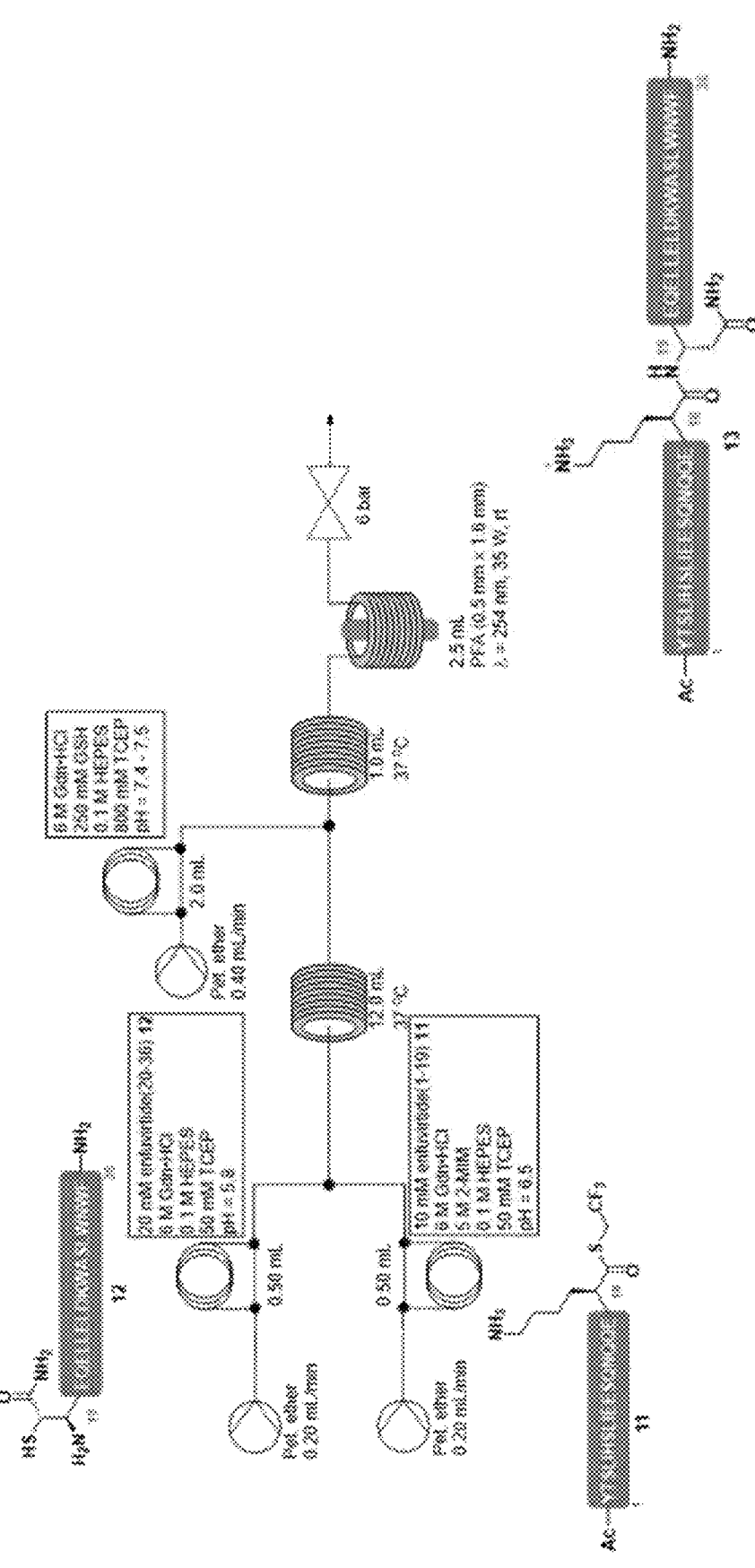

FIG. 36: Flow system used for the synthesis of enfuvirtide 13.

Figure 37:
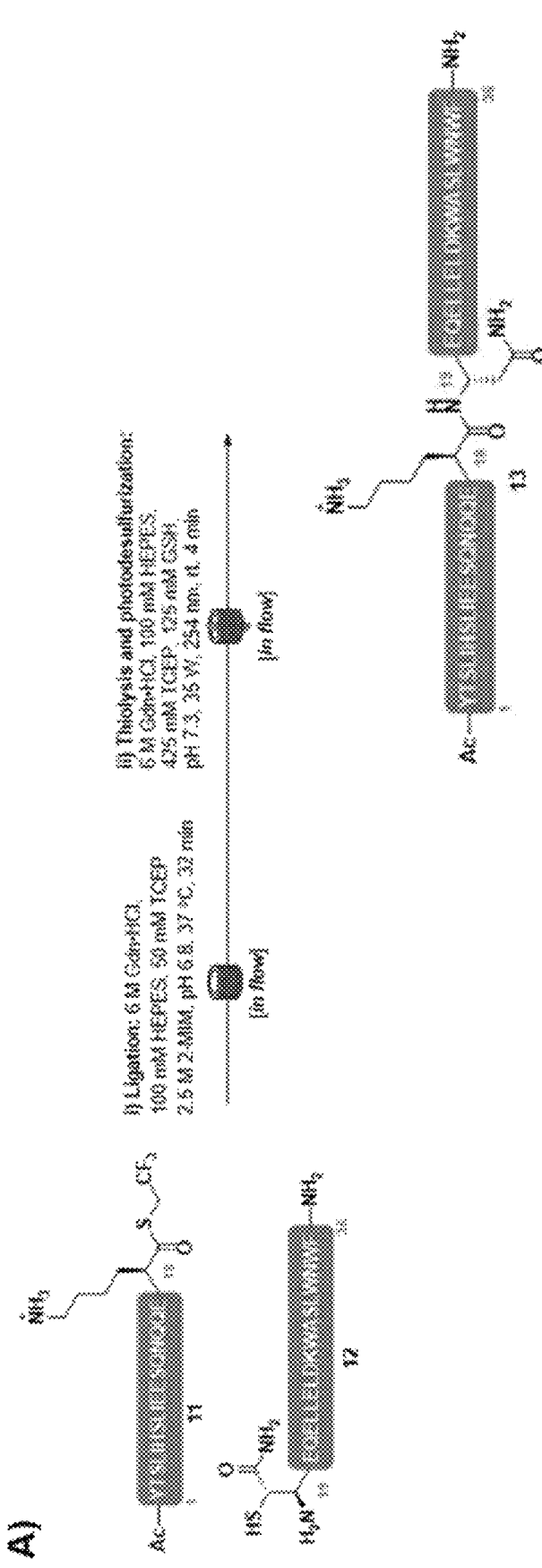
Figure 37:
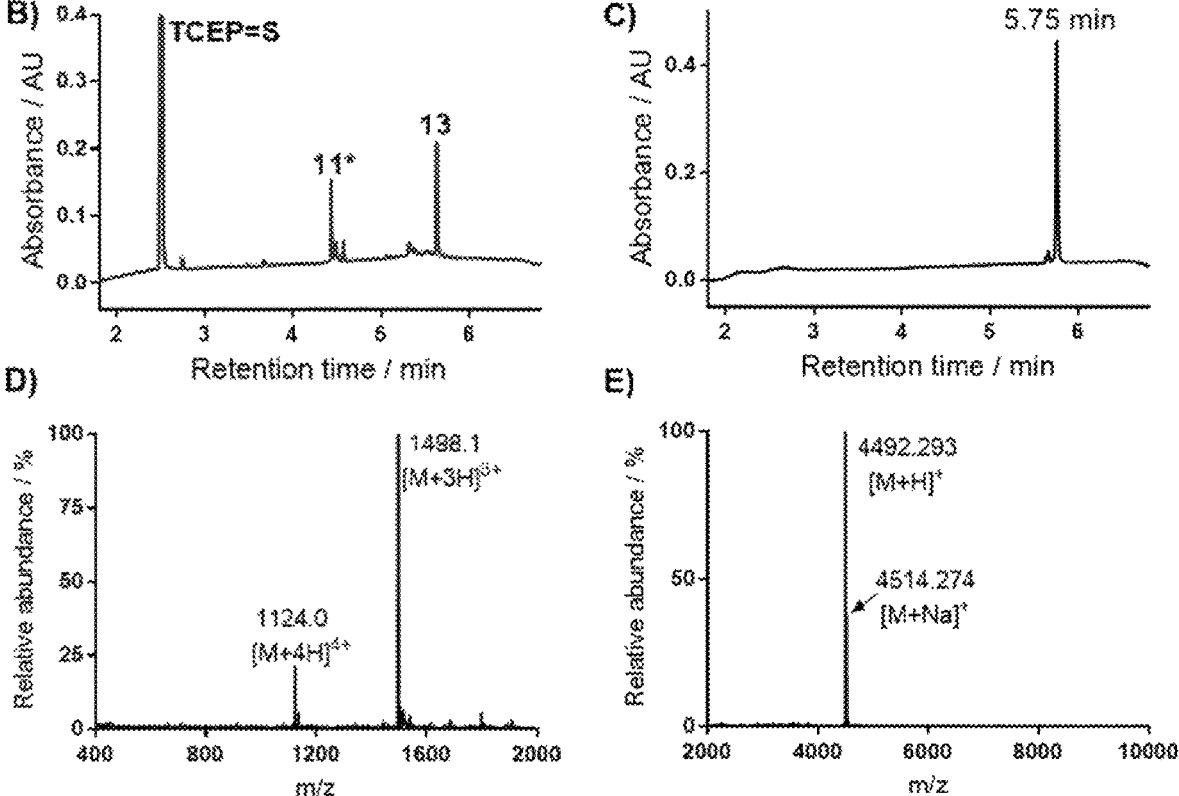

FIG. 37: A) Synthetic scheme for the flow synthesis of enfuvirtide 13. B) Crude UPLC trace ($\lambda$=214 nm, 0 to 70% B over 5 min, 0.1% TFA) of the ligation-photodesulfurization solution. * GSH thioester of 11 C) UPLC trace $\lambda$=214 nm, 0 to 70% B over 5 min, 0.1% TFA) of the purified peptide. D) ESI-MS of the purified product. E) MALDI-TOF: Calculated Mass for $C_{204}H_{302}N_{51}O_{64}^+$ [M+H]$^+$: 4492.200, $C_{204}H_{301}N_{51}O_{64}Na^+$ [M+Na]$^+$: 4514.190; Mass Found; 4492.293 [M+H]$^+$, 4514.274 [M+Na]$^+$. MALDI-TOF data were obtained as outlined under general synthetic procedures using a matrix of saturated $\alpha$-cyano-4-hydroxy-cinnamic acid in TA30 (30% acetonitrile/70% $H_2O$ containing 0.1% TFA).

Figure 38:
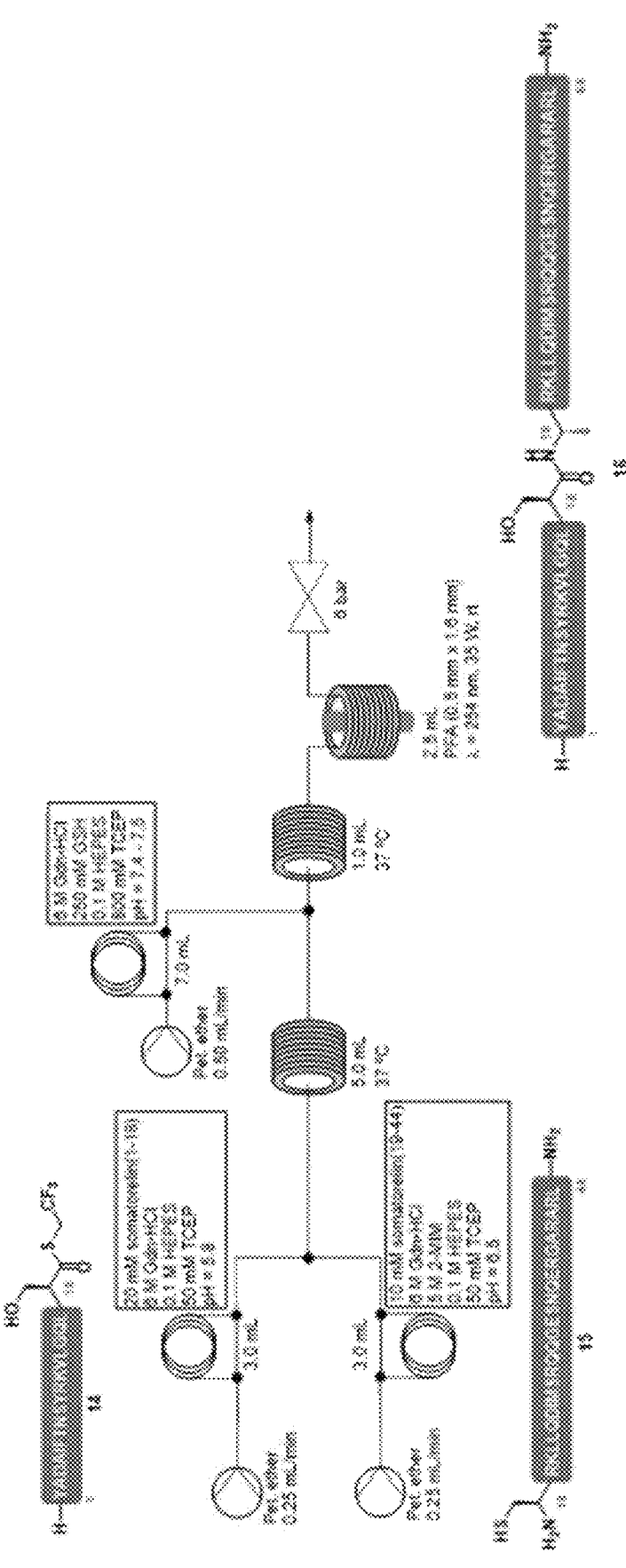

FIG. 38: Flow system used for the synthesis of somatorelin 16.

Figure 39:
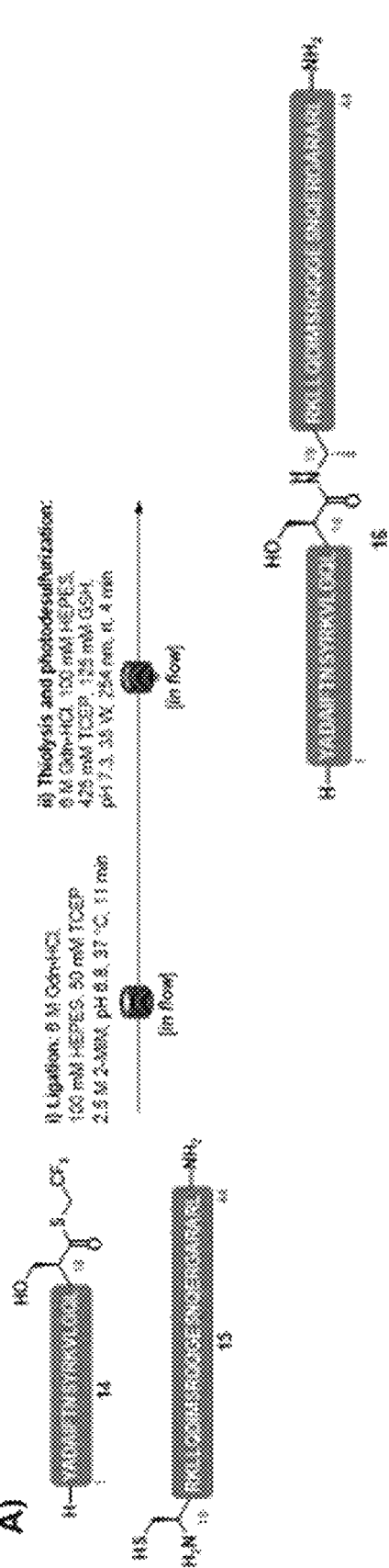
Figure 39:
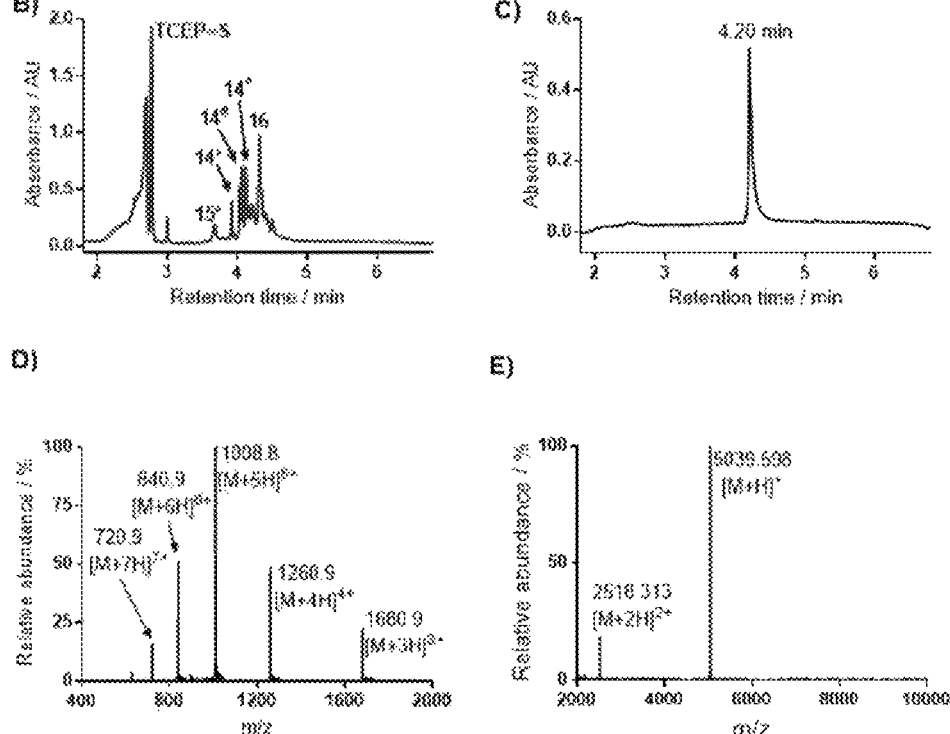

FIG. 39: A) Synthetic scheme for the flow synthesis of somatorelin 16. B) Crude UPLC trace ($\lambda$=214 nm, 0 to 70% B over 5 min, 0.1% TFA) of the ligation-photodesulfurization solution. 14*: glutathione thioester of 14; 14$^\#$: hydrolysed 14; 14$^\circ$: lactam of 14 C) UPLC trace ($\lambda$=214 nm, 0 to 70% B over 5 min, 0.1% TFA) of the purified peptide. D) ESI-MS of the purified product. E) MALDI-TOF: Calculated Mass for $C_{215}H_{359}N_{72}O_{66}S^+$ [M+H]$^+$: 5039.672, $C_{204}H_{360}N_{72}O_{66}S_2^+$ [M+2H]$^{2+}$: 2520.340; Mass Found; 5039.598 [M+H]$^+$, 2518.313 [M+2H]$^{2+}$. MALDI-TOF data were obtained as outlined under general synthetic procedures using a matrix of 2',4',6'-Trihydroxyacetophenone (THAP)/di-ammonium hydrogen citrate (18 mg/7 mg in 500 $\mu$L of TA30).

Figure 40:
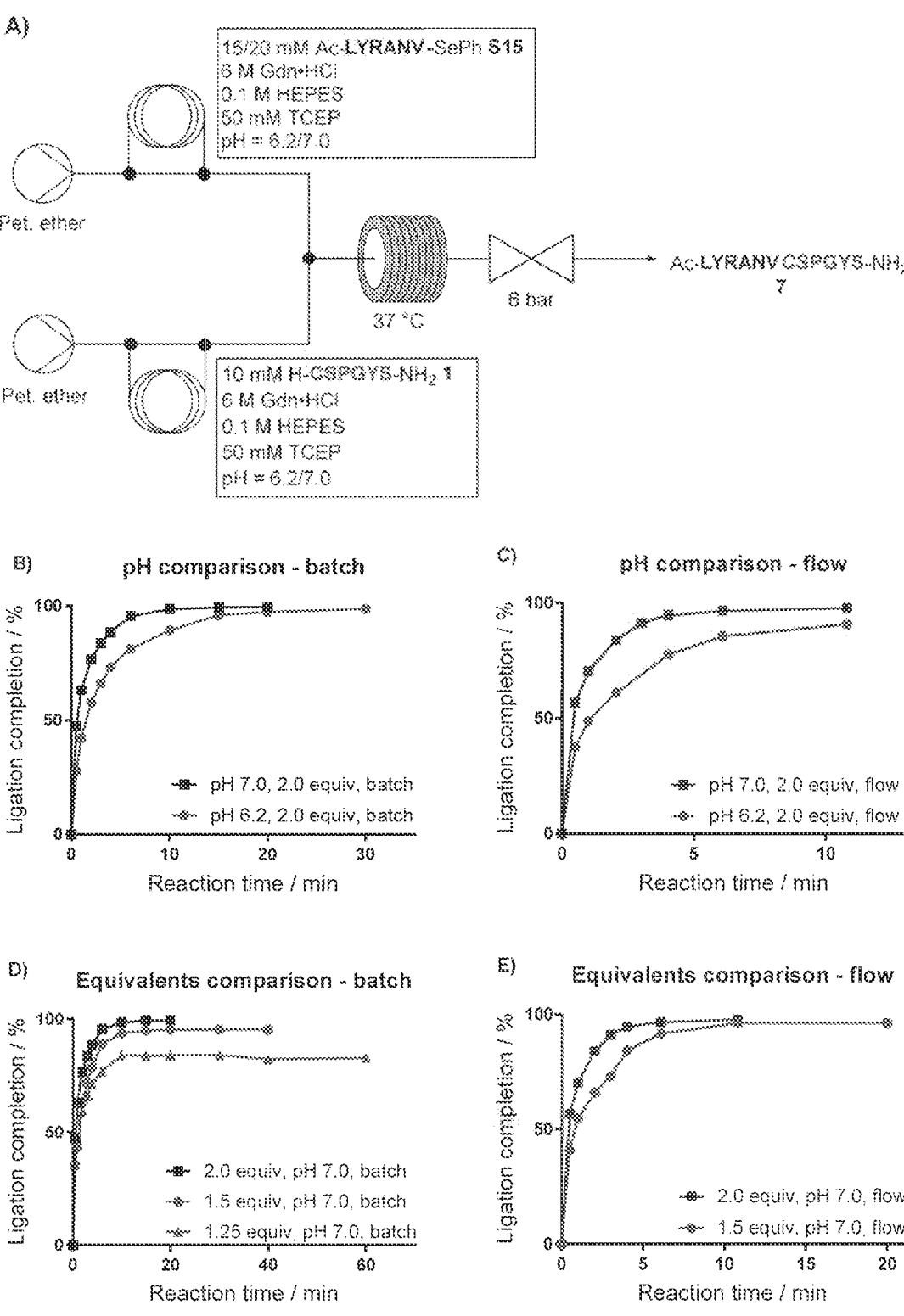

FIG. 40: A) Schematic representation of experimental setup used to perform NCL in flow between H-CSPGYS-NH$_2$ (SEQ ID NO: 1) 1 and Ac-LYRANV-SePh (SEQ ID NO: 27) S15. B) Kinetics of ligation between H-CSPGYS-NH$_2$ (SEQ ID NO: 1) 1 (5 mM) and Ac-LYRANV-SePh (SEQ ID NO: 27) S15 (2.0 eq., 10 mM) at pH 6.2 and pH 7.0 in batch. C) Kinetics of ligation between H-CSPGYS-NH$_2$ (SEQ ID NO: 1) 1 (5 mM) and Ac-LYRANV-SePh (SEQ ID NO: 27) S15 (2.0 eq., 10 mM) at pH 6.2 and pH 7.0 in flow. D) Kinetics of ligation between H-CSPGYS-NH$_2$ (SEQ ID NO: 1) 1 (5 mM) and Ac-LYRANV-SePh (SEQ ID NO: 27) S15 (1.25 eq., 1.5 eq., 2.0 eq.) at pH 7.0 in batch. E) Kinetics of ligation between H-CSPGYS-NH$_2$ (SEQ ID NO: 1) 1 (5 mM) and Ac-LYRANV-SePh (SEQ ID NO: 27) S15 (1.5 eq., 2.0 eq.) at pH 7.0 in flow. Percentage ligation is calculated by integrating UPLC chromatogram peaks at $\lambda$=280 nm.

Figure 41:
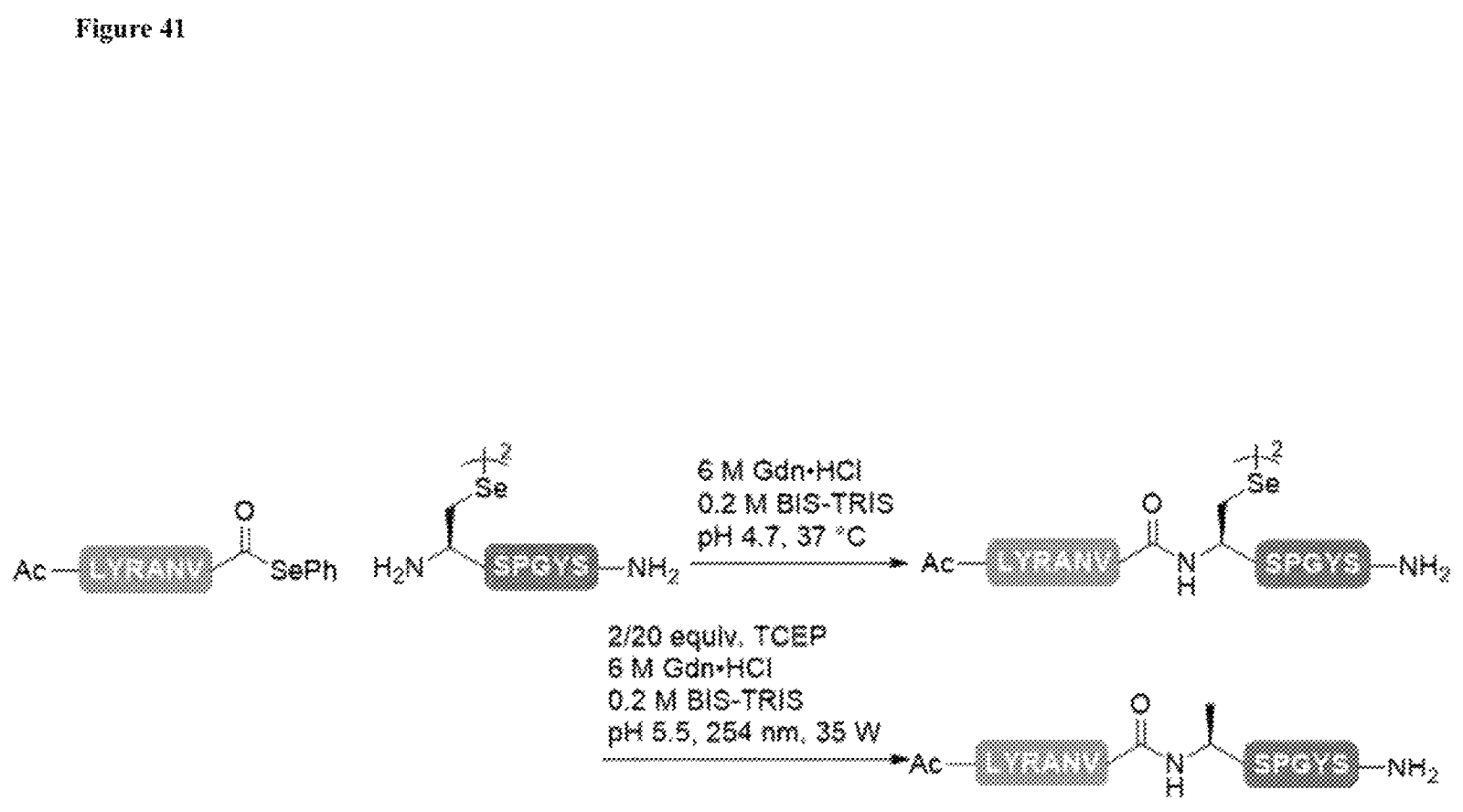

FIG. 41: Scheme for the one-pot diselenide-selenoester ligation-deselenization procedure.

Figure 42:
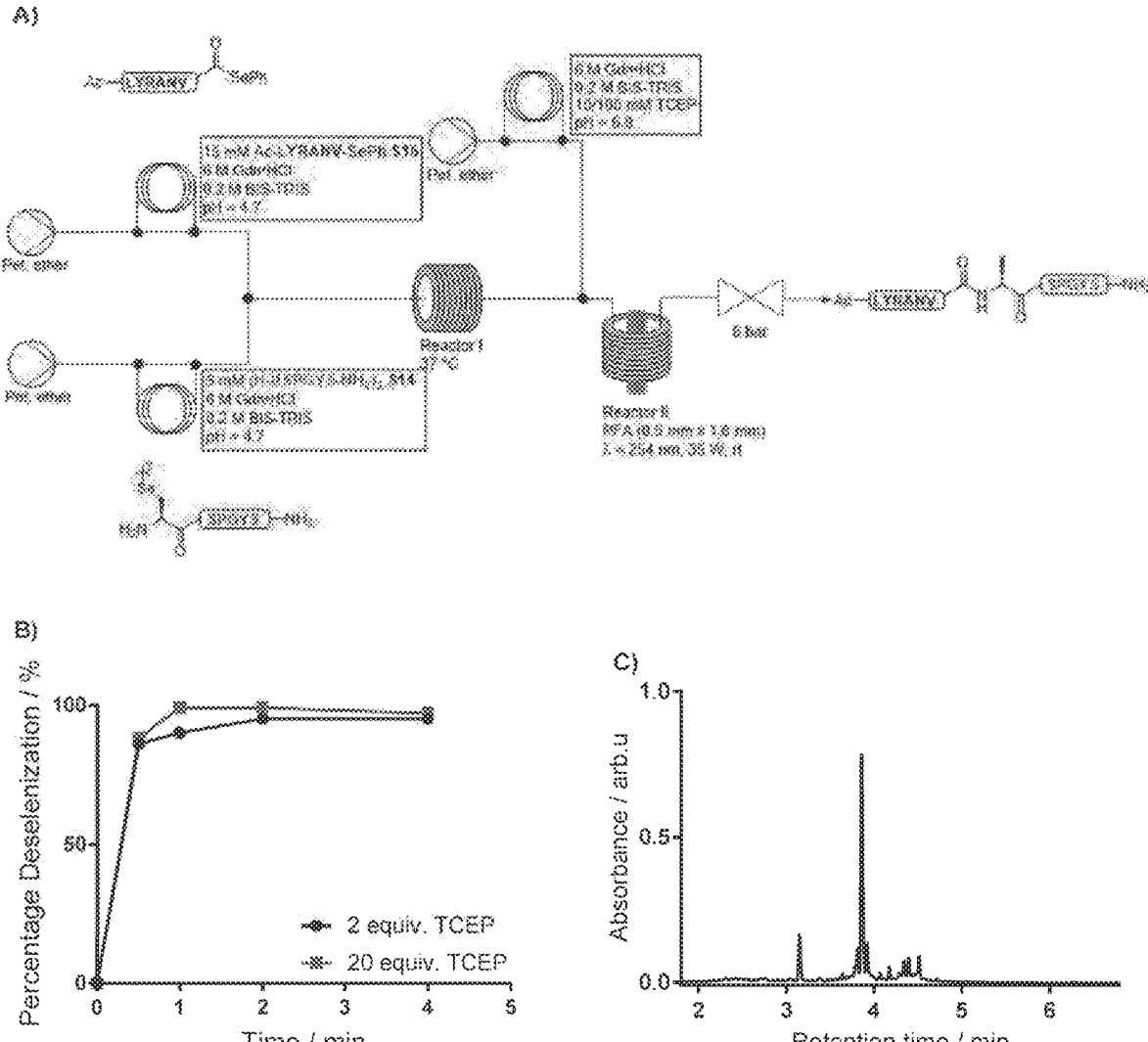

FIG. 42: A) Schematic representation of experimental setup used for in-line flow diselenide-selenoester ligation-deselenization. B) Percentage deselenization at various time points using either 2 equiv. or 20 equiv. TCEP relative to the monomer of S14. Percentage deselenization is calculated by integrating UPLC chromatogram peaks at $\lambda$=280 nm. C) UPLC chromatogram ($\lambda$=280 nm, 0 to 28% B over 5 min, 0.1% TFA) of the crude reaction mixture from the in-line flow procedure using 20 equiv. TCEP after 2.2 min deselenization.

Figure 43:
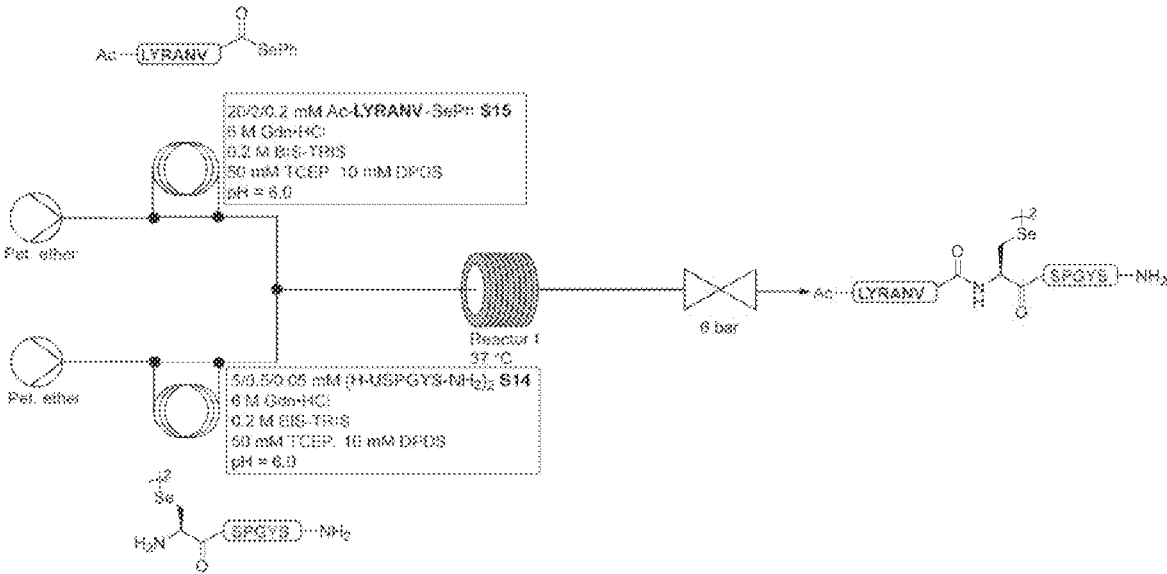

FIG. 43: Schematic representation of experimental setup used for in-line flow diselenide-selenoester ligation at dilution.

Figure 44:
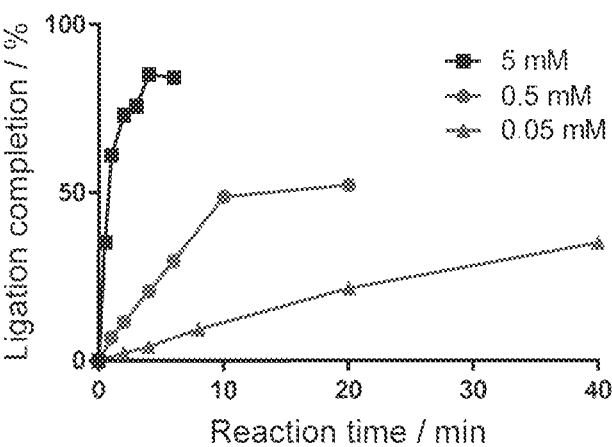

FIG. 44: Percentage ligation for reductive DSL at various residence times in flow at the specified concentration of diselenide. Percentage ligation is calculated by integrating UPLC chromatogram peaks at $\lambda$=280 nm.

Figure 45:
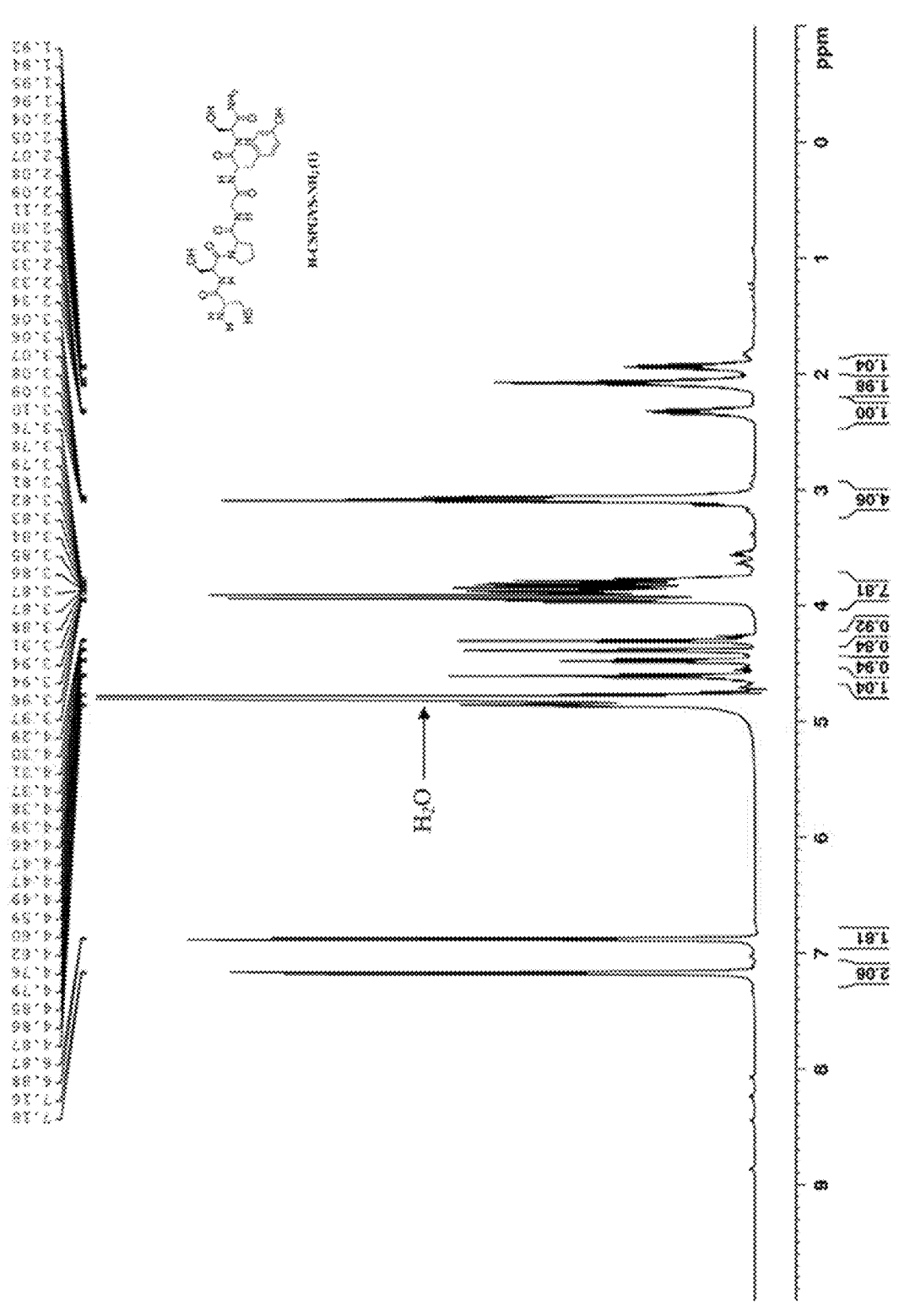

FIG. 45: $^1$H NMR spectrum (D$_2$O, 500 MHZ) of H-CSPGYS-NH$_2$ (1, SEQ ID NO: 1).

Figure 46:
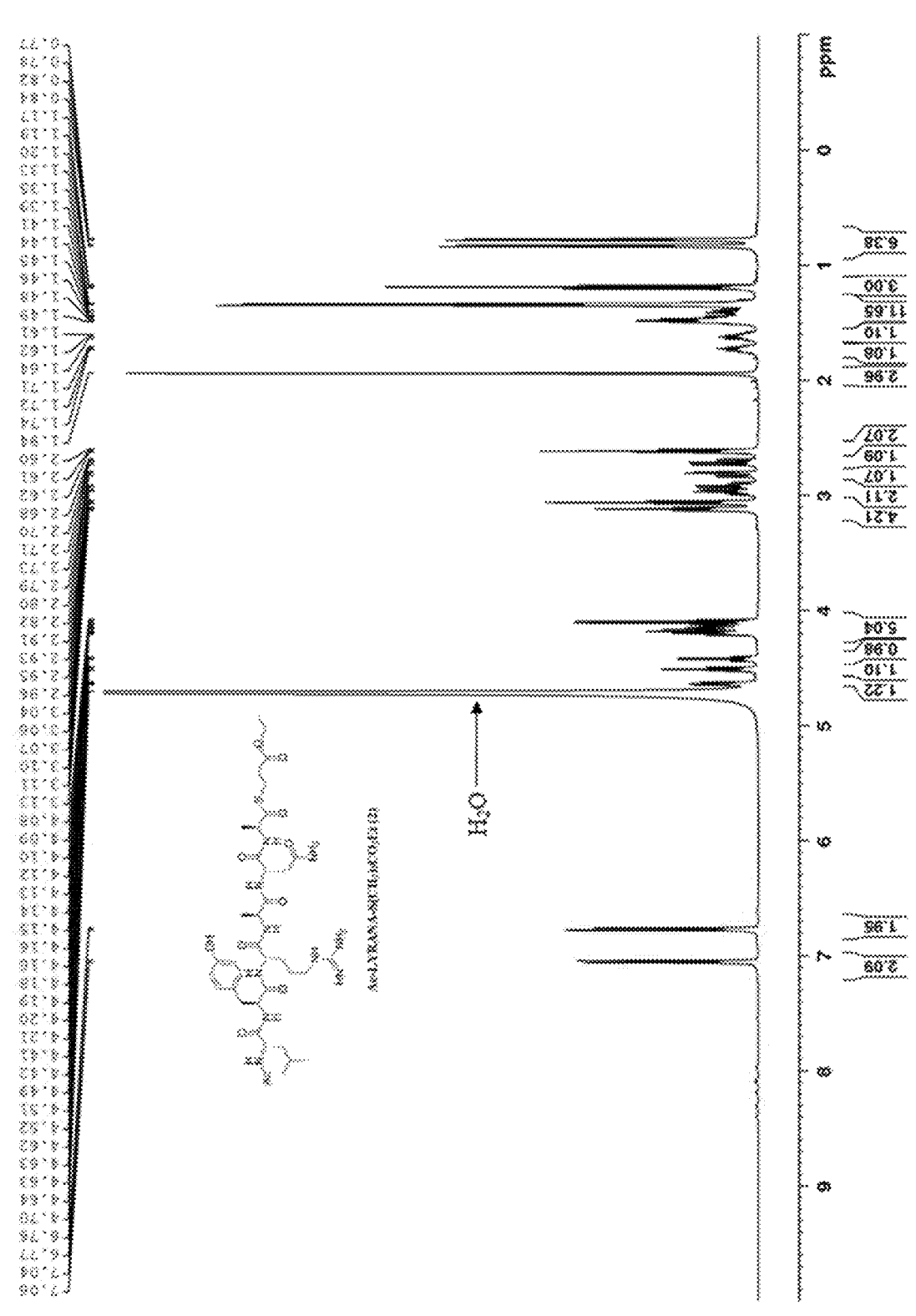

FIG. 46: $^1$H NMR spectrum (D$_2$O, 500 MHZ) of Ac-LYRANA-S(CH$_2$)$_2$CO$_2$Et (2, SEQ ID NO: 2).

Figure 47:
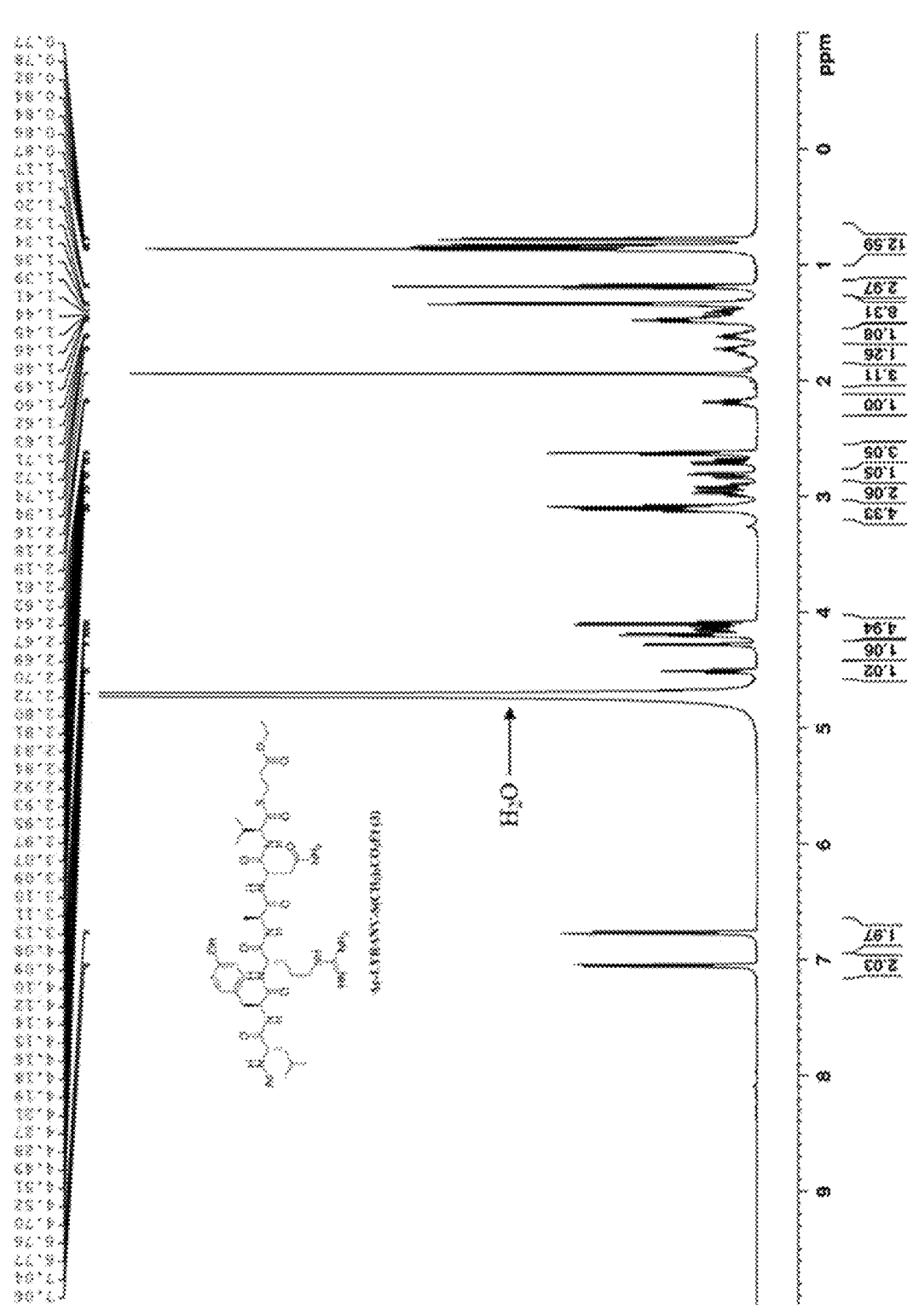

FIG. 47: $^1$H NMR spectrum (D$_2$O, 500 MHZ) of Ac-LYRANV-S(CH$_2$)$_2$CO$_2$Et (3, SEQ ID NO: 3).

Figure 48:
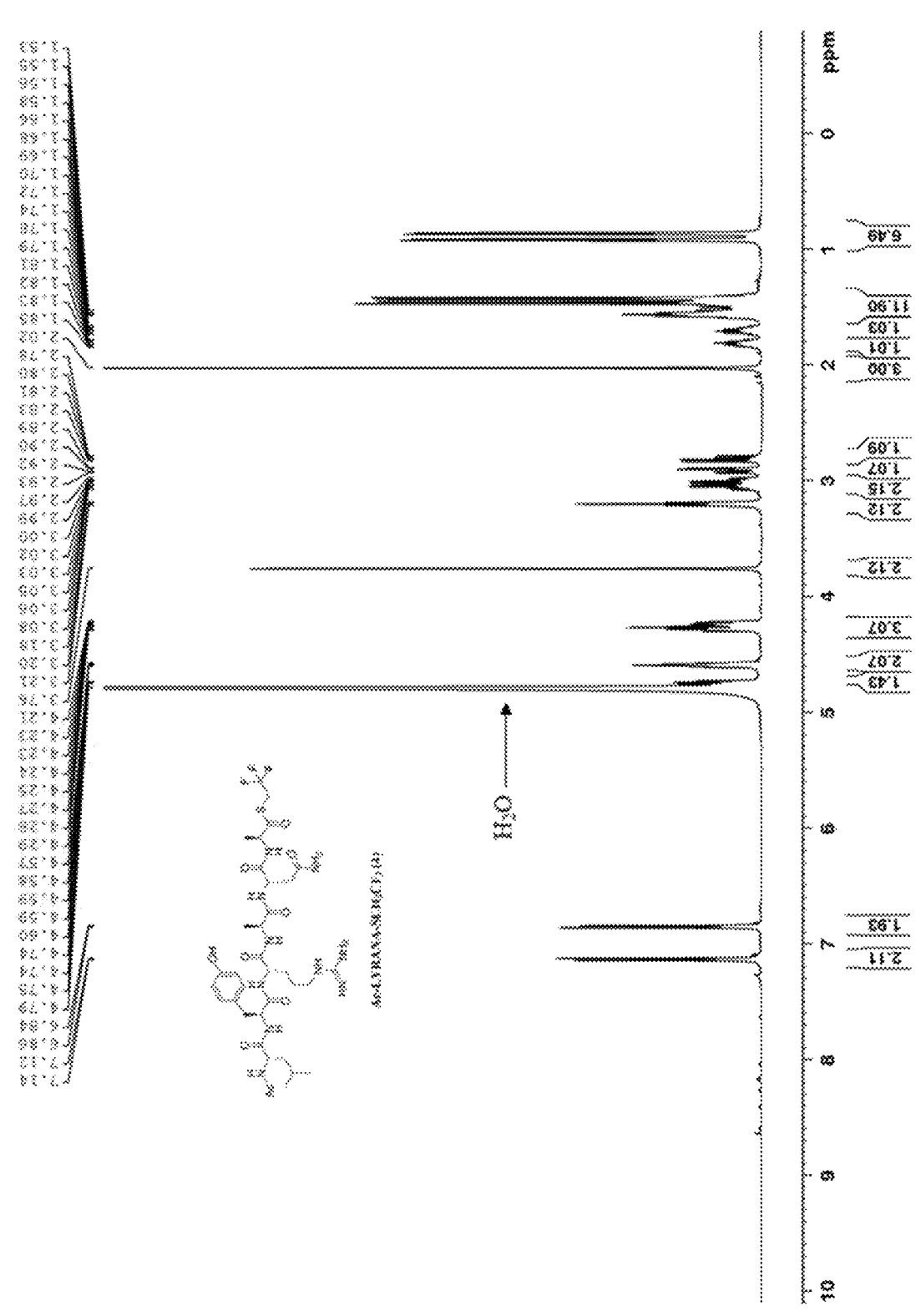

FIG. 48: $^1$H $\{^{19}$F$\}$ NMR spectrum (D$_2$O, 500 MHZ) of Ac-LYRANA-SCH$_2$CF$_3$ (4, SEQ ID NO: 4).

Figure 49:
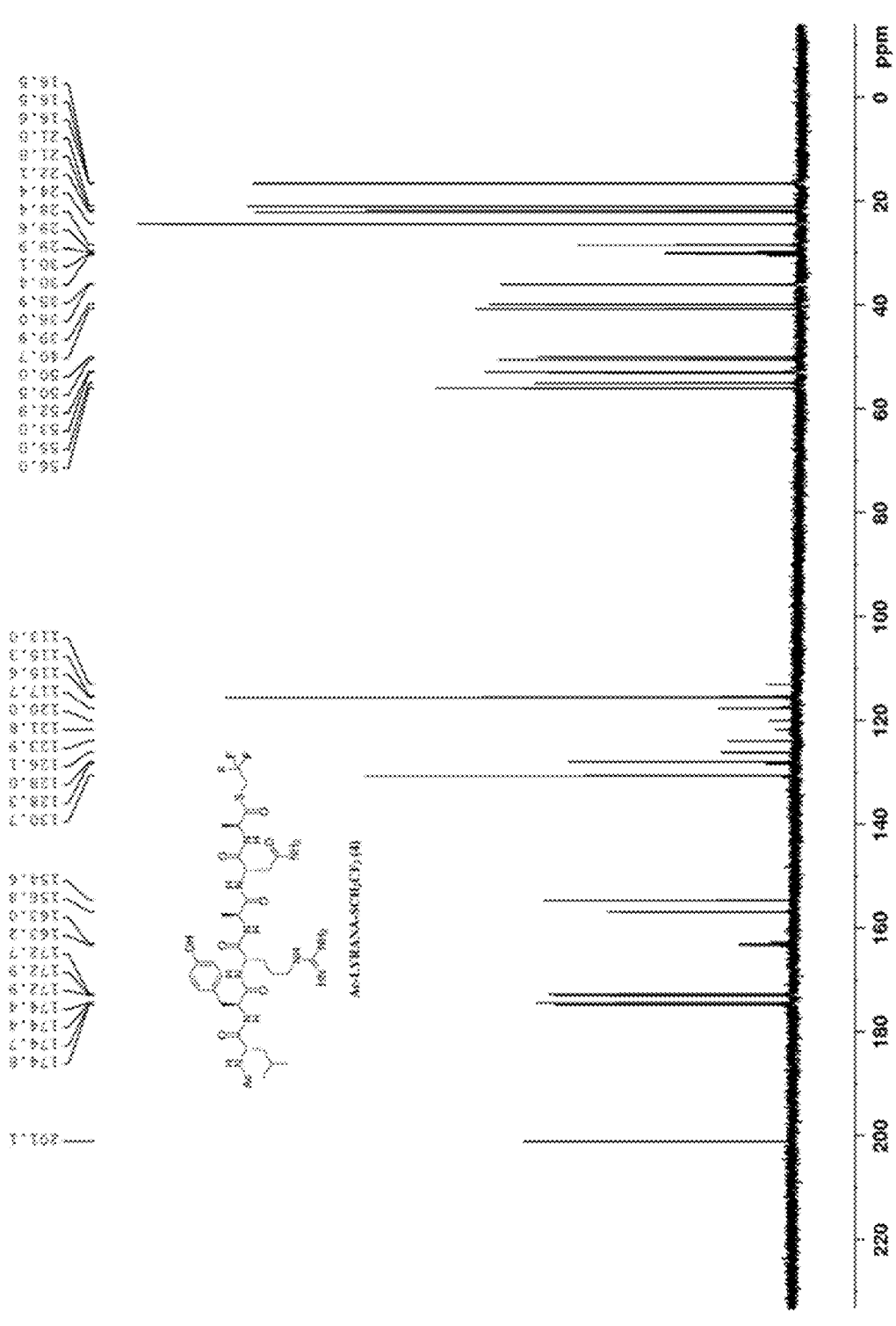

FIG. 49: $^{13}$C$\{^1$H$\}$ NMR spectrum (D$_2$O, 126 MHz) of Ac-LYRANA-SCH$_2$CF$_3$ (4, SEQ ID NO: 4).

Figure 50:
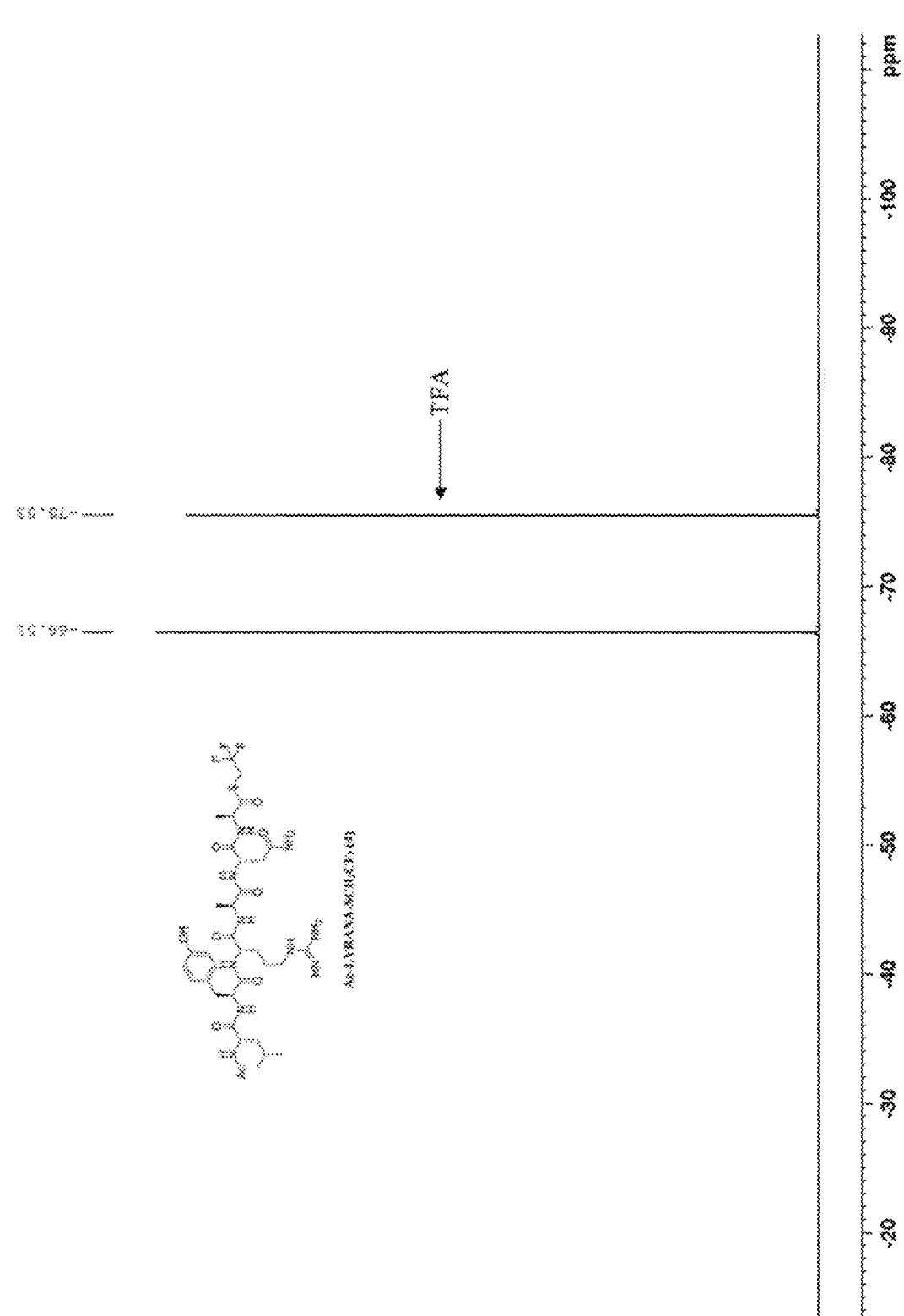

FIG. 50: $^{19}$F $\{^1$H$\}$ NMR spectrum (D$_2$O, 471 MHz) of Ac-LYRANA-SCH$_2$CF$_3$ (4, SEQ ID NO: 4).

Figure 51:
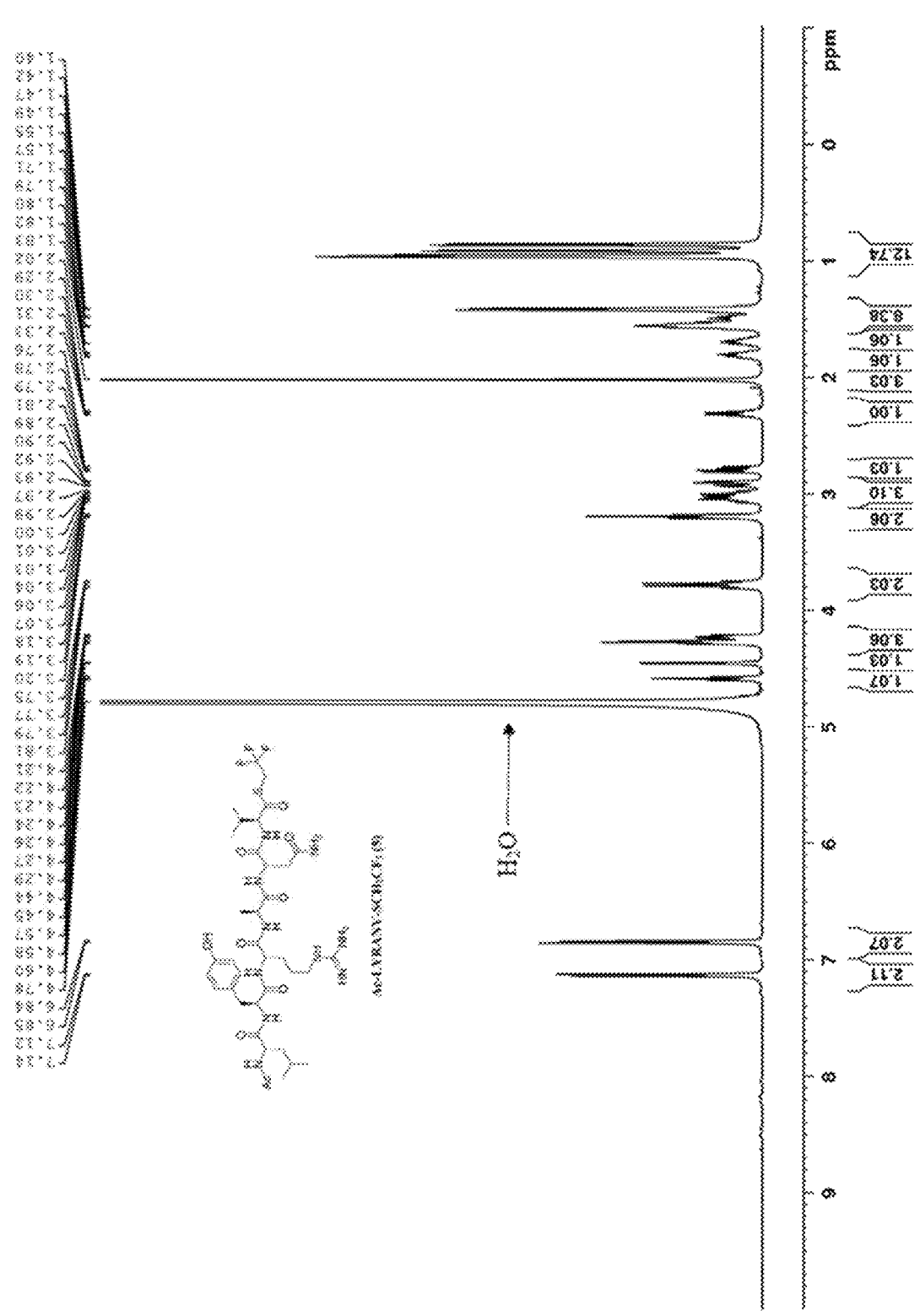

FIG. 51: $^1$H $\{^{19}$F$\}$ NMR spectrum (D$_2$O, 500 MHZ) of Ac-LYRANV-SCH$_2$CF$_3$ (5, SEQ ID NO: 5).

Figure 52:
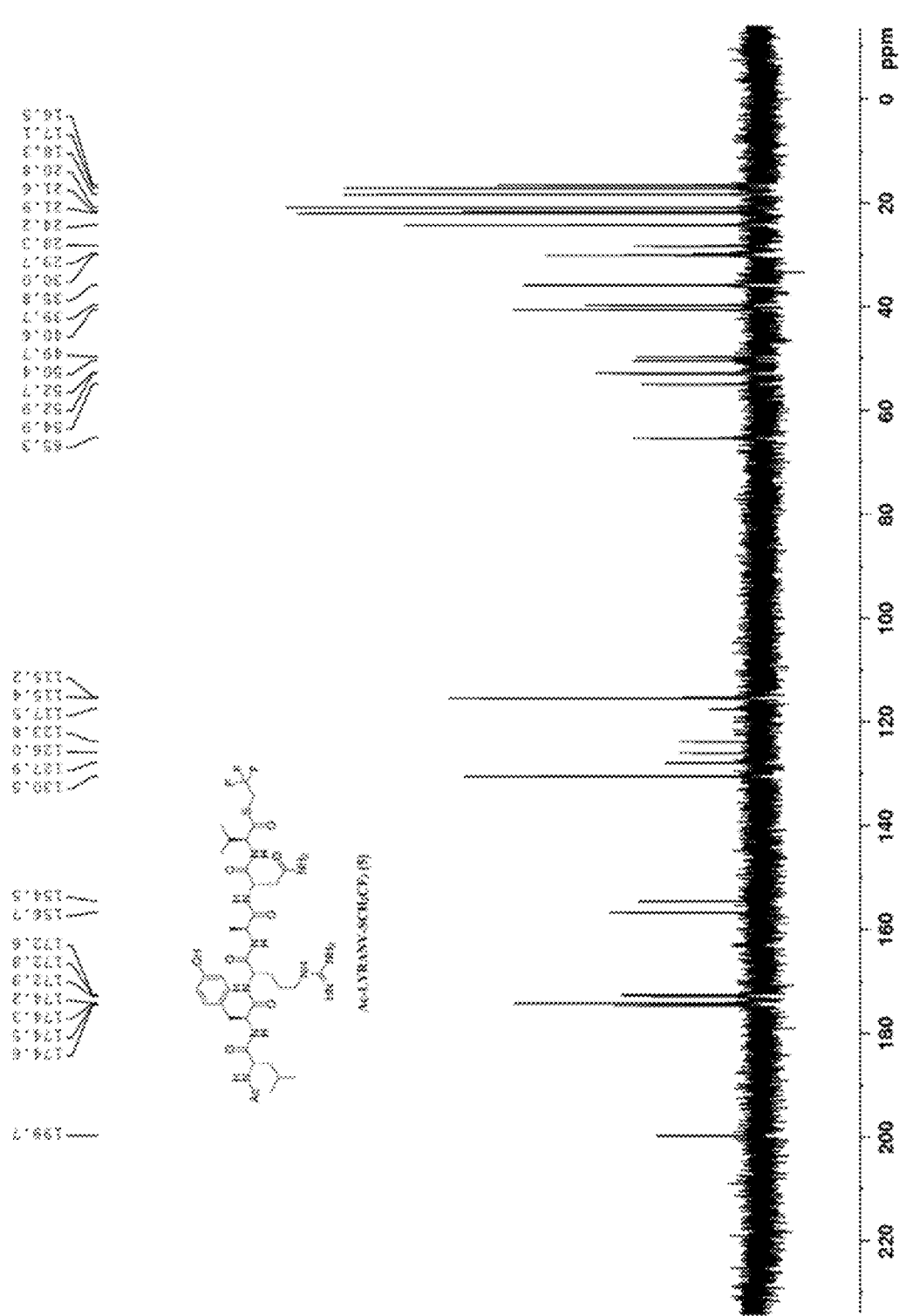

FIG. 52: $^{13}$C$\{^1$H$\}$ NMR spectrum (D$_2$O, 126 MHz) of Ac-LYRANV-SCH$_2$CF$_3$ (5, SEQ ID NO: 5).

Figure 53:
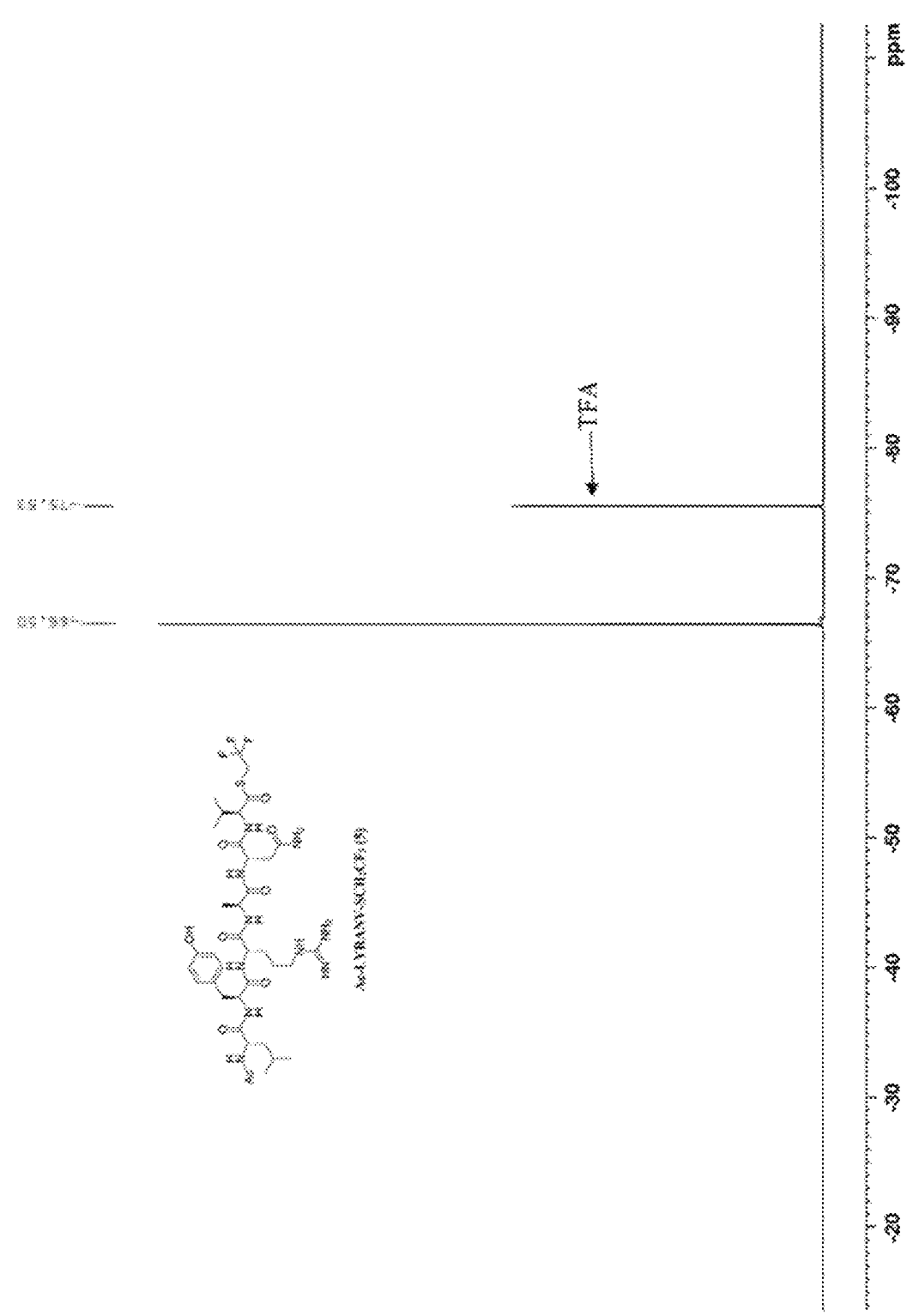

FIG. 53: $^{19}$F $\{^1$H$\}$ NMR spectrum (D$_2$O, 471 MHz) of Ac-LYRANV-SCH$_2$CF$_3$ (5, SEQ ID NO: 5).

Figure 54:
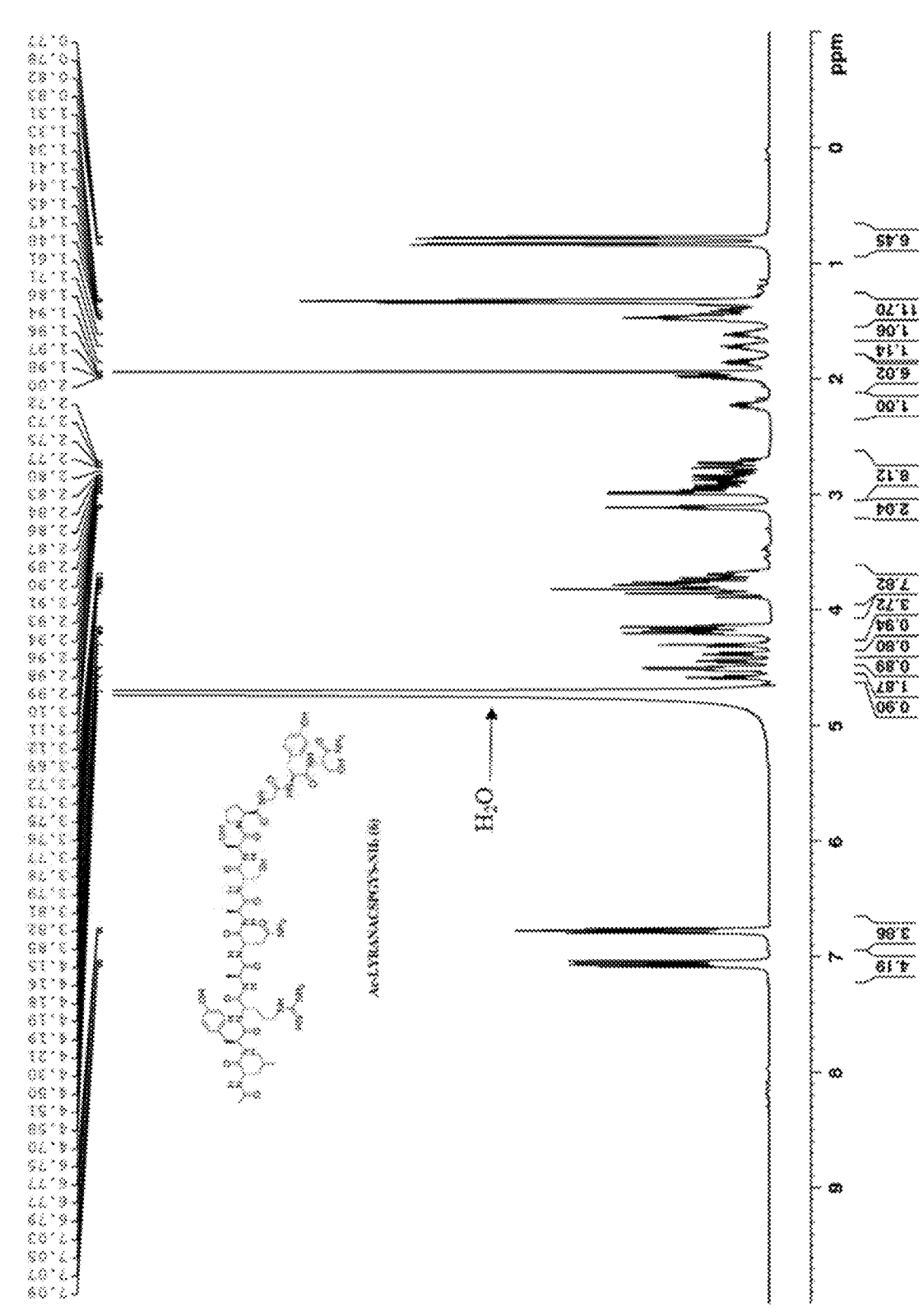

FIG. 54: $^1$H NMR spectrum (D$_2$O, 500 MHZ) of Ac-LYRANACSPGYS-NH$_2$ (6, SEQ ID NO: 6).

Figure 55:
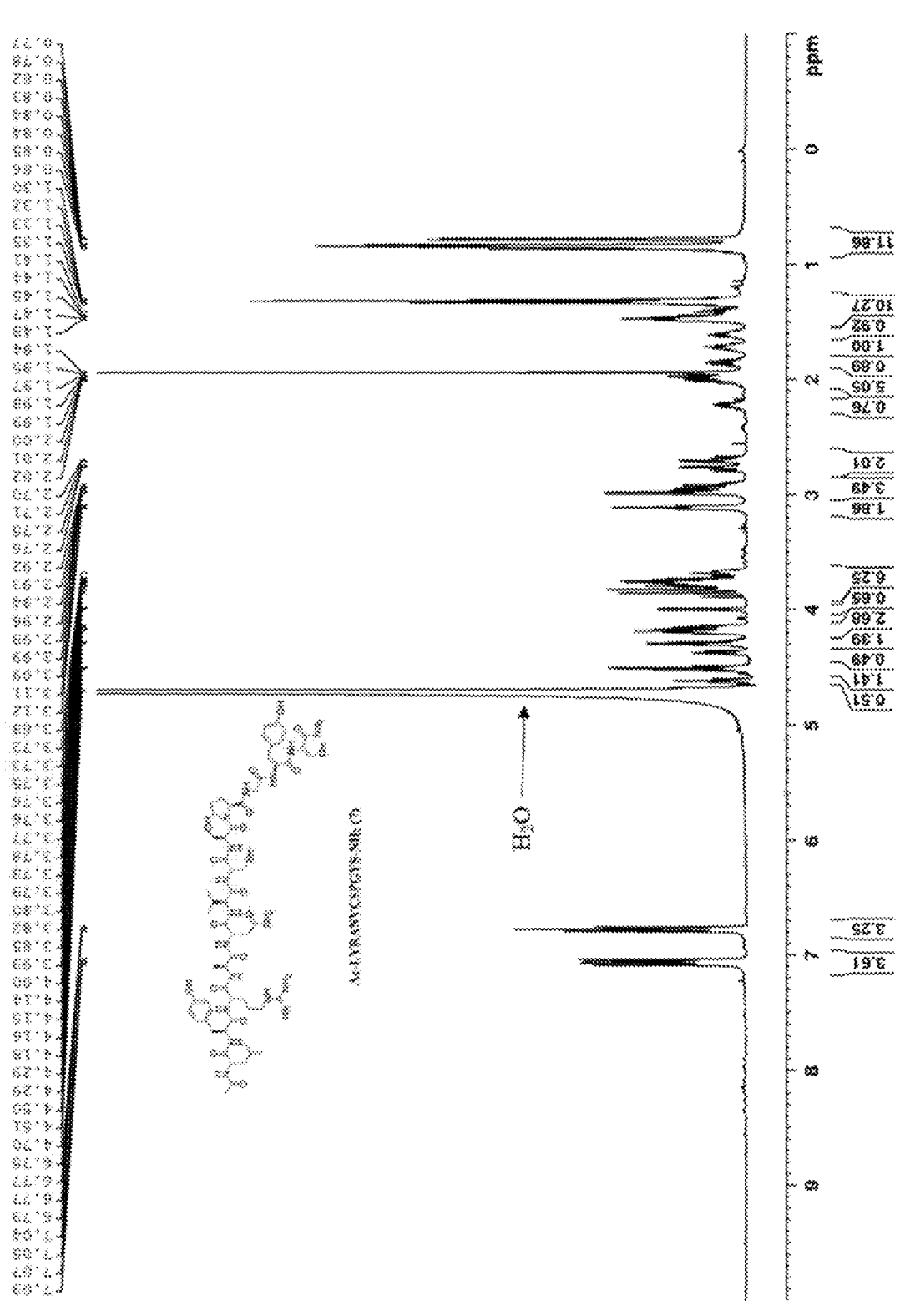

FIG. 55: $^1$H NMR spectrum (D$_2$O, 500 MHZ) of Ac-LYRANVCSPGYS-NH$_2$ (7, SEQ ID NO: 7).

Figure 56:
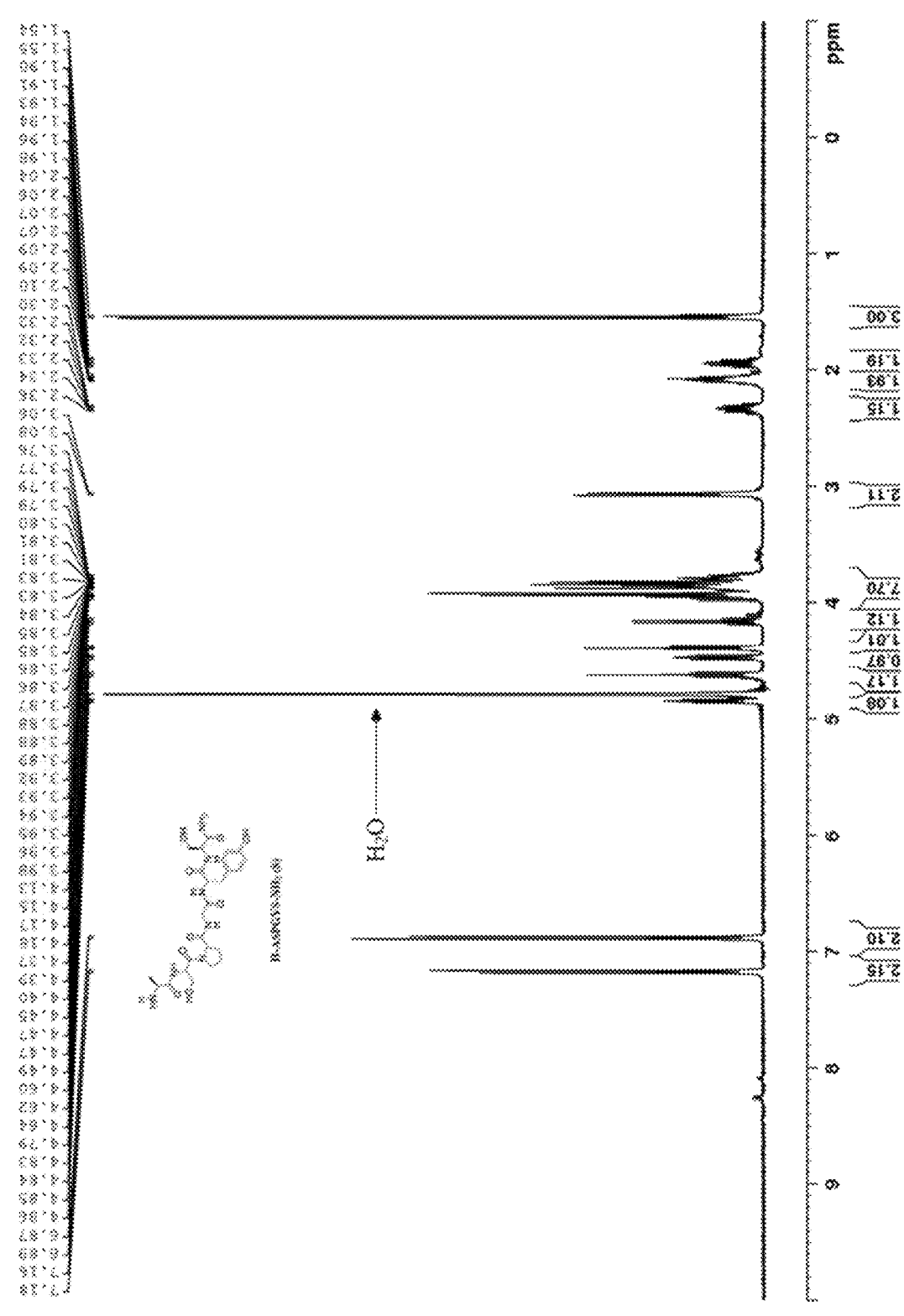

FIG. 56: $^1$H NMR spectrum (D$_2$O, 400 MHz) of H-AS-PGYS-NH$_2$ (8, SEQ ID NO: 8).

Figure 57:
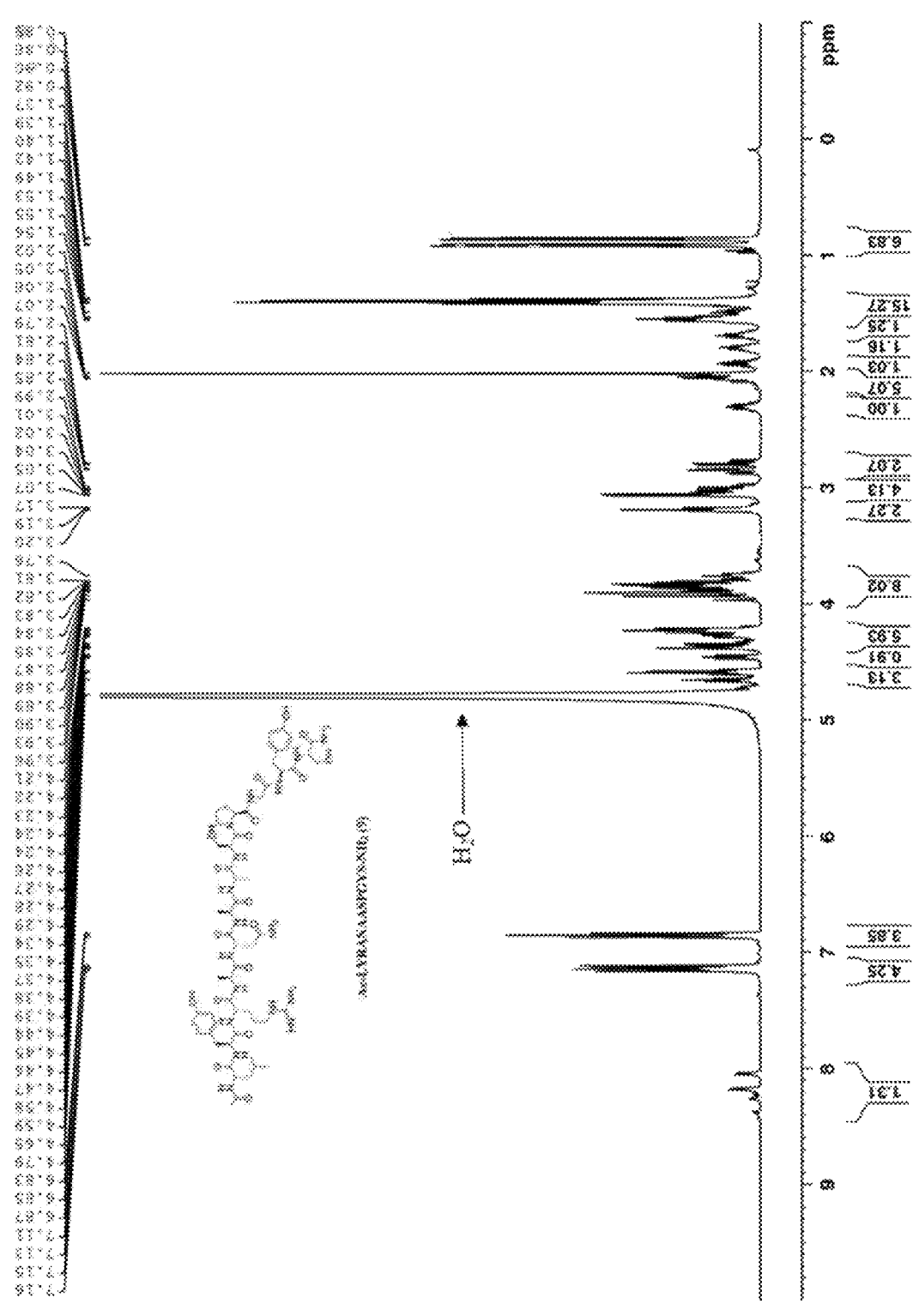

FIG. 57: $^1$H NMR spectrum (D$_2$O, 500 MHZ) of Ac-LYRANAASPGYS-NH$_2$ (9, SEQ ID NO: 9).

Figure 58:
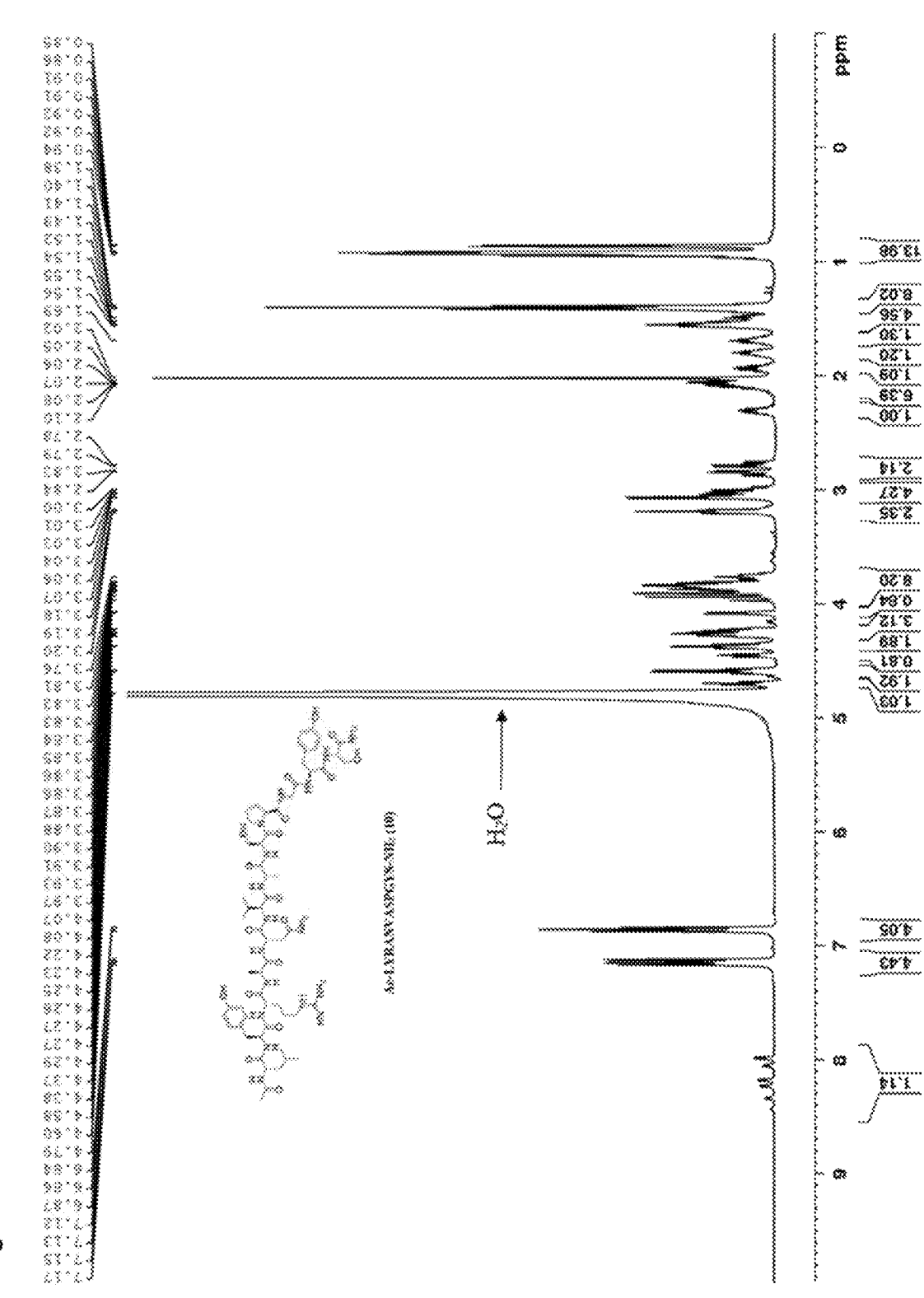

FIG. 58: $^1$H NMR spectrum (D$_2$O, 500 MHZ) of Ac-LYRANVASPGYS-NH$_2$ (10, SEQ ID NO: 10).

Figure 59:
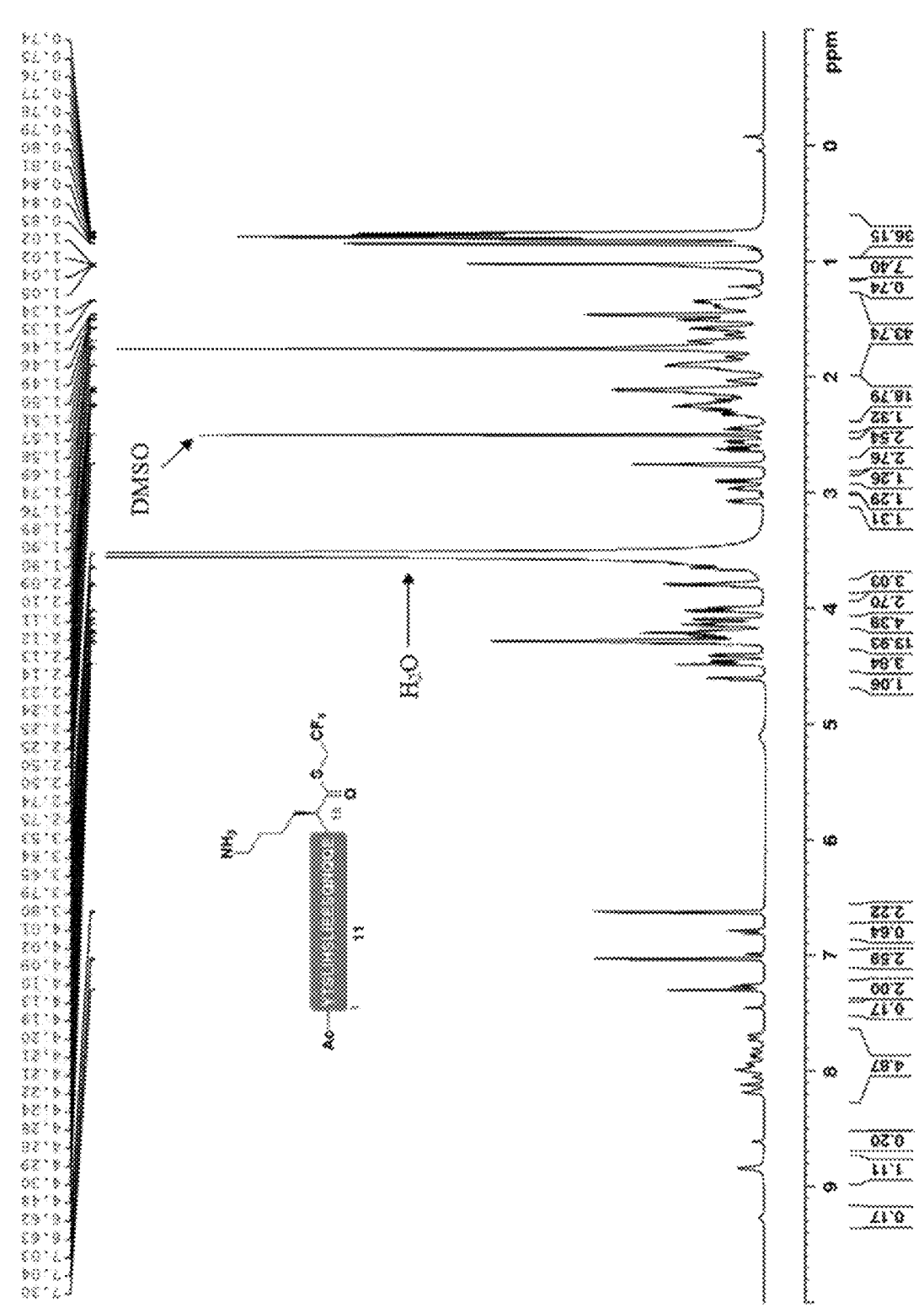

FIG. 59: $^1$H NMR spectrum (95% d$_6$-DMSO+5% D$_2$O, 800 MHZ) of enfuvirtide(1-18) (11, SEQ ID NO: 11).

Figure 60:
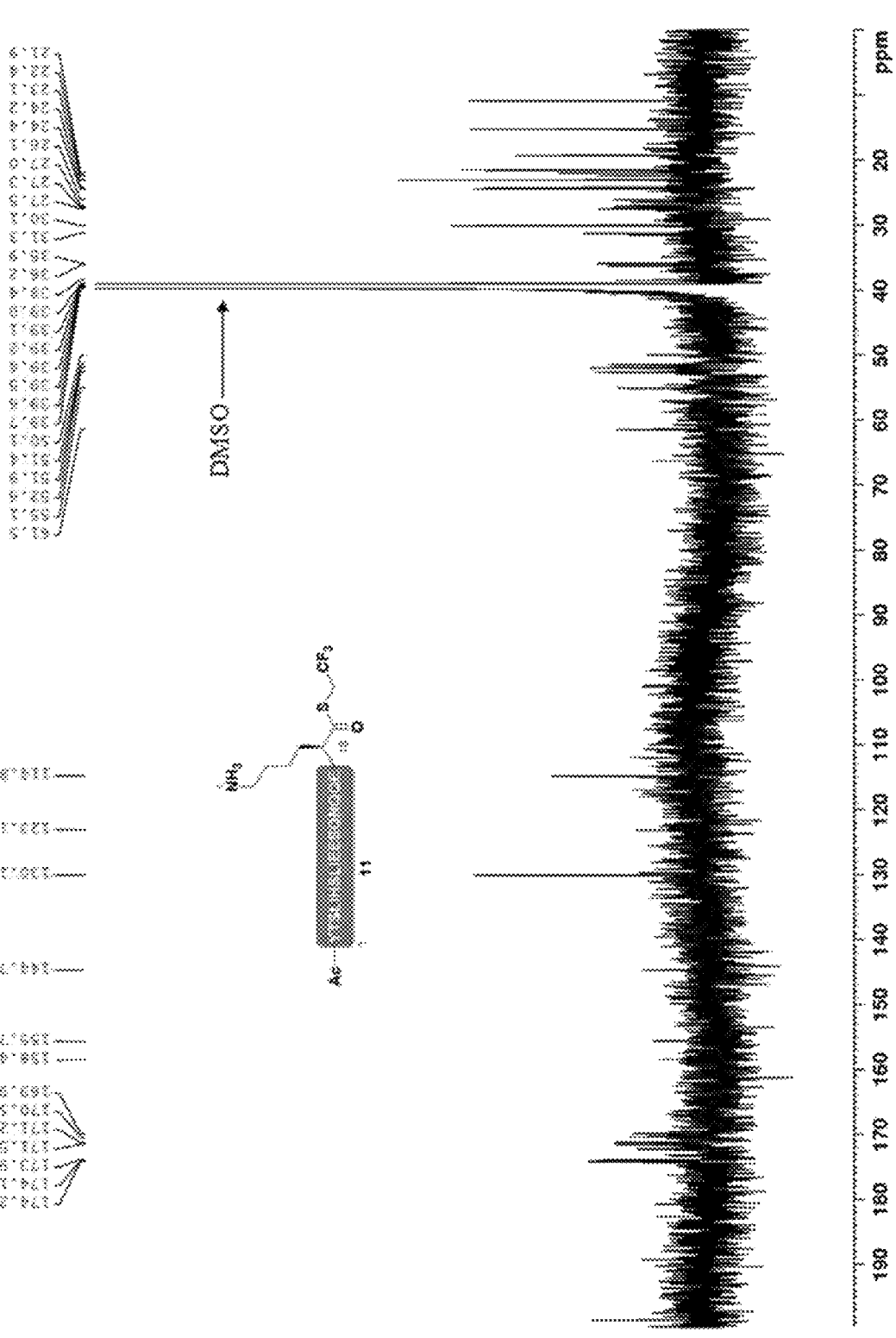

FIG. 60: $^{13}$C$\{^1$H$\}$ NMR spectrum (95% d$_6$-DMSO+5% D$_2$O, 201 MHZ) of enfuvirtide(1-18) (11, SEQ ID NO: 11).

Figure 61:
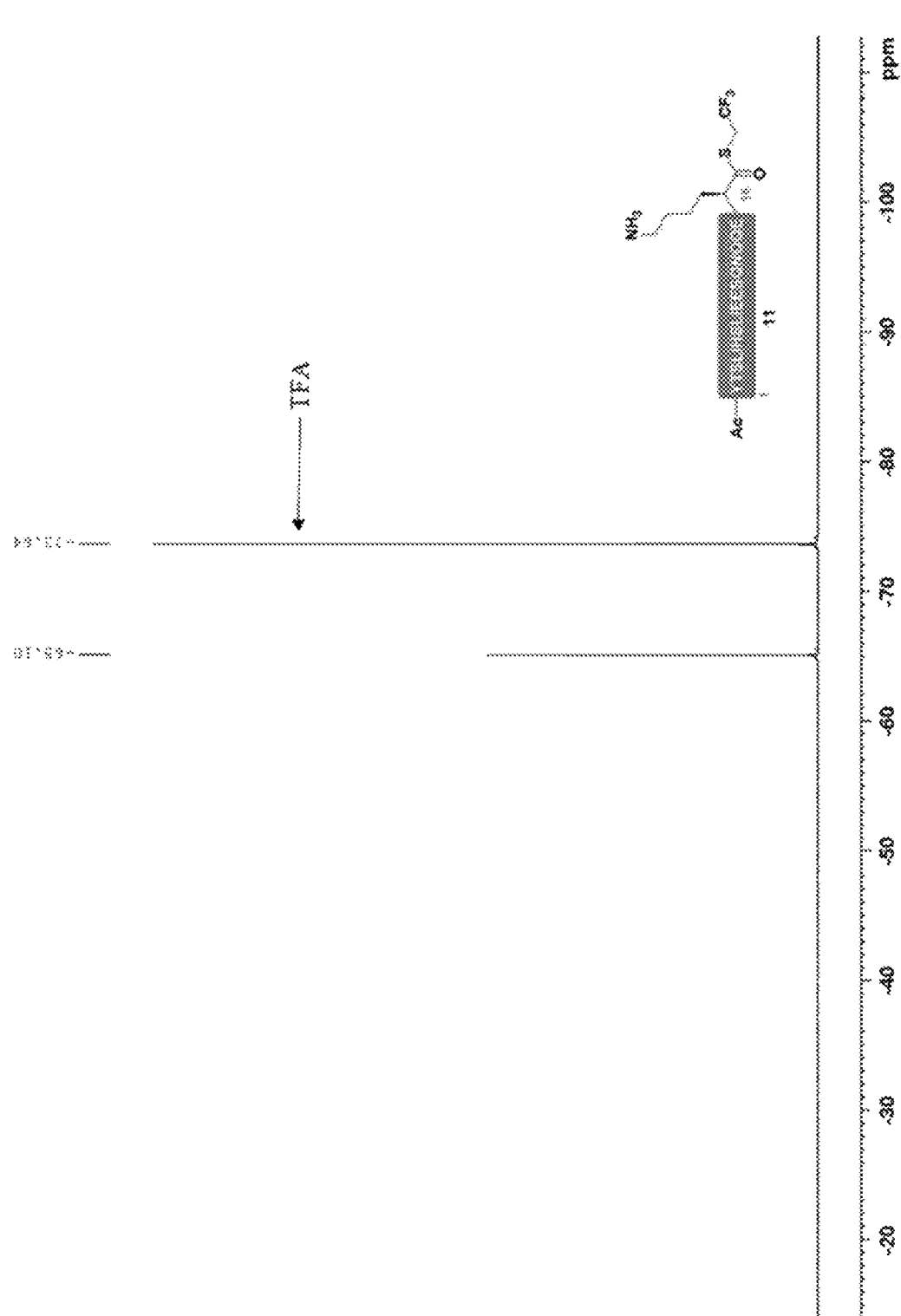

FIG. 61: $^{19}$F $\{^1$H$\}$ NMR spectrum (95% d$_6$-DMSO+5% D$_2$O, 376 MHZ) of enfuvirtide(1-18) (11, SEQ ID NO: 11).

Figure 62:
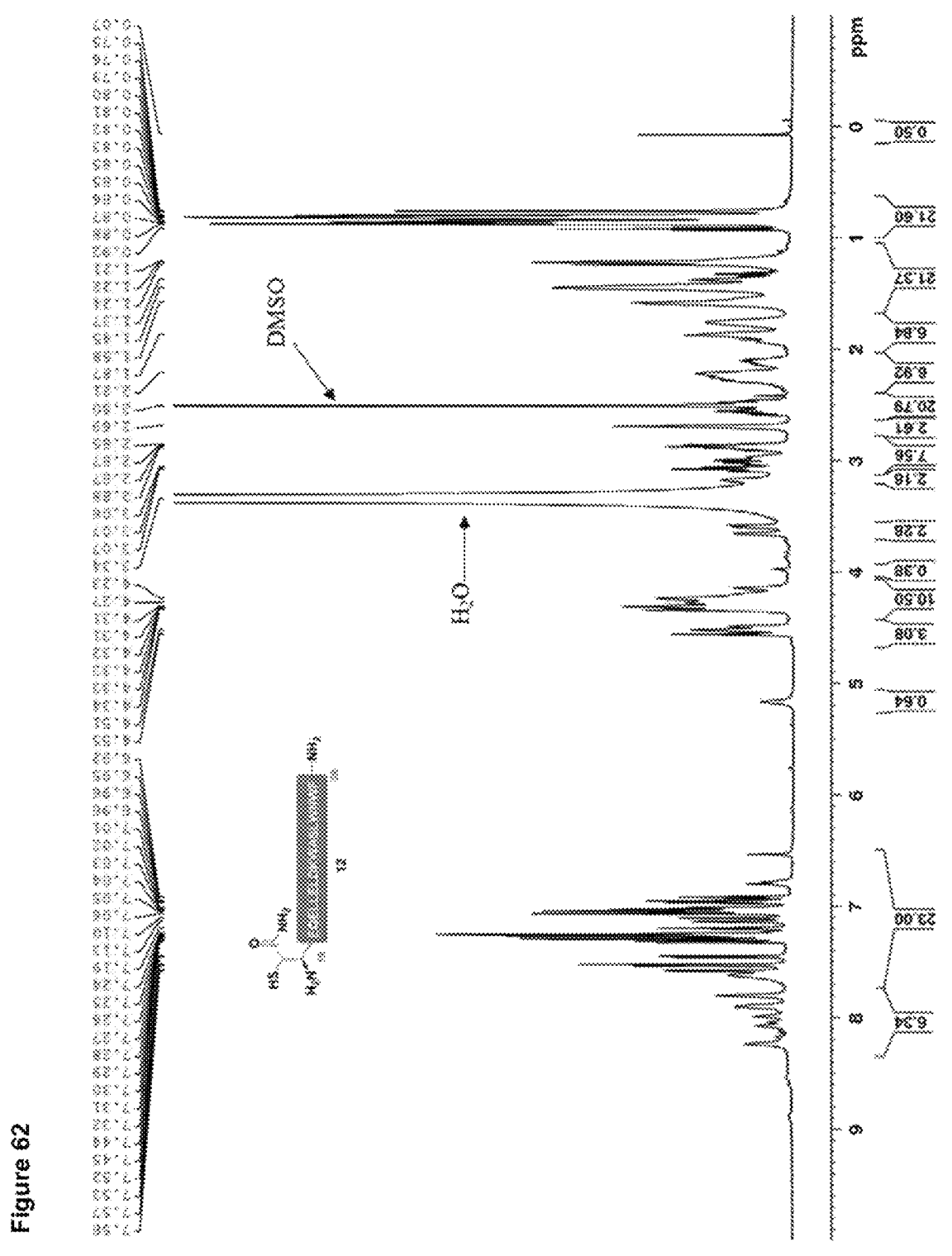

FIG. 62: $^1$H NMR spectrum (95% d$_6$-DMSO+5% D$_2$O, 800 MHZ) of enfuvirtide(19-36) (12, SEQ ID NO: 12).

Figure 63:
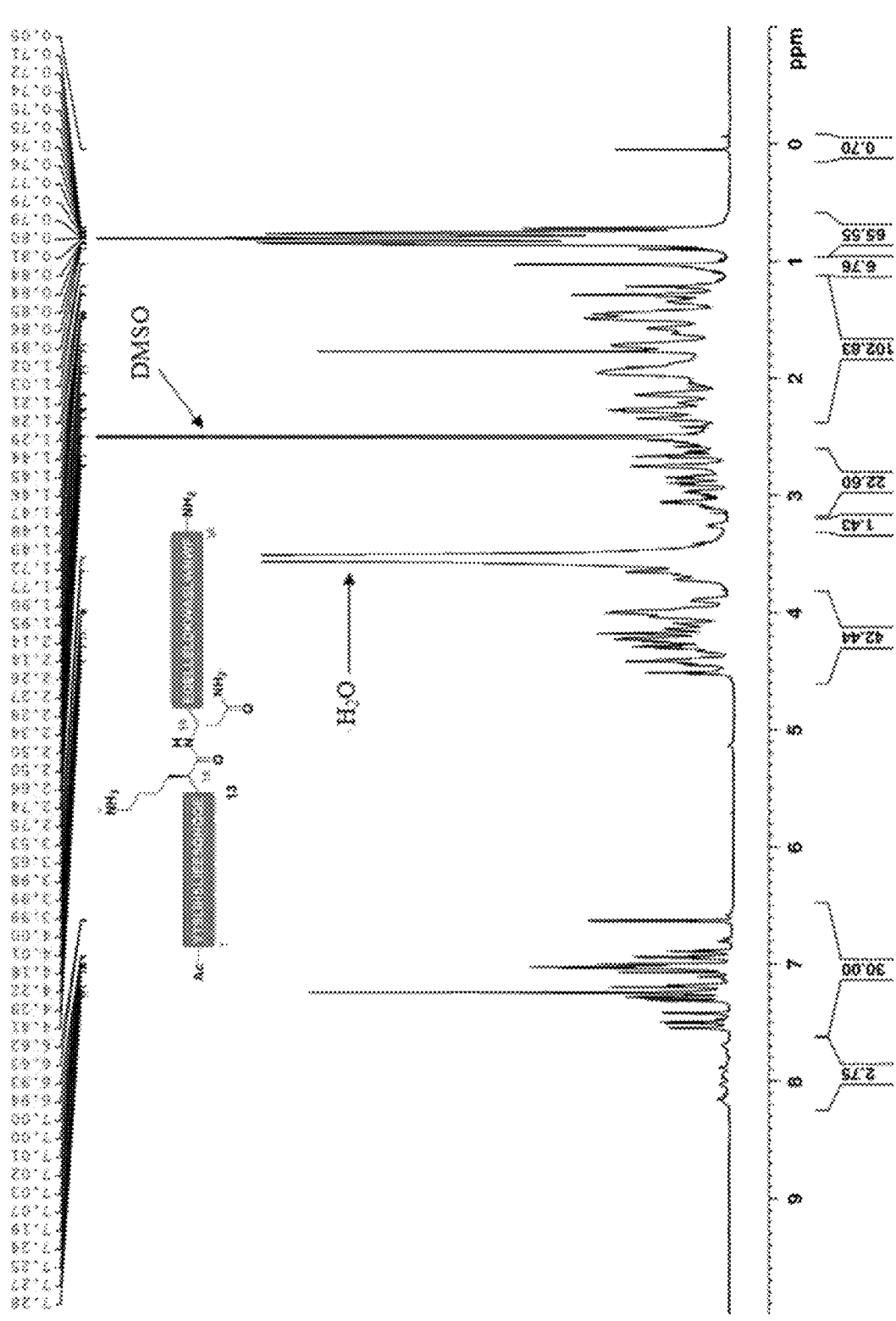

FIG. 63: $^1$H NMR spectrum (95% d$_6$-DMSO+5% D$_2$O, 800 MHZ) of enfuvirtide(13, SEQ ID NO: 13).

Figure 64:
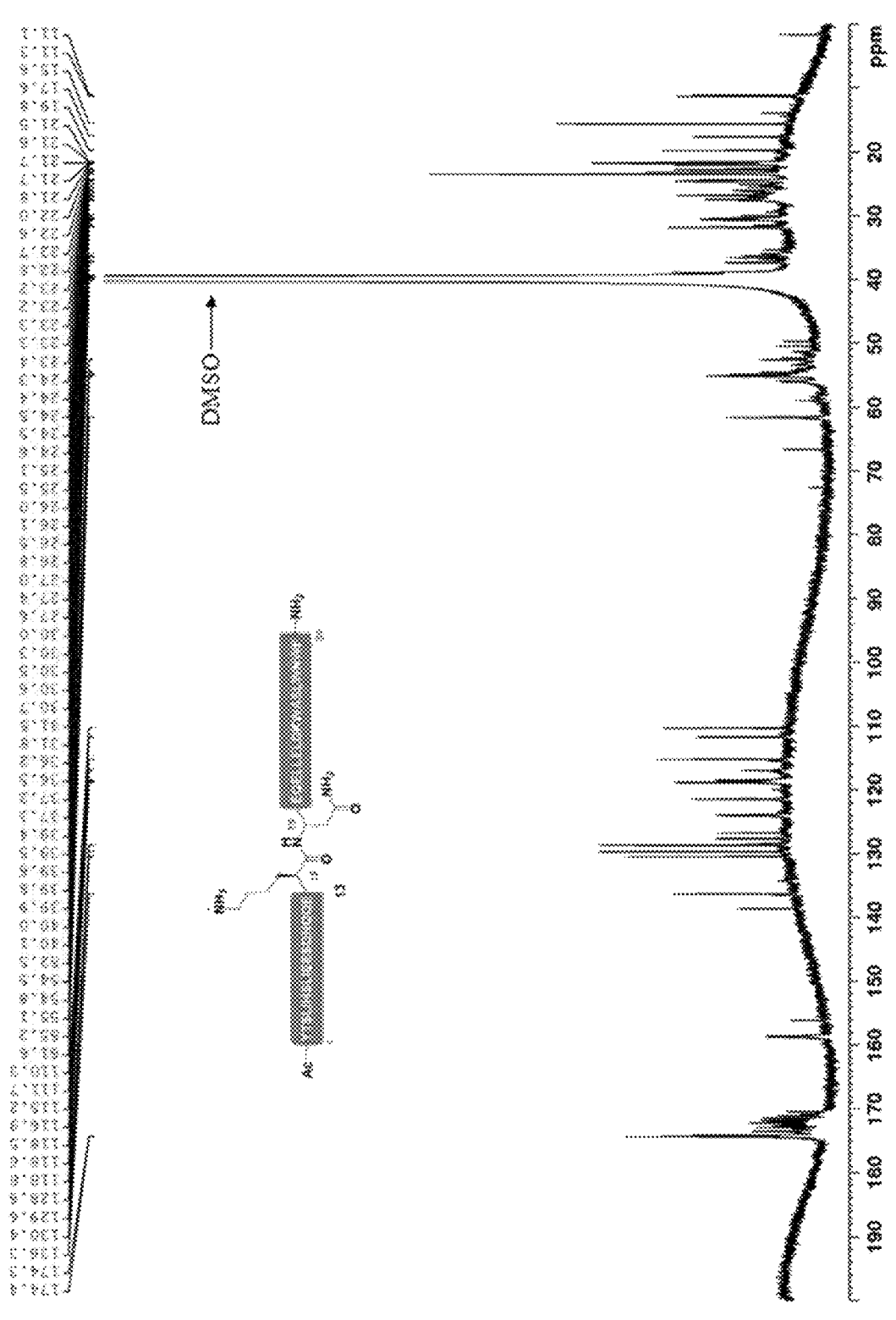

FIG. 64: $^{13}$C$\{^1$H$\}$ NMR spectrum (95% d$_6$-DMSO+5% D$_2$O, 201 MHZ) of enfuvirtide(13, SEQ ID NO: 13).

Figure 65:
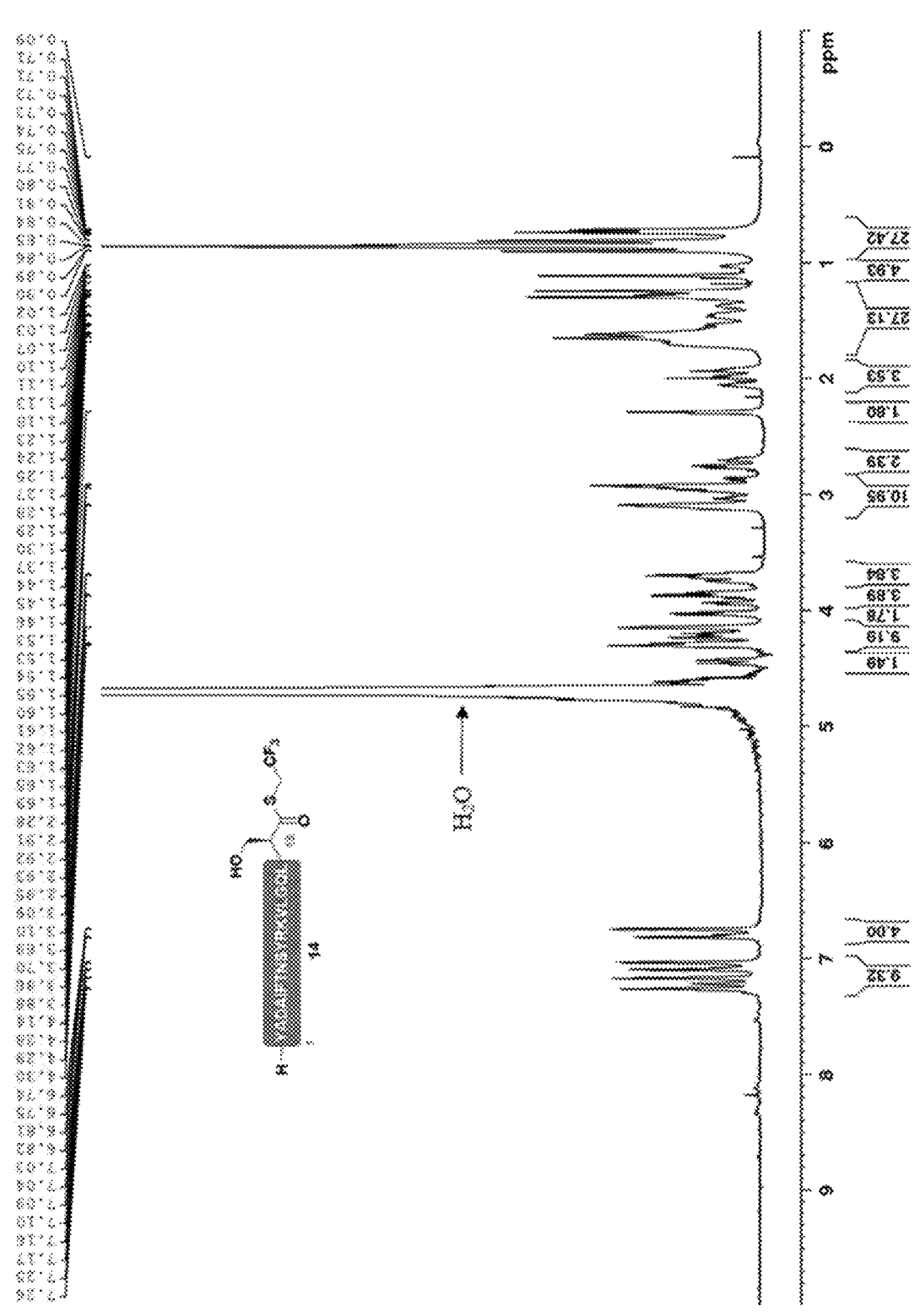

FIG. 65: $^1$H NMR spectrum (D$_2$O, 800 MHZ) of somatorelin(1-18) (14, SEQ ID NO: 14).

Figure 66:
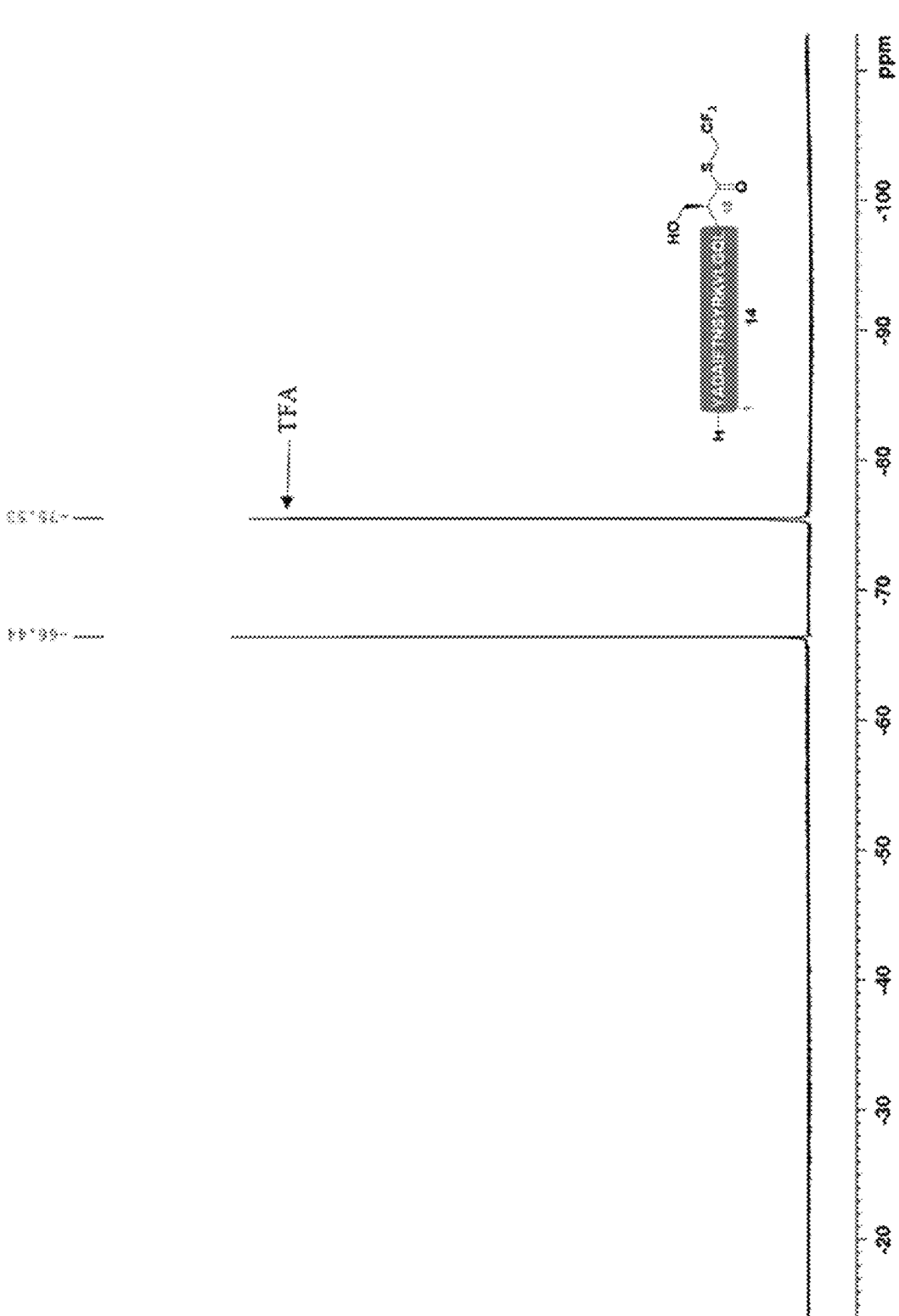

FIG. 66: $^{19}$F $\{^1$H$\}$ NMR spectrum (D$_2$O, 471 MHZ) of somatorelin(1-18) (14, SEQ ID NO: 14).

Figure 67:
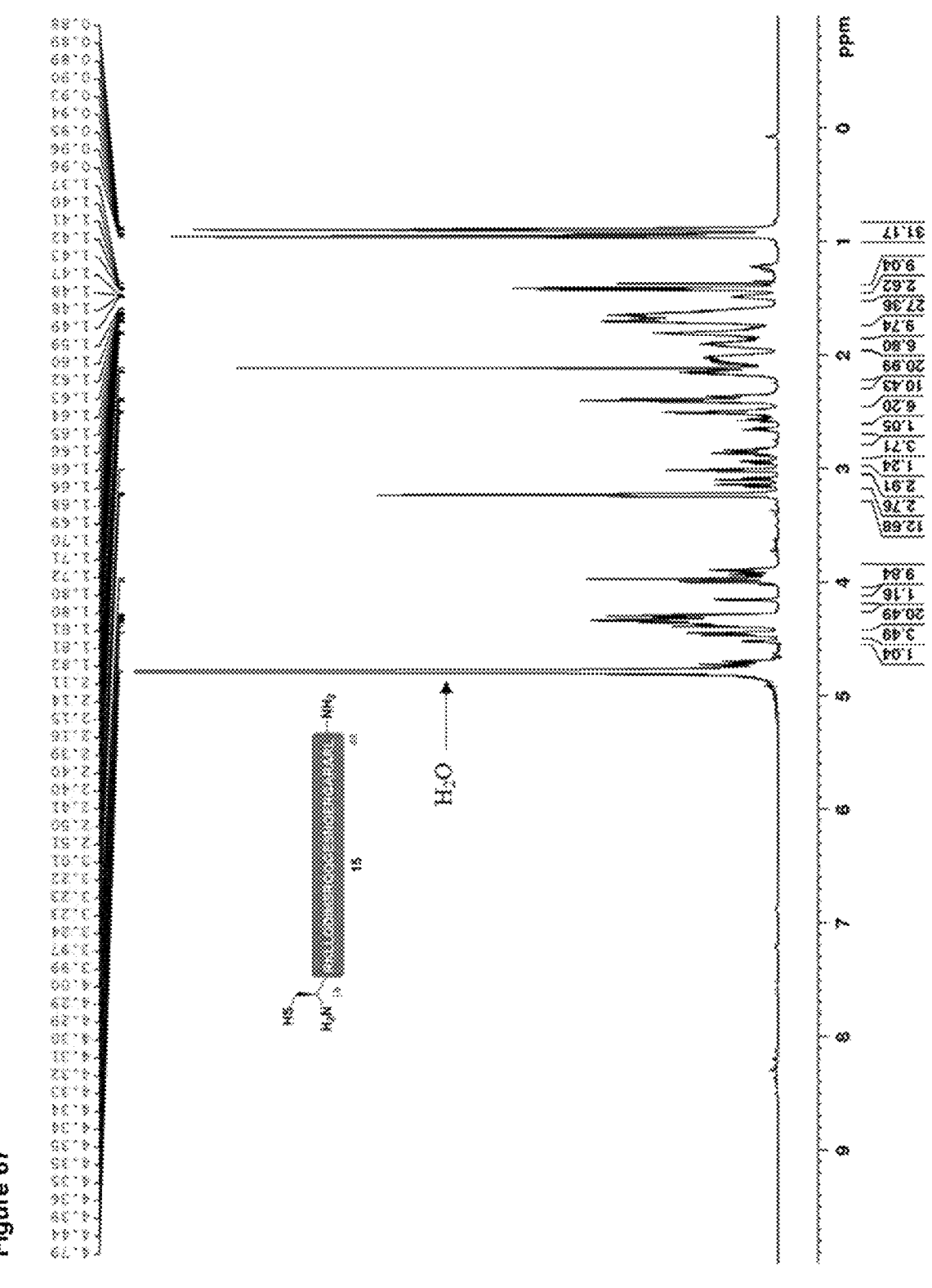

FIG. 67: $^1$H NMR spectrum (D$_2$O, 800 MHZ) of somatorelin(19-44) (15, SEQ ID NO: 15).

Figure 68:
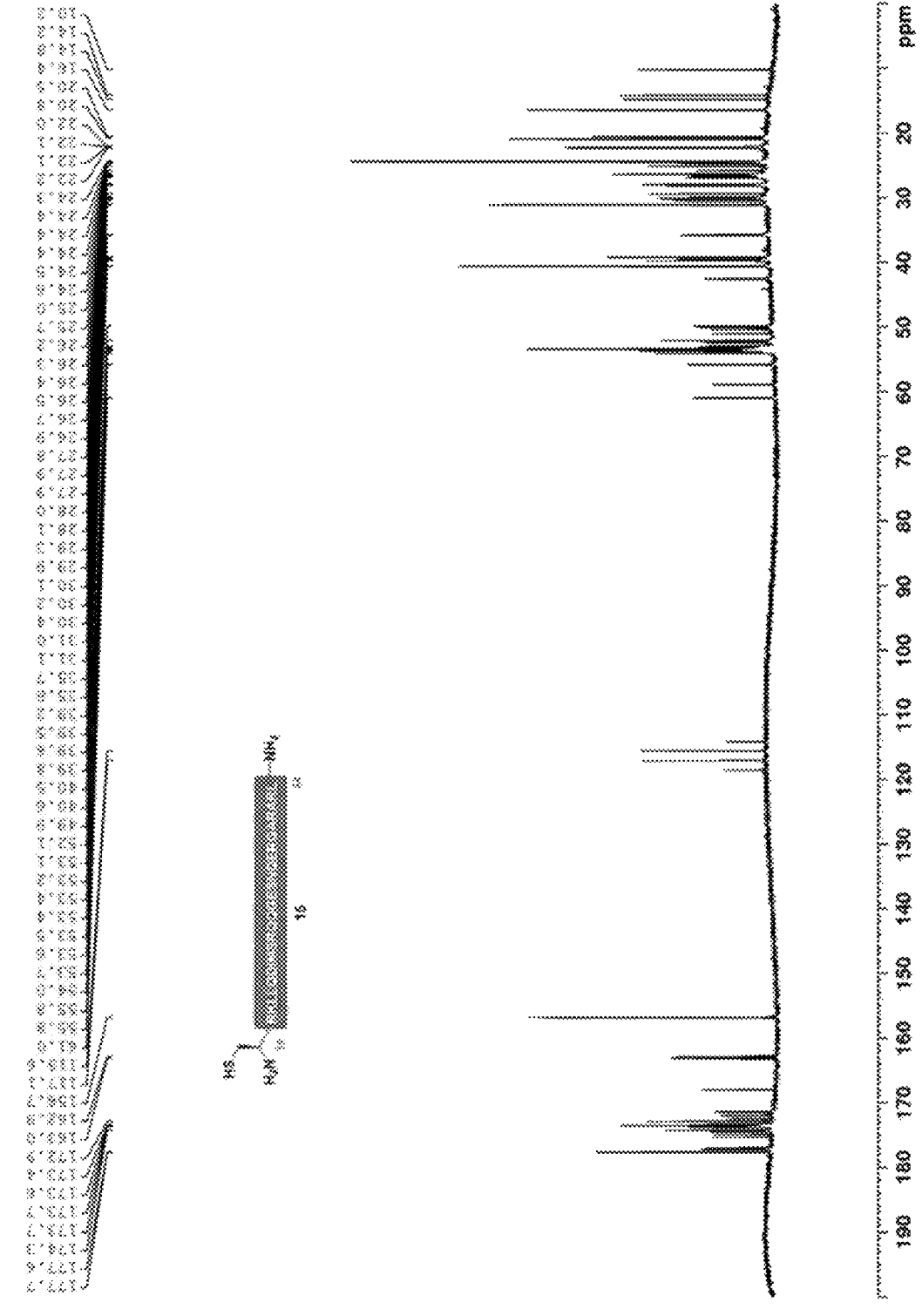

FIG. 68: $^{13}$C$\{^1$H$\}$ NMR spectrum (D$_2$O, 201 MHZ) of somatorelin(19-44) (15, SEQ ID NO: 15).

Figure 69:
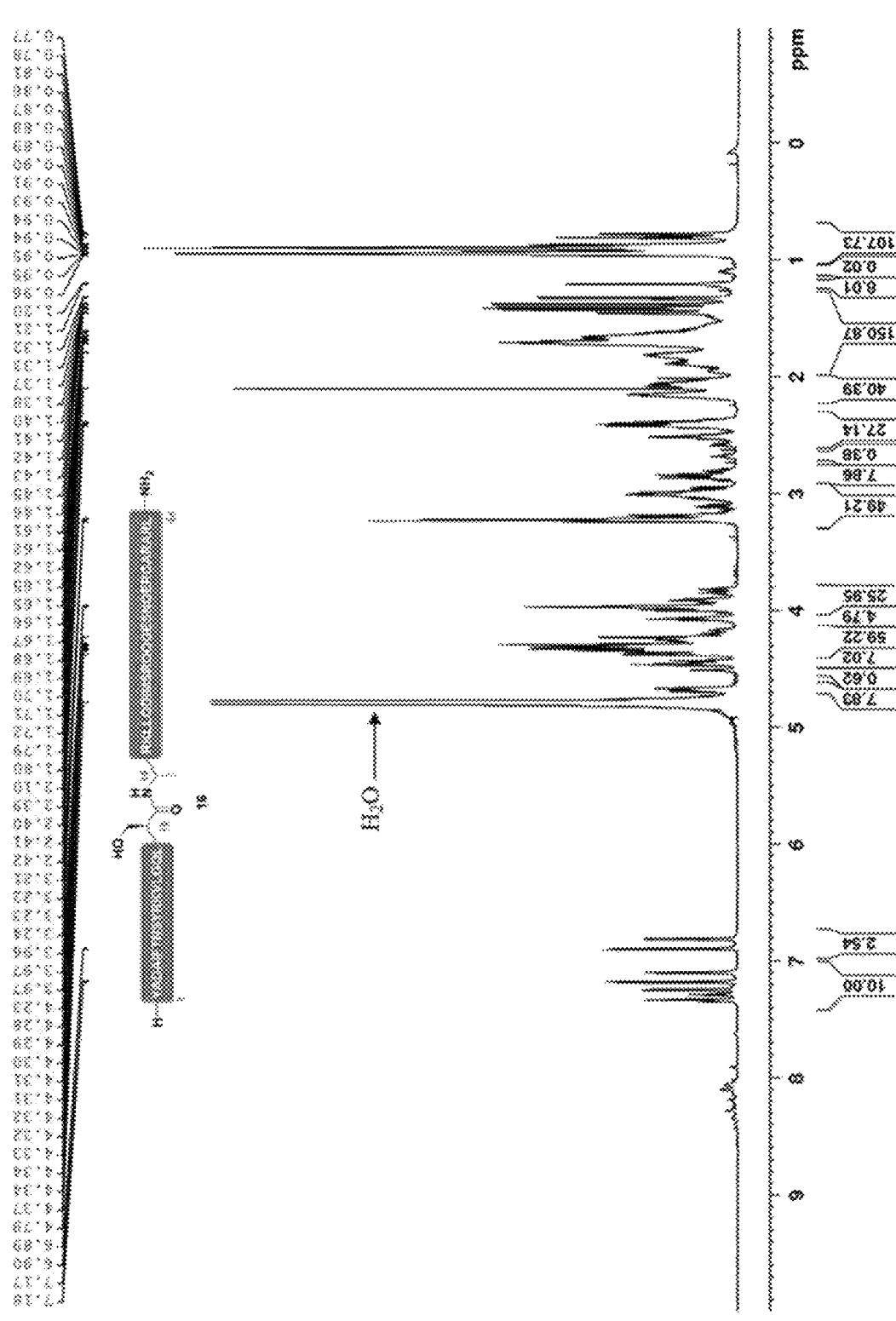

FIG. 69: $^1$H NMR spectrum (D$_2$O, 800 MHZ) of somatorelin(16, SEQ ID NO: 16).

Figure 70:
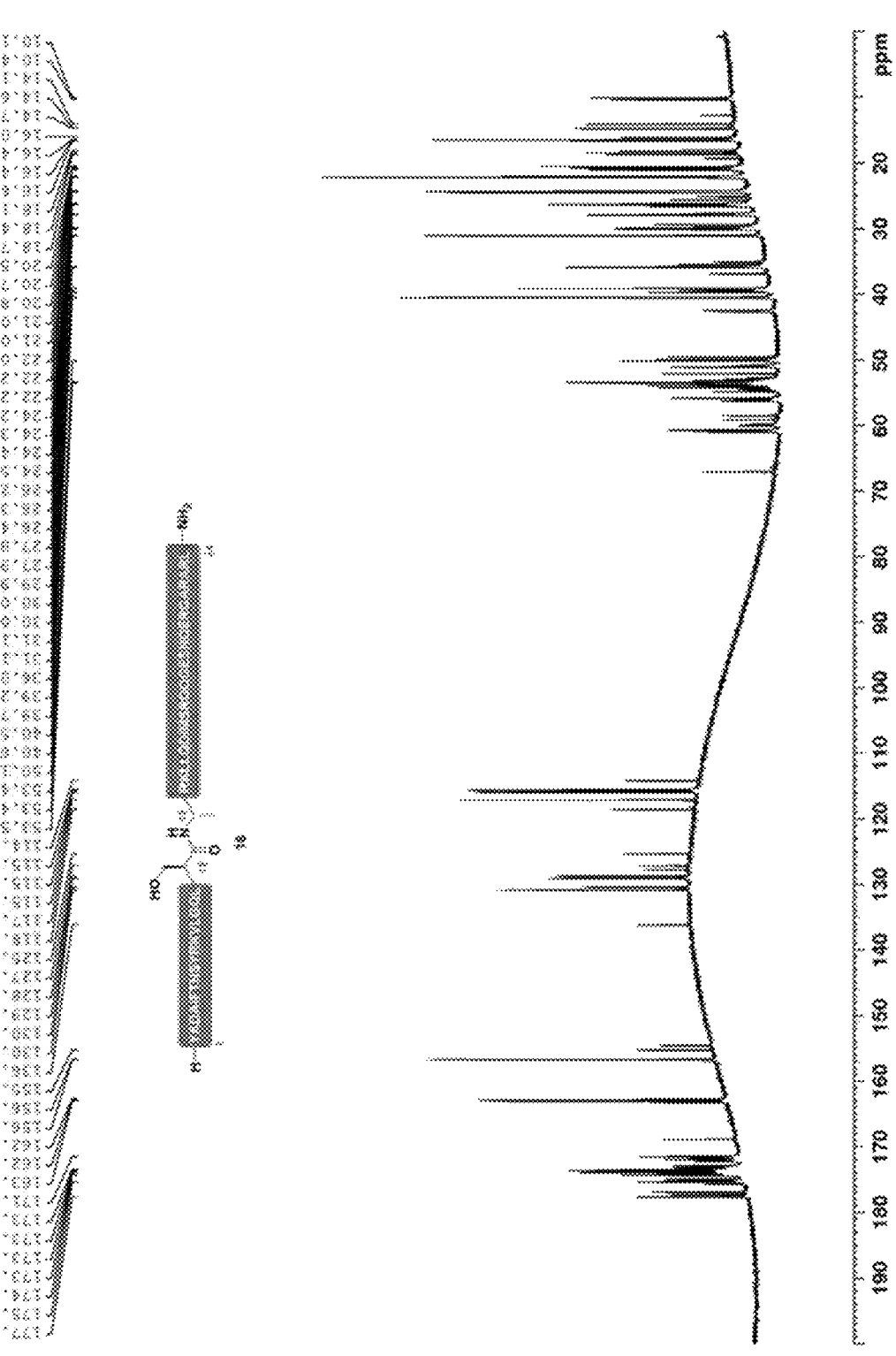

FIG. 70: $^{13}$C$\{^1$H$\}$ NMR spectrum (D$_2$O, 201 MHZ) of somatorelin(16, SEQ ID NO: 16).

Figure 71:
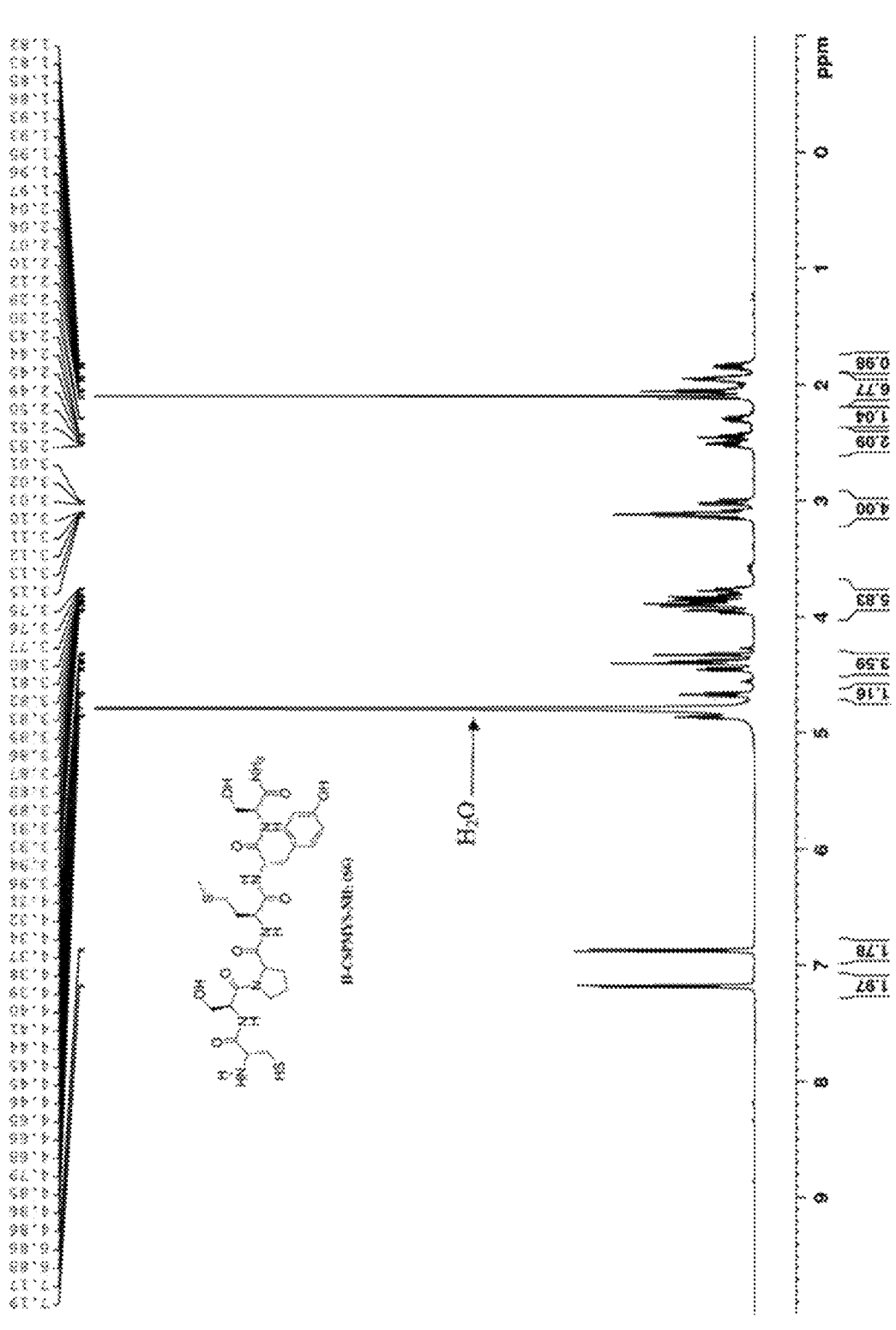

FIG. 71: $^1$H NMR spectrum (D$_2$O, 500 MHZ) of H-CSPMYS-NH$_2$ (S6, SEQ ID NO: 18).

Figure 72:
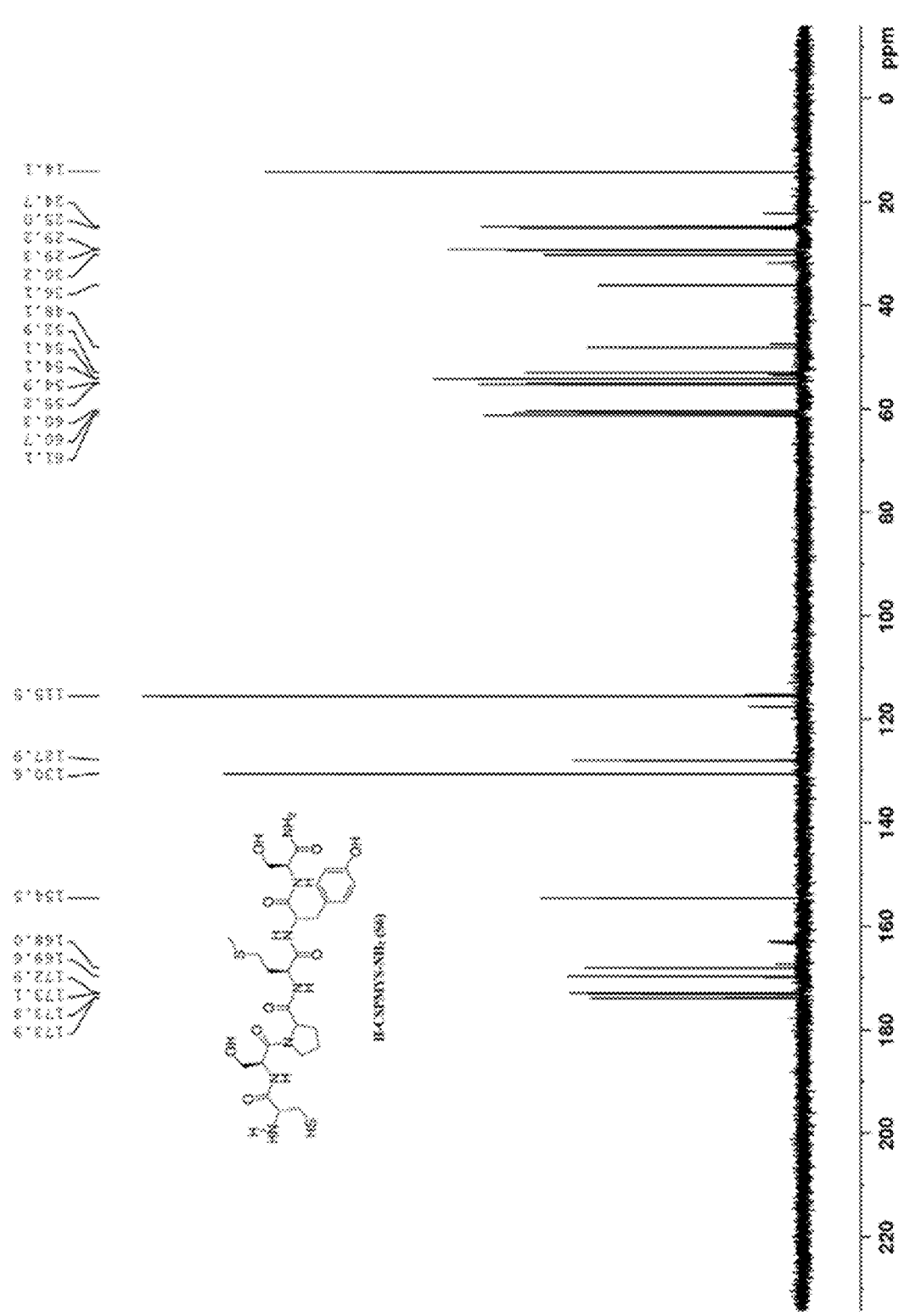

FIG. 72: $^{13}$C$\{^1$H$\}$ NMR spectrum (D$_2$O, 126 MHz) of H-CSPMYS-NH$_2$ (S6, SEQ ID NO: 18).

Figure 73:
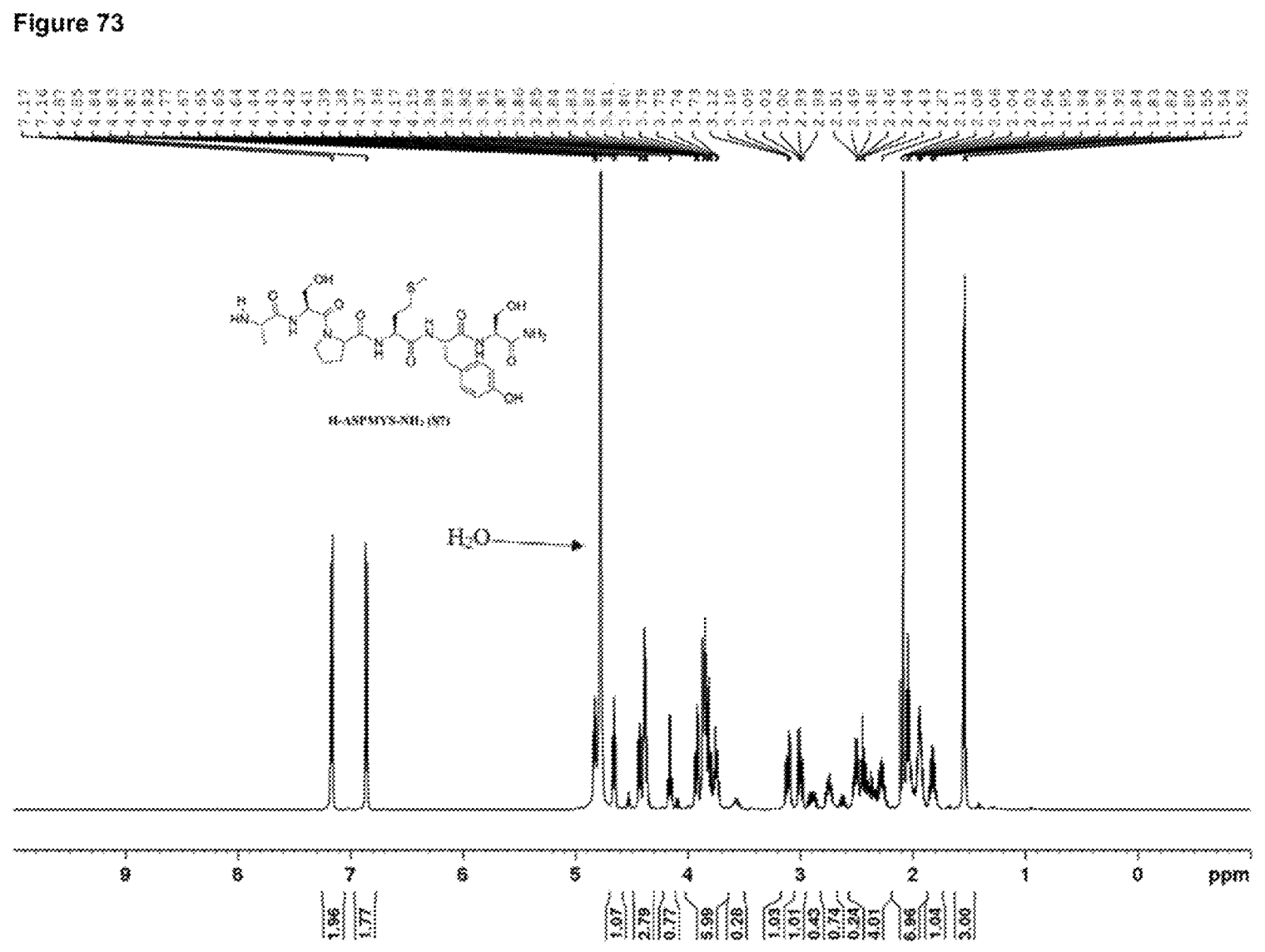

FIG. 73: $^1$H NMR spectrum (D$_2$O, 500 MHZ) of H-AS-PMYS-NH$_2$ (S7, SEQ ID NO: 19).

Figure 74:
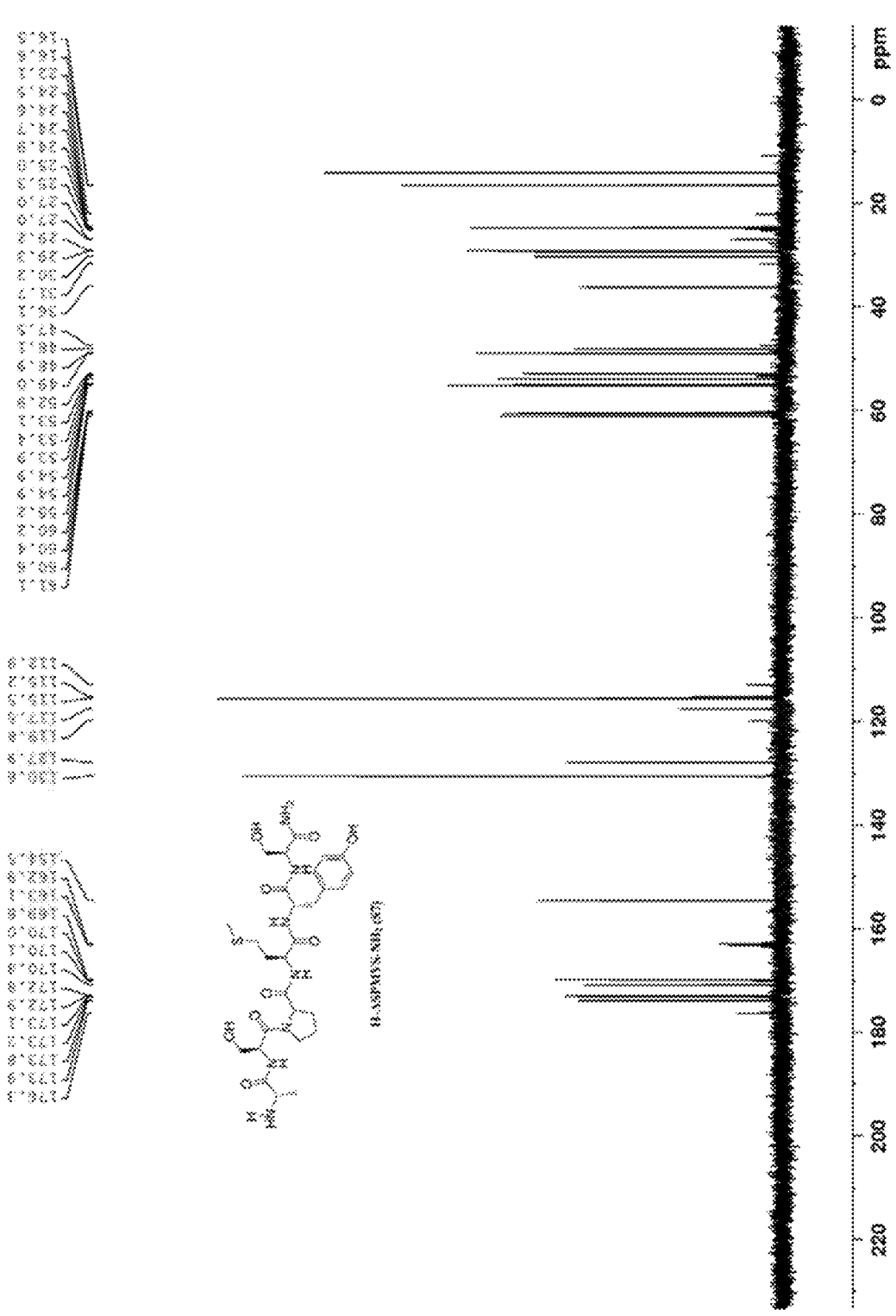

FIG. 74: $^{13}$C$\{^1$H$\}$ NMR spectrum (D$_2$O, 126 MHz) of H-ASPMYS-NH$_2$ (S7, SEQ ID NO: 19).

Figure 75:
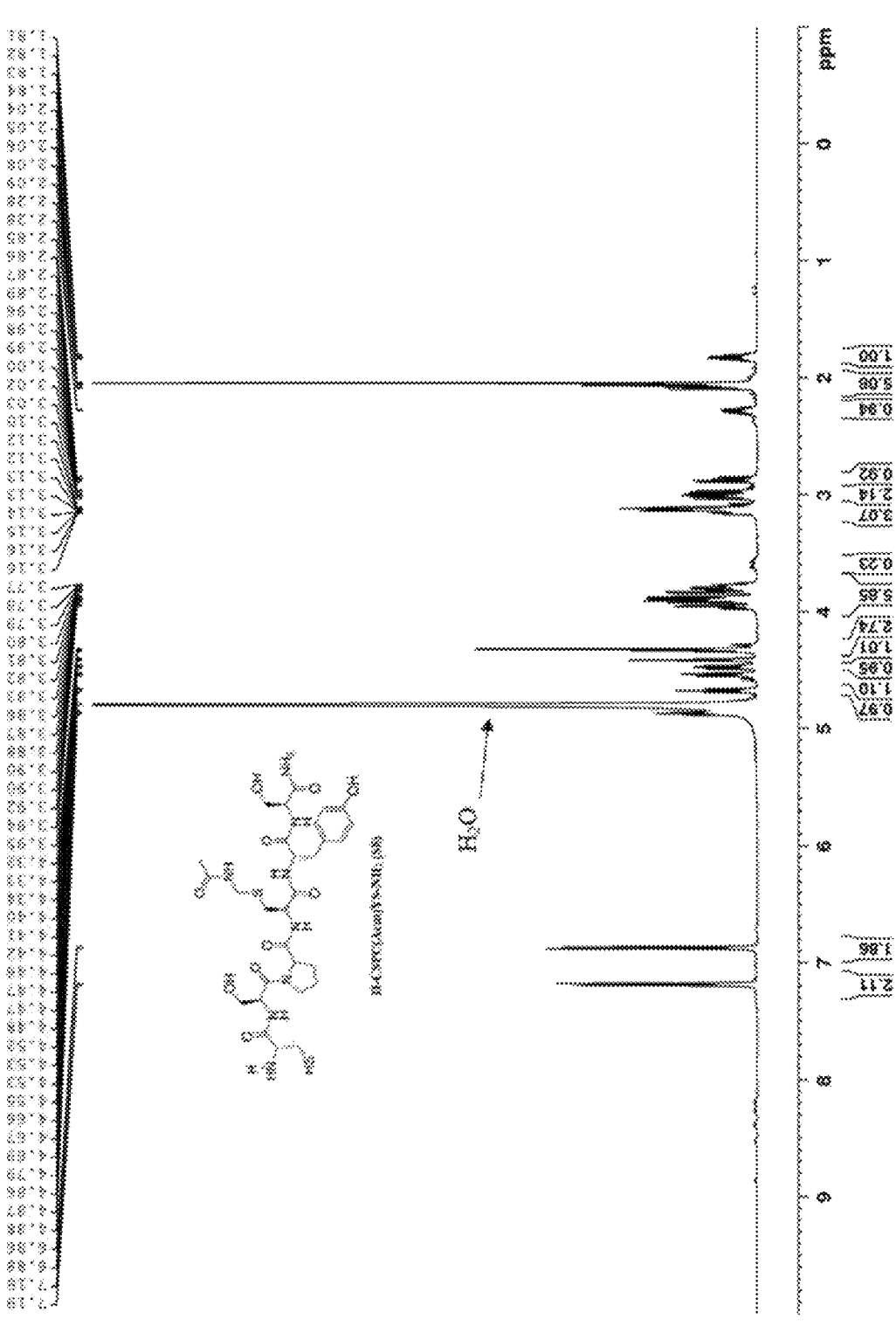

FIG. 75: $^1$H NMR spectrum (D$_2$O, 500 MHZ) of H-CSPC(Acm)YS-NH$_2$ (S8, SEQ ID NO: 20).

Figure 76:
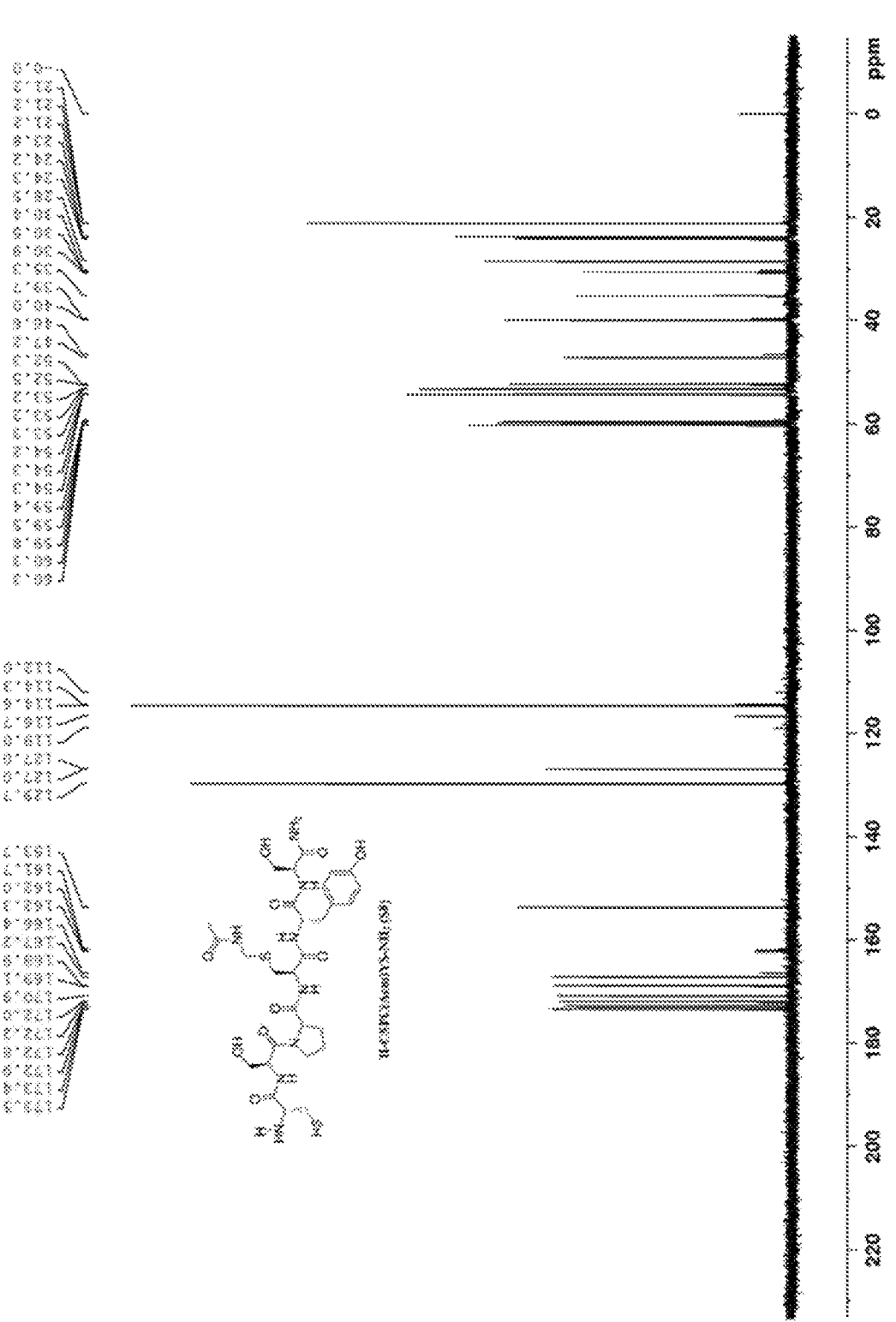

FIG. 76: $^{13}$C$\{^1$H$\}$ NMR spectrum (D$_2$O, 126 MHz) of H-CSPC(Acm)YS-NH$_2$ (S8, SEQ ID NO: 20).

Figure 77:
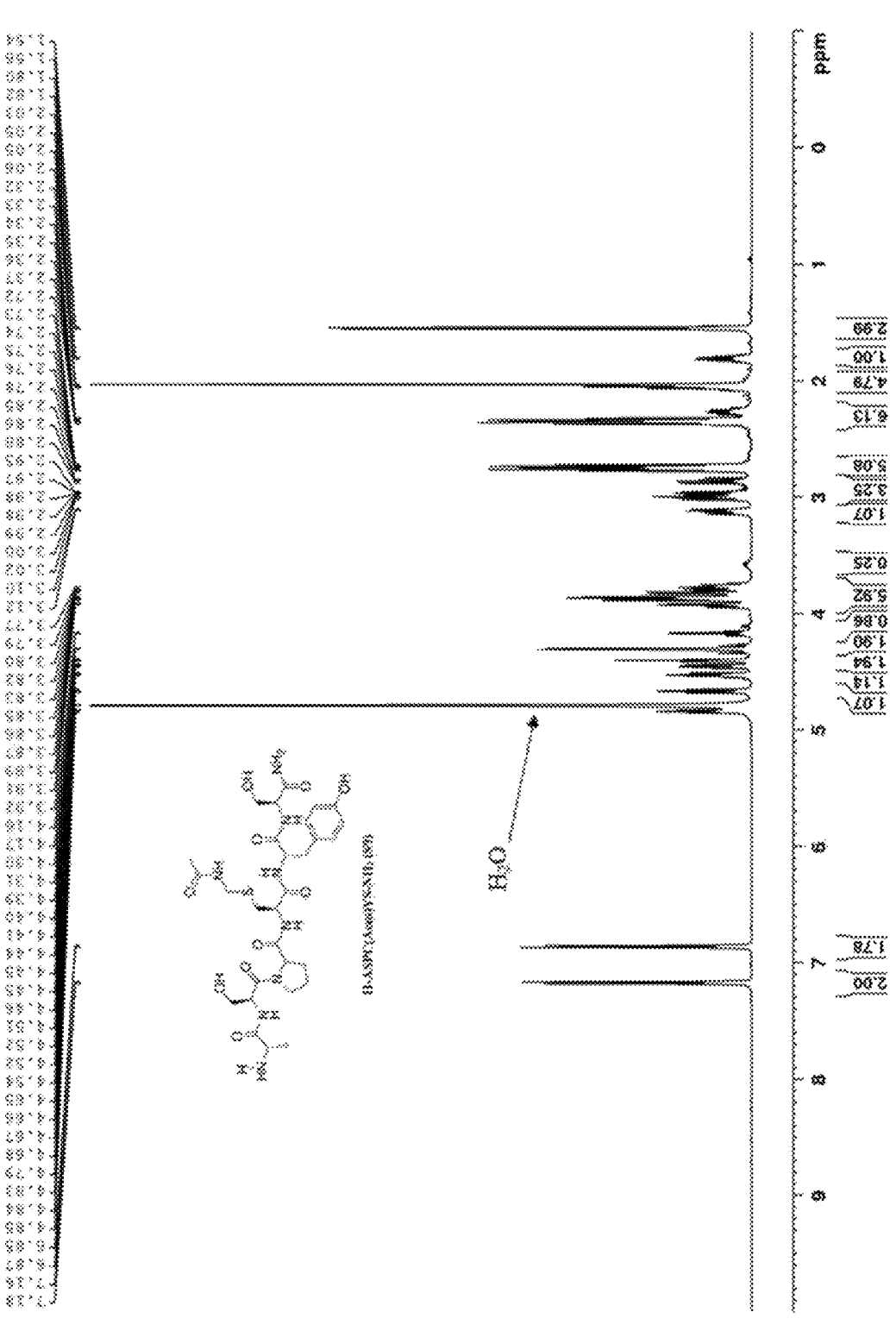

FIG. 77: $^1$H NMR spectrum (D$_2$O, 500 MHZ) of H-ASPC(Acm)YS-NH$_2$ (S9, SEQ ID NO: 21).

Figure 78:
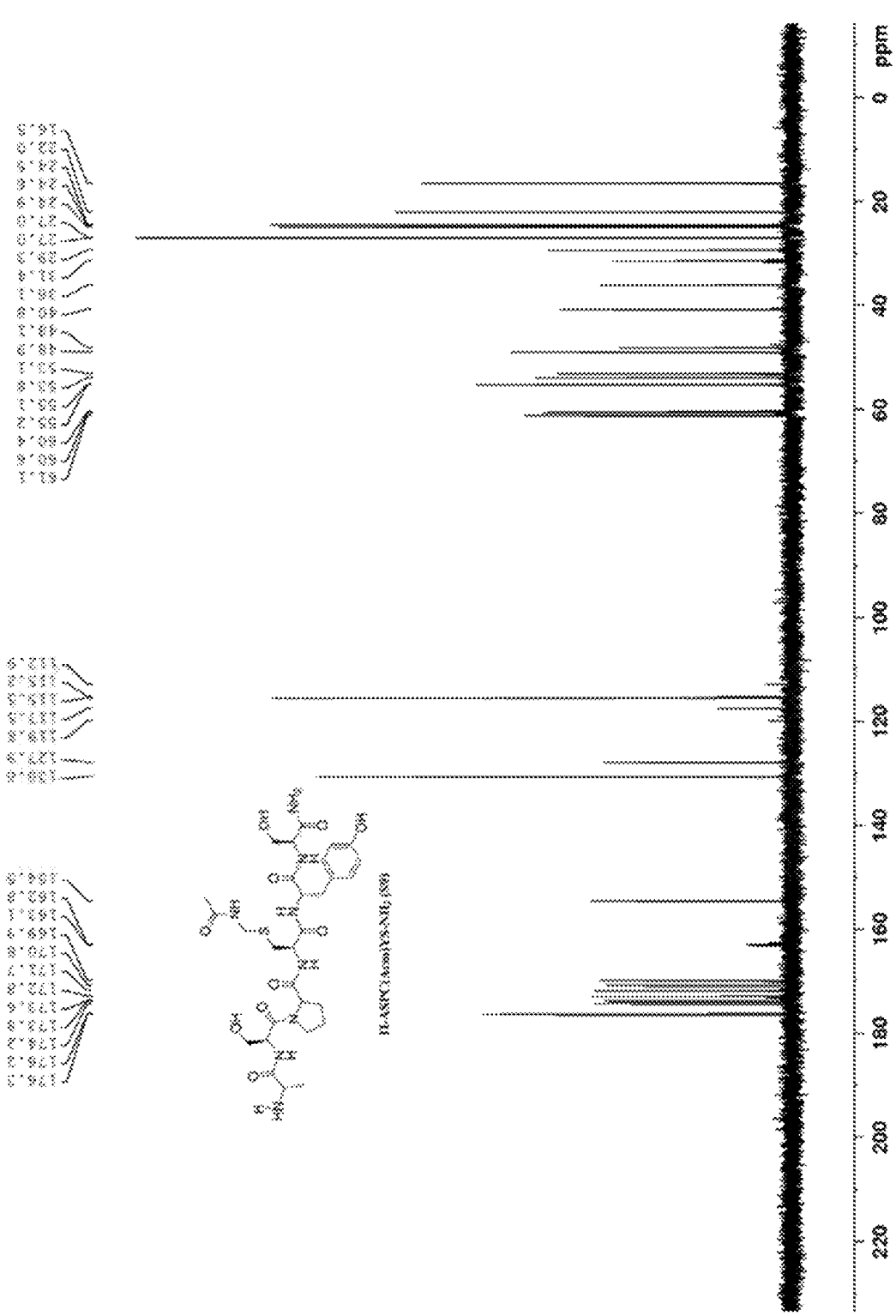

FIG. 78: $^{13}$C$\{^1$H$\}$ NMR spectrum (D$_2$O, 126 MHz) of H-ASPC(Acm)YS-NH$_2$ (S9, SEQ ID NO: 21).

Figure 79:
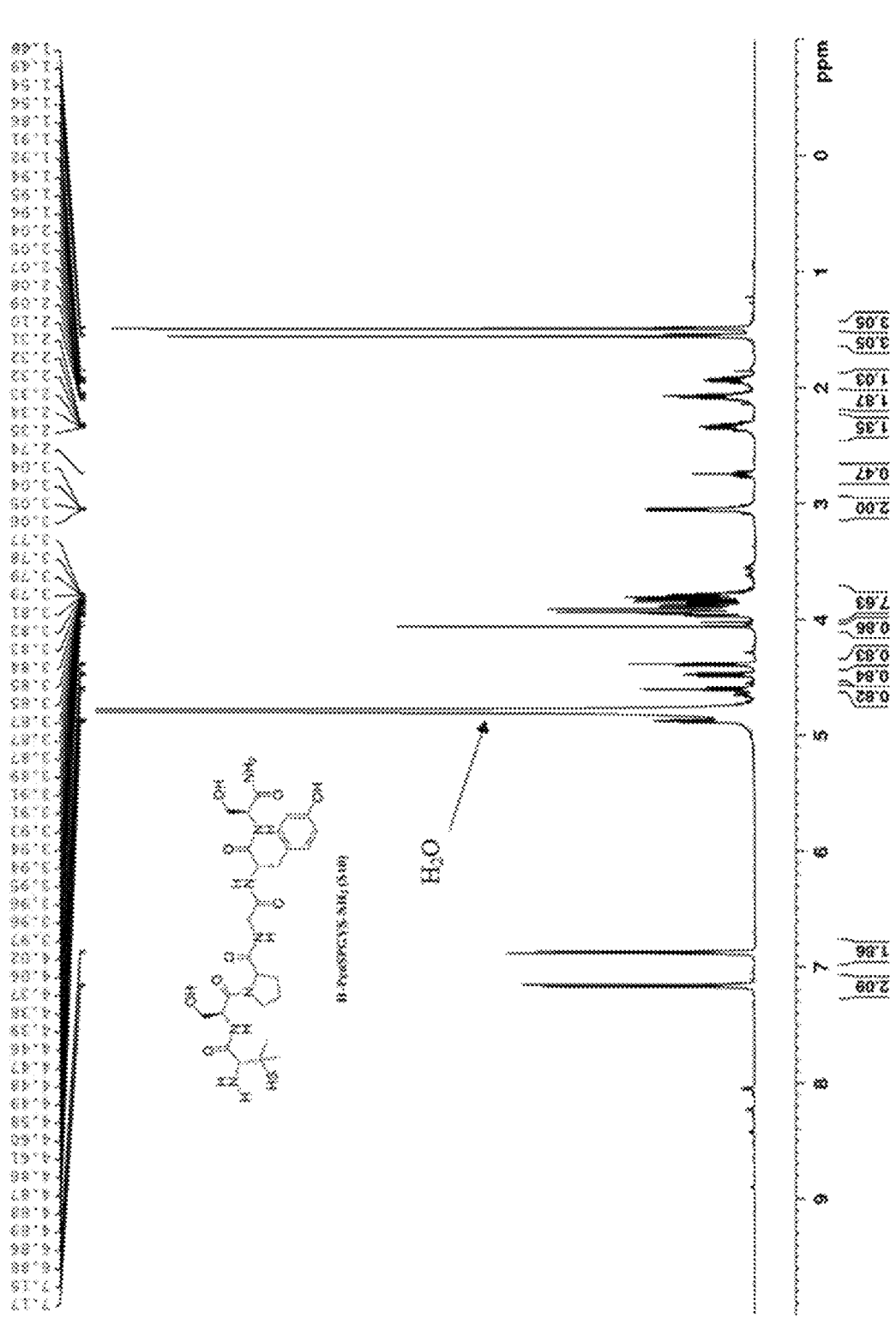

FIG. 79: $^1$H NMR spectrum (D$_2$O, 500 MHz) of H-Pen-SPGYS-NH$_2$ (S10, SEQ ID NO: 22).

Figure 80:
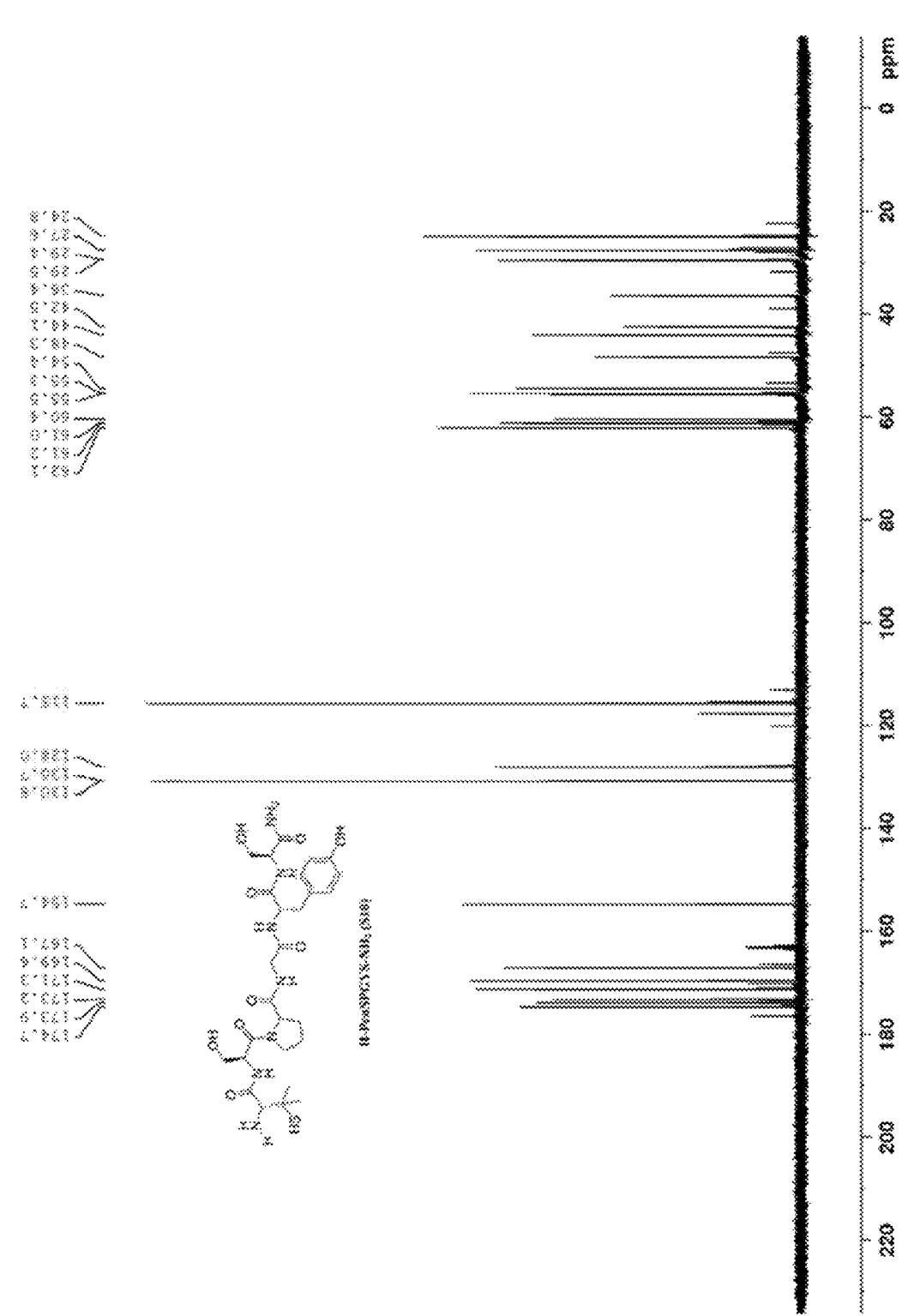

FIG. 80: $^{13}$C{$^1$H} NMR spectrum (D$_2$O, 126 MHZ) of H-PenSPGYS-NH$_2$ (S10, SEQ ID NO: 22).

Figure 81:
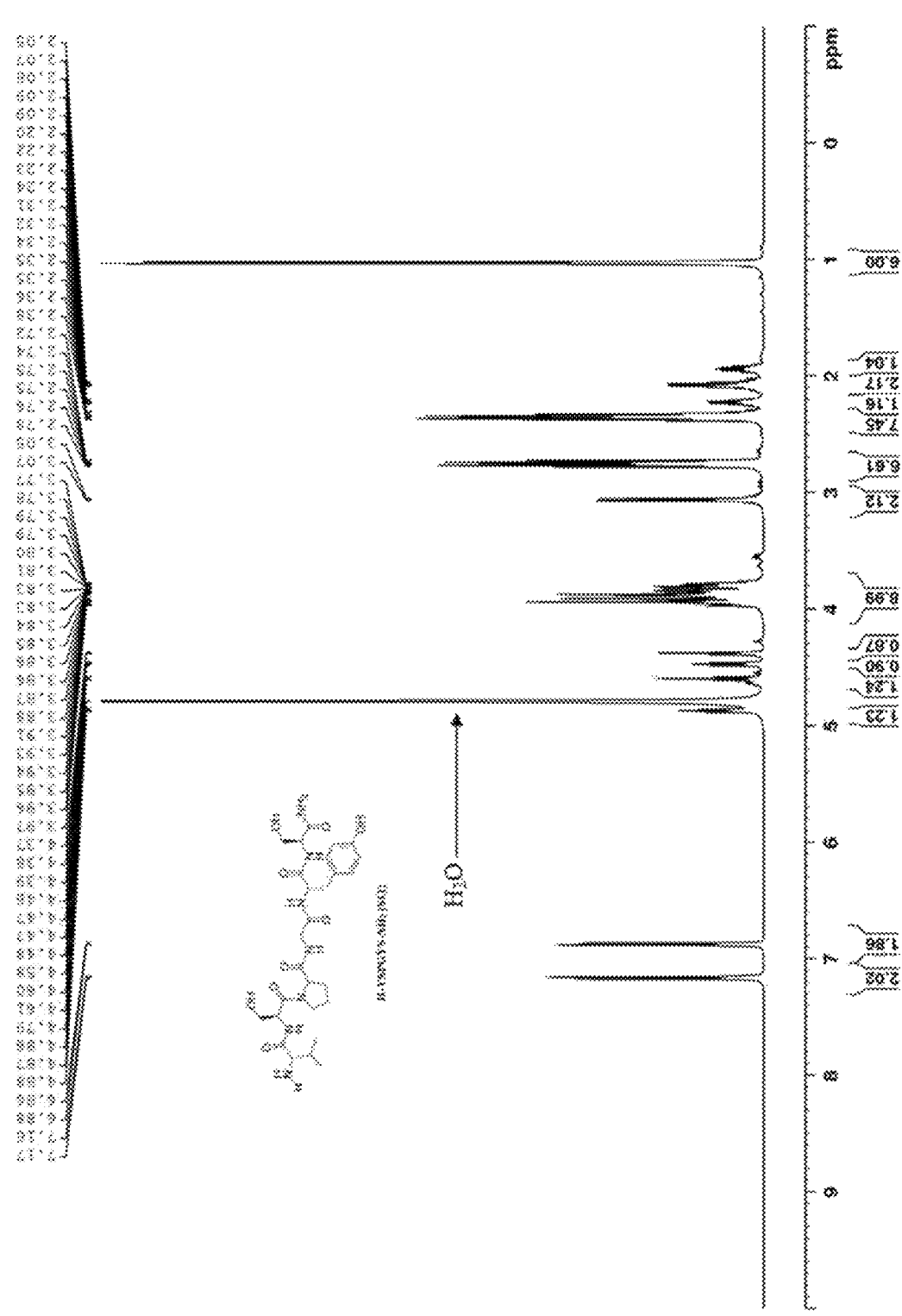

FIG. 81: $^1$H NMR spectrum (D$_2$O, 500 MHZ) of H-VSPGYS-NH$_2$ (S11, SEQ ID NO: 23).

Figure 82:
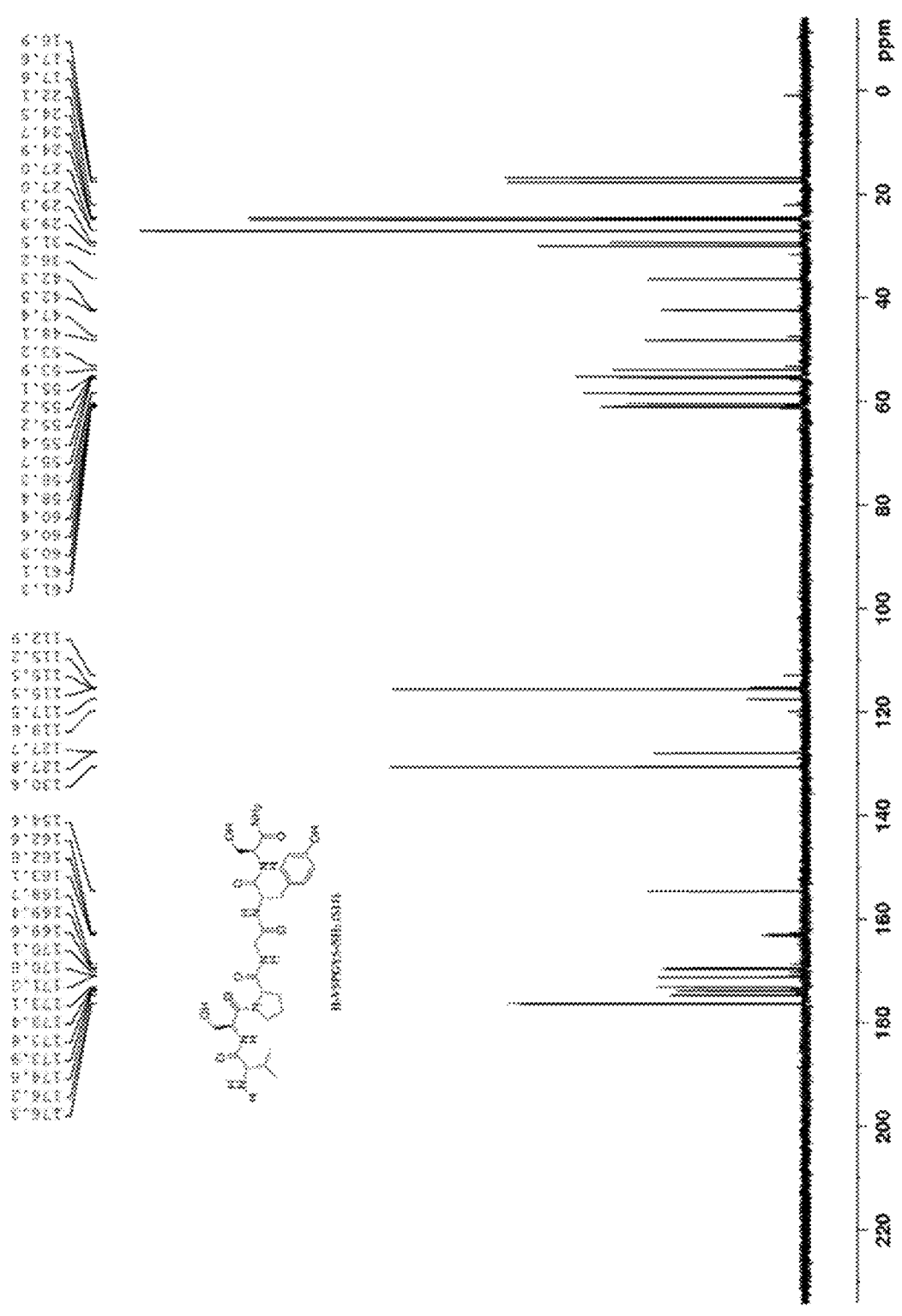

FIG. 82: $^{13}$C{$^1$H} NMR spectrum (D$_2$O, 126 MHZ) of H-VSPGYS-NH$_2$ (S11, SEQ ID NO: 23).

Figure 83:
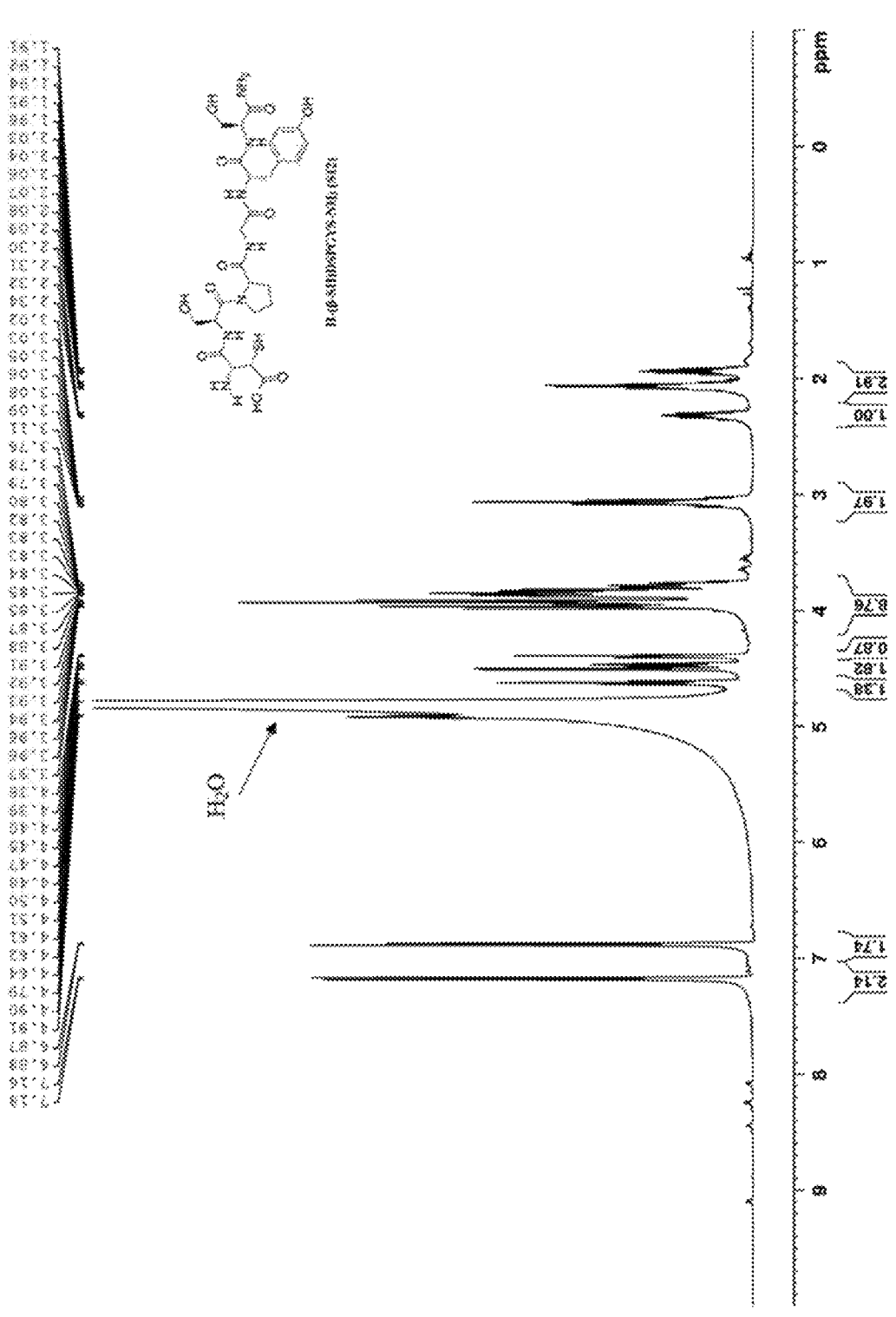

FIG. 83: $^1$H NMR spectrum (D$_2$O, 500 MHZ) of H-(β-SH) DSPGYS-NH$_2$ (S12, SEQ ID NO: 24).

Figure 84:
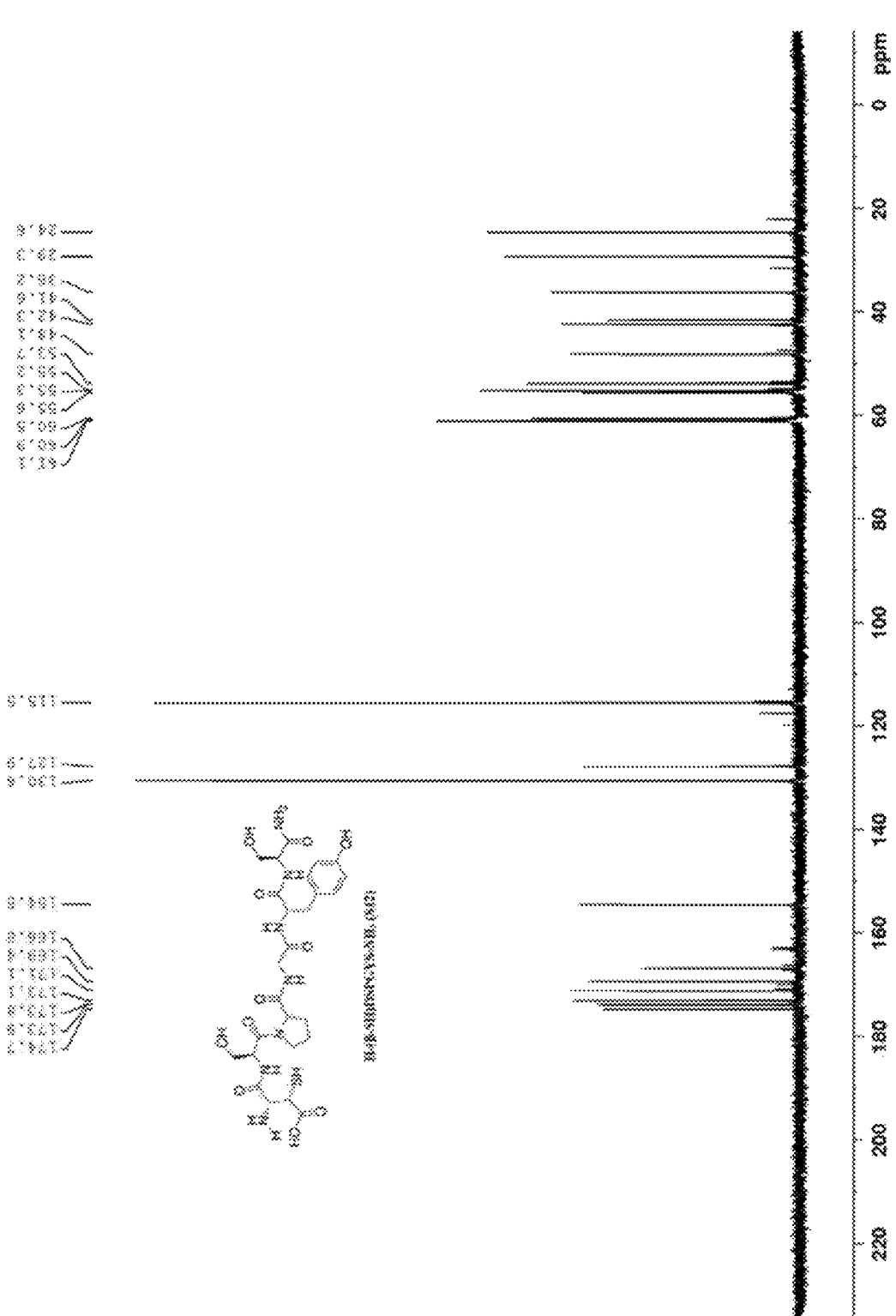

FIG. 84: $^{13}$C{$^1$H} NMR spectrum (D$_2$O, 126 MHZ) of H-(β-SH) DSPGYS-NH$_2$ (S12, SEQ ID NO: 24).

Figure 85:
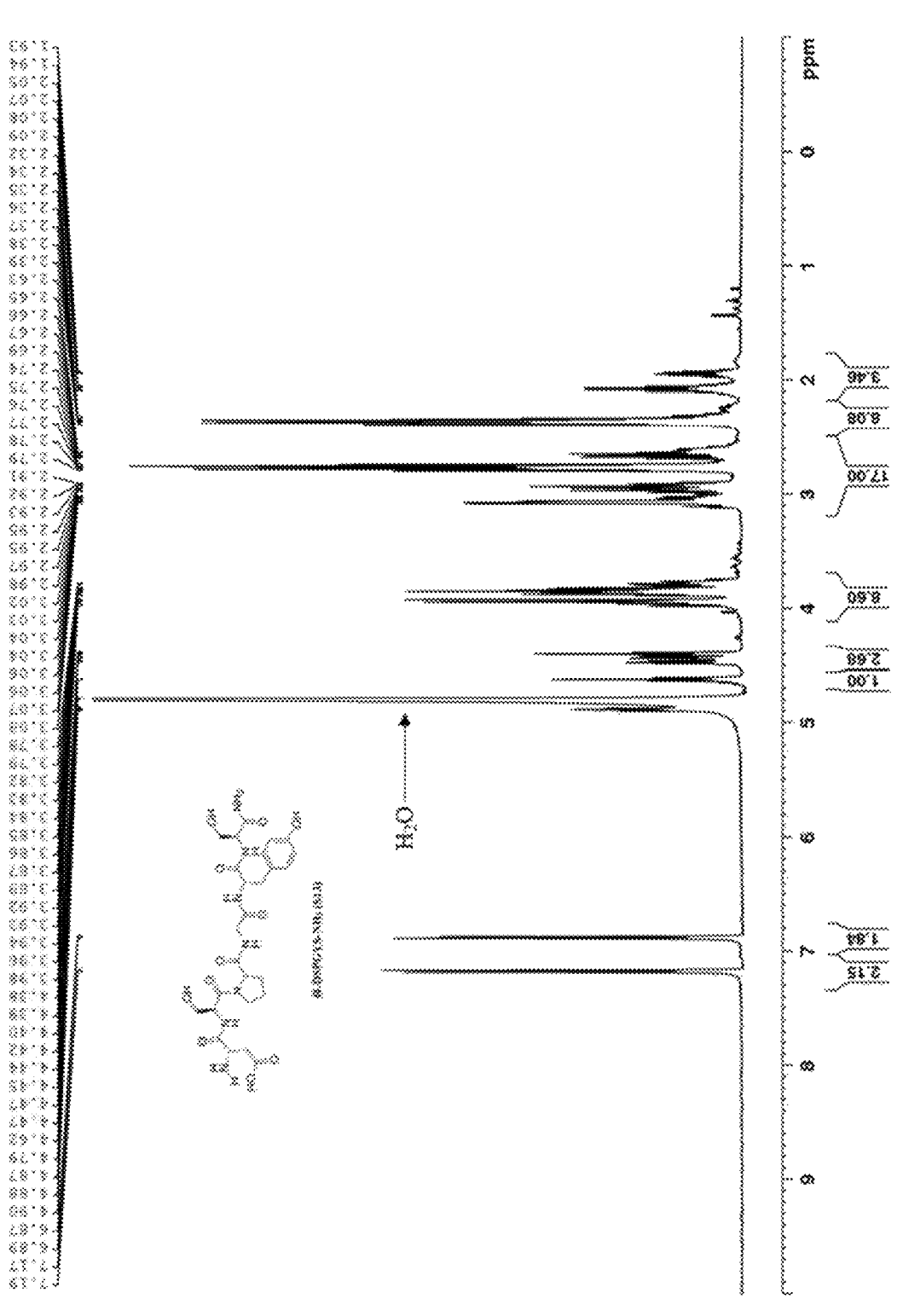

FIG. 85: $^1$H NMR spectrum (D$_2$O, 500 MHZ) of H-DSPGYS-NH$_2$ (S13, SEQ ID NO: 25).

Figure 86:
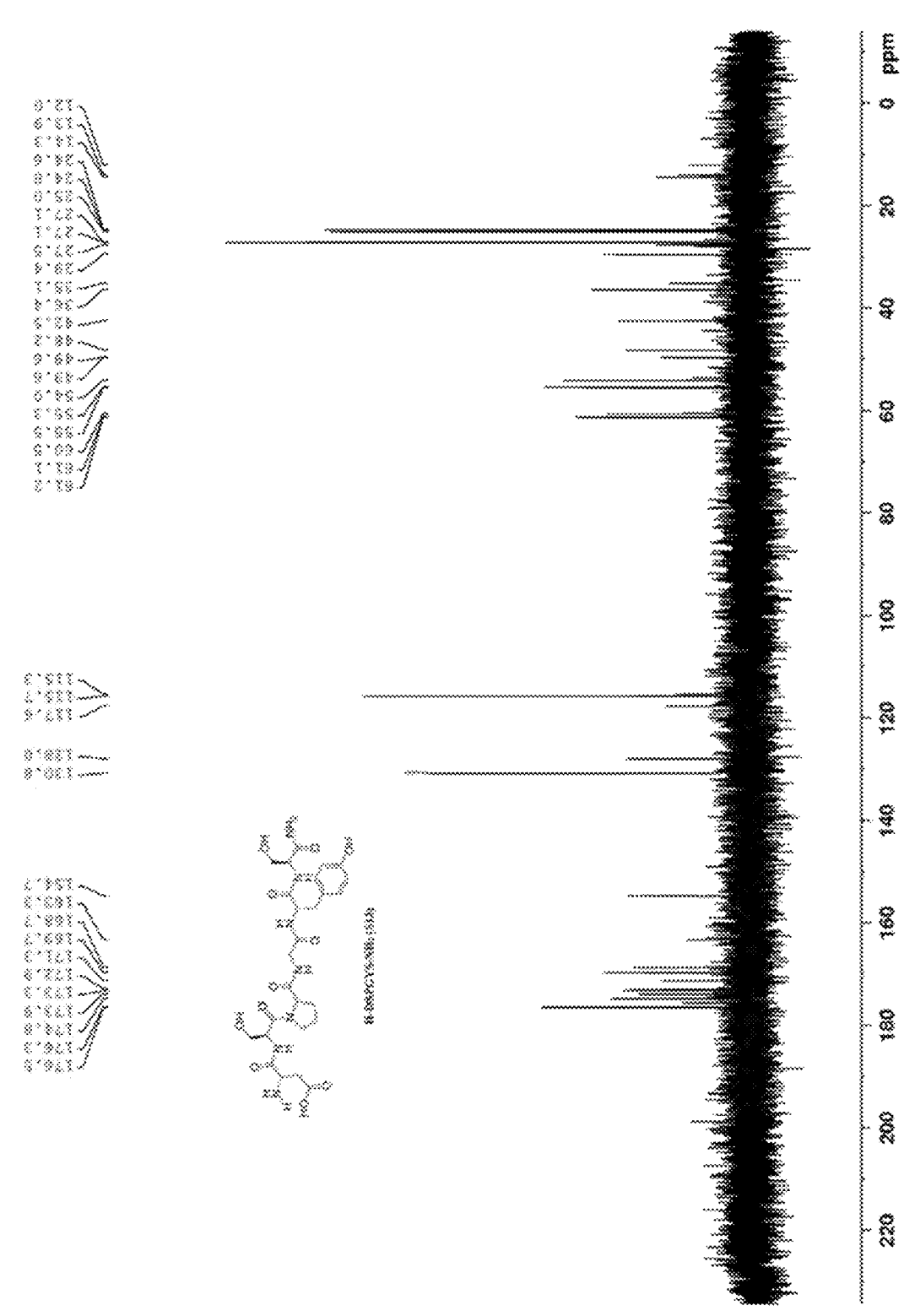

FIG. 86: $^{13}$C{$^1$H} NMR spectrum (D$_2$O, 126 MHZ) of H-DSPGYS-NH$_2$ (S13, SEQ ID NO: 25).-

Figure 87:
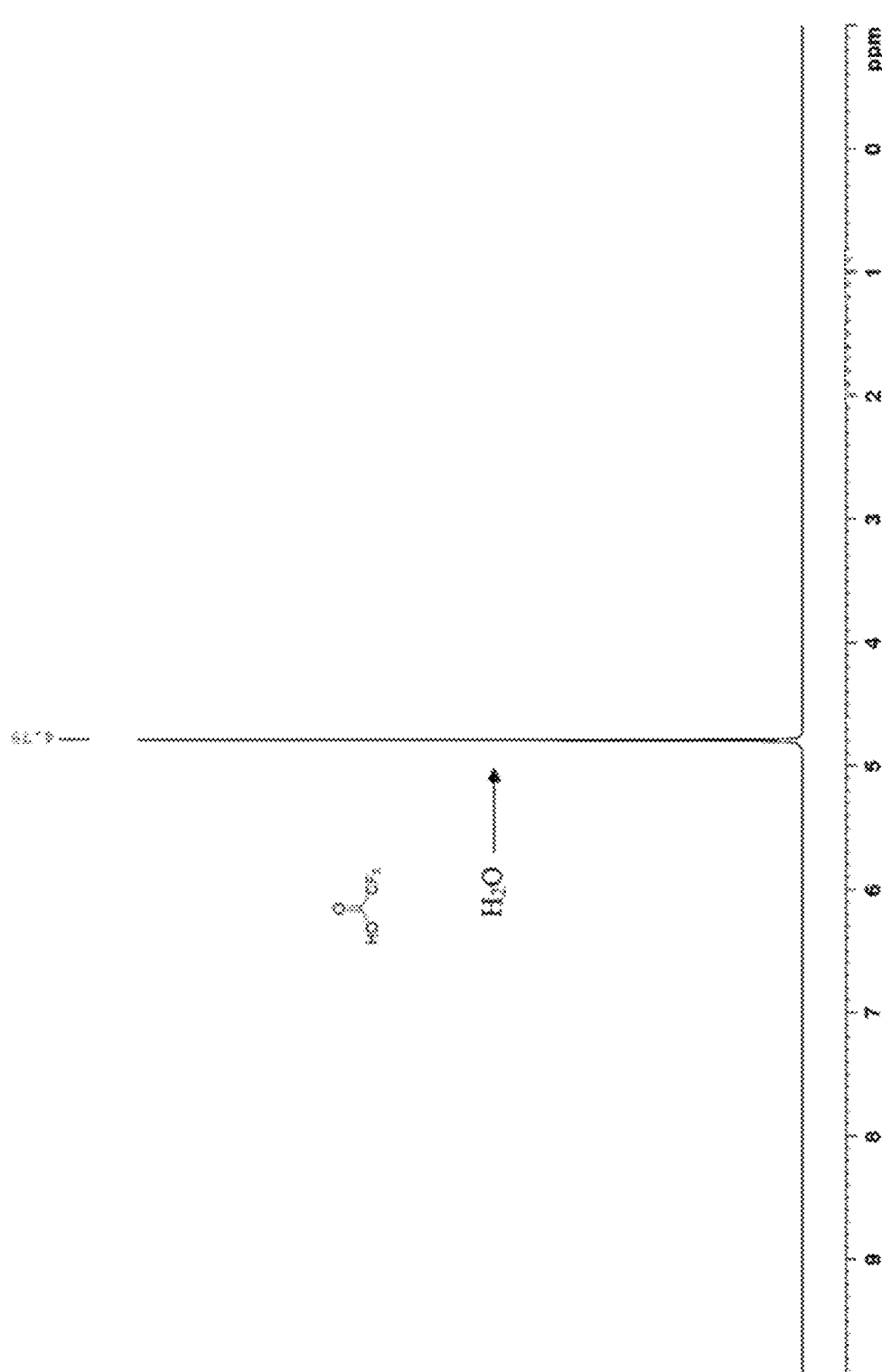

FIG. 87: $^1$H {$^{19}$F} NMR spectrum (D$_2$O, 500 MHZ) of trifluoroacetic acid.

Figure 88:
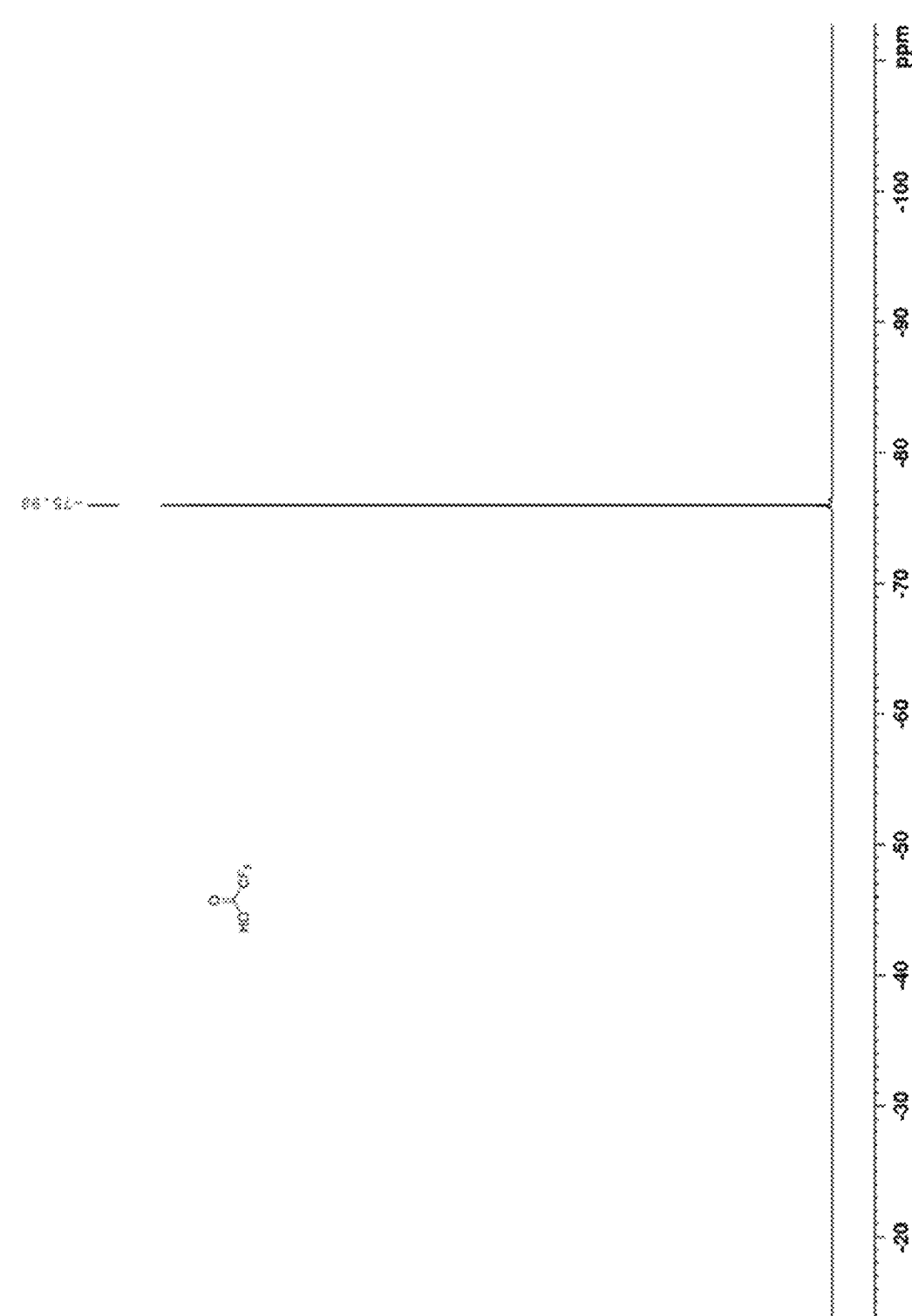

FIG. 88: $^{19}$F {$^1$H} NMR spectrum (D$_2$O, 471 MHZ) of trifluoroacetic acid.

Figure 89:
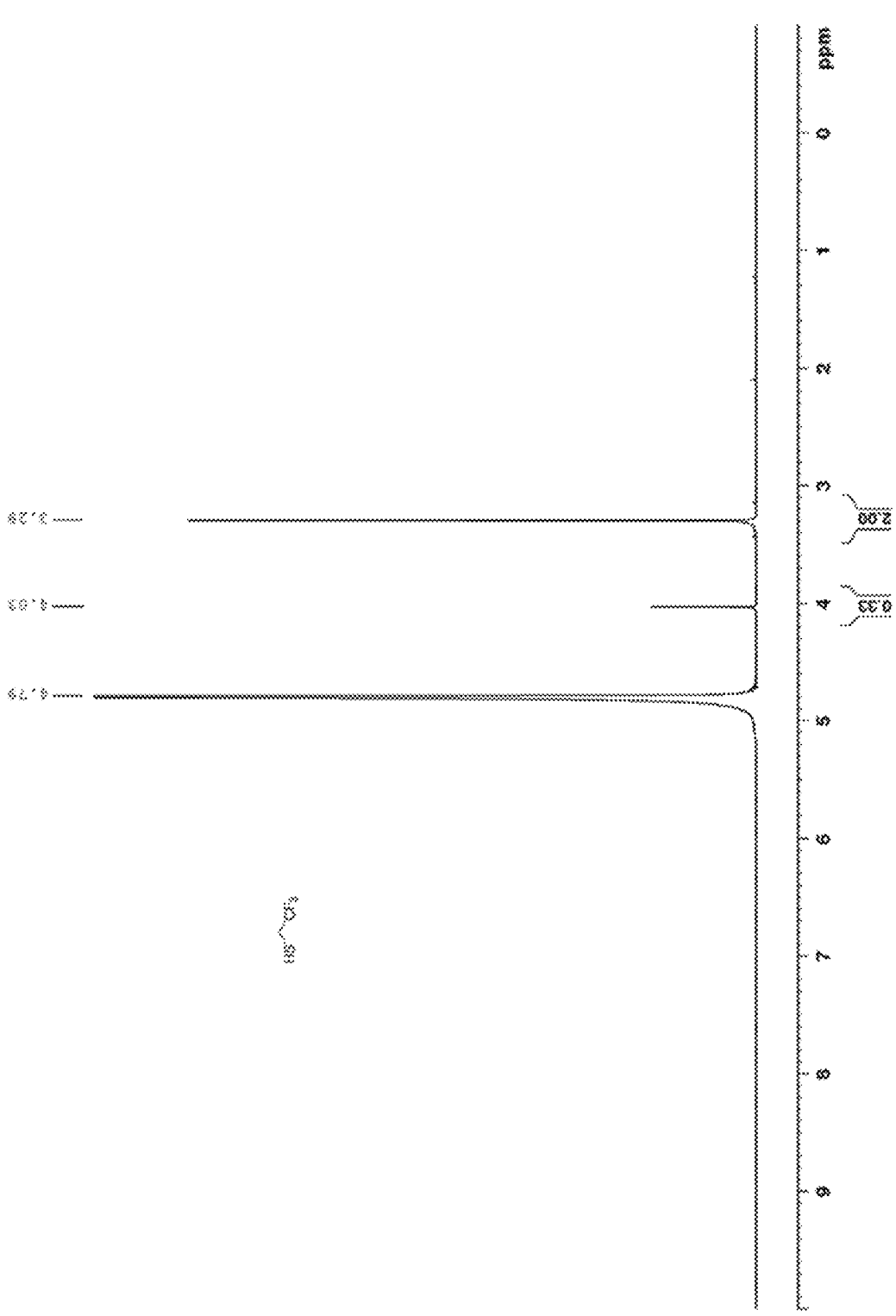

FIG. 89: $^1$H {$^{19}$F} NMR spectrum (D$_2$O, 500 MHZ) of trifluoroethanethiol.

Figure 90:
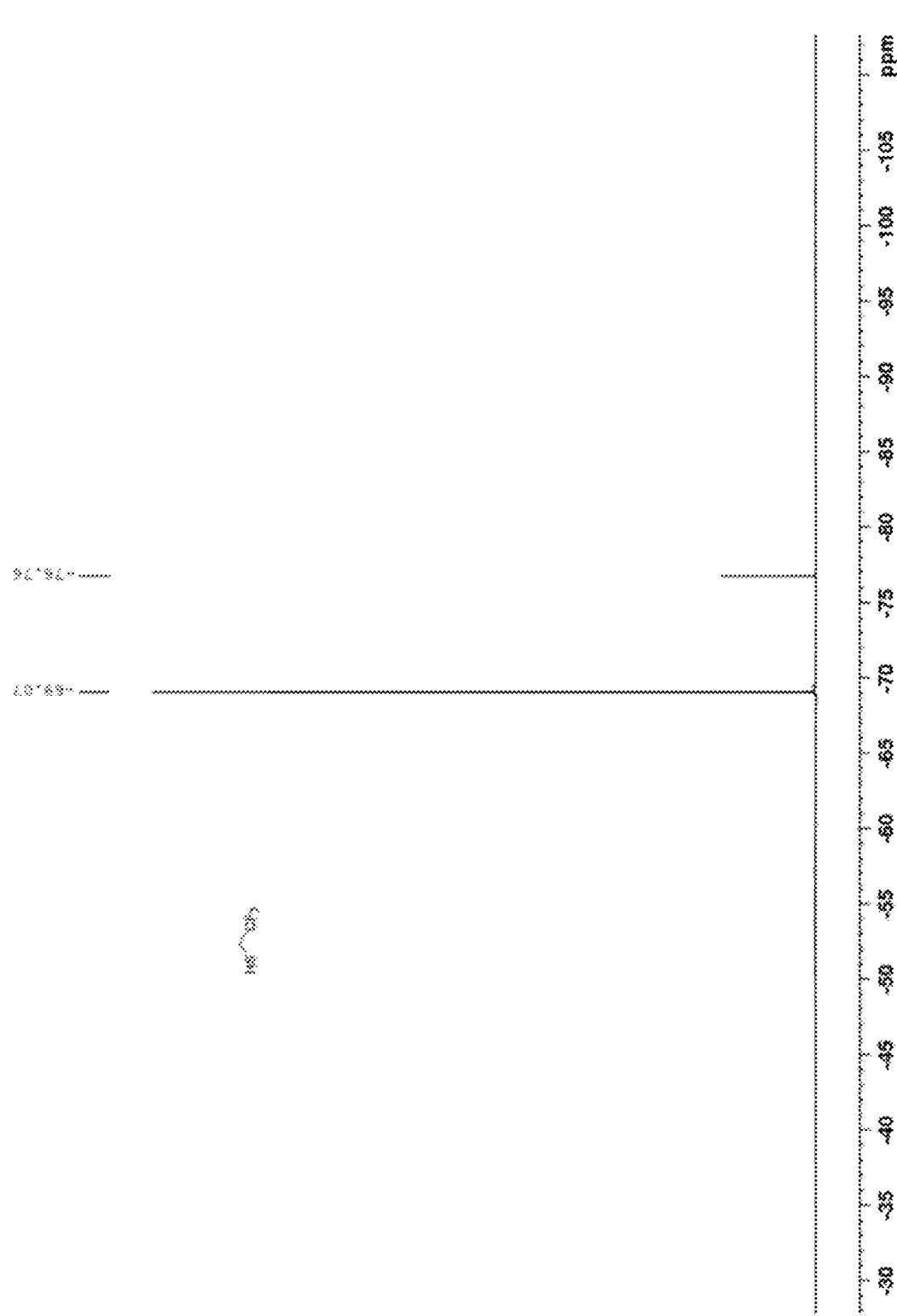

FIG. 90: $^{19}$F {$^1$H} NMR spectrum (D$_2$O, 471 MHZ) of trifluoroethanethiol.

Figure 91:
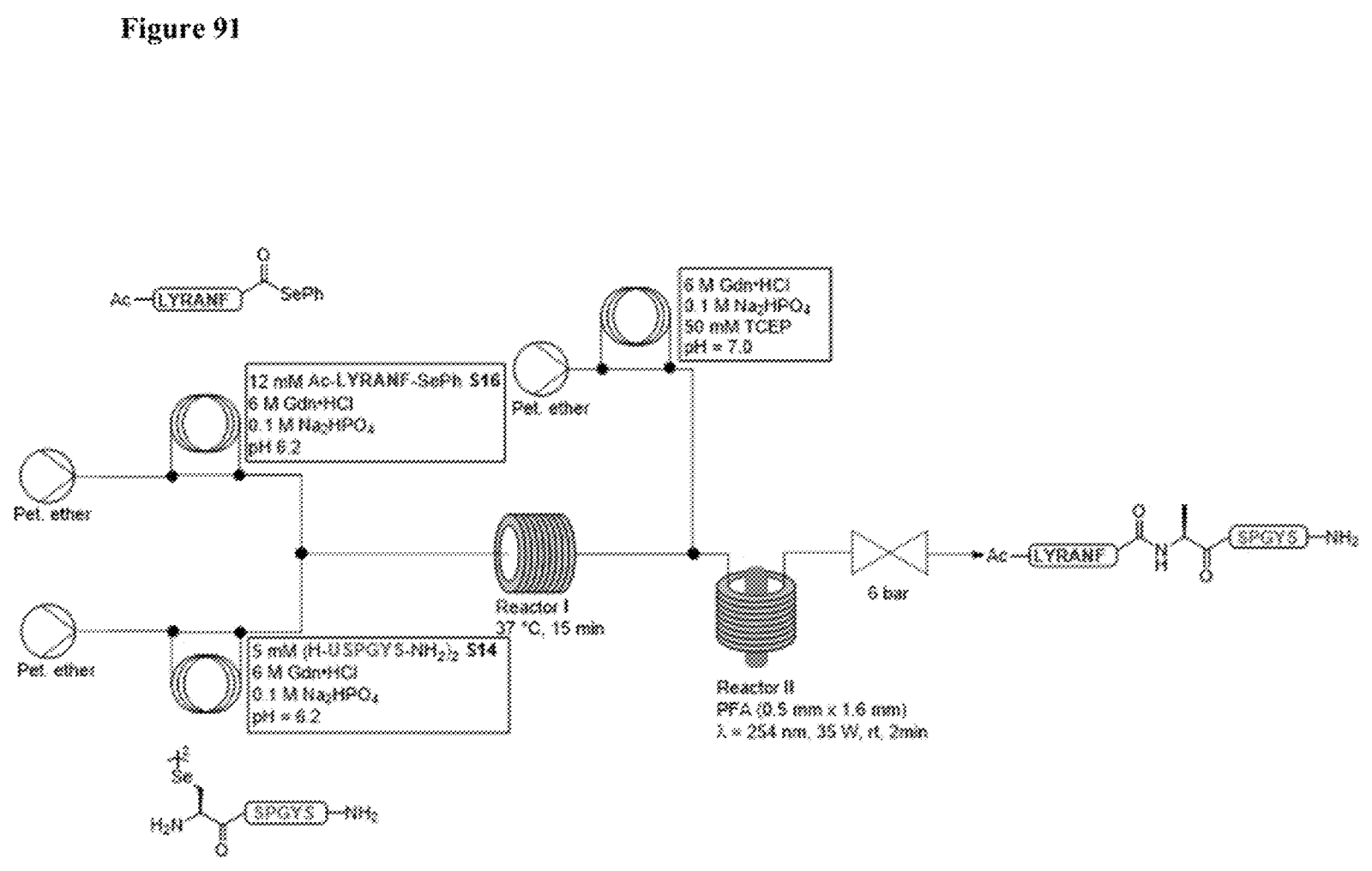

FIG. 91: Schematic of batch diselenide-selenoester ligation (DSL) between H-USPGYS-NH$_2$ (SEQ ID NO: 26) and Ac-LYRANF-SePh (SEQ ID NO: 28) followed by one-pot deselenization in flow without intermediary purification.

Figure 92:
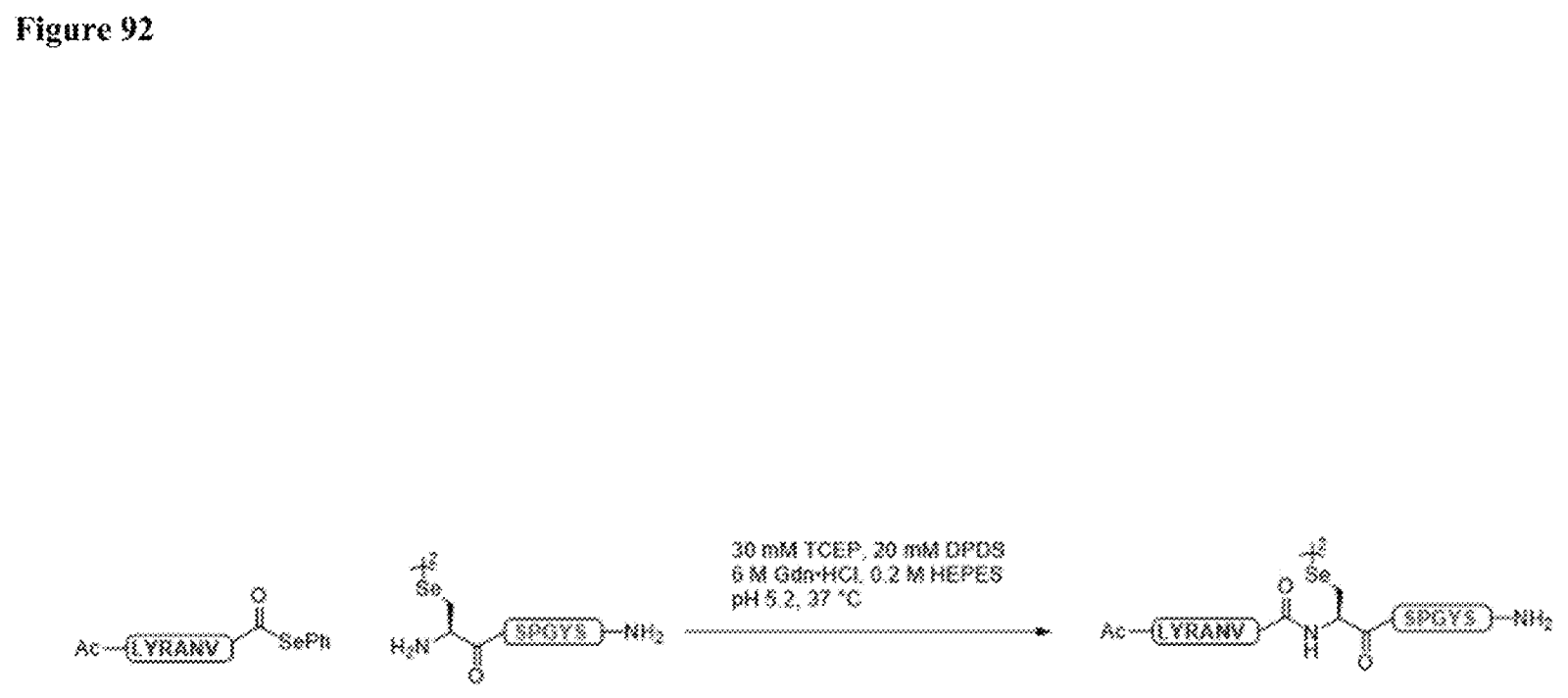

FIG. 92: Reaction scheme for reductive diselenide-selenoester ligation.

Figure 93:
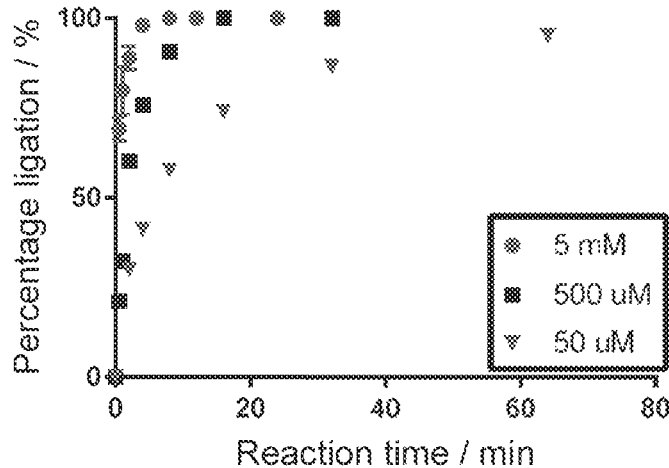
Figure 93:
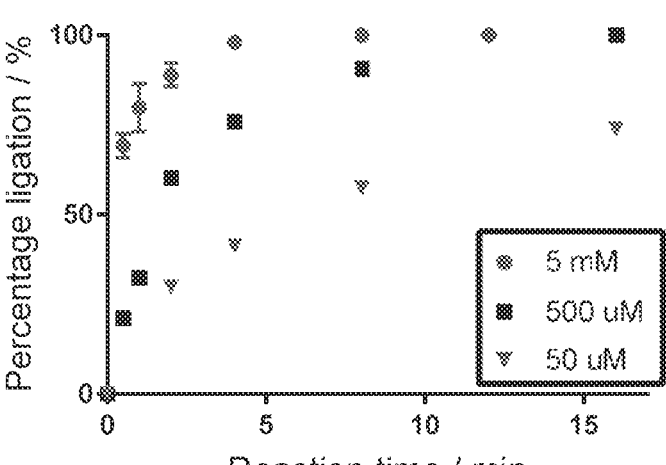

FIG. 93: A) Kinetic data for ligation between (H-US-PGYS-NH$_2$)$_2$ S14 (SEQ ID NO: 26) at varying concentrations of the monomer and Ac-LYRANV-SePh S15 (SEQ ID NO: 27) (2 eq. relative to the monomer) in batch. B) Expanded view of the kinetic data for reaction times from 0 to 17 min. Percentage ligation was calculated from integrating UPLC chromatogram peaks at λ=280 nm for 5 mM and 500 μM concentrations. For 50 μM concentrations, ligations were monitored by HPLC with an FLR detector using an excitation wavelength of 280 nm. Error bars represent one standard deviation above and below the mean calculated from three independent experiments.

DETAILED DESCRIPTION OF THE EMBODIMENTS

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. For example, reference to "a protein" includes a plurality of proteins; reference to "a cell" includes populations of a plurality of cells.

In the present specification, the term "additive" refers to any means for promoting a reaction and/or preventing a side reaction that is added separately, from an external source, to a reaction mixture. The reaction mixture contains reagents. The reaction mixture may include a solvent. The skilled addressee would appreciate that the solvent may include an aqueous solution. The aqueous solution may include buffering salts and a denaturing agent. By way of illustration an additive may refer to an exogenous molecule that is added to the reaction mixture. An additive may also refer to the addition of electrons as required in an electrochemical reduction. Some non-limiting examples of additives are nucleophiles and reductants. For illustration, some thiol group containing reductants that have been traditionally used in NCL are MPAA, thiophenol, trifluoroethanethiol (TFET), methylthioglycolate, benzylmercaptan and MESNa. Reductants that may be used for the ligation reactions disclosed herein include, but are not limited to, TCEP (tris(2-carboxyethyl)phosphine), THPP (tris(3-hydroxypropyl)phosphine), DTT (dithiothreitol), NaBH$_4$, NaHBH$_3$CN and ascorbic acid. Alternatively, thiol-based or selenol-based nucleophiles or reductants, and/or imidazole-based nucleophiles may also be used. The methods disclosed herein may be performed in the absence of an additive unless explicitly stated otherwise.

In the context of the specification a "thiol additive" refers to a thiol-based additive or a disulfide-based additive, and a "selenol additive" refers to a selenol-based additive or a diselenide-based additive. The "thiol additive" and the "selenol additive" may accelerate the rate-limiting transesterification step in the ligation reaction. A "thiol additive" or a "selenol additive" is used to transform a less reactive ester into a reactive ester. Specifically, a "thiol additive" is used to transform a less reactive thioester into a reactive thioester, and a "selenol additive" is used to transform a less reactive thioester into a reactive selenoester or less reactive selenoester into reactive selenoester. Examples of thiol additives include but are not limited to trifluoroethanethiol (TFET), 4-mercaptophenyl acetic acid (MPAA), mercaptoethylsulfonate, methylthioglycolate, thiophenol, and benzylmercaptan. Examples of selenol additives include aryl selenols, more particularly phenylselenol or 4-selenophenyl acetic acid.

In the present specification, the term "amino acid" refers to a molecule containing both an amino group and a carboxy group. For example, in an α-amino acid, there is an "α-amino group" attached directly to the carbon atom bearing both an amino and a carboxyl group and an "α-carboxyl group" attached directly to the carbon atom bearing both an amino and a carboxyl group. The term "carboxyl" may refer to either a COOH group or a —COO— group. α-amino acids are of the general form H$_2$N—CHR—COOH, where R is a side chain or H. The side chain in general is an alkyl chain, which is optionally substituted, commonly but not necessarily at its distal end. The N terminus of the amino acid (or of a peptide) is that end at which the amine functionality (optionally ionised or substituted/protected) is located, and the C terminus is the end at which the carboxyl functionality (optionally ionised or substituted/protected) is located.

As used herein, the term "peptide" refers to a chain comprising (or consisting of) at least two amino acid residues joined by amide bond(s). They may be dipeptides, oligopeptides, polypeptides, proteins, glycopeptides, glycoproteins etc. The terms "peptide", "polypeptide" and "protein" are used interchangeably herein and include a molecular chain of two or more amino acids linked covalently through peptide bonds. The terms do not refer to a specific length of the product. The terms include post-translational modifications of the peptide, for example, glycosylations, acetylations, biotinylations, 4-pentynoylations, PEGylations, phosphorylations, sulfations and the like. In addition, protein fragments, analogs, mutated or variant proteins, fusion proteins and the like are included within the meaning of polypeptide. The terms also include molecules in which one or more amino acid analogs or non-canonical or unnatural amino acids are included. It will be understood that proteins, either natural or synthetic, come within the scope of the term "peptide". Within the context of the disclosure, natural proteins and peptides include recombinantly expressed proteins and peptides such as enzymes, hormones, structural proteins, transport proteins, signal proteins, antigens, and antibodies. Preferably, "peptide" includes synthetic and expressed peptides and proteins, such as selenoproteins, cysteinyl proteins, protein hydrazides, protein selenoesters, and protein thioesters. In addition, peptides can be derivatized as described herein by well-known organic chemistry techniques set forth, for example, in Smith, M. B. March's Advanced Organic Chemistry: Reactions, Mechanisms, and Structure, Seventh Edition; John Wiley & Sons, Inc.: Hoboken, NJ, 2013; Fmoc Solid Phase Peptide Synthesis, A Practical Approach; Chan, W. C., White, P. D., Eds.; Oxford University Press, 2000 (chapter 6, pages 137-178; chapter 9, pages 215-227, chapter 11, pages 243-262); and Peptide Synthesis and Applications, Second Edition (Methods in Molecular Biology); Jensen, K. J., Shelton, P. T., Pedersen, S. L., Eds.; Humana Press, 2013 (chapter 8, pages 119-130).

The term "aryl", alone or in combination, means a carbocyclic aromatic moiety containing one, two or even three rings wherein such rings may be attached together in a fused manner. Thus the term "aryl" embraces aromatic radicals such as phenyl, naphthyl, indenyl, tetrahydronaphthyl, anthracenyl, and indanyl. Said "aryl" group may have 1 or more substituents such as lower alkyl, hydroxyl, halo, haloalkyl, nitro, cyano, alkoxy and lower alkylamino, and the like. Phenyl substituted with —O—CH$_2$—O— forms an aryl benzodioxolyl substituent. Aryl as used herein, implies a fully unsaturated ring.

Groups that are displaceable, "displaceable groups", generally refer to groups that are displaceable from a molecule during the course of a reaction.

"Leaving groups" generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH$_3$), thiolate, selenoates, N-hydroxysuccinimide, N-hydroxybenzotriazole, and the like.

"Nucleophiles" are species that are capable of attacking a molecule at the point of attachment of the leaving group causing displacement of the leaving group. Nucleophiles are known in the art. Examples of nucleophilic groups include, but are not limited to, amines, thiols, alcohols, selenols, Grignard reagents, anionic species (e.g., alkoxides, amides, carbanions) and the like.

In the context of the specification a "first nucleophilic agent" refers to a nucleophilic agent that accelerates the rate of the ligation reaction. Examples of a suitable first nucleophilic agent include an imidazole. In a preferred embodiment, the first nucleophilic agent is selected from the group consisting of 2-methylimidazole, imidazole, and combinations thereof. In the context of the specification, the first nucleophilic agent is distinct from the thiol additive or selenol additive. The first nucleophilic agent may comprise a thiol or selenol moiety.

In the context of the specification a "second nucleophilic agent" refers to a nucleophilic agent that may be used to thiolyze, aminolyze, hydrolyze or hydrazinolyze product ester formed between the amide containing compound and the ester. Examples of suitable second nucleophilic agents include but are not limited to reduced glutathione (GSH), dithiothreitol (DTT), cysteine, an imidazole, an amine, hydroxide ion, hydrazine, and combinations thereof. The second nucleophilic agent may be added before, during, or after the ligation reaction, or a combination thereof. Accordingly, the ligation reaction may be conducted in the presence of the second nucleophilic agent. Alternatively, thiolysis, aminolysis, hydrolysis or hydrazinolysis may be an additional step performed after completion of the ligation reaction. In a preferred embodiment, the second nucleophilic agent is added to the ligation reaction mixture after completion of the ligation reaction.

The thiol additive or selenol additive, the first nucleophilic agent and the second nucleophilic agent may be used independently. In one embodiment, when the ester is a reactive ester, the reaction is conducted in the absence of a thiol additive or selenol additive, but in the presence of a first nucleophilic agent. In this form of the embodiment, the first nucleophilic agent may include a thiol or selenol moiety. In another embodiment, when the ester is a less reactive ester, the reaction is conducted in the presence of a thiol additive or selenol additive, and in the presence of a first nucleophilic agent.

The first nucleophilic agent and the second nucleophilic agent may be used independently. In one embodiment, the flow ligation method includes the first nucleophilic agent and not the second nucleophilic agent. In another embodiment, the flow ligation method includes the second nucleophilic agent and not the first nucleophilic agent. In yet another embodiment, the flow ligation method includes both the first nucleophilic agent and the second nucleophilic agent. In further describing the peptides described herein, a one-letter abbreviation system is frequently applied to designate the identities of the twenty "canonical" or proteogenic amino acid residues and the 21$^{st}$ amino acid selenocysteine that are generally incorporated into naturally occurring peptides and proteins (Table 1). Such one-letter abbreviations are entirely interchangeable in meaning with three-letter abbreviations, or non-abbreviated amino acid names.

Non-canonical or non-proteogenic amino acid residues can be incorporated into a peptide by employing the techniques disclosed herein. The term "non-canonical amino acid residue" refers to amino acid residues in D- or L-form that are not among the 20 canonical amino acids generally incorporated into naturally occurring proteins, for example, β-amino acids, homoamino acids, cyclic amino acids, seleno amino acids, thio amino acids, and amino acids with derivatized side chains such as those described in US 2015/0023988.

TABLE 1

Three and one-letter abbreviations for the twenty canonical/naturally-occurring amino acids and the twenty first amino acid Selenocysteine.

| Amino acid | Three-letter abbreviation | One-letter abbreviation |
| --- | --- | --- |
| Alanine | Ala | A |
| Glutamine | Gln | Q |
| Leucine | Leu | L |
| Serine | Ser | S |
| Arginine | Arg | R |
| Glutamic Acid | Glu | E |
| Lysine | Lys | K |
| Threonine | Thr | T |
| Asparagine | Asn | N |
| Glycine | Gly | G |
| Methionine | Met | M |
| Tryptophan | Trp | W |
| Aspartic Acid | Asp | D |
| Histidine | His | H |

TABLE 1-continued

Three and one-letter abbreviations for the twenty
canonical/naturally-occurring amino acids and
the twenty first amino acid Selenocysteine.

| Amino acid | Three-letter abbreviation | One-letter abbreviation |
|---|---|---|
| Phenylalanine | Phe | F |
| Tyrosine | Tyr | Y |
| Cysteine | Cys | C |
| Isoleucine | Ile | I |
| Proline | Pro | P |
| Valine | Val | V |
| Selenocysteine | Sec | U |

Nomenclature and Symbolism for Amino Acids and Peptides by the IUPAC-IUB Joint Commission on Biochemical Nomenclature (JCBN) have been published in the following documents: Biochem. J., 1984, 219, 345-373; Eur. J. Biochem., 1984, 138, 9-37; 1985, 152, 1; 1993, 213, 2; Internat. J. Pept. Prot. Res., 1984, 24, following page 84; J. Biol. Chem., 1985, 260, 14-42; Pure Appl. Chem., 1984, 56, 595-624; Amino Acids and Peptides, 1985, 16, 387-410; Biochemical Nomenclature and Related Documents, 2nd edition, Portland Press, 1992, pages 39-69 which are all referenced herein by their entirety.

As stated herein above, in accordance with the present disclosure, the peptides described can also be chemically derivatized at one or more amino acid residues by known organic chemistry techniques. "Derivative" or "derivatized" refers to a subject peptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-benzylhistidine. Also included as chemical derivatives are those peptides which contain one or more naturally occurring amino acid derivatives of the twenty canonical amino acids, whether in L- or D-form. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Useful derivatizations include modification of an N-terminal free amino group for attachment of an imaging agent, e.g. a fluorescent dye, an MRI contrast agent, a PET contrast agent, or a therapeutic agent whose activity adds to the potential therapeutic activity of the peptide. The N-terminus can be acylated or modified to a substituted amine, or derivatized with another functional group, such as an aromatic moiety (e.g., an indole acid, benzyl (Bzl or Bn), dibenzyl (DiBzl or Bn$_2$), or benzyloxycarbonyl (Cbz or Z)), N,N-dimethylglycine or creatine. For example, in some embodiments, an acyl moiety, such as, but not limited to, a formyl, acetyl (Ac), propanoyl, butanyl, pentanyl, heptanyl, hexanoyl, octanoyl, or nonanoyl, can be covalently linked to the N-terminal end of the peptide. Other exemplary N-terminal derivative groups include —NRR$_1$ (other than-NH$_2$), —NRC(O)R$_1$, —NRC(O)OR$_1$, —NRS(O)$_2$R$_1$, —NHC(O) NHR$_1$, succinimide, or benzyloxycarbonyl-NH-(Cbz- NH—), wherein R and R$_1$ are each independently hydrogen or lower alkyl or phenyl and wherein the phenyl ring may be substituted with 1 to 5 substituents selected from C$_1$-C$_4$ alkyl, C$_1$-C$_4$ alkoxy, chloro, and bromo.

In some embodiments, one or more peptidyl [—C(O) NR—] linkages (bonds) between amino acid residues can be replaced by a non-peptidyl linkage. Exemplary non-peptidyl linkages are —CH$_2$-carbamate [—CH$_2$—OC(O)NR—], phosphonate, —CH$_2$— sulfonamide [—CH$_2$—S(O)$_2$ NR—], thiourea [—NHC(S)NH—], urea [—NHC(O) NH—], —CH$_2$— secondary amine, and alkylated peptide [—C(O)NR$_6$, wherein R$_6$ is lower alkyl].

The above examples of derivatizations are not intended to be an exhaustive treatment, but merely illustrative. The skilled addressee would appreciate that one or more individual amino acids can be derivatized by well-known organic chemistry techniques as described for example in Smith, M. B. March's Advanced Organic Chemistry: Reactions, Mechanisms, and Structure, Seventh Edition; John Wiley & Sons, Inc.: Hoboken, NJ, 2013; and that various derivatizing agents are known to react with selected side chains or terminal residues as described for example in Fmoc Solid Phase Peptide Synthesis, A Practical Approach; Chan, W. C., White, P. D., Eds.; Oxford University Press, 2000; Peptide Synthesis and Applications, Second Edition (Methods in Molecular Biology); Jensen, K. J., Shelton, P. T., Pedersen, S. L., Eds.; Humana Press, 2013.

It will be understood that the invention disclosed and defined in this specification extends to all alternative combinations of two or more of the individual features mentioned or evident from the text or drawings. All of these different combinations constitute various alternative aspects of the invention.

The invention relates to a method of preparing an amide containing compound in flow comprising the step of reacting:

(i) an ester, with (ii) a molecule comprising a terminal amino acid selected from the group consisting of cysteine, cystine, a thiol-derivatized amino acid, a disulfide-derivatized amino acid, selenocysteine, selenocystine, a selenol-derivatized amino acid, and a diselenide-derivatized amino acid;

wherein the ester is a thioester or selenoester.

The ester may be a molecule comprising an ester functional group. The ester may be selected from a polymer (including a peptide), a small molecule (including a therapeutic agent, or a diagnostic agent such as a fluorescent dye, radioisotope, MRI contrast agent, or PET contrast agent), or an antibody. Preferably, the ester is a peptide.

The ester is preferably a reactive ester. A reactive ester is capable of reacting with the terminal amino acid in the molecule in the absence of a thiol additive or a selenol additive and accelerates the rate-limiting trans-esterification step. Preferably the reactive ester is selected from the group consisting of trifluoroethyl thioester, 4-mercaptophenyl acetic acid thioester, mercaptoethylsulfonate thioester, methylthioglycolate thioester, thiophenyl thioester, benzylmercaptan thioester, phenylselenoester, and 4-selenophenyl acetic acid selenoester. Preferably, when the ester is a reactive ester the reaction is conducted in the absence of a thiol additive or selenol additive.

In another embodiment, the ester may be a less reactive ester. The ester may be transformed into a reactive ester by reacting the ester with a thiol additive or selenol additive. Examples of less reactive esters include: ethyl 3-mercaptopropionate thioester, reduced L-glutathione (GSH) thioester, dithiothreitol (DTT) thioester, mercaptopropionic acid-leucine thioester, tert-butylthiol thioester, mercaptopropanoyl glycine thioester, selenoacetamide selenoester, selenopropionic acid-isoleucine selenoester, and (9-fluorenylmethyl) selenoester. In this embodiment, the reaction is conducted in the presence of a thiol additive or a selenol additive. In one embodiment, the ester is a thioester and the reaction is conducted in the presence of a thiol additive or a selenol additive. Preferably, the thiol additive is selected from the group consisting of trifluoroethanethiol, 4-mercaptophenyl acetic acid, mercaptoethylsulfonate, methylthioglycolate, thiophenol, and benzylmercaptan. In another embodiment, the ester is a selenoester and the reaction is conducted in the presence of a selenol additive. Preferably, the selenol additive is an aryl selenol, more preferably phenylselenol or 4-selenophenyl acetic acid.

The molecule comprising a terminal amino acid selected from the group consisting of cysteine, cystine, a thiol-derivatized amino acid, a disulfide-derivatized amino acid, selenocysteine, selenocysteine, a selenol-derivatized amino acid, and a diselenide-derivatized amino acid may be selected from a polymer (including a peptide), a small molecule (including a therapeutic agent, or a diagnostic agent such as a fluorescent dye, radioisotope, MRI contrast agent, or PET contrast agent), or an antibody. Preferably, the molecule is a peptide.

It would be understood that amino acids comprising a thiol functional group may be in either the reduced form (cysteine or a thiol-derivatized amino acid) or oxidized form (cystine or a disulfide-derivatized amino acid). In the oxidized form, the thiol functional group may form a disulfide bond with a second amino acid comprising an oxidized thiol functional group and form a dimer. For example, the molecule may form a dimer of formula (IV):

wherein $AA_{lig}$ is selected from cystine and a disulfide-derivatized amino acid.

It would be understood that amino acids comprising a selenol functional group may be in either the reduced form (selenocysteine or a selenol-derivatized amino acid) or oxidized form (selenocystine or a diselenide-derivatized amino acid). In the oxidized form, the selenol functional group may form a diselenide bond with a second amino acid comprising an oxidized selenol functional group and form a dimer. For example, the molecule may form a dimer of formula (IV):

wherein $AA_{lig}$ is selected from selenocystine and a diselenide-derivatized amino acid.

The amide containing compound is the product of the ligation reaction between the ester and the molecule. Preferably, the amide containing compound is a polypeptide. Preferably, the ester and the molecule are independently selected from synthetic and natural peptides. The present disclosure contemplates the synthesis of natural and non-natural peptides. Natural peptides comprise naturally occurring amino acids which have L stereochemistry. Non-natural peptides include peptides comprising one or more non-natural amino acids, including amino acids with D stereochemistry or derivatized amino acids, including amino acids that incorporate a diagnostic agent (e.g., a fluorescent dye, radioisotope, MRI contrasting agent, or PET contrasting agent) or a therapeutic agent (e.g., a drug, or antibody). Non-natural peptides also include peptides where one or more peptidyl linkages between amino acid residues have been replaced by a non-peptidyl linkage. The amino acids used in the present invention may be L or may be D or may be racemic. The presently described chemistry may preserve the stereochemistry of the amino acid.

In a particularly preferred embodiment, the polypeptide is defined by formula (I):

the ester is defined by formula (II):

the molecule comprising a terminal amino acid selected from the group consisting of cysteine, a thiol-derivatized amino acid, selenocysteine, and a selenol-derivatized amino acid is defined by formula (III):

the molecule comprising a terminal amino acid selected from the group consisting of cystine, a disulfide-derivatized amino acid, selenocystine and a diselenide-derivatized amino acid is defined by formula (IV):

IV wherein:

$N_{term}$ is the N-terminus of the polypeptide;

$C_{term}$ is the C-terminus of the polypeptide;

AA is an amino acid;

n is an integer;

$(AA)_n$ represents a polypeptide comprising n number of amino acid monomers;

DG is a displaceable group selected from a thiolate and a selenoate; and is a thiol, disulfide, selenol or diselenide functionalised amino acid residue at the ligation site selected from the group consisting of cysteine, cystine, a thiol-derivatized amino acid, a disulfide-derivatized amino acid, selenocysteine, selenocystine, a selenol-derivatized amino acid, and a diselenide-derivatized amino acid.

It would be understood that the polypeptide of formula (I) may be in either the reduced form or oxidized form. In the reduced form, the polypeptide of formula (I) is monomeric. In the oxidized form, $AA_{lig}$ of the polypeptide of formula (I) may form a bond with $AA_{lig}$ of a second polypeptide of formula (I) and form a dimer.

Preferably, the reaction is conducted using a concentration of the molecule comprising the terminal amino acid of about 5 mM to about 20 mM. In another embodiment, the reaction may be conducted at high dilution using a concentration of the molecule comprising the terminal amino acid of less than about 1 mM, preferably less than about 500 μM, more preferably less than about 100 μM, more preferably less than about 50 M. Preferably, the reaction comprises at least about a 1.2 molar equivalent, more preferably about a 2 molar equivalent, of the ester.

Preferably, the reaction is conducted in an aqueous solution. The aqueous solution is preferably a buffer selected from HEPES, $Na_2HPO_4$, MOPS, and Tris, more preferably HEPES.

Preferably, the aqueous solution has a pH in the range of about 4 to 9, preferably about 6 to 8.

The aqueous solution may optionally include a denaturing agent. Preferably, the denaturing agent is 6 M guanidine hydrochloride or urea, more preferably 6 M guanidine hydrochloride.

The aqueous solution may optionally include a reductant. Preferably, the reductant is selected from the group consisting of tris-(2-carboxyethyl)phosphine (TCEP), dithiothreitol (DTT) and L-glutathione (GSH), more preferably TCEP.

The reaction may be conducted at moderately elevated temperatures, or at room temperature or below. In general, the ligation reactions described herein are conducted at room temperature. Nonetheless, the skilled addressee would understand that the reactions can be run at a lower temperature to minimise side reactions or run at elevated temperatures to, for example, further accelerate the rate of reaction. Suitable lower temperatures are below room temperature, below 0° C. down to about –100° C.; for example, –10, –20, –50 or –70° C., or about-100 to about 0° C., or about-100 to –50, –100 to –70, –50 to 0, –20 to 0 or –80 to –60° C., e.g. about 100, 90, –80, –78, –70, –60, –50, –40, –30, –20, –10 or 0° C. Suitable elevated temperatures are above room temperature, above about 30, 40, 50, 60, 70, up to about 80° C. About 10 to about 80° C., or about 20 to 80, 50 to 80, 70 to 80, 10 to 30, 10 to 50, 30 to 60, 30 to 40, 40 to 70 or 50 to 70° C., e.g. about 10, 15, 20, 25, 30, 35, 40, 45, 50, 55, 60, 65, 70, 75 or 80° C.

The ligation reaction is preferably commenced by combining a solution of the ester with a solution of the molecule comprising a terminal amino acid selected from the group consisting of cysteine, cystine, a thiol-derivatized amino acid, a disulfide-derivatized amino acid, selenocysteine, selenocystine, a selenol-derivatized amino acid, and a diselenide-derivatized amino acid, in flow, and then allowed to proceed to completion as measured by an analytical technique. Preferably the ligation reaction may be allowed to proceed to about 100% completion. It would be understood that the ligation reaction may be allowed to proceed to at least 90% completion, at least 85% completion, at least 80% completion, at least 75% completion, at least 70% completion, at least 65% completion, at least 60% completion, at least 55% completion, at least 50% completion, at least 45% completion, at least 40% completion, at least 35% completion, at least 30% completion, at least 25% completion. Preferably, the ligation reaction may be allowed to proceed to at least 90% completion, more preferably about 100% completion.

The reaction is preferably complete within about 10 minutes as measured by noting the product formation by HPLC-MS, except those reactions where $AA_{lig}$ is selected from Ile or Val wherein the reaction is complete within about 40 minutes as measured by HPLC-MS.

In one embodiment, the reaction is conducted in the presence of a first nucleophilic agent. The first nucleophilic agent accelerates the rate of the ligation reaction. Preferably, the first nucleophilic agent comprises an imidazole. More preferably, the first nucleophilic agent is selected from the group consisting of 2-methylimidazole, imidazole and combinations thereof.

The ligation reaction between the ester and the molecule produces an amide containing compound. The amide containing compound may react with excess ester in the ligation reaction mixture to form a product ester.

In one embodiment, a second nucleophilic agent may be used to thiolyze, aminolyze, hydrolyze or hydrazinolyze product ester formed between the amide containing compound and the ester. In a preferred embodiment, the second nucleophilic agent is selected from the group consisting of reduced glutathione (GSH), dithiothreitol (DTT), cysteine, an imidazole, an amine, hydroxide ion, hydrazine, and combinations thereof. Preferably, the second nucleophilic agent is GSH. Preferably, the second nucleophilic agent is added to the ligation reaction mixture after completion of the ligation reaction.

The ligation reaction conducted in flow proceeds quickly using unprotected peptide fragments, in aqueous buffer with broad pH range at room temperature.

Following the ligation reaction, the crude reaction mixture may be subjected, without purification of intermediates (but optionally with at least partial removal of at least one reagent or catalyst used in the ligation reaction), to suitable desulfurization or deselenization conditions and reagents. The resulting ligated and selectively desulfurized or deselenized product peptide may be obtained from the resulting reaction mixture following a suitable time for reaction.

In one embodiment, the method additionally comprises the step of desulfurizing or deselenizing the amide containing compound in flow. In a preferred embodiment, when $AA_{lig}$ is a thiol or disulfide functionalised amino acid residue at the ligation site selected from the group consisting of cysteine, cystine, a thiol-derivatized amino acid, and a disulfide-derivatized amino acid, the method additionally comprises the step of desulfurizing the amide containing compound in flow.

In another preferred embodiment, when $AA_{lig}$ is a selenol or diselenide functionalised amino acid residue at the ligation site selected from the group consisting of selenocysteine, selenocystine, a selenol-derivatized amino acid, and a diselenide-derivatized amino acid, the method additionally comprises the step of deselenizing the amide containing compound in flow.

In one embodiment, the desulfurization or deselenization step comprises adding a chemical radical initiator to the amide containing compound in flow. A non-limiting example of a water-soluble radical initiator is 2,2'-azobis(2-(2-imidazolin-2-yl)propane)dihydrochloride (VA-044).

In a preferred embodiment, the desulfurization or deselenization step comprises exposing the compound to UV irradiation in the presence of a phosphine source.

Preferably, the photodesulfurization or photodeselenization step is conducted in the absence of a chemical radical initiator.

In another aspect of the invention, there is provided a method of desulfurizing an amide containing compound comprising a thiol group or a disulfide group in flow. Preferably, the amide containing compound is the reaction product of a native chemical ligation reaction. In one embodiment, the desulfurization comprises adding a chemical radical initiator to the amide containing compound in flow. Preferably, the desulfurization comprises exposing the compound to UV irradiation in the presence of a phosphine source.

In yet another aspect of the invention, there is provided a method of deselenizing an amide containing compound comprising a selenol group or a diselenide group in flow. Preferably, the amide containing compound is the reaction product of a native chemical ligation reaction. In one embodiment, the deselenization comprises adding a chemical radical initiator to the amide containing compound in flow. Preferably, the deselenization comprises exposing the compound to UV irradiation in the presence of a phosphine source.

In another aspect of the invention, there is provided a method of desulfurizing an amide containing compound comprising a thiol group or a disulfide group, wherein the desulfurization comprises exposing the compound to UV irradiation in the presence of a phosphine source. The method may be performed in batch or in flow.

In yet another aspect of the invention, there is provided a method of deselenizing an amide containing compound comprising a selenol group or a diselenide group, wherein the deselenization comprises exposing the compound to UV irradiation in the presence of a phosphine source. The method may be performed in batch or in flow.

The desulfurization or deselenization reaction is preferably commenced by exposing a solution comprising the amide containing compound comprising a thiol group, a disulfide group, a selenol group or a diselenide group to UV irradiation in the presence of a phosphine source, preferably in flow, and then allowed to proceed to completion as measured by an analytical technique. Preferably the desulfurization or deselenization reaction may be allowed to proceed to about 100% completion. It would be understood that the desulfurization or deselenization reaction may be allowed to proceed to at least 90% completion, at least 85% completion, at least 80% completion, at least 75% completion, at least 70% completion, at least 65% completion, at least 60% completion, at least 55% completion, at least 50% completion, at least 45% completion, at least 40% completion, at least 35% completion, at least 30% completion, at least 25% completion. Preferably, the desulfurization or deselenization reaction may be allowed to proceed to at least 90% completion, more preferably about 100% completion.

The phosphine is preferably water soluble. Examples of suitable water soluble phosphines include, but are not limited to, Bis(p-sulfonatophenyl)phenylphosphine dihydrate dipotassium salt, Bis(4,6-dimethyl-3-sulfonatophenyl) (2,4-disodium salt hydrate, 1,2-Bis(di-4-dimethylphenyl)phosphine, sulfonatophenylphosphino)benzene tetrasodium salt, Bis(3-sulfonatophenyl) (3,5-di-trifluoromethylphenyl)phosphine, disodium salt monohydrate, Bis(p-sulfonatophenyl) phenylphosphine dihydrate dipotassium salt, Bis(3-sulfonatophenyl) (2-trifluoromethylphenyl)phosphine, disodium dehydrate, Bis(3-sulfonatophenyl) (4-trifluoromethylphenyl)phosphine disodium dihydrate, Di-t-butyl (3-sulfonatopropyl)phosphine, 2'-Dicyclohexylphosphino-2,6-dimethoxy-3-sulfonato-1,1'-biphenyl hydrate sodium salt, 2'-Dicyclohexylphosphino-2,6-di-i-propyl-4-sulfonato-1,1'-biphenyl hydrate sodium salt, Diphenyl(m-sulfonatophenyl)phosphine dihydrate sodium salt, 2-(Dicyclohexylphosphino)ethyl]trimethylammonium chloride, Diphenyl (p-sulfonatophenyl)phosphine monohydrate dimethylsulfoxide adduct, potassium salt, Dicyclohexyl-{9-[3-(4-sulfonylphenyl) propyl]-2-sulfonylfluoren-9-yl}phosphonium hydrogen sulfate, Tetrabutylphosphonium chloride, 1,3,5-Triaza-7-phosphaadamantane, Tris(2-carboxyethyl)phosphine (TCEP), Tris(4,6-dimethyl-3-sulfonatophenyl)phosphine trisodium salt hydrate, Tris(hydroxymethyl) phosphine, Tris(3-hydroxypropyl)phosphine, and Tris(3-sulfonatophenyl)phosphine hydrate, sodium salt. Preferably, the phosphine source is TCEP.

In another preferred embodiment, the desulfurization or deselenization further comprises a hydrogen atom source. Preferably, the hydrogen atom source is selected from the group consisting of reduced L-glutathione (GSH), dithiothreitol (DTT), tert-butylthiol, cysteine, and combinations thereof. Preferably, the hydrogen atom source is GSH.

In another preferred embodiment, the photodesulfurization or photodeselenization is conducted in the absence of a chemical radical initiator.

The invention also relates to an amide containing compound prepared by reacting an ester with a molecule comprising a terminal amino acid selected from the group consisting of cysteine, cystine, a thiol-derivatized amino acid, a disulfide-derivatized amino acid, selenocysteine, selenocystine, a selenol-derivatized amino acid, and a diselenide-derivatized amino acid in flow.

The invention also relates to a desulfurized or deselenized amide containing compound prepared by the methods described herein.

Experimental

The illustrative examples below relate to use of synthetic peptides. A skilled person would understand the disclosure is not limited to synthetic peptides, and includes expressed peptides and proteins.

General Synthetic Procedures

Nuclear magnetic resonance (NMR) spectroscopy was conducted at 300 K using either a Bruker Avance DPX 400, 500 or 800 spectrometer in $D_2O$ or $d_6$-DMSO as specified in the figure legends for individual spectra, calibrating to residual solvent peaks as internal references. High resolution mass spectra were acquired in reflectron mode on a Bruker (MA, USA) Autoflex™ Speed MALDI-TOF using either a matrix of saturated α-cyano-4-hydroxycinnamic acid in 3:7 MeCN:$H_2O$ containing 0.1% TFA (TA30), or 2',4',6'-trihydroxyacetophenone (THAP)/di-ammonium hydrogen citrate (18 mg/7 mg in 500 μL of TA30). Equal volumes of the sample in TA30 and the matrix were mixed well and spotted to a ground steel MALDI plate then allowed to dry. Data was acquired with Protein 1 calibrants (Bruker) then analyzed using Flexanalysis (Bruker) software.

Analytical UPLC was performed on a Waters Acquity UPLC system equipped with a Sample Manager FTN, Quaternary Solvent Manager (H-Class) and a PDA ex detector (λ=210-400 nm). Analysis was performed using a Waters Acquity UPLC C-18 BEH (130 Å, 1.7 μm) 2.1 mm×50 mm column operating at 0.60 mL/min. Preparative reverse-phase HPLC (RP-HPLC) was performed on a Waters 2535 Quaternary Gradient system interfaced with a Waters 2489 UV/Vis Detector module operating at 230 nm and 280 nm and a Waters Fraction Collector III. A Waters Sunfire C-18 OBD (100 Å, 5 μm), 30×150 mm column was employed at a flow rate of 38.0 mL/min unless otherwise stated. Both instruments utilized a mobile phase composed of 0.1 vol. % TFA in Milli-Q water (A/Solvent A) and 0.1 vol. % TFA in HPLC grade acetonitrile (B/Solvent B) operating using a linear gradient. Chromatogram analysis was performed using Empower 3 Pro software (2010).

UPLC-MS was performed using Shimadzu LC-30AD Liquid Chromatography pump modules with a DGU-20A5R degassing unit and SPD-M30A Diode Array Detector. A CTO-20A Column Oven was employed with a Waters C-18 BEH (130 Å, 1.7 μm) 2.1×50 mm column operating at 0.60 mL/min. These components were interfaced with a CBM-20A Communications Bus Module alongside a Nexera X2 SIL-30AC Autosampler and a Shimadzu LCMS-2020 mass spectrometer operating in positive mode. Peptides were analyzed using a mobile phase of 0.1 vol. % formic acid in Milli-Q water and 0.1 vol. % formic acid in HPLC grade acetonitrile operating with a linear gradient. Analysis was performed using Shimadzu LabSolutions software. ESI-MS spectra of purified proteins were obtained by averaging the total ion count over the entire gradient and wash cycle.

Flow experiments were performed using a Vapourtec RS-200 Automated control system alongside a Stainless Steel $R_2$-series pumping module and an $R_4$ convection heating module with a Vapourtec Standard Coiled Tube Reactor. These modules were interfaced with preinstalled Flow Commander software alongside an R-2S pumping module with two V-3 peristaltic pumps. Polytetrafluoroethylene (PTFE) tubing (0.50 mm id×1.60 mm od) or polyfluoroalkoxy (PFA) tubing (0.50 mm id×1.60 mm od) were used as specified, alongside PTFE injection loops of 100 μL, 500 μL, 2.0 mL (0.50 mm id×1.60 mm od) and 5.0 mL (0.75 mm id×1.60 mm od) volume. A Rayonet RPR-100 photoreactor was used at λ=254 nm, 302 nm, and 365 nm (35 W).

Ligation progression of model systems was calculated based on the integration of peaks in the UPLC chromatogram at λ=280 nm, corresponding to the absorbance of tyrosine residues (cTyr=1280 $M^{-1}$ $cm^{-1}$) in the model peptides used. Reported reaction yields are calculated from the mass of isolated peptide relative to the theoretical reaction yield. Yields are adjusted to compensate for any aliquots removed for reaction monitoring.

Materials

Commercial materials were used as received unless otherwise noted. Amino acids, coupling reagents and resins were obtained from Novabiochem or GL Biochem. Reagents that were not commercially available were synthesized following literature procedures as indicated in the experimental. N,N-dimethylformamide (DMF) was obtained as peptide synthesis grade from Merck or Labscan.

Compound S1 was synthesized as reported in Sayers 2015.

Compound S2 was synthesized as reported in Thompson 2013.

Fmoc SPPS Procedures

All reagent equivalents are reported relative to the moles of amino acid loaded to the resin.

Resin Loading

Rink Amide Resin

Rink amide resin (copoly(styrene-1% DVB) 100-200 mesh) (200 μmol) was swollen with $CH_2Cl_2$ for 30 min then washed with DMF (5×5 mL). The resin was Fmoc-deprotected with 20 vol. % piperidine in DMF (2×5 mL, 3 min) before washing with DMF (5×5 mL), $CH_2Cl_2$ (5×5 mL) and DMF (5×5 mL). PyBOP (4 equiv.) and NMM (8 equiv.) were added to Fmoc-Xaa-OH (4 equiv.) in DMF (0.125 M of Fmoc-Xaa-OH) and added to the resin at rt with agitation for 2 h. The loading solution was removed and the resin washed with DMF (5×5 mL), $CH_2Cl_2$ (5×5 mL) and DMF (5×5 mL) then capped with $Ac_2O$ (0.125 M) and $iPr_2EtN$ (0.125 M) in DMF (5 mL). The resin was washed with DMF (5×5 mL), $CH_2Cl_2$ (5×5 mL) and DMF (5×5 mL).

2-Chlorotrityl Chloride RESIN 2-chlorotrityl chloride resin (copoly(styrene-1% DVB) 100-200 mesh) (200 μmol) was swollen in $CH_2Cl_2$ for 30 min. A solution of Fmoc-Xaa-OH (2 equiv.) and $iPr_2EtN$ (4 equiv.) in $CH_2Cl_2$ (0.125 M of Fmoc-Xaa-OH) was added to the resin and agitated at rt for 16 h. The loading solution was removed and the resin washed with DMF (5×5 mL), $CH_2Cl_2$ (5×5 mL), and DMF (5×5 mL). The resin was treated with a solution of $CH_2Cl_2/CH_3OH/iPr_2EtN$ (17:2:1 v/v/v, 5 mL) for 1 h and washed with DMF (5×5 mL), $CH_2Cl_2$ (5×5 mL), and DMF (5×5 mL).

Derivatization of 2-Chlorotrityl Chloride Resin with Hydrazine

This procedure was adapted from Zheng et al. 2013. 2-chlorotrityl chloride resin (copoly(styrene-1% DVB) 100-200 mesh) (200 μmol) was swollen in $CH_2Cl_2$ for 30 min. A solution of 5 vol. % $N_2H_4 \cdot H_2O$ in DMF was added to the resin and gently agitated for 30 minutes. The resin was washed with DMF (5×5 mL), $CH_2Cl_2$ (5×5 mL), and DMF (5×5 mL), followed by a repeated hydrazine treatment and washing. A capping solution of 5 vol. % $CH_3OH$ in DMF was added to the resin and agitated for 10 minutes. The resin was then washed with DMF (5×5 mL), $CH_2Cl_2$ (5×5 mL), and DMF (5×5 mL) to afford a light yellow-green resin. Standard peptide coupling procedures were then immediately performed.

Quantification of Resin Loading

Resin (10 mg)) was treated with a solution of 2 vol. % 1,8-diazabicyclo(5.4.0) undec-7-ene (DBU) in DMF (2 mL) and agitated for 30 min before adding 8 mL acetonitrile. A 1 mL aliquot of the resultant solution was taken and diluted to 12.5 mL with acetonitrile. The absorbance of the DBU-fulvene adduct ( ) 304, $ι$=9254 $M^{-1}$ $cm^{-1}$) was measured to estimate loading.

Iterative Peptide Assembly (Fmoc SPPS)

Deprotection

The resin (200 μmol initial loading) was treated with 20 vol. % piperidine in DMF (2×5 mL, 3 min) and washed with DMF (5×5 mL), $CH_2Cl_2$ (5×5 mL), and DMF (5×5 mL).

General Amino Acid Coupling

A solution of Fmoc-Xaa-OH (4 equiv.), PyBOP (4 equiv.) and NMM (8 equiv.) in DMF (0.125 M of Fmoc-Xaa-OH) was added to the resin (200 μmol initial loading) and agitated at rt for 1 h. The resin was then washed with DMF (5×5 mL), $CH_2Cl_2$ (5×5 mL), and DMF (5×5 mL).

Capping

A solution of $Ac_2O$ (0.125 M) and $iPr_2EtN$ (0.125 M) in DMF (5 mL) was added to the resin. After 3 min the resin (200 μmol initial loading) was washed with DMF (5×5 mL), $CH_2Cl_2$ (5×5 mL), and DMF (5×5 mL).

Cleavage from Resin without Side-Chain Deprotection and Work Up

The resin (200 μmol initial loading) was treated with HFIP/$CH_2Cl_2$ (3:7, v/v, 5 mL) and agitated at rt for 40 min. The resin was filtered and washed with $CH_2Cl_2$ (5×5 mL). The combined filtrates were concentrated under nitrogen flow.

Cleavage from Resin with Full Side-Chain Deprotection and Work Up

A mixture of TFA:$iPr_3SiH$:$H_2O$ (90:5:5 v/v//v) was added to the resin (200 μmol initial loading). After 2 h the resin was filtered and washed with TFA (3×5 mL). The combined filtrates were concentrated under nitrogen flow to less than 5 mL. Diethyl ether (40 mL) was added and the solution cooled to −20° C. for 15 minutes. The precipitate was pelleted by centrifugation at 4000 rcf for 8 min and the supernatant decanted.

Automated SPPS

Automated Fmoc-SPPS was performed on a Gyros Protein Technologies Symphony Automated Synthesizer. General synthetic protocols for Fmoc-deprotection using 20 vol. % piperidine in DMF, and capping using $Ac_2O$ (0.3 M) and $iPr_2EtN$ (0.3 M) in DMF, were performed as above. Coupling solutions were prepared for Fmoc-Xaa-OH (0.3 M) in DMF, OxymaPure® (0.3 M) in DMF, and DIC (0.3 M) in DMF.

Microwave-Assisted Peptide Synthesis

Microwave-assisted peptide synthesis was performed at either 90° or 50° C. on a CEM Liberty Blue automated microwave peptide synthesizer (USA, NC). High temperature coupling used a 4 minute coupling method: [2 min coupling (90° C.), 1 min deprotection (90° C.), 1 min associated washes and liquid handling] while synthesis on 2-chlorotrityl chloride resin (N-terminal segment) was performed at 50° C. using a 30 min coupling method: [20 min coupling (50° C.), 2×3 min deprotection (rt), 4 min associated washes and liquid handling]. Both methods used a 4-fold excess of Fmoc-Xaa-OH, Oxyma and DIC. Capping of unreacted N-terminal amines was achieved using N-acetylglycine, Oxyma and DIC at a 5-fold molar excess using 90° C. coupling for 1 min, or 50° C. coupling for 3 min.

Solution-Phase Thioesterification

Crude side-chain protected peptides were dissolved in dry DMF (20 mM) and cooled to −30° C. To this was added ethyl 3-mercaptopropionate (30 equiv.) followed by PyBOP (5 equiv.) and $iPr_2EtN$ (5 equiv.) with stirring over 3 h under an argon atmosphere. The solution was warmed to rt and concentrated under nitrogen flow. Deprotection and work-up was achieved using the acidic deprotection conditions described for fully protected peptides on-resin. No epimerization was observed using this procedure.

Diazotization and Thioesterification of Peptide Hydrazides

Conversion of peptide hydrazides to peptide thioesters was performed using a slightly modified procedure to that reported by Zheng 2013. Fully deprotected peptides bearing C-terminal acyl hydrazides were solvated in aqueous ligation buffer (6 M Gdn·HCl, 0.1 M HEPES) to a 40 mM concentration. This solution was adjusted to pH 3.0 and cooled to −15° C. To this was added an aqueous solution of $NaNO_2$ (12 M, 10 equiv.). After 10 minutes, distilled TFET (10 equiv. for Ala thioester, 20 equiv. for Val thioester) was added (warning: TFET is pungent and acutely toxic and should be used in a fume cupboard). The solution was adjusted to pH 6.8-7.0 and warmed to rt. After 10 minutes, the resulting peptide trifluoroethyl thioester was purified by HPLC.

Native Chemical Ligation in Flow

Figure 1:
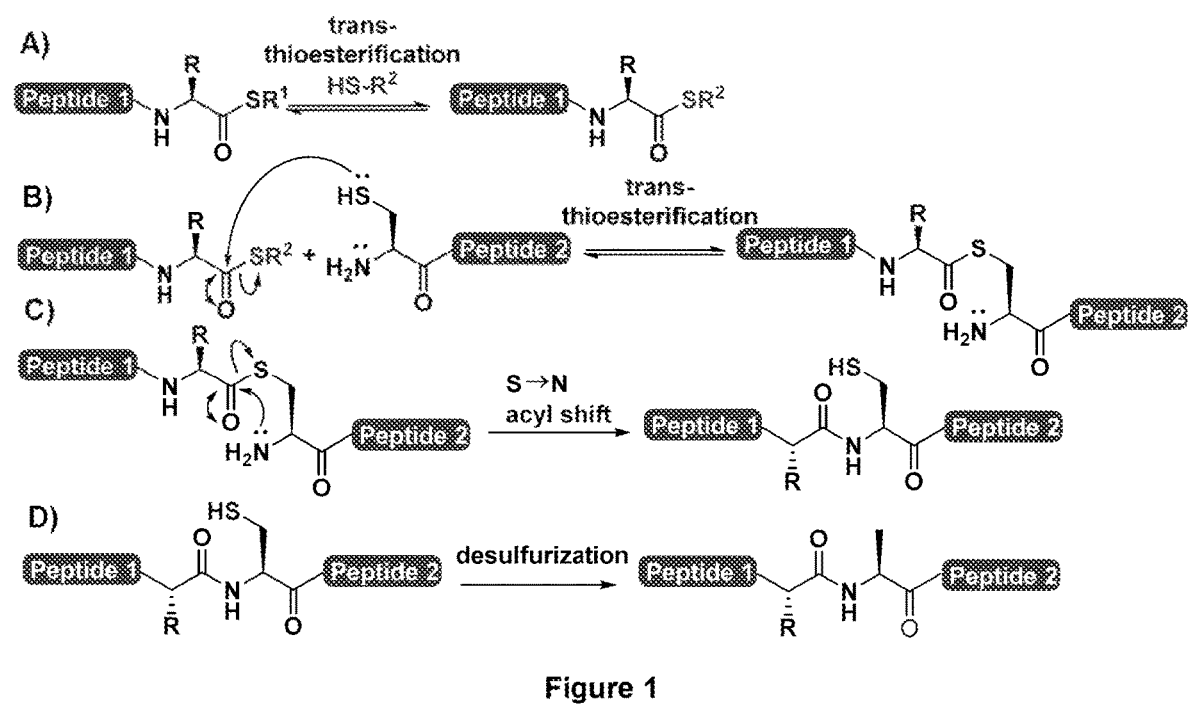

Native chemical ligation is performed between a peptide containing an N-terminal cysteine (Cys) residue and a peptide functionalized as a C-terminal thioester (FIG. 1). Mechanistically, the reaction proceeds through an initial trans-thioesterification step followed by a rapid S→N acyl rearrangement to afford a native peptide bond. Usually a suitable thiol additive is required to generate a reactive thioester (SR2) that accelerates the rate-limiting trans-thio-esterification step.

Figure 2:
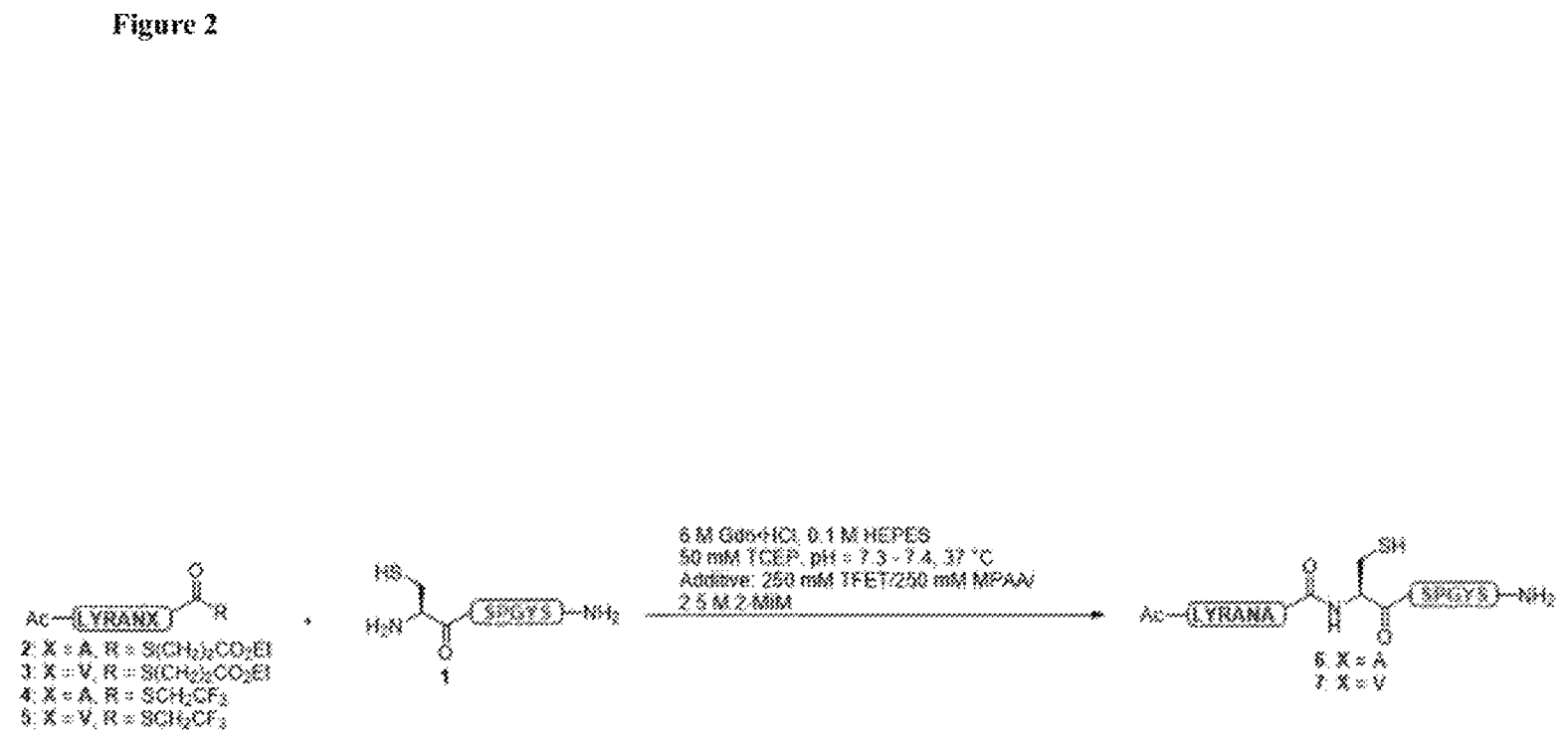
Figure 3:
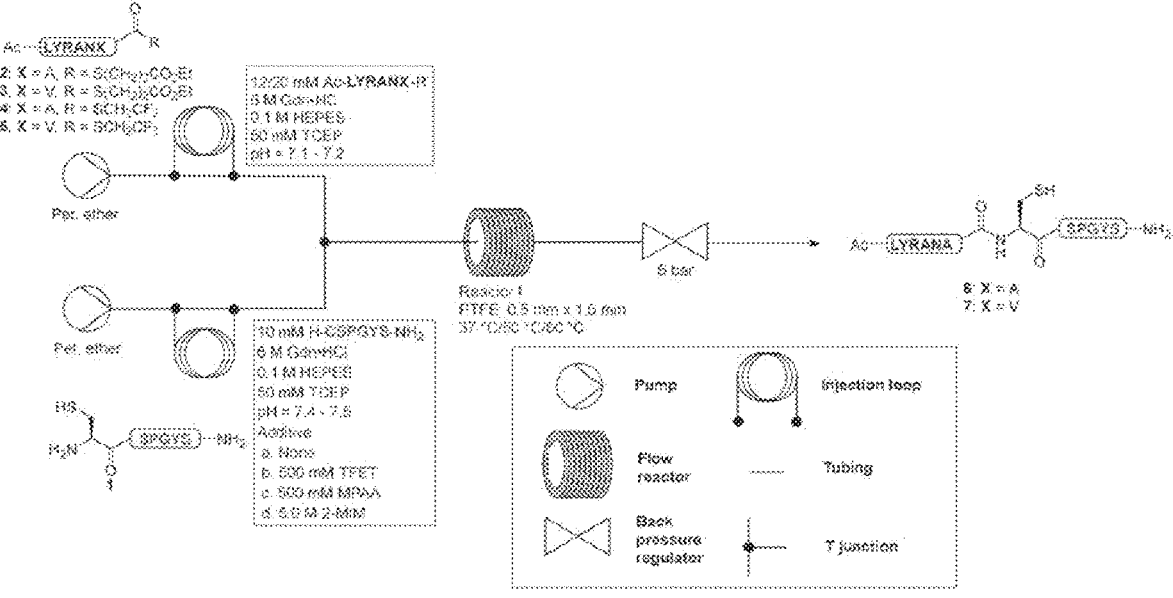
FIG. 3: (Top) Flow schematic used to perform NCL optimization experiments, with legend for flow symbols. (Bottom) The physical flow apparatus used to perform flow experiments: i) computer interface with FlowCommander software; ii) analog buttons for manual control; iii) master control dial with visual monitors of system parameters; iv) system solvent reservoirs; v) piston pump; vi) six-valved rheodyne; viii) T-junction; ix) heated reactor module; x) back pressure regulator; xi) collection vessel; xii) peristaltic pump; xiii) Rayonet RPR-100 photoreactor.
Figure 3:
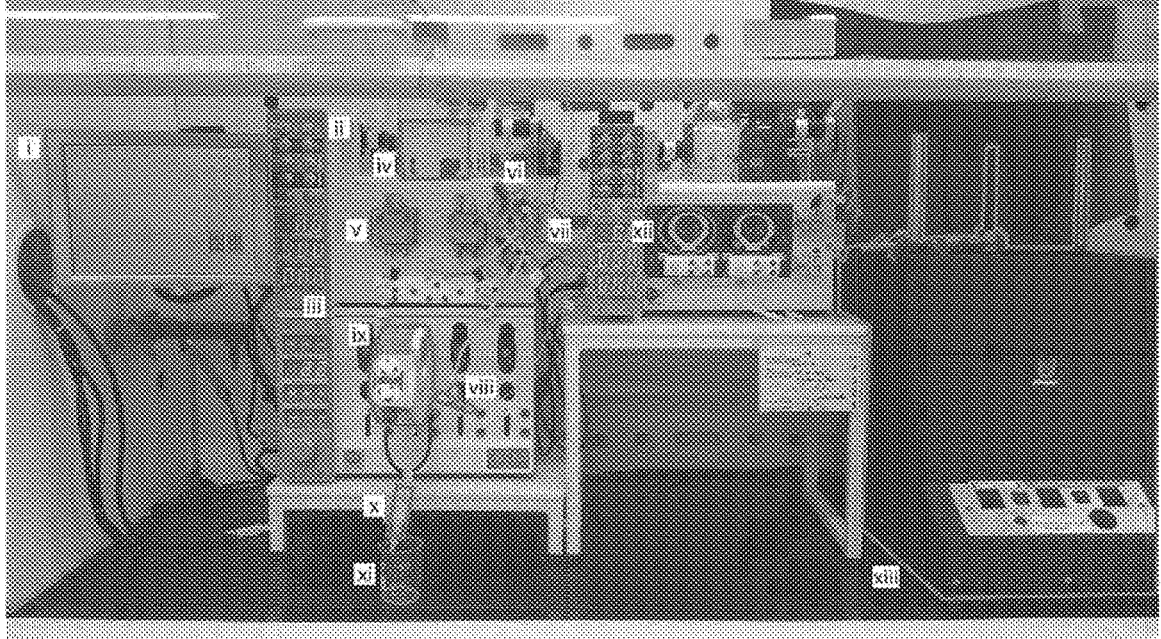
Figure 4:
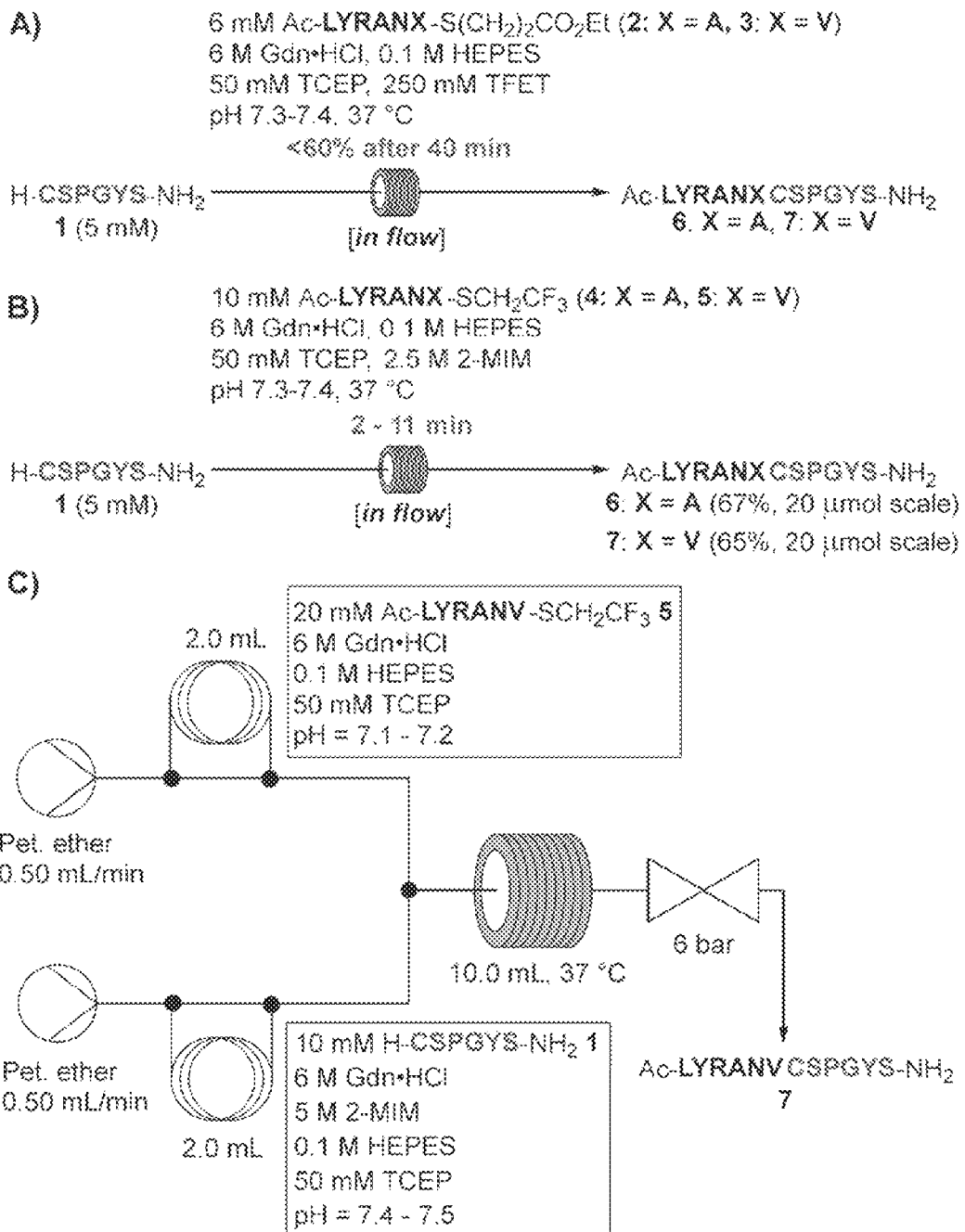
FIG. 4: A) Flow NCL between peptide 1 and thioesters 2 and 3; B) Flow NCL between model peptide 1 and trifluoroethyl thioesters 4 and 5; C) Schematic diagram of the optimized NCL flow system for the reaction between peptide 1 and peptide thioester 5.

A model NCL reaction in flow between model peptide H-CSPGYS-$NH_2$ (1 (SEQ ID NO: 1) and model peptide thioesters Ac-LYRANX-S($CH_2$)$_2$$CO_2$Et (2: X=A (SEQ ID NO: 2) 3: X=V (SEQ ID NO: 3)) was conducted (FIGS. 2-4).

Any additives employed were solvated in degassed ligation buffer (500 mM MPAA, 500 mM TFET, 5.0 M 2-MIM)

(warning: TFET is pungent and acutely toxic and should be used in a fume cupboard) comprising 6 M Gdn·HCl, 0.1 M HEPES and 50 mM TCEP (pH 7.4-7.5). This solution was added to model peptide 1 (10 mM, 1.0 equiv.). A second solution was prepared of model peptide thioester 2 or 3 (1.2 equiv. or 2.0 equiv.) in degassed ligation buffer (10 mM) comprising 6 M Gdn·HCl, 0.1 M HEPES and 50 mM TCEP (pH 7.1-7.2). These solutions were inserted into injection loops and combined at a T piece on a 150 µL scale using petroleum ether as the system solvent (FIG. 3A). The resulting reaction stream entered PTFE coil reactor I (0.5 mm×1.6 mm) at 37° C. (6 bar BPR). The reaction solution was quenched directly upon collection using an equal volume of 7 vol. % $N_2H_4 \cdot H_2O$ in Milli Q water. Ligation time-courses were obtained via altering the volume of reactor I and the flow rate to modulate the residence time. Aliquots of 10 µL were taken of the quenched solution and diluted with 40 µL of 0.1% TFA in Milli-Q water then analyzed by UPLC. Conversion estimates were based on the relative peak areas of the starting material 1 and the desired ligation product 6 or 7 at λ=280 nm [$\varepsilon_{280}(1)$=1280 $M^{-1}$ $cm^{-1}$, $\varepsilon_{280}(6, 7)$=2560 $M^{-1}$ $cm^{-1}$.]

Native Chemical Ligation in Batch

A comparative NCL reaction in batch between model peptide H-CSPGYS-NH$_2$ (1, SEQ ID NO: 1) and model peptide thioesters Ac-LYRANX-S(CH$_2$)$_2$CO$_2$Et (2: X=A (SEQ ID NO: 2), 3: X=V (SEQ ID NO: 3)) was conducted.

Any additives employed were solvated in degassed ligation buffer (500 mM MPAA, 500 mM TFET, 5.0 M 2-MIM) (warning: TFET is pungent and acutely toxic and should be used in a fume cupboard) comprising 6 M Gdn·HCl, 0.1 M HEPES and 50 mM TCEP (pH 7.4-7.5). This solution was added to model peptide 1 (10 mM, 1.0 equiv.). A second solution of model peptide thioester 2 or 3 (1.2 equiv. or 2.0 equiv.) was prepared in degassed ligation buffer comprising 6 M Gdn·HCl, 0.1 M HEPES and 50 mM TCEP (pH 7.1-7.2). These solutions were combined (1:1 vol/vol) and gently agitated before incubation at 37° C. (Scheme S1). Ligation time-courses were plotted by taking 5 µL aliquots at various timepoints and quenching with 5 µL of 7 vol. % $N_2H_4 \cdot H_2O$ in Milli-Q water. This solution was diluted with 40 L of 0.1% TFA in Milli-Q water then analyzed by UPLC. Conversion estimates were based on the relative peak areas of the starting material 1 and the desired ligation product 6 or 7 at λ=280 nm [$\varepsilon_{280}(1)$=1280 $M^{-1}$ $cm^{-1}$, $\varepsilon_{280}(6, 7)$=2560 $M^{-1}$ $cm^{-1}$].

Figure 5:
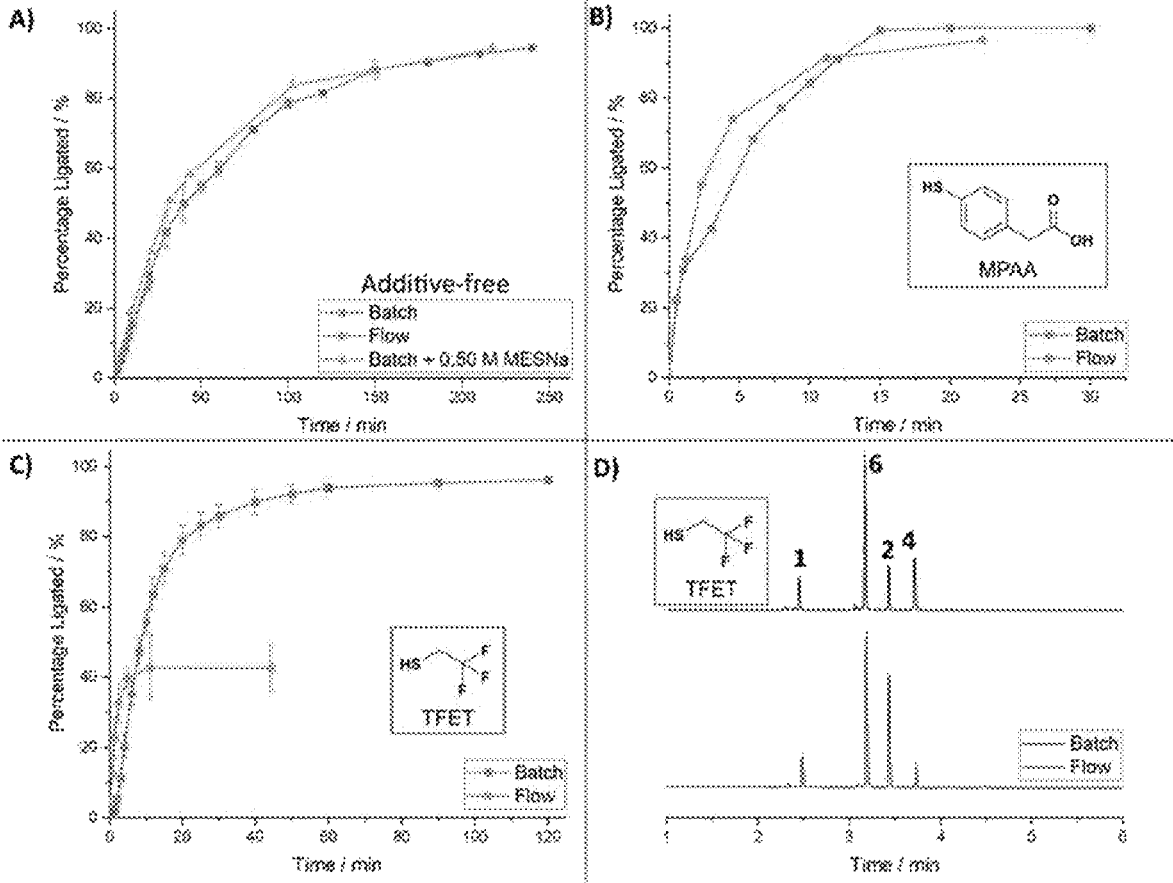
FIG. 5: Ligations of H-CSPGYS-NH$_2$ (SEQ ID NO: 1) 1 and Ac-LYRANA-S(CH$_2$)$_2$CO$_2$Et (SEQ ID NO: 2)$_2$: A) With either no thiol additive or with MESNa (500 mM); B) with MPAA (250 mM); C) with TFET (250 mM); and D) UPLC chromatograms ($\lambda$=280 nm, 0 to 30% B over 5 min, 0.1% TFA) of the TFET-additive ligation after 10 minutes, in batch and flow. Peak 1: H-CSPGYS-NH$_2$ (SEQ ID NO: 1), peak 6: Ac-LYRANACSPGYS-NH$_2$ (SEQ ID NO: 6), peak 2: Ac-LYRANA-S(CH$_2$)$_2$CO$_2$Et (SEQ ID NO: 2), peak 4: Ac-LYRANA-SCH$_2$CF$_3$. (SEQ ID NO: 4) Percentage ligation was calculated by integrating peaks from analytical UPLC chromatograms at $\lambda$=280 nm. Error bars represent one standard deviation above and below the mean calculated from three independent experiments.

The kinetics of the ligation reactions between model peptide 1 and model peptide thioester 2, in batch and in flow, either in the absence or presence of a thiol additive selected from trifluoroethanethiol (TFET), 4-mercaptophenylacetic acid (MPAA) and MESNa are shown in FIG. 5.

Native Chemical Ligation in Flow Using a Preformed Reactive Thioester

An NCL flow strategy was developed whereby preformed trifluoroethyl thioesters Ac-LYRANX-SCH$_2$CF$_3$ (4: X=A, SEQ ID NO: 4; 5: X=V, SEQ ID NO: 5) were ligated with 1 using 2-methylimidazole (2-MIM) as an optional additive (FIG. 4B). Using the same flow set-up as described above, these conditions led to complete ligation between peptide 1 and thioester 4 in 2 min, and with thioester 5 in 11 min (see FIGS. 4B and 4C, FIG. 6).

Native Chemical Ligation in Batch Using a Preformed Reactive Thioester

A comparative NCL reaction in batch between preformed trifluoroethyl thioesters Ac-LYRANX-SCH$_2$CF$_3$ (4: X=A, SEQ ID NO: 4; 5: X=V, SEQ ID NO: 5) ligated with 1 using 2-methylimidazole (2-MIM) as an optional additive was conducted.

Figure 6:
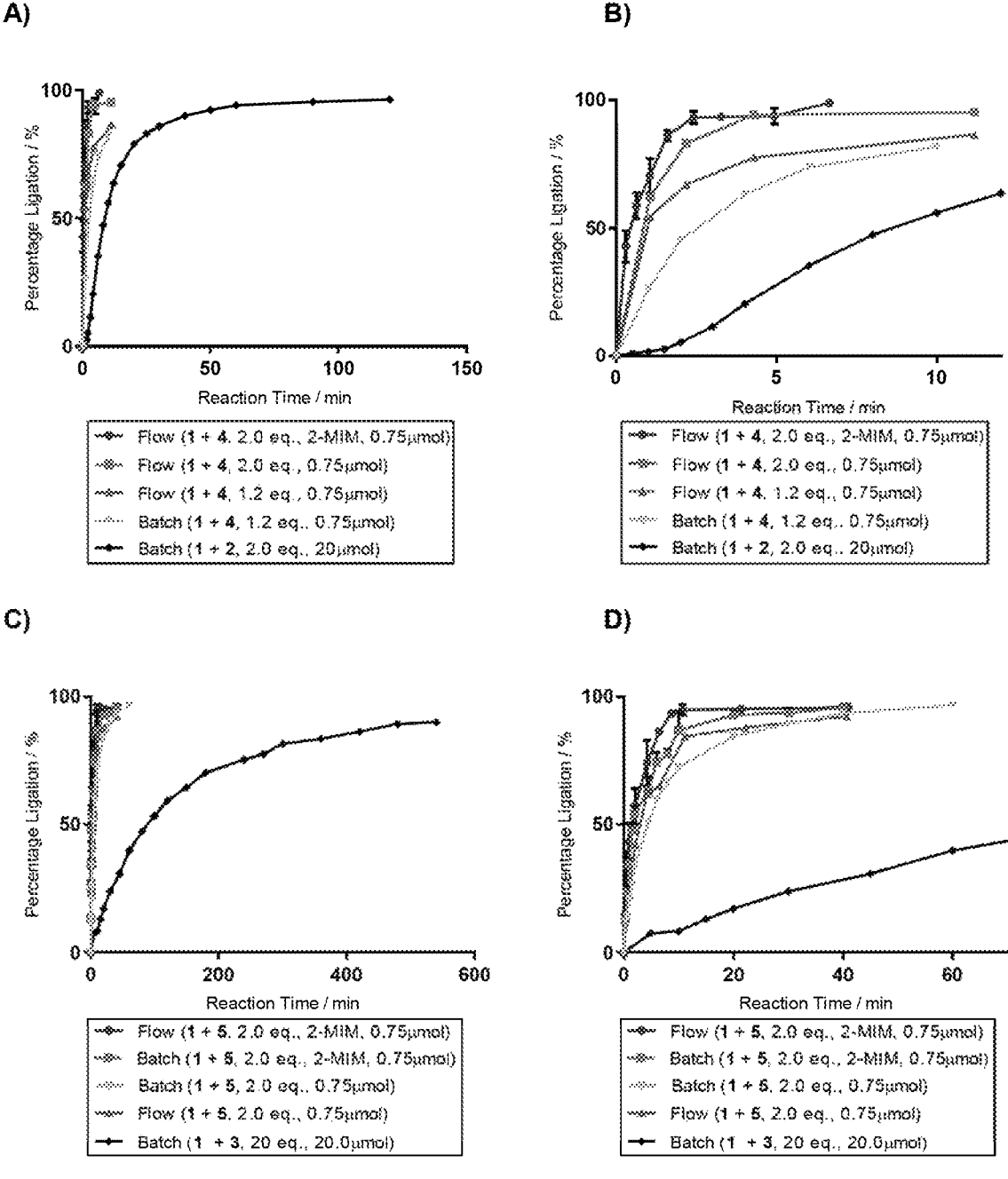
FIG. 6: A) Kinetics of ligation between H-CSPGYS-NH$_2$ (SEQ ID NO: 1) 1 and Ac-LYRANA-S(CH$_2$)$_2$CO$_2$Et (SEQ ID NO: 2)$_2$ or Ac-LYRANA-SCH$_2$CF$_3$ (SEQ ID NO: 4) 4 using different equivalents of thioester with or without 2.5 M 2-MIM as an additive. B) Expanded section of kinetic data from FIG. 6A spanning 0-12 min. C) Kinetics of ligation between H-CSPGYS-NH$_2$ (SEQ ID NO: 1) 1 and Ac-LYRANV-S(CH$_2$)$_2$CO$_2$Et (SEQ ID NO: 3) 3 or Ac-LYRANV-SCH$_2$CF$_3$ (SEQ ID NO: 5) 5 with or without 2.5 M 2-MIM as an additive. D) Expanded section of kinetic data from FIG. 6C spanning 0-70 min. Percentage ligation was calculated through integrating peaks from analytical UPLC chromatograms at $\lambda$=280 nm. Error bars represent one standard deviation above and below the mean calculated from three independent experiments.
Figure 7:
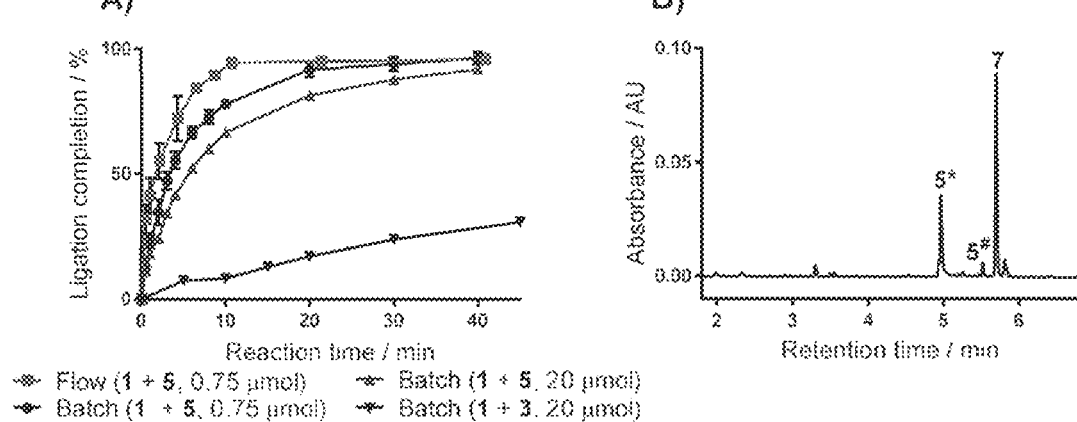
FIG. 7: A) Reaction of peptide 1 and peptide trifluoroethyl thioester 5 with 2-MIM as an additive (2.5 M) to generate 7 on a 0.75 µmol scale in batch (blue) and flow (red), on a 20 µmol scale in batch (green), and reaction of 1 and 3 to generate 7 using TFET as an exogenous additive on a 20 µmol scale in batch (black). B) UPLC of the crude eluent from the optimized flow ligation between 1 and 5. (gradient: 0 to 28% B over 5 min, $\lambda$=214 nm). * peak corresponds to the acyl hydrazide derivative of 5 following quenching with hydrazine; # peak corresponds to hydrolyzed 5.

The reaction rates for batch and flow ligation reactions between 1 and thioester 3 with TFET as an additive, and between 1 and pre-activated trifluoroethyl thioester 4 or 5 were compared (FIGS. 6 and 7). General batch and flow ligations were performed according to the above procedure, using either 1.2 equiv. or 2.0 equiv. of Ac-LYRANX-SCH$_2$CF$_3$ (4: X=A, SEQ ID NO: 4; 5: X=V, SEQ ID NO: 5) thioesters 4 and 5, with or without 2.5 M 2-MIM. Rate accelerations were observed for experiments performed in flow vs batch, for 2.0 equiv. or 1.2 equiv., and with 2-MIM as an additive.

The optimized flow procedure using the pre-activated thioester proved to be substantially faster than the corresponding batch reactions (4-50 fold), the rate difference being more pronounced on a larger scale (20 µmol) despite active mixing (FIG. 7A). The reaction endpoints of flow ligations did not change upon scale-up (see FIG. 7B for crude UPLC trace of the ligation between 1 and 5, after quenching with 3 vol % hydrazine), and led to excellent isolated yields upon direct HPLC purification of the flow eluent (18 mg, 67% for 6 and 18 mg, 65% for 7).

Native Chemical Ligation in Flow at Dilution

Two 0.5 mL solutions were prepared, one containing H-CSPGYS-NH$_2$ (SEQ ID NO: 1) 1 (1 mM or 0.1 mM) and TCEP (50 mM) in ligation buffer (6 M Gdn·HCl, 0.1 M HEPES, pH 6.0), and the other containing 2 equiv. Ac-LYRANA-SCH$_2$CF$_3$ 4 (SEQ ID NO: 4; 2 mM or 0.2 mM) and TCEP (50 mM) in ligation buffer (6 M Gdn·HCl, 0.1 M HEPES, pH 6.0). These solutions were inserted into injection loops and combined at a T-piece using petroleum ether as the system solvent. The resulting reaction stream entered PTFE coil reactor I (0.5 mm×1.6 mm) at 37° C. (6 bar BPR). The reaction solution was collected into a quenching solution of aqueous hydrazine monohydrate (7 vol. %) and analysed by UPLC and UPLC-MS. Conversion estimates were based on the relative peak areas of the starting material and the desulfurized product at λ=280 nm [£280 (1)=1280 $M^{-1}$ $cm^{-1}$, $\varepsilon_{280}(6)$=2560 $M^{-1}$ $cm^{-1}$].

Figure 8:
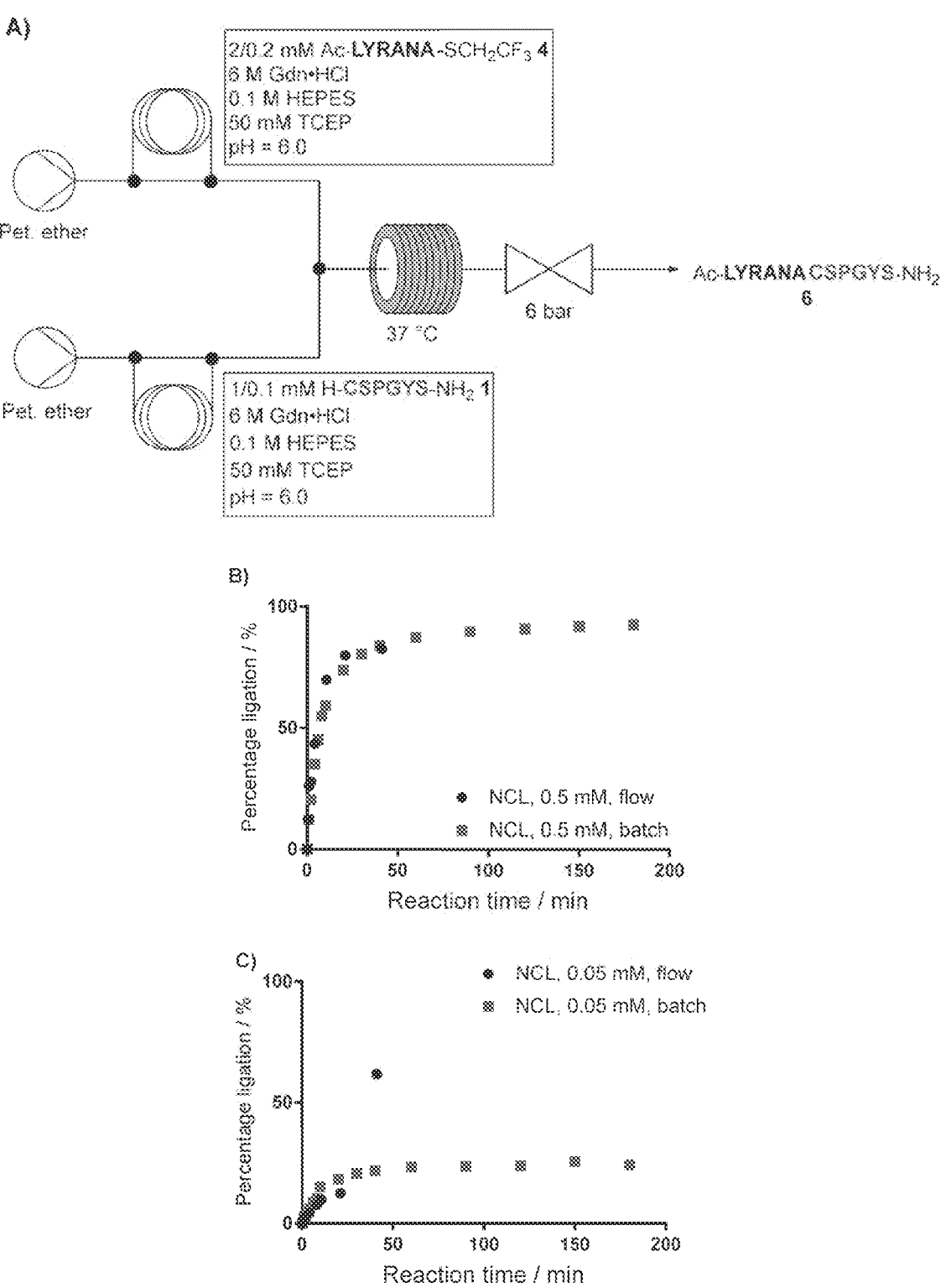
FIG. 8: A) Schematic representation of experimental setup for NCL in flow at high dilutions. B) Kinetics of ligation between H-CSPGYS-NH$_2$ (SEQ ID NO: 1) 1 (0.5 mM) and Ac-LYRANA-SCH$_2$CF$_3$ (SEQ ID NO: 4) 4 (2 eq., 1.0 mM) in batch and flow. C) Kinetics of ligation between H-CSPGYS-NH$_2$ (SEQ ID NO: 1) 1 (0.05 mM) and Ac-LYRANA-SCH$_2$CF$_3$ (SEQ ID NO: 4) 4 (2 eq., 0.10 mM) in batch and flow. Percentage ligation is calculated by integrating UPLC chromatogram peaks at $\lambda$=280 nm.

The kinetics of the ligation reactions between dilute solutions of model peptide 1 and model peptide thioester 2, in batch and in flow, without any thiol or selenol additives are shown in FIG. 8.

Standard Desulfurization in Flow

Figure 9:
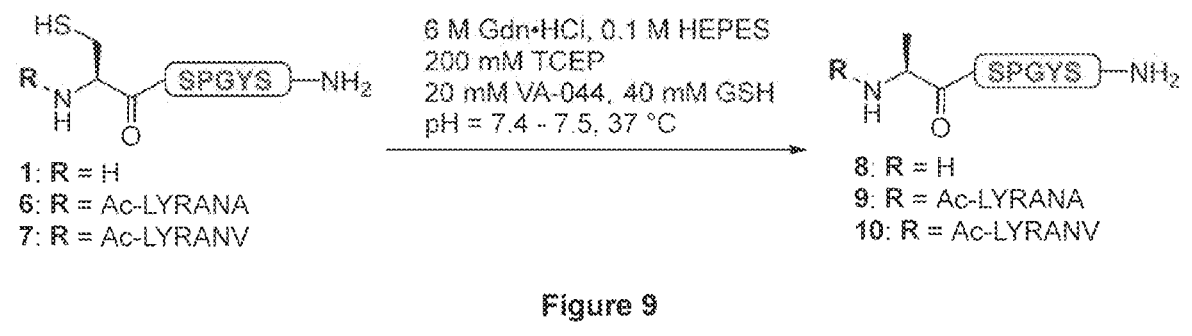

Having established an optimized protocol for NCL in flow the inventors investigated whether desulfurization could be carried out under a similar manifold. A general scheme for the desulfurization of Cys-containing peptides 1, 6 or 7 is shown in FIG. 9.

Figure 10:
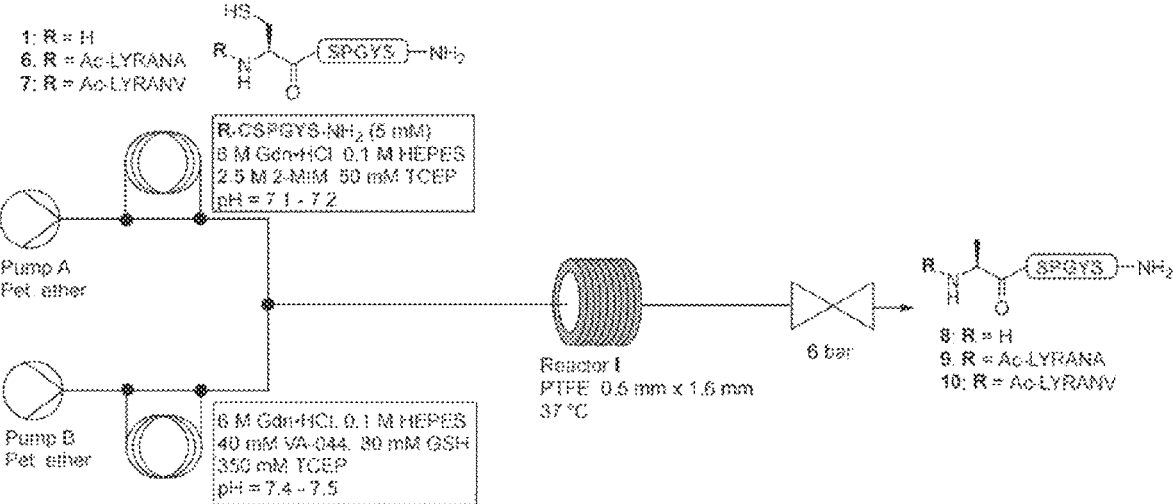
FIG. 10: Flow system used to perform standard desulfurization within a flow manifold.

Cys-containing peptide 1, 6 or 7 was solvated in degassed ligation buffer (5 mM) containing 6 M Gdn·HCl, 0.1 M HEPES, 50 mM TCEP and 2.5 M 2-MIM (pH 7.3-7.4). A second solution was prepared containing 40 mM VA-044 and 80 mM GSH in degassed ligation buffer comprising 6 M Gdn·HCl, 0.1 M HEPES and 350 mM TCEP (pH 7.4-7.5). These two solutions were inserted into injection loops and combined at a T-piece on a 150 µL scale using petroleum ether as the system solvent (FIG. 10). The resulting reaction stream then entered PTFE coil reactor I heated to 37° C. Desulfurization time-courses were obtained via altering the reactor volume and flow rate to modulate the residence time. The reaction solution exited the system through a 6 bar BPR and was quenched in an equal volume of neutral 15 mM MPAA solution in Milli-Q water. A 5 µL aliquot of this solution was diluted with 40 µL of 0.1% TFA in Milli-Q water and analyzed by UPLC. Conversion estimates were based on the relative peak areas of the starting material and the desulfurized product at $\lambda=280$ nm [$\varepsilon_{280}(1, 8)=1280$ M$^{-1}$ cm$^{-1}$, $\varepsilon_{280}(6, 7, 9, 10)=2560$ M$^{-1}$ cm$^{-1}$].

Standard Desulfurization in Batch

A comparative desulfurization reaction of Cys-containing peptides 1, 6 or 7 in batch was conducted.

Cys-containing peptide 1, 6 or 7 was solvated in degassed ligation buffer (5 mM) containing 6 M Gdn·HCl, 0.1 M HEPES and 50 mM TCEP (pH 7.3-7.4). A second solution was prepared containing 40 mM VA-044 and 80 mM reduced L-glutathione (GSH) in 6 M Gdn·HCl, 0.1 M HEPES and 350 mM TCEP (pH 7.4-7.5). These solutions were combined at a 150 μL scale (1:1 vol/vol) in a polypropylene microcentrifuge tube and gently agitated before incubation at 37° C. (FIG. 9). Desulfurization time-courses were obtained by quenching 5 μL aliquots with 3 μL of a neutral 25 mM MPAA solution in Milli-Q water at various timepoints. This solution was diluted with 40 UL of 0.1% TFA in Milli-Q water and analyzed by UPLC. Conversion estimates were based on the relative peak areas of the starting material and the desulfurized product at $\lambda=280$ nm [£280 (1, 8)=1280 M$^{-1}$ cm$^{-1}$, $\varepsilon_{280}(6, 7, 9, 10)=2560$ M$^{-1}$ cm$^{-1}$].

Figure 11:
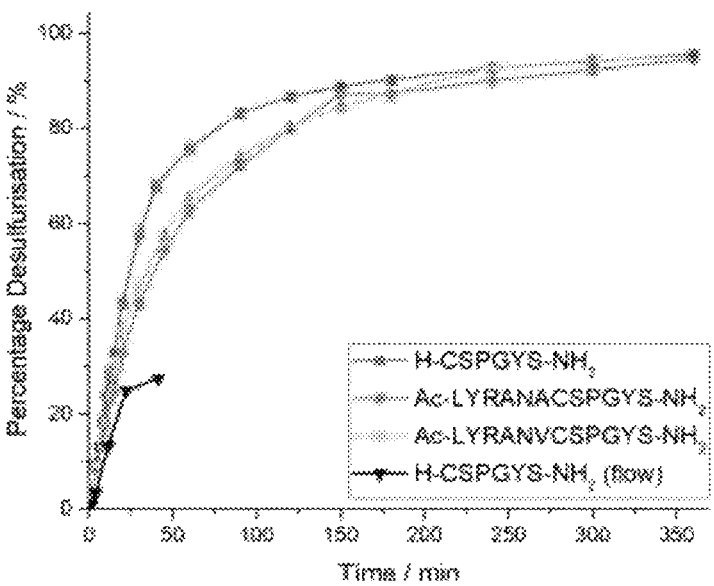
FIG. 11: Kinetics of desulfurization of 1, 6 and 7 in batch, and 1 in flow when using VA-044 to chemically initiate desulfurization without UV irradiation
Figure 12:
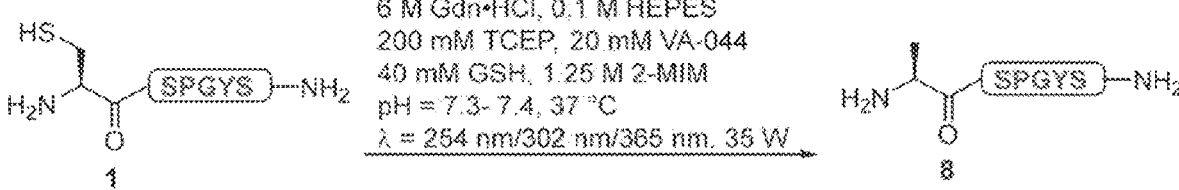
FIG. 12: General scheme for the photodesulfurization of 1 with VA-044 and UV photoirradiation.
Figure 13:
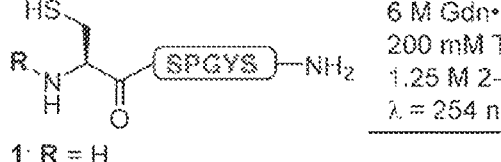
FIG. 13: General scheme for the photodesulfurization of 1, 6 and 7 with UV photoirradiation in the absence of VA-044.
Figure 14:
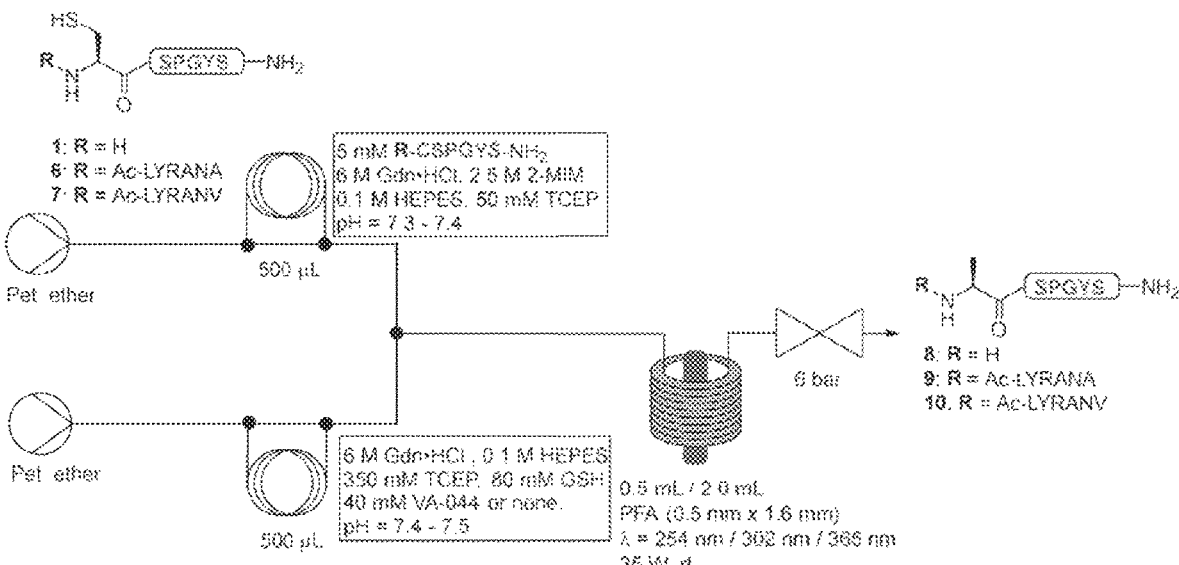
FIG. 14: Flow system used to perform photodesulfurization of peptides 1, 6 and 7.
Figure 15:
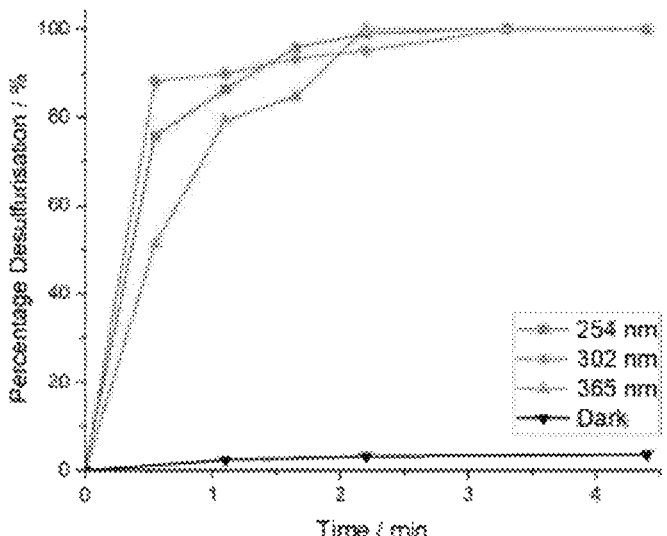
FIG. 15: Kinetics in flow of desulfurization of H-CSPGYS-NH$_2$ (SEQ ID NO: 1) 1 in the presence of 20 mM VA-044 at different wavelengths of UV irradiation inside a Rayonet RPR-100 UV photoreactor (35 W, rt).

The results for desulfurization performed in batch and flow using the chemical radical initiator VA-044 (20 mM) and 40 mM GSH, are set out in FIG. 11.

Photodesulfurization in Flow

A protocol for desulfurizing in the presence or absence of a chemical radical inhibitor was developed.

Cys-containing peptide 1, 6 or 7 was solvated in degassed ligation buffer (5 mM) containing 6 M Gdn·HCl, 0.1 M HEPES, 50 mM TCEP and 2.5 M 2-MIM (pH 7.3-7.4). A second solution was prepared containing 40 mM VA-044 or no VA-044, and 80 mM GSH in degassed ligation buffer comprising 6 M Gdn·HCl, 0.1 M HEPES and 350 mM TCEP. These two solutions were inserted into injection loops and combined at a T-piece on a 150 μL scale using petroleum ether as the system solvent (FIGS. 12-17). The resulting reaction stream entered a PFA coil reactor inside a Rayonet RPR-100 UV photoreactor at $\lambda=254$ nm, 302 nm, or 365 nm (35 W, rt). Desulfurization time-courses were obtained via altering the reactor volume and flow rate to modulate the residence time. The reaction solution exited the system through a 6 bar BPR and was quenched in an equal volume of neutral 25 mM MPAA solution in Milli-Q water. A 5 μL aliquot of this solution was diluted with 40 UL of 0.1% TFA in Milli-Q water and analyzed by UPLC. Conversion estimates were based on the relative peak areas of the starting material and the desulfurized product at $\lambda=280$ nm [$\varepsilon_{280}(1, 8)=1280$ M$^{-1}$ cm$^{-1}$, $\varepsilon_{280}(6, 7, 9, 10)=2560$ M$^{-1}$ cm$^{-1}$].

Photodesulfurization in Batch

A comparative photodesulfurization reaction of Cys-containing peptides 1, 6 or 7 in batch was conducted.

Cys-containing peptides 1, 6 or 7 were solvated in degassed ligation buffer (5 mM) containing 6 M Gdn·HCl, 0.1 M HEPES, 50 mM TCEP and 2.5 M 2-MIM (pH 7.3-7.4). A second solution was prepared containing 40 mM VA-044 (FIG. 12) or no VA-044 (FIG. 13), and 80 mM GSH in degassed ligation buffer comprising 6 M Gdn·HCl, 0.1 M HEPES and 350 mM TCEP (pH 7.4-7.5). These solutions were combined at a 150 μL scale (1:1 vol/vol) in a polypropylene microcentrifuge tube and gently agitated prior to photoirradiation using a Rayonet RPR-100 UV photoreactor at $\lambda=254$ nm, 302 nm, or 365 nm (35 W, rt). Desulfurization time-courses were obtained via quenching 5 μL aliquots with 3 L of a neutral 25 mM MPAA solution in Milli-Q water at various timepoints. This solution was diluted with 40 μL of 0.1% TFA in Milli-Q water and analyzed by UPLC. Conversion estimates were based on the relative peak areas of the starting material and the desulfurized product at $\lambda=280$ nm [$\varepsilon_{280}(1, 8)=1280$ M$^{-1}$ cm$^{-1}$, $\varepsilon^{280}(6, 7, 9, 10)=2560$ M$^{-1}$ cm$^{-1}$].

In the absence of the chemical radical initiator VA-044, clean conversion of 1 to the desulfurized product 8 was observed in only 15 sec upon photo-irradiation at A=254 nm (35 W) at rt (FIGS. 17A & B). Products 6 and 7 (possessing internal Cys residues) from the earlier flow NCL reactions were also submitted to these photodesulfurization conditions and cleanly generated 9 and 10 in 60-90 sec (FIG. 17C). The reaction was also chemoselective in the presence of potentially reactive side chains, e.g. methionine and side chain protected Cys residues (FIGS. 18-20). Finally, peptides bearing penicillamine and β-thiol-aspartate residues were photodesulfurized cleanly in <1 min to afford native valine and aspartate residues, respectively (FIGS. 21 and 22). Photoirradiation under flow minimised product degradation compared to batch reactions.

The inventors have developed a novel method for desulfurizing an amide containing compound comprising a thiol group. The method comprises exposing the compound to UV irradiation in the presence of a phosphine source, optionally further including a hydrogen atom source. The method is suitable for batch and flow. Surprisingly no chemical radical initiator is required.

Ligation-Photodesulfurization in Flow

Having optimized the ligation and photodesulfurization reactions in flow, these were then combined into an "in-line" ligation-photodesulfurization 20 μmol flow experiment.

A 20 μmol flow experiment was performed whereby a solution of 1 (10 mM in ligation buffer with 5 M 2-MIM and 50 mM TCEP) was mixed at a T-piece with thioesters 4 or 5 (20 mM in ligation buffer with 50 mM TCEP, FIG. 23). After passing through a PTFE coil reactor at 37° C. (4:3 min, 5:11 min), the product was mixed at a second T-piece with a stream of 250 mM GSH and 350 mM TCEP in ligation buffer and directed to a second PTFE reactor at 37° C. (4:1 min, 5:6 min) to thiolyze any product thioesters generated by trans-thioesterification between the internal Cys of the ligation product 6 or 7 and excess thioesters 4 or 5 (FIGS. 24-28). Finally, the reaction mixture was photoirradiated ($\lambda=254$ nm) for 1 min to facilitate photodesulfurization before collection (see FIGS. 23B and 23C and FIGS. 29-30). Following HPLC purification, the desired products were isolated in excellent yields over the two steps (9:17 mg, 65%, 10:17 mg, 63%). The peptides were also generated on rapid timescales; a total reaction time of 5 min for 9 and only 18 min for 10 was required, the latter representing one of the most challenging ligation junctions (Val thioester).

One-Pot Ligation-Photodesulfurization in Batch

A one-pot ligation-photodesulfurization procedure was performed on a 20 μmol scale in batch.

Two 2.0 mL solutions were prepared, one containing 10 mM H-CSPGYS-NH$_2$ (SEQ ID NO: 1) 1, 50 mM TCEP and 5.0 M 2-MIM in degassed ligation buffer (6 M Gdn·HCl, 0.1 M HEPES, pH 7.4-7.5), and the other containing 20 mM Ac-LYRANX-SCH$_2$CF$_3$ (4: X=A, SEQ ID NO: 4; 5: X=V, SEQ ID NO: 5) and 50 mM TCEP in ligation buffer (6 M Gdn·HCl, 0.1 M HEPES, pH 7.1-7.2). A desulfurization solution was prepared, containing GSH (250 mM) and TCEP (350 mM) in 5.0 mL ligation buffer (6 M Gdn·HCl, 0.1 M HEPES, pH 7.4-7.5). Upon degassing, the two ligations solutions were combined and actively mixed at 37° C. Upon complete ligation as determined by UPLC (X=A:

6 min, X=V: 40 min), the reaction solution was transferred to a 15 mL Corning™ Falcon™ polypropylene conical centrifuge tube and combined with 4.0 mL of the desulfurization solution. This mixture was photoirradiated at λ=254 nm (35 W, rt) (FIG. 31). Upon completion by UPLC (X=A: 2.5 h; X=V: 2.5 h), the product was immediately isolated using RP-HPLC (X=A: 9, total processing time of 2.6 h, isolated yield 66%; X=V: 10, total processing time of 3.2 h, isolated yield 66%. Processing time refers to the total time taken for complete injection and reaction).

Notably, an order of magnitude increase in the reaction time was observed when using pre-activated thioesters (4:2.6 h, 5:3.2 h, FIGS. 31 and 32) in batch compared to flow. Furthermore, the flow NCL-photodesulfurization process was two orders of magnitude faster compared to a traditional ligation-desulfurization reaction in batch (with thioesters 2 or 3 and TFET as an additive), whilst affording comparable isolated yields (FIGS. 33-35).

Synthesis of Enfuvirtide

Enfuvirtide is a clinically approved 36-residue peptide HIV entry inhibitor. It is produced commercially by the condensation of three protected fragments in organic solvent. Enfuvirtide was prepared by NCL-photodesulfurization in flow by reacting peptide 11 (enfuvirtide 1-18, SEQ ID NO: 11) bearing a C-terminal lysine, derivatized as a trifluoroethyl thioester, with peptide 12 (enfuvirtide 19-36, SEQ ID NO: 12) bearing an N-terminal β-thiol-asparagine residue (FIG. 36).

Both peptides were made using Fmoc-SPPS.

Enfuvirtide(1-18) Trifluoroethyl Thioester (SEQ ID NO: 11)

Hydrazine-derived 2-chlorotrityl chloride resin (copoly (styrene-1% DVB) 100-200 mesh) was loaded with Fmoc-Lys (Boc)-OH (125 µmol, 1.6 mmol/g) and the peptide was elongated using automated Fmoc-SPPS, as described in the general procedures. The fully assembled resin-bound peptide was cleaved from the resin via treatment with TFA/iPr$_3$SiH/H$_2$O (90:5:5 v/v/v) with concomitant deprotection of all side-chain protecting groups. The reaction was stirred at room temperature for 2 h and concentrated in vacuo. The fully deprotected peptide acyl hydrazide was solvated in aqueous ligation buffer (6 M Gdn·HCl, 0.1 M HEPES, pH 3.0) to 10 mM concentration and cooled to −15° C. To this was added an aqueous solution of NaNO$_2$ (1 M, 10 equiv., 1.25 mL). After 10 minutes TFET (20 equiv., 221 µL) was added (warning: TFET is pungent and acutely toxic and should be used in a fume cupboard). The solution was allowed to warm to room temperature and stirred for 45 min. Complete conversion to the thioester was confirmed by UPLC-MS and the crude material was purified by HPLC (20-60% B over 40 min, 0.1% TFA) to afford peptide 11 as a white solid following lyophilization (70 mg, 22% yield based on original resin loading). UPLC: Rt 4.52 min (λ=230 nm, 0 to 60% B over 5 min, 0.1% TFA); Calculated Mass [M+2H]2+: 1144.5, [2M+3H]3+: 1525.7, [3M+4H]4+: 1716.0, [4M+5H]5+: 1830.6. Mass Found (ESI+): 1144.7 [M+2H]2+, 1526.0 [2M+3H]3+, 1716.7 [3M+4H]4+, 1831.0 [4M+5H]5+ (ESI-MS data was collected over the entire gradient and wash cycle of the UPLC-MS). 19F{1H} NMR (376 MHZ, d6-DMSO) δ −65.1 ppm. NMR spectra of enfuvirtide(1-18) 11 is shown in FIGS. 59-61.

Enfuvirtide(19-36)

(SEQ ID NO: 12)

Fmoc-Phe-OH was loaded onto Rink amide resin (copoly (styrene-1% DVB) 100-200 mesh) (100 µmol) and the peptide was elongated using automated Fmoc-SPPS as outlined in the general procedures. A preactivated solution of β-thiol asparagine S11 (1.20 equiv.), PyAOP (1.20 equiv.), and NMM (2.40 equiv.) in DMF (final concentration 0.1 M) was added to the resin. After 2 h of gentle agitation at room temperature, the resin was washed with DMF (5×3 mL), CH2Cl2 (5×3 mL) and DMF (5×3 mL). The fully protected resin-bound peptide was cleaved from the solid-support and deprotected using a solution of TFA/iPr$_3$SiH/H$_2$O/EDT (89: 5:5:1 v/v/v/v). The reaction was agitated at room temperature for 2 h and concentrated in vacuo. Crude peptide 12 was precipitated from cold Et$_2$O, and the crude product purified by preparative reverse-phase (20-80% B over 40 min, 0.1% TFA) to yield peptide 12 as a white solid following lyophilization (51.6 mg, 20% yield based on original resin loading). UPLC: Rt 4.43 min (λ=214 nm, 0 to 60% B over 5 min, 0.1% TFA); Calculated Mass [M+2H]2+: 1177.1, [2M+3H]3+: 1569.1. Mass Found (ESI+): 1177.2 [M+2H] 2+, 1569.3 [2M+3H]3+. (ESI-MS data was collected over the entire gradient and wash cycle of the UPLC-MS). NMR spectrum of enfuvirtide(19-36) 12 is shown in FIG. 62.

Enfuvirtide (SEQ ID NO: 13)

A solution of enfuvirtide(19-36) 12 (5 μmol, 12.9 mg, 10 mM) was prepared in ligation buffer (6 M Gdn·HCl, 0.1 M HEPES) containing 50 mM TCEP and 5.0 M 2-MIM (pH 7.0). A second solution of enfuvirtide(1-18) 11 (10 μmol, 25.1 mg, 20 mM) was prepared in ligation buffer (6 M Gdn·HCl, 0.1 M HEPES) containing 50 mM TCEP (pH 6.2). A desulfurization solution was prepared in ligation buffer (6 M Gdn·HCl, 0.1 M HEPES) containing 800 mM TCEP and 250 mM GSH (pH 7.5). The ligation solutions were inserted into 0.50 mL injection loops, and the desulfurization solution was inserted into a 2.0 mL injection loop (FIG. 36). The two peptide solutions were first combined (0.20 mL/min) at a T-piece on a 5 μmol scale using petroleum ether as the system solvent. The resulting reaction stream entered a PTFE coil reactor (0.5 mm×1.6 mm, 12.0 mL) at 37° C. The reaction solution was then combined with the desulfurization solution (0.40 mL/min) at a second T-piece and entered a second PTFE coil reactor (0.5 mm×1.6 mm, 1.0 mL) at 37° C., followed by a final PFA coil reactor (0.5 mm×1.6 mm, 2.5 mL) inside a Rayonet RPR-100 photoreactor (λ=254 nm, 35 W, rt). The reaction mixture was collected through a 6 bar BPR (total processing time 38 min) and immediately purified using RP-HPLC to afford a fluffy white solid (9.7 mg, 40%, 0.8 μmol/min). UPLC: Rt 5.75 min (λ=214 nm, 0 to 70% B over 5 min, 0.1% TFA); Calculated Mass [M+3H]3+: 1498.1, [M+4H]4+: 1123.8; Mass Found (ESI+); 1498.1 [M+3H]3+, 1124.0 [M+4H]4+. (ESI-MS data was collected over the entire gradient and wash cycle of the UPLC-MS) (FIG. 37). NMR spectra of enfuvirtide 13 is shown in FIGS. 63 and 64.

This result clearly demonstrates the utility of the flow methodology in complex target assembly, as well as the compatibility with thiolated amino acids in addition to Cys. Synthesis of Somatorelin Somatorelin is a 44-residue peptide used as a diagnostic agent for determining growth hormone deficiency. Somatorelin was prepared by NCL-photodesulfurization in flow by reacting peptide 14 (somatorelin 1-18, SEQ ID NO: 14), bearing a C-terminal thioester, and peptide 15 (somatorelin 19-44, SEQ ID NO: 15), containing an N-terminal Cys residue (FIG. 38).

Both peptides were prepared using Fmoc-SPPS. Somatorelin(1-18) Trifluoroethyl Thioester (SEQ ID NO: 14)

Hydrazine-derived 2-chlorotrityl chloride resin (copoly (styrene-1% DVB) 100-200 mesh) was loaded with Fmoc-Ser (OtBu)-OH (250 μmol, 1.1 mmol/g) and the peptide was elongated using microwave-assisted automated Fmoc-SPPS, as described in the general procedures. Double coupling was performed at position 1-8, 11-13 and 15-16 of the N-terminal segment with N-acetylglycine capping performed from position 13 (Valine). After synthesis the resin was washed with DMF (5×10 mL) and CH2Cl2 (5×10 mL) before drying in vacuo. The full-length resin-bound peptide was then cleaved from the resin via treatment with TFA/iPr$_3$SiH/H$_2$O (90:5:5 v/v/v) for 2 h which led to concomitant deprotection of all side-chain protecting groups. The cleavage cocktail was concentrated in vacuo then the crude peptide was precipitated from cold Et$_2$O, and dried in vacuo. Fully deprotected peptide acyl hydrazide (225 mg) was solvated in aqueous ligation buffer (6 M Gdn·HCl, 0.1 M HEPES, pH 3.0) to a concentration of 10 mM and cooled to −15° C. To this was added an aqueous solution of NaNO$_2$ (1 M, 10 equiv., 1.125 mL). After 10 minutes TFET (20 equiv., 186 μL) was added and the solution allowed to warm to room temperature and stirred for 45 min (warning: TFET is pungent and acutely toxic and should be used in a fume cupboard).

Complete conversion to the thioester was confirmed by UPLC-MS and the product was purified by preparative reverse-phase HPLC (20-35% B over 40 min, 0.1% TFA) to yield peptide 14 as a fluffy white solid following lyophilization (3×250 μmol syntheses; 272.0 mg, 14.6% yield based on original resin loading). UPLC: Rt 4.25 min (λ=214 nm, 0 to 50% B over 5 min, 0.1% TFA); Calculated Mass [M+3H]3+: 715.7, [M+2H]2+: 1073.0, [2M+3H]3+: 1430.4. Mass Found (ESI+): 715.8 [M+3H]3+, 1073.3 [M+2H]2+, 1430.7 [2M+3H]3+ (ESI-MS data was collected over the entire gradient and wash cycle of the UPLC-MS). 19F{1H}

NMR (471 MHZ, D2O) δ −66.4 ppm. NMR spectra of somatorelin(1-18) 14 is shown in FIGS. 65 and 66.
Somatorelin(19-44)

(SEQ ID NO: 15)

Fmoc-Leu-OH was loaded to Rink amide resin (copoly (styrene-1% DVB) 100-200 mesh) (250 μmol) and the peptide was elongated using microwave-assisted automated Fmoc-SPPS as outlined in the general procedures. All residues in the sequence were double coupled, except for Fmoc-(DMB) Gly-OH at position 32 which was installed by single coupling. Capping was performed using N-acetylglycine after the incorporation of this residue. After synthesis the resin was washed well with DMF (5×10 mL) then CH2Cl2 (5×10 mL) then dried in vacuo, and the fully protected resin-bound peptide was cleaved from the solid-support and deprotected using a solution of TFA/iPr₃SiH/ H₂O/thioanisole/2,2'-(ethylenedioxy)diethanethiol (90:2.5: 2.5:2.5:2.5 v/v/v/v/v). The reaction was agitated at room temperature for 2 h and concentrated in vacuo. Crude peptide 15 was precipitated from cold Et₂O, and the product purified by preparative reverse-phase HPLC (5-30% B over 40 min, 0.1% TFA) to yield peptide 15 as a white solid following lyophilization (234.0 mg, 24% yield based on original resin loading). UPLC: Rt 3.35 min (λ=214 nm, 0 to 50% B over 5 min, 0.1% TFA); Calculated Mass [M+6H]6+: 508.1, [M+5H]5+: 609.5, [M+4H]4+: 761.7, [M+3H]3+: 1015.2, [M+2H]2+: 1522.3. Mass Found (ESI+): 508.2 [M+6H]6+, 609.7 [M+5H]5+, 761.9 [M+4H]4+, 1015.5 [M+3H]3+, 1522.6 [M+2H]2+. (ESI-MS data was collected over the entire gradient and wash cycle of the UPLC-MS). NMR spectra of somatorelin(19-44) 15 is shown in FIGS. 67 and 68.
Somatorelin stream entered a PTFE coil reactor (0.5 mm×1.6 mm, 5.0 mL) at 37° C. The reaction solution was then combined with the desulfurization solution (0.10 mL/min) at a second T-piece and entered a second PTFE coil reactor (0.5 mm×1.6 mm, 1.0 mL) at 37° C., followed by a final PFA coil reactor (0.5 mm×1.6 mm, 2.5 mL) inside a Rayonet RPR-100 photoreactor (λ=254 nm, 35 W, rt). The reaction mixture was collected through a 6 bar BPR (total processing time 27 min) and immediately purified using RP-HPLC to afford a fluffy white solid (102.9 mg, 57%, 1.4 μmol/min). UPLC: Rt 4.20 min (λ=214 nm, 0 to 70% B over 5 min, 0.1% TFA); Calculated Mass [M+7H]7+: 720.8, [M+6H]6+: 840.8, [M+5H]5+: 1008.7, [M+4H]4+: 1260.7, [M+3H]3+: 1680.6. Mass Found (ESI+): 720.9 [M+7H]7+, 840.9 [M+6H]6+, 1008.8 [M+5H]5+, 1260.9 [M+4H]4+, 1680.9 [M+3H]3+. (ESI-MS data was collected over the entire gradient and wash cycle of the UPLC-MS). (FIG. 39). NMR spectra of somatorelin 16 is shown in FIGS. 69 and 70.

Model Peptides and Peptide Thioesters

H-CSPGYS-NH₂ (1, SEQ ID NO: 1)

A solution of somatorelin(19-44) 15 (30 μmol, 115.2 mg, 10 mM) was prepared in ligation buffer (6 M Gdn·HCl, 0.1 M HEPES) containing 50 mM TCEP and 5.0 M 2-MIM (pH 7.0). A second solution of somatorelin(1-18) trifluoroethyl thioester 14 (60 μmol, 149.1 mg, 20 mM) was prepared in ligation buffer (6 M Gdn·HCl, 0.1 M HEPES) containing 50 mM TCEP (pH 6.2). A desulfurization solution was prepared in ligation buffer (6 M Gdn·HCl, 0.1 M HEPES) containing 800 mM TCEP and 250 mM GSH (pH 7.5). The peptide solutions were inserted into 3.0 mL injection loops, and the desulfurization solution into a 7.0 mL injection loop (Scheme S24). The two peptide solutions were first combined (0.25 mL/min) at a T-piece on a 30 μmol scale using petroleum ether as the system solvent. The resulting reaction Peptide 1 was synthesized using the outlined procedure for Fmoc-strategy SPPS on Rink amide resin (730 μmol). The peptide was cleaved from resin and deprotected under acidic conditions according to general procedures. Purification via preparative reverse-phase HPLC (0 to 20% B over 40 min, 0.1% TFA) followed by lyophilization afforded peptide 1 as a white solid (257 mg, 57% yield). UPLC: Rt 3.99 min (0 to 15% B over 5 min, 0.1% TFA, λ=214 nm); Calculated Mass [M+H]⁺: 612.2. Mass Found (ESI⁺): 612.5 [M+H]⁺. (ESI-MS data was collected over the entire gradient and wash cycle of the UPLC-MS). ¹H NMR spectrum (D₂O, 500 MHZ) of H-CSPGYS-NH₂ (1, SEQ ID NO: 1) is shown in FIG. 45.

Ac-LYRANA-S(CH$_2$)$_2$CO$_2$Et (2, SEQ ID NO: 2)

The fully sidechain protected peptide 2 was synthesized using the outlined procedure for Fmoc-strategy SPPS on 2-CTC resin (730 μmol). The protected peptide was cleaved from resin, thioesterified and deprotected according to general procedures. Purification via preparative reverse-phase HPLC (0 to 40% B over 40 min, 0.1% TFA) followed by lyophilization afforded peptide 2 as a white solid (288 mg, 46% yield). UPLC: Rt 3.63 min (0 to 30% B over 5 min, 0.1% TFA, λ=214 nm); Calculated Mass [M+H]$^+$: 865.4, [M+2H]$^{2+}$: 433.2. Mass Found (ESI$^+$): 865.8 [M+H]$^+$, 433.4 [M+2H]$^{2+}$. (ESI-MS data was collected over the entire gradient and wash cycle of the UPLC-MS). $^1$H NMR spectrum (D$_2$O, 500 MHZ) of Ac-LYRANA-S(CH$_2$)$_2$CO$_2$Et (2, SEQ ID NO: 2) is shown in FIG. 46.

Ac-LYRANV-S(CH$_2$)$_2$CO$_2$Et (3, SEQ ID NO: 3)

The fully sidechain protected peptide 3 was synthesized using the outlined procedure for Fmoc-strategy SPPS on 2-CTC resin (350 μmol). The protected peptide was cleaved from resin, thioesterified and deprotected according to general procedures. Purification via preparative reverse-phase HPLC (0 to 40% B over 40 min, 0.1% TFA) followed by lyophilization afforded peptide 3 as a white solid (128 mg, 41% yield). UPLC: Rt 3.89 min (0 to 30% B over 5 min, 0.1% TFA, λ=214 nm); Calculated Mass [M+H]$^+$: 893.5, [M+2H]$^{2+}$: 447.2. Mass Found (ESI$^+$): 893.9 [M+H]$^+$, 447.4 [M+2H]$^{2+}$. (ESI-MS data was collected over the entire gradient and wash cycle of the UPLC-MS). $^1$H NMR spectrum (D$_2$O, 500 MHZ) of Ac-LYRANV-S(CH$_2$)$_2$CO$_2$Et (3, SEQ ID NO: 3) is shown in FIG. 47.

Ac-LYRANA-SCH$_2$CF$_3$ (4, SEQ ID NO: 4)

The peptide acyl hydrazide of 4 was synthesized using the outlined procedure for Fmoc-strategy SPPS on 2-CTC resin (480 μmol) functionalized with hydrazine. Cleavage from the resin and global deprotection was afforded under acidic conditions according to the general procedures, followed by diazotization and thioesterification of the crude product. Purification via preparative reverse-phase HPLC (0 to 40% B over 40 min, 0.1% TFA) followed by lyophilization afforded peptide 4 as a white solid (351 mg, 86% yield). UPLC: Rt 3.73 min (0 to 30% B over 5 min, 0.1% TFA, λ=214 nm); Calculated Mass [M+H]$^+$: 847.4, [M+2H]$^{2+}$: 424.2. Mass Found (ESI$^+$): 847.7 [M+H]$^+$, 424.4 [M+2H]$^{2+}$ (ESI-MS data was collected over the entire gradient and wash cycle of the UPLC-MS). $^{19}$F{$^1$H} NMR (471 MHZ, D$_2$O) δ −66.5 ppm. NMR spectra of AC-LYRANA-SCH$_2$CF$_3$ (4, SEQ ID NO: 4) is shown in FIGS. 48-50.

Ac-LYRANV-SCH$_2$CF$_3$ (5, SEQ ID NO: 5)

The peptide acyl hydrazide of 5 was synthesized using the outlined procedure for Fmoc-strategy SPPS on 2-CTC resin (640 μmol) functionalized with hydrazine. Cleavage from the resin and global deprotection was afforded under acidic conditions according to the general procedures, followed by diazotization and thioesterification of the crude product. Purification via preparative reverse-phase HPLC (0 to 40% B over 40 min, 0.1% TFA) followed by lyophilization afforded peptide 5 as a white solid (431 mg, 77% yield). UPLC: Rt 4.05 min (0 to 30% B over 5 min, 0.1% TFA, λ=214 nm); Calculated Mass [M+H]$^+$: 875.4, [M+2H]$^{2+}$: 438.2. Mass Found (ESI$^+$): 875.8 [M+H]$^+$, 438.4 [M+2H]$^{2+}$ (ESI-MS data was collected over the entire gradient and wash cycle of the UPLC-MS). $^{19}$F{$^1$H} NMR (471 MHZ, D$_2$O) δ −66.5 ppm. NMR spectra of Ac-LYRANV-SCH$_2$CF$_3$ (5, SEQ ID NO: 5) is shown in FIGS. 51-53.

Ac-LYRANACSPGYS-NH$_2$ (6, SEQ ID NO: 6)

Batch synthesis of 6: Ligation of H-CSPGYS-NH$_2$ (SEQ ID NO: 1) 1 (12.2 mg, 20 µmol, 5 mM) and Ac-LYRANA-SCH$_2$CF$_3$ (SEQ ID NO: 4) 4 (33.9 mg, 40 µmol, 10 mM) in batch (2.5 M 2-MIM, 37° C., t=6.0 min) was performed according to general procedures with active stirring of the reaction solution. Purification via preparative reverse-phase HPLC (0 to 40% B over 40 min, 0.1% TFA) followed by lyophilization afforded peptide 6 as a white solid (18.3 mg, 68% yield). UPLC: Rt 5.23 min (0 to 28% B over 5 min, 0.1% TFA, λ=214 nm); Calculated Mass [M+H]$^+$: 1342.6, [M+2H]$^{2+}$: 671.8. Mass Found (ESI$^+$): 1343.6 [M+H]$^+$, 672.4 [M+2H]$^{2+}$. (ESI-MS data was collected over the entire gradient and wash cycle of the UPLC-MS).

Flow synthesis of 6: Ligation of H-CSPGYS-NH$_2$ (SEQ ID NO: 1) 1 (12.2 mg, 20 µmol, 5 mM) and Ac-LYRANA-SCH$_2$CF$_3$ (SEQ ID NO: 4) 4 (33.9 mg, 40 µmol, 10 mM) was performed with 2.5 M 2-MIM in flow (Pump A, B: 0.50 mL/min, Reactor I: 3.0 mL, T=37° C., τI (residence time)= 3.3 min) according to general procedures. Purification via preparative reverse-phase HPLC (0 to 40% B over 40 min, 0.1% TFA) followed by lyophilization afforded peptide 6 as a white solid (18.0 mg, 67% yield, 3.4 µmol/min). Analytical data is identical to 6 as prepared above. $^1$H NMR spectrum (D$_2$O, 500 MHZ) of Ac-LYRANACSPGYS-NH$_2$ (6, SEQ ID NO: 6) is shown in FIG. 54.

Ac-LYRANVCSPGYS-NH$_2$ (7, SEQ ID NO: 7)

Batch synthesis of 7: Peptide ligation of H-CSPGYS-NH$_2$ (SEQ ID NO: 1) 1 (12.2 mg, 20 μmol, 5 mM) and Ac-LYRANV-SCH$_2$CF$_3$ (SEQ ID NO: 5) 5 (35.0 mg, 40 μmol, 10 mM) was performed in batch (37° C., 2.5 M 2-MIM, t=40.0 min) according to general procedures with active mixing of the reaction solution. Purification via preparative reverse-phase HPLC (0 to 40% B over 40 min, 0.1% TFA) followed by lyophilization afforded peptide 7 as a white solid (18.6 mg, 67% yield). UPLC: Rt 5.80 min (0 to 28% B over 5 min, 0.1% TFA, λ=214 nm); Calculated Mass [M+H]$^+$: 1370.7, [M+2H]$^{2+}$: 685.8. Mass Found (ESI$^+$): 1372.1 [M+H]$^+$, 686.3 [M+2H]$^{2+}$. (ESI-MS data was collected over the entire gradient and wash cycle of the UPLC-MS).

(λ=254 nm, 125 mM GSH, t=1.0 min) according to the general procedure outlined above. Purification via preparative reverse-phase HPLC (0 to 20% B over 30 min, 0.1% TFA) followed by lyophilization afforded peptide 8 as a white solid (2.5 mg, 82% yield). UPLC: Rt 3.72 min (0 to 15% B over 5 min, 0.1% TFA, λ=214 nm); Calculated Mass [M+H]$^+$: 580.3. Mass Found (ESI$^+$): 580.4 [M+H]$^+$. (ESI-MS data was collected over the entire gradient and wash cycle of the UPLC-MS). $^1$H NMR spectrum (D$_2$O, 400 MHZ) of H-ASPGYS-NH$_2$ (8, SEQ ID NO:8) is shown in FIG. 56.

Ac-LYRANAASPGYS-NH$_2$ (9, SEQ ID NO: 9)

Flow synthesis of 7: Ligation of H-CSPGYS-NH$_2$ 1 (SEQ ID NO: 1; 12.2 mg, 20 μmol, 5 mM) and Ac-LYRANV-SCH$_2$CF$_3$ 5 (SEQ ID NO: 5; 35.0 mg, 40 μmol, 10 mM) was performed with 2.5 M 2-MIM in flow (Pump A, B: 0.50 mL/min, Reactor I: 10.0 mL, T=37° C., τI=10.8 min) according to general procedures. Purification via preparative reverse-phase HPLC (0 to 40% B over 40 min, 0.1% TFA) followed by lyophilization afforded peptide 7 as a white solid (18.0 mg, 65% yield, 3.3 μmol/min). Analytical data was identical to 7 as prepared above. $^1$H NMR spectrum (D$_2$O, 500 MHZ) of Ac-LYRANVCSPGYS-NH$_2$ (7, SEQ ID NO: 7) is shown in FIG. 55.

H-ASPGYS-NH$_2$ (8, SEQ ID NO: 8)

Photodesulfurization of H-CSPGYS-NH$_2$ 1 (SEQ ID NO: 1; 3.2 mg, 5.2 μmol, 2.5 mM) was performed in batch Batch synthesis of 9, i: Ligation of H-CSPGYS-NH$_2$ 1 (SEQ ID NO: 1; 12.2 mg, 20 μmol, 5 mM) and Ac-LYRANA-S(CH$_2$)$_2$CO$_2$Et 2 (SEQ ID NO: 2; 34.6 mg, 40 μmol, 10 mM) was performed in batch (250 mM TFET, 25 min) (warning: TFET is pungent and acutely toxic and should be used in a fume cupboard) followed by in situ desulfurization (20 mM VA-044, 40 mM GSH, 37° C., t=16 h) with active mixing, according to general procedures. Purification via preparative reverse-phase HPLC (0 to 40% B over 40 min, 0.1% TFA) followed by lyophilization afforded peptide 9 as a white solid (18.1 mg, 69% yield). UPLC: Rt 5.15 min (0 to 28% B over 5 min, 0.1% TFA, λ=214 nm); Calculated Mass [M+H]$^+$: 1310.6, [M+2H]$^{2+}$: 655.8. Mass Found (ESI): 1311.4 [M+H]$^+$, 656.4 [M+2H]$^{2+}$. (ESI-MS data was collected over the entire gradient and wash cycle of the UPLC-MS).

Batch synthesis of 9, ii: Ligation of H-CSPGYS-NH$_2$ 1 (SEQ ID NO: 1; 12.2 mg, 20 μmol, 5 mM) and Ac-LYRANA-SCH$_2$CF$_3$ 4 (SEQ ID NO: 4; 33.9 mg, 40 μmol, 10 mM) was performed in batch with active mixing (2.5 M 2-MIM, 37° C., 6.0 min) followed by in situ photodesulfurization (125 mM GSH, λ=254 nm, rt, t=2.5 h) in a 15 mL Corning™ Falcon™ polypropylene conical centrifuge tube according to general procedures. Purification via preparative reverse-phase HPLC (0 to 40% B over 40 min, 0.1% TFA) followed by lyophilization afforded peptide 9 as a white solid (17.3 mg, 66% yield). Analytical data was identical to 9 prepared above.

Flow synthesis of 9: Ligation of H-CSPGYS-NH$_2$ 1 (SEQ ID NO: 1; 12.2 mg, 20 μmol, 5 mM) and Ac-LYRANA-SCH$_2$CF$_3$ 4 (SEQ ID NO: 4; 33.9 mg, 40 μmol, 10 mM) was performed in flow (2.5 M 2-MIM, Pump A, B: 0.25 mL/min, Reactor I: 1.5 mL, 37° C.) followed by novel in situ photodesulfurization (125 mM GSH, Pump C: 0.50 mL/min, Reactor II: 1.0 mL, Reactor III: 1.0 mL, λ=254 nm, rt) according to general procedures (τtotal=5.0 min). Purification via preparative reverse-phase HPLC (0 to 40% B over 40 min, 0.1% TFA) followed by lyophilization afforded peptide 9 as a white solid (17.0 mg, 65% yield, 1.6 μmol/min). Analytical data was identical to 9 prepared above. $^1$H NMR spectrum (D$_2$O, 500 MHZ) of Ac-LYRA-NAASPGYS-NH$_2$ (9, SEQ ID NO: 9) is shown in FIG. 57.

Ac-LYRANVASPGYS-NH$_2$ (10, SEQ ID NO: 10)

Batch synthesis of 10, i: Ligation of H-CSPGYS-NH$_2$ 1 (SEQ ID NO: 1; 12.2 mg, 20 μmol, 5 mM) and Ac-LYRANV-S(CH$_2$)$_2$CO$_2$Et 3 (SEQ ID NO: 3; 35.7 mg, 40 μmol, 10 mM) was performed in batch (250 mM TFET, t=9 h) (warning: TFET is pungent and acutely toxic and should be used in a fume cupboard) followed by in situ desulfurization (20 mM VA-044, 40 mM GSH, 37° C., t=16 h) with active mixing according to general procedures. Purification via preparative reverse-phase HPLC (0 to 40% B over 40 min, 0.1% TFA) followed by lyophilization afforded peptide 10 as a white solid (16.4 mg, 61% yield). UPLC: Rt 5.47 min (0 to 28% B over 5 min, 0.1% TFA, λ=214 nm); Calculated Mass [M+H]$^+$: 1338.7, [M+2H]$^{2+}$: 669.8. Mass Found (ESI$^+$): 1339.6 [M+H]$^+$, 670.3 [M+2H] $^{2+}$. (ESI-MS data was collected over the entire gradient and wash cycle of the UPLC-MS).

Batch synthesis of 10, ii: Ligation of H-CSPGYS-NH$_2$ 1 (SEQ ID NO: 1; 12.2 mg, 20 μmol, 5 mM) and Ac-LYRANV-SCH$_2$CF$_3$ 5 (SEQ ID NO: 5; 35.0 mg, 40 μmol, 10 mM) was performed in batch with active mixing (2.5 M 2-MIM, 37° C., t=40.0 min) followed by in situ photodesulfurization (125 mM GSH, λ=254 nm, rt, t=2.5 h) in a 15 mL Corning™ Falcon™ polypropylene conical centrifuge tube according to general procedures. Purification via preparative reverse-phase HPLC (0 to 40% B over 40 min, 0.1% TFA) followed by lyophilization afforded peptide 10 as a white solid (17.7 mg, 66% yield). Analytical data is identical to 10 prepared above.

Flow synthesis of 10: Ligation of H-CSPGYS-NH$_2$ 1 (SEQ ID NO: 1; 12.2 mg, 20 μmol, 5 mM) and Ac-LYRANV-SCH$_2$CF$_3$ 5 (SEQ ID NO: 5; 35.0 mg, 40 μmol, 10 mM) was performed in flow (2.5 M 2-MIM, Pump A, B: 0.20 mL/min, Reactor I: 4.0 mL, T=37° C.) followed by in situ photodesulfurization (125 mM GSH, Pump C: 0.40 mL/min, Reactor II: 5.0 mL, Reactor III: 1.0 mL, λ=254 nm, rt) according to general procedures (τtotal=17.5 min). Purification via preparative reverse-phase HPLC (0 to 40% B over 40 min, 0.1% TFA) followed by lyophilization afforded peptide 10 as a white solid (16.9 mg, 63% yield, 1.3 μmol/min). Analytical data is identical to 10 prepared above. $^1$H NMR spectrum (D$_2$O, 500 MHZ) of Ac-LYRAN-VASPGYS-NH$_2$ (10, SEQ ID NO: 10) is shown in FIG. 58.

Additional Characterization

Ac-(LYRANA)$_2$CSPGYS-NH$_2$ (S3, SEQ ID NO: 16)

Peptide ligation of H-CSPGYS-NH$_2$ 1 (SEQ ID NO: 1; 4.1 mg, 6.70 μmol, 5 mM) 1 and Ac-LYRANA-SCH$_2$CF$_3$ 4 (SEQ ID NO: 4; 11.3 mg, 13.4 μmol, 10 mM) in batch was performed as detailed under the general procedures (37° C., t=12.0 min), without hydrazinolysis of the product thioester. Purification via preparative reverse-phase HPLC (0 to 40% B over 40 min, 0.1% TFA) followed by lyophilization afforded peptide S3 as a white solid (8.6 mg, 62% yield).

UPLC: Rt 3.54 min (0 to 30% B over 5 min, 0.1% TFA, λ=214 nm); Calculated Mass [M+H]$^+$: 2073.0, [M+2H]$^{2+}$: 1037.0, [M+3H]$^{3+}$: 691.7. Mass Found (ESI$^+$): 1037.9 [M+2H]$^{2+}$, 692.2 [M+3H]$^{3+}$. (ESI-MS data was collected over the entire gradient and wash cycle of the UPLC-MS).

Ac-(LYRANV)$_2$CSPGYS-NH$_2$ (S4, SEQ ID NO: 17)

51

Peptide ligation of H-CSPGYS-NH₂ 1 (SEQ ID NO: 1; 4.4 mg, 7.2 μmol, 5 mM) and Ac-LYRANV-SCH₂CF₃ 5 (SEQ ID NO: 5; 12.6 mg, 14.4 μmol, 10 mM) in batch was performed as detailed under the general procedures (37° C., t=60.0 min), without hydrazinolysis of the product thioester. Purification via preparative reverse-phase HPLC (0 to 40% B over 40 min, 0.1% TFA) followed by lyophilization afforded peptide S4 as a white solid (8.9 mg, 58% yield). UPLC: Rt 3.62 min (0 to 30% B over 5 min, 0.1% TFA, λ=214 nm); Calculated Mass [M+2H]²⁺: 1065.0, [M+3H]³⁺: 710.4. Mass Found (ESI⁺): 1066.2 [M+2H]²⁺, 711.0 [M+3H]³⁺. (ESI-MS data was collected over the entire gradient and wash cycle of the UPLC-MS).

N,N'-bis(tert-butyloxycarbonyl)-L-penicillamine Dimer (S5)

1.5 equiv. of Boc-anhydride (439 mg. 2.01 mmol) was added to L-penicillamine (200 mg, 1.34 mmol) in 2 mL THF and 2 mL of sat. sodium bicarbonate, and reacted for 18 h (rt). The resultant solution was cooled to 0° C. and 0.5 equiv. of hydrogen peroxide (30 wt %, 68 μl, 0.67 mmol) added dropwise with mixing and reacted for 5 min. The solution was then acidified with aq. 1 M HCl and the compound extracted 3 times with equal volumes of ethyl acetate. The organic layer was dried over MgSO₄, concentrated and then purified by silica gel flash chromatography (0-10% methanol in CH₂Cl₂ with 1% acetic acid) affording compound S5 as an amorphous white solid (185 mg, 55%), $[\alpha]_D$+127.9 (c 1.0, CH₂Cl₂); IR Vmax 2977, 2931, 1712, 1655, 1498, 1456, 1393, 1367, 1327, 1247, 1158, 1116, 1050, 1027; 1H NMR (400 MHZ, MeOD) δ 4.23 (s, 2H), 1.45 (s, 18H), 1.41 (s, 6H), 1.38 (s, 6H) ppm; ¹³C NMR (101 MHZ, MeOD) δ 173.5, 157.6, 80.9, 62.4, 52.0, 28.7, 26.8, 24.9 ppm; HRMS (ESI+) Calculated mass for $C_{20}H_{36}N_2O_8S_2Na$ [M+Na]⁺: 519.1805; mass found [M+Na]⁺: 519.1813.

H-CSPMYS-NH₂ (S6, SEQ ID NO: 18)

52

Peptide S6 was synthesized using the outlined procedure for Fmoc-strategy SPPS on Rink amide resin (100 μmol). The peptide was cleaved from resin and deprotected under acidic conditions according to general procedures. Purification via preparative reverse-phase HPLC (0 to 20% B over 40 min, 0.1% TFA) followed by lyophilization afforded peptide S6 as a white solid (17.4 mg, 22% yield). UPLC: Rt 4.26 min (0 to 15% B over 5 min, 0.1% TFA, λ=214 nm); Calculated Mass [M+H]⁺: 686.8, [2M+H]⁺: 1371.5. Mass Found (ESI⁺): 686.4 [M+H]⁺, 1372.0 [2M+H]⁺. (ESI-MS data was collected over the entire gradient and wash cycle of the UPLC-MS). NMR spectra of H-CSPMYS-NH₂ (S6, SEQ ID NO: 18) is shown in FIGS. 71 and 72.

H-ASPMYS-NH₂ (S7, SEQ ID NO: 19)

Photodesulfurization of H-CSPMYS-NH₂ S6 (SEQ ID NO: 18; 14.77, 18.4 μmol, 2.5 mM) was performed in flow (λ=254 nm, 125 mM GSH, t=1.0 min) according to the general procedure outlined above. Purification via preparative reverse-phase HPLC (2 to 20% B over 40 min, 0.1% TFA) followed by lyophilization afforded peptide S7 as a white solid (10.5 mg, 74% yield). UPLC: Rt 5.10 min (0 to 15% B over 5 min, 0.1% TFA, λ=214 nm); Calculated Mass [M+H]⁺: 654.3, [M+Na]⁺: 677.3, [2M+H]⁺: 1307.6. Mass Found (ESI⁺): 654.4 [M+H]⁺, 676.4 [M+Na]⁺, 1308.3 [2M+H]⁺. (ESI-MS data was collected over the entire gradient and wash cycle of the UPLC-MS). NMR spectra of H-ASPMYS-NH₂ (S7, SEQ ID NO: 19) is shown in FIGS. 73 and 74.

H-CSPC(Acm)YS-NH₂ (S8, SEQ ID NO: 20)

Peptide S8 was synthesized using the outlined procedure for Fmoc-strategy SPPS on Rink amide resin (100 μmol). The peptide was cleaved from resin and deprotected under acidic conditions according to general procedures. Purification via preparative reverse-phase HPLC (0 to 20% B over 40 min, 0.1% TFA) followed by lyophilization afforded peptide S8 as a white solid (39.8 mg, 47% yield). UPLC: Rt 4.89 min (0 to 15% B over 5 min, 0.1% TFA, λ=214 nm); Calculated Mass [M+H]⁺: 729.8, [2M+H]⁺: 1457.5. Mass Found (ESI⁺): 729.5 [M+H]⁺, 1457.9 [2M+H]⁺. (ESI-MS data was collected over the entire gradient and wash cycle of the UPLC-MS). NMR spectra of H-CSPC(Acm)YS-NH₂ (S8, SEQ ID NO: 20) is shown in FIGS. 75 and 76.

H-ASPC(Acm)YS-NH₂ (S9, SEQ ID NO: 21)

Photodesulfurization of H-CSPC(Acm)YS-NH₂ S8 (SEQ ID NO: 20; 38.9 mg, 46.2 μmol, 2.5 mM) was performed in flow (λ=254 nm, 125 mM GSH, t=1.0 min) according to the general procedure outlined above. Purification via preparative reverse-phase HPLC (2 to 20% B over 40 min, 0.1% TFA) followed by lyophilization afforded peptide S9 as a white solid (30.6 mg, 82% yield). UPLC: Rt 4.41 min (0 to 15% B over 5 min, 0.1% TFA, λ=214 nm); Calculated Mass [M–Acm+H]⁺: 626.3, [M+H]⁺: 697.3, [M+Na]⁺: 719.3, [2M+H]⁺: 1393.6. Mass Found (ESI⁺): 626.4 [M–Acm+H]⁺, 697.5 [M+H]⁺, 719.4 [M+Na]⁺, 1393.5 [2M+H]⁺. (ESI-MS data was collected over the entire gradient and wash cycle of the UPLC-MS). NMR spectra of H-ASPC (Acm)YS-NH₂ (S9, SEQ ID NO: 21) is shown in FIGS. 77 and 78.

H-PenSPGYS-NH₂ (S10, SEQ ID NO: 22)

Peptide S10 was synthesized using the outlined procedure for Fmoc-strategy SPPS on Rink amide resin (100 μmol). The final coupling was performed using 1.1 equiv. of N,N'-bis(tert-butyloxycarbonyl)-L-penicillamine dimer S5 (54.6 mg, 110 μmol) with 1.1 equiv. of HOAt (15.0 mg, 110 μmol) and 1.1 equiv. of DIC (17.0 μL, 110 μmol) at rt for 18 h. The peptide was cleaved from resin and deprotected under acidic conditions according to general procedures. The crude product (6 mM) was dissolved in an aqueous solution of TCEP (300 mM, 8 mL) and adjusted to pH 12 followed by incubation at rt. Purification via preparative reverse-phase HPLC (0 to 20% B over 40 min, 0.1% TFA) followed by lyophilization afforded peptide S10 as a white solid (18.1 mg, 28% yield). UPLC: Rt 4.40 min (0 to 15% B over 5 min, 0.1% TFA, λ=214 nm); Calculated Mass [M+H]⁺: 640.7, [2M+H]⁺: 1279.5. Mass Found (ESI⁺): 640.3 [M+H]⁺, 1279.6 [2M+H]⁺. (ESI-MS data was collected over the entire gradient and wash cycle of the UPLC-MS). NMR spectra of H-PenSPGYS-NH₂ (S10, SEQ ID NO: 22) is shown in FIGS. 79 and 80.

H-VSPGYS-NH₂ (S11, SEQ ID NO: 23)

Photodesulfurization of H-PenSPGYS-NH₂ S10 (SEQ ID NO: 22, 16.9 mg, 22.4 μmol, 2.5 mM) was performed in flow (λ=254 nm, 125 mM GSH, t=1.0 min) according to the general procedure outlined above. Purification via preparative reverse-phase HPLC (2 to 20% B over 40 min, 0.1% TFA) followed by lyophilization afforded peptide S11 as a white solid (13.5 mg, 83% yield). UPLC: Rt 4.24 min (0 to 15% B over 5 min, 0.1% TFA, λ=214 nm); Calculated Mass [M+H]⁺: 608.3, [M+Na]⁺: 630.3, [2M+H]⁺: 1215.6. Mass Found (ESI⁺): 608.3 [M+H]⁺, 630.4 [M+Na]⁺, 1216.2 [2M+H]⁺. (ESI-MS data was collected over the entire gradient and wash cycle of the UPLC-MS). NMR spectra of H-VSPGYS-NH₂ (S11, SEQ ID NO: 23) is shown in FIGS. 81 and 82.

H-(β-SH) DSPGYS-NH₂ (S12, SEQ ID NO: 24)

Peptide S12 was synthesized using the outlined procedure for Fmoc-strategy SPPS on Rink amide resin (50 μmol). For the final coupling, 1.1 equiv. of N-(tert-butyloxycarbonyl)-3-(2,4,6-trimethoxybenzylthiol)-L-aspartic acid (27.6 mg, 55 μmol) was coupled with 1.1 equiv. of HOAt (7.5 mg, 55 μmol) and 1.1 equiv. of DIC (8.6 μL, 55 μmol) at rt for 18 h. The peptide was cleaved from resin and deprotected under acidic conditions according to general procedures. Purification via preparative reverse-phase HPLC (0 to 20% B over 40 min, 0.1% TFA) followed by lyophilization afforded peptide S12 as a white solid (11.8 mg, 36% yield). UPLC: Rt 3.59 min (0 to 15% B over 5 min, 0.1% TFA, λ=214 nm); Calculated Mass [M+H]⁺: 656.2, [2M+H]⁺: 1311.5. Mass Found (ESI⁺): 656.4 [M+H]⁺, 1311.4 [2M+H]⁺. (ESI-MS data was collected over the entire gradient and wash cycle of the UPLC-MS). NMR spectra of H-(β-SH) DSPGYS-NH₂ (S12, SEQ ID NO: 24) is shown in FIGS. 83 and 84.

H-DSPGYS-NH$_2$ (S13, SEQ ID NO: 25)

Photodesulfurization of H-(β-SH) DSPGYS-NH$_2$ S12 (SEQ ID NO: 24, 11.1 mg, 14.4 μmol, 2.5 mM) was performed in flow (λ=254 nm, 125 mM GSH, t=0.5 min) according to the general procedure outlined above. Purification via preparative reverse-phase HPLC (2 to 20% B over 40 min, 0.1% TFA) followed by lyophilization afforded peptide S13 as a white solid (5.7 mg, 50% yield). UPLC: Rt 3.65 min (0 to 15% B over 5 min, 0.1% TFA, λ=214 nm); Calculated Mass [M+H]$^+$: 624.3, [M+Na]$^+$: 646.2, [2M+H]$^+$: 1247.5. Mass Found (ESI+): 625.3 [M+H]$^+$, 647.0 [M+Na]$^+$, 1248.6 [2M+H]$^+$. (ESI-MS data was collected over the entire gradient and wash cycle of the UPLC-MS). NMR spectra of H-DSPGYS-NH$_2$ (S13, SEQ ID NO: 25) is shown in FIGS. 85 and 86.

Thiolysis of the Product Thioester

Product thioester species were observed to form during the ligation.

Kinetic Studies of Thiolysis and Hydrazinolysis in Batch

A solution of product thioester S3 or S4 was prepared in degassed ligation buffer (5 mM) containing 6 M Gdn·HCl, 0.1 M HEPES, 50 mM TCEP and 2.5 M 2-MIM (pH 7.3-7.4). A second solution containing a thiolysis reagent (250 mM GSH or 250 mM DTT) or 7 vol. % N$_2$H$_4$·H$_2$O was prepared in ligation buffer containing 6 M Gdn·HCl, 0.1 M HEPES and 350 mM TCEP (pH 7.4-7.5). Equal volumes of the two solutions were combined and incubated at 37° C. Aliquots of 5 μL were taken at time points and diluted with 45 μL of 0.1% TFA in Milli-Q water prior to immediate UPLC analysis. Conversion estimates were based on the relative peak areas of the starting product thioester and the resultant ligated peptide at λ=280 nm [ε$_{280}$(S2, S3)=3840 M$^{-1}$ cm$^{-1}$, λ$_{280}$(6, 7)=2560 M$^{-1}$ cm$^{-1}$].

Kinetic Studies of Thiolysis in Flow

An aqueous stream of model peptide thioester 4 or 5 (20 mM) in ligation buffer containing 6 M Gdn·HCl, 0.1 M HEPES and 50 mM TCEP (pH 7.1-7.2) was combined with an aqueous stream of model peptide 1 (10 mM) in ligation buffer containing 6 M Gdn·HCl, 0.1 M HEPES, 50 mM TCEP and 5.0 M 2-MIM (pH 7.4-7.5) on a 150 μL scale at a T-piece using petroleum ether as the system solvent (individual pump rates; X=A: 0.25 mL/min, X=V: 0.20 mL/min) (see FIG. 27 for the flow system used). This reaction stream entered PTFE coil reactor I (0.5 mm×1.6 mm, X=A: 1.5 mL, X=V: 4.0 mL) operated at 37° C. A third solution of TCEP (350 mM) and GSH (250 mM) in ligation buffer containing 6 M Gdn·HCl and 0.1 M HEPES (pH 7.4-7.5) was combined with the ligated mixture at a second T-piece (individual pump rates; X=A: 0.50 mL/min, X=V: 0.40 mL/min). This reaction stream entered PTFE coil reactor II (0.5 mm×1.6 mm, 37° C.) then entered PFA reactor III (0.5 mm×1.6 mm, 1.0 mL) and was irradiated in a Rayonet RPR-100 photoreactor at λ=254 nm (35 W, rt). The reaction solution was collected through a 6 bar BPR into an equal volume of neutral MPAA (15 mM) in Milli-Q water. Aliquots of 5 μL were taken at time points and diluted with 45 UL of 0.1% TFA in Milli-Q water prior to immediate UPLC analysis. Thiolysis time-courses were obtained by modifying the volume of reactor II. Conversion estimates were based on the relative peak areas of the product thioester (S2, S3) and ligated product (6, 7) to the resultant desulfurized peptide (9, 10) at λ=280 nm [ε$_{280}$(S2, S3)=3840 M$^{-1}$ cm$^{-1}$, ε$_{280}$(9, 10)=2560 M$^{-1}$ cm$^{-1}$].

Preparative Scale Reactions of Model System

The novel native chemical ligation procedure was performed in batch and flow on a 20 μmol scale.

Native Chemical Ligation in Batch

Two 2.0 mL solutions were prepared, one containing 10 mM H-CSPGYS-NH$_2$ 1 (SEQ ID NO:1), 50 mM TCEP and 5.0 M 2-MIM in ligation buffer (6 M Gdn·HCl, 0.1 M HEPES, pH 7.4-7.5), and the other containing 20 mM Ac-LYRANX-SCH$_2$CF$_3$ (4: X=A, SEQ ID NO: 4; 5: X=V, SEQ ID NO: 5) and 50 mM TCEP in ligation buffer (6 M Gdn·HCl, 0.1 M HEPES, pH 7.1-7.2). In batch an equal volume of these reaction solutions was actively mixed and, upon completion, quenched with aqueous hydrazine monohydrate in Milli-Q water (7 vol. %) and immediately purified using RP-HPLC (X=A: 6, 6 min, isolated yield 68%; X=V: 7, 40 min, isolated yield 67%).

Native Chemical Ligation in Flow

Two 2.0 mL solutions were prepared, one containing 10 mM H-CSPGYS-NH$_2$ 1 (SEQ ID NO: 1), 50 mM TCEP and 5.0 M 2-MIM in ligation buffer (6 M Gdn·HCl, 0.1 M HEPES, pH 7.4-7.5), and the other containing 20 mM Ac-LYRANX-SCH$_2$CF$_3$ (4: X=A (SEQ ID NO: 4), 5: X=V (SEQ ID NO: 5)) and 50 mM TCEP in ligation buffer (6 M Gdn·HCl, 0.1 M HEPES, pH 7.1-7.2). These solutions were inserted into injection loops and combined at a T-piece (0.50 mL/min) on a 20 μmol scale using petroleum ether as the system solvent. The resulting reaction stream entered PTFE coil reactor 1 (0.5 mm×1.6 mm, X=A: 3.0 mL, X=V: 10.0 mL) at 37° C. (6 bar BPR). The reaction solution was collected into a quenching solution of aqueous hydrazine monohydrate (7 vol. %) and immediately purified using RP-HPLC (X=A: 6, total processing time of 6 min, isolated yield 67%, production rate 3.4 μmol/min; X=V: 7, total processing time of 15 min, isolated yield 65%, production rate 3.3 μmol/min. Processing time refers to the total time taken for complete injection and reaction.)

Standard One-Pot Ligation-Desulfurization in Batch

The standard one-pot ligation-desulfurization batch procedure developed by Thompson et al. was investigated to provide a comparison to the flow methodology reported here. This standard procedure was performed in batch at a 20 μmol scale at both alanine and valine junctions. Two ligation solutions were prepared, one containing H-CSPGYS-NH$_2$ 1 (SEQ ID NO:1, 10 mM) and TCEP (50 mM) in ligation buffer (6 M Gdn·HCl, 0.1 M HEPES, pH 7.4-7.5) and the other containing Ac-LYRANX-S(CH$_2$)$_2$CO$_2$Et (20 mM, X=A: 2, SEQ ID NO:2; X=V: 3, SEQ ID NO:3) and TCEP (50 mM) in ligation buffer (6 M Gdn·HCl, 0.1 M HEPES, pH 7.4-7.5). A desulfurization solution containing VA-044 (40 mM), GSH (80 mM) and TCEP (350 mM) was also prepared in 4.0 mL ligation buffer (6 M Gdn·HCl, 0.1 M HEPES, pH 7.5). All solutions were degassed for 10 minutes, then the two ligation solutions combined and TFET (250 mM) immediately added (warning: TFET is pungent and acutely toxic and should be used in a fume cupboard). The ligation mixture was actively mixed at 37° C. and reaction progression monitored by UPLC. Upon completion (X=A: 25 min, X=V: 9 h) the desulfurization solution was added and the reaction mixture actively mixed at 37° C. Upon completion as judged by UPLC analysis (X=A: 16 h, X=V: 16 h) the pure desulfurized peptides were isolated using RP-HPLC (X=A: 9, total processing time of 16.5 h, isolated yield 69%; X=V: 10, total processing time of 25.0 h, isolated yield 61%. Processing time refers to the total time taken for complete injection and reaction).

One-Pot Ligation-Photodesulfurization in Batch

The one-pot ligation-photodesulfurization procedure was performed on a 20 µmol scale in batch and flow.

Two 2.0 mL solutions were prepared, one containing 10 mM H-CSPGYS-NH$_2$ 1 (SEQ ID NO:1), 50 mM TCEP and 5.0 M 2-MIM in degassed ligation buffer (6 M Gdn·HCl, 0.1 M HEPES, pH 7.4-7.5), and the other containing 20 mM Ac-LYRANX-SCH$_2$CF$_3$ (4: X=A, SEQ ID NO:4; 5: X=V, SEQ ID NO:5) and 50 mM TCEP in ligation buffer (6 M Gdn·HCl, 0.1 M HEPES, pH 7.1-7.2). A desulfurization solution was prepared, containing GSH (250 mM) and TCEP (350 mM) in 5.0 mL ligation buffer (6 M Gdn·HCl, 0.1 M HEPES, pH 7.4-7.5). Upon degassing, the two ligations solutions were combined and actively mixed at 37° C. Upon complete ligation as determined by UPLC (X=A: 6 min, X=V: 40 min), the reaction solution was transferred to a 15 mL Corning™ Falcon™ polypropylene conical centrifuge tube and combined with 4.0 mL of the desulfurization solution. This mixture was photoirradiated at λ=254 nm (35 W, rt). Upon completion by UPLC (X=A: 2.5 h; X=V: 2.5 h), the product was immediately isolated using RP-HPLC (X=A: 9, total processing time of 2.6 h, isolated yield 66%; X=V: 10, total processing time of 3.2 h, isolated yield 66%. Processing time refers to the total time taken for complete injection and reaction).

Ligation-Photodesulfurization in Flow

Two 2.0 mL solutions were prepared, one containing 10 mM H-CSPGYS-NH$_2$ 1 (SEQ ID NO: 1), 50 mM TCEP and 5.0 M 2-MIM in degassed ligation buffer (6 M Gdn·HCl, 0.1 M HEPES, pH 7.4-7.5), and the other containing 20 mM Ac-LYRANX-SCH$_2$CF$_3$ (4: X=A, SEQ ID NO: 4; 5: X=V, SEQ ID NO:5) and 50 mM TCEP in ligation buffer (6 M Gdn·HCl, 0.1 M HEPES, pH 7.1-7.2). A desulfurization solution was prepared, containing GSH (250 mM) and TCEP (350 mM) in 5.0 mL degassed ligation buffer (6 M Gdn·HCl, 0.1 M HEPES, pH 7.4-7.5). These solutions were loaded into injection loops, and the two peptide solutions combined (X=A: 0.25 mL/min, X=V: 0.20 mL/min) at a T-piece on a 20 µmol scale using petroleum ether as the system solvent. The resulting reaction stream entered PTFE coil reactor I (0.5 mm×1.6 mm, X=A: 1.5 mL, X=V: 4.0 mL) at 37° C. The reaction solution was then combined with the desulfurization solution (X=A: 0.50 mL/min; X=V: 0.40 mL/min) at a second T-piece and entered a second PTFE coil reactor II (0.5 mm×1.6 mm, X=A: 1.0 mL, X=V: 5.0 mL) at 37° C., followed by a final PFA coil reactor III (0.5 mm×1.6 mm, 1.0 mL) inside a Rayonet RPR-100 photoreactor (λ=254 nm, 35 W, rt). The reaction mixture was collected through a 6 bar BPR and immediately purified using RP-HPLC (X=A: 9, total processing time 0.26 h, isolated yield 65%, production rate 1.6 µmol/min; X=V: 10, total processing time 0.46 h, isolated yield 63%, production rate 1.3 µmol/min. Processing time refers to the total time taken for complete injection and reaction).

Native Chemical Ligation in Flow Using a Selenoester

A model NCL reaction in flow between model peptide H-CSPGYS-NH$_2$ 1 (SEQ ID NO: 1) and model peptide Ac-LYRANV-SePh S15 (SEQ ID NO: 27) was conducted (FIG. 40A).

Model peptide H-CSPGYS-NH$_2$ 1 (SEQ ID NO: 1) was solvated in ligation buffer (10 mM, 1.0 equiv.) comprising 6 M Gdn·HCl, 0.1 M HEPES and 50 mM TCEP (pH 6.2 or 7.0). A second solution was prepared of model peptide Ac-LYRANV-SePh S15 (SEQ ID NO: 27) in ligation buffer (20 mM, 2.0 equiv.; or 15 mM, 1.5 equiv.) comprising 6 M Gdn·HCl, 0.1 M HEPES and 50 mM TCEP (pH 6.2 or 7.0). Model peptide Ac-LYRANV-SePh S15 (SEQ ID NO: 27) was prepared according to the methods described in WO2016/138563. These solutions were inserted into injection loops and combined at a T piece on a 150 µL scale using petroleum ether as the system solvent. The resulting reaction stream entered a PTFE coil reactor (0.5 mm×1.6 mm) at 37° C. (6 bar BPR). The reaction solution was quenched upon collection using an equal volume of 7 vol. % N$_2$H$_4$·H$_2$O in Milli Q water. Ligation time-courses were obtained via altering the reactor volume and the flow rate to modulate the residence time. Aliquots of 10 µL were taken of the quenched solution and diluted with 40 L of 0.1% TFA in Milli-Q water then analyzed by UPLC. Conversion estimates were based on the relative peak areas of the starting material H-CSPGYS-NH$_2$ 1 (SEQ ID NO: 1) and the desired ligation product Ac-LYRANVCSPGYS-NH$_2$ (SEQ ID NO: 7) at λ=280 nm [$\varepsilon_{280}$(H-CSPGYS-NH$_2$ (SEQ ID NO: 1)=1280 M$^{-1}$ cm$^{-1}$, $\varepsilon_{280}$(Ac-LYRANVCSPGYS-NH$_2$ (SEQ ID NO: 7)=2560 M$^{-1}$ cm$^{-1}$].

Native Chemical Ligation in Batch Using a Selenoester

Model peptide H-CSPGYS-NH$_2$ 1 (SEQ ID NO: 1) was solvated in ligation buffer (10 mM, 1.0 equiv.) comprising 6 M Gdn·HCl, 0.1 M HEPES and 50 mM TCEP (pH 6.2 or 7.0). A second solution was prepared of model peptide Ac-LYRANV-SePh S15 (SEQ ID NO: 27) in ligation buffer (20 mM, 2.0 equiv.; or 15 mM, 1.5 equiv.; or 12.5 mM, 1.25 equiv.) comprising 6 M Gdn·HCl, 0.1 M HEPES and 50 mM TCEP (pH 6.2 or 7.0). Model peptide Ac-LYRANV-SePh (SEQ ID NO: 27) was prepared according to the methods described in WO2016/138563. These solutions were combined and incubated at 37° C. Ligation time-courses were obtained via quenching aliquots of 5 µL with an equal volume of 7 vol. % N$_2$H$_4$·H$_2$O in Milli Q water. This solution was diluted with 40 UL of 0.1% TFA in Milli-Q water then analyzed by UPLC. Conversion estimates were based on the relative peak areas of the starting material H-CSPGYS-NH$_2$ 1 (SEQ ID NO: 1) and the desired ligation product Ac-LYRANVCSPGYS-NH$_2$ (SEQ ID NO: 7) at λ=280 nm [$\varepsilon_{280}$(H-CSPGYS-NH$_2$ (SEQ ID NO: 1)=1280 M$^{-1}$ cm$^{-1}$, $\varepsilon_{280}$(AC-LYRANVCSPGYS-NH$_2$ (SEQ ID NO: 7)=2560 M$^{-1}$ cm$^{-1}$].

The kinetics of the ligation reactions between model peptide 1 and model peptide S15, in batch and in flow, without thiol or selenol additives are shown in FIG. 40B-E.

Photodeselenization in Flow

H-USPGYS-NH$_2$ dimer S14 (SEQ ID NO: 26) was solvated in degassed ligation buffer (2.5 mM) containing 6 M Gn. HCl, 0.1 M HEPES (pH 6.2-6.3). A second solution was prepared containing Ac-LYRANF-SePh S16 (SEQ ID NO: 28) 6 mM, 1.2 eq.) solvated in degassed ligation buffer comprising 6 M Gn·HCl, 0.1 M HEPES (pH 6.2-6.3). These two solutions were mixed and incubated at 37° C. for 15 min at which point analysis by UPLC-MS (1/10 dilution in H$_2$O, Gradient: 0-40% MeCN in H$_2$O [0.1% FA] over 5 min) showed the ligation has proceeded to completion. An equivalent volume of petroleum ether was added to the ligation mixture and subsequently decanted to remove precipitated DPDS. The extracted ligation mixture was then inserted into an injection loop and into a second injection loop was inserted a solution of tris(2-carboxylethyl)phosphine (TCEP) (50 mM, 10 eq.) in 6 M Gn·HCl, 0.1 M HEPES (pH 7.0-7.2) buffer. These loops were then injected into the flow system at individual flow rates to give the desired residence time and using petroleum ether as the immiscible system solvent. The two solutions were mixed at a T-piece and the resulting reaction stream entered a PFA coil reactor inside a Rayonet RPR-100 UV photoreactor at λ=254 nm (35 W, 37° C.) for a residence time of 2 min. The reaction solution then exited the system through a 6 bar back-pressure regulator (BPR) and reaction completion judged by UPLC-MS analysis (1/10 dilution in H$_2$O, Gradient: 0-40% MeCN in H2O [0.1% FA] over 5 min).

Diselenide Seleneoester Ligation—Photodeselenization in Flow

Two 0.5 mL solutions were prepared, one containing 5 mM of the dimer (H-USPGYS-NH$_2$)$_2$ S14 (SEQ ID NO: 26) in degassed ligation buffer (6 M Gdn·HCl, 0.2 M BIS-TRIS, pH 4.7), and the other containing 12.5 mM Ac-LYRANV-SePh S15 (SEQ ID NO: 27) in ligation buffer (6 M Gdn·HCl, 0.2 M BIS-TRIS, pH 4.7). A deselenization solution was prepared, containing TCEP (10 mM or 100 mM) in 1.0 mL degassed ligation buffer (6 M Gdn·HCl, 0.2 M BIS-TRIS, pH 5.5). These peptide solutions were loaded into injection loops, and the two peptide solutions combined at a T-piece using petroleum ether as the system solvent. The resulting reaction stream entered PTFE coil reactor I (0.5 mm×1.6 mm, 5 min) at 37° C. The reaction solution was then combined with the deselenization solution at a second T-piece and entered a second PTFE coil reactor II (0.5 mm×1.6 mm) inside a Rayonet RPR-100 photoreactor ( )=254 nm, 35 W, rt). The reaction mixture was collected through a 6 bar BPR and immediately analysed by UPLC. Conversion estimates were based on the relative peak areas of the ligated product (Ac-LYRANVUSPGYS-NH$_2$)$_2$ (SEQ ID NO: 29) and the desired deselenized product Ac-LYRANVASPGYS-NH$_2$ at λ=280 nm (SEQ ID NO: 10) [ε$_{280}$((Ac-LYRANVUSPGYS-NH$_2$)$_2$ (SEQ ID NO: 29)=5120 M$^{-1}$ cm$^{-1}$, ε$_{280}$ (Ac-LYRANVASPGYS-NH$_2$ (SEQ ID NO: 10)=2560 M$^{-1}$ cm$^{-1}$].

Reductive Diselenide-Selenoester Ligation in Flow

Two 0.5 mL solutions were prepared, one containing (H-USPGYS-NH$_2$)$_2$ S14 (SEQ ID NO: 26) 5 mM, 0.5 mM, 0.05 mM; with respects to the dimer), TCEP (50 mM), and DPDS (10 mM) in degassed ligation buffer (6 M Gdn·HCl, 0.2 M BIS-TRIS, pH 6.0), and the other containing 1.25 equiv. Ac-LYRANV-SePh S15 (SEQ ID NO: 27; 12.5 mM, 1.25 mM, 0.125 mM), TCEP (50 mM), and DPDS (10 mM) in ligation buffer (6 M Gdn·HCl, 0.2 M BIS-TRIS, pH 6.0). These solutions were loaded into injection loops, and the two peptide solutions combined at a T-piece using petroleum ether as the system solvent. The resulting reaction stream entered PTFE coil reactor I (0.5 mm×1.6 mm) at 37° C. The reaction mixture was collected through a 6 bar BPR and immediately analysed by UPLC. Conversion estimates were based on the relative peak areas of the starting material (H-USPGYS-NH$_2$)$_2$ (SEQ ID NO: 26) S14 and the desired ligation product (Ac-LYRANVUSPGYS-NH$_2$)$_2$ (SEQ ID NO: 29) at λ=280 nm [ε$_{280}$(S14)=2560 M$^{-1}$ cm$^{-1}$, ε$_{280}$((Ac-LYRANVUSPGYS-NH$_2$)$_2$ (SEQ ID NO: 29)=5120 M$^{-1}$ cm$^{-1}$].

Solution-Phase Selenoesterification

Crude side-chain protected peptides were dissolved in dry DMF (20 mM) and cooled to 0° C. To this was added DPDS (30 equiv.) followed by BusP (30 equiv.) with stirring over 3 h under an argon atmosphere. The solution was warmed to rt and concentrated under nitrogen flow. Deprotection and work-up was achieved using the acidic deprotection conditions described for fully protected peptides on-resin. No epimerization was observed using this procedure.

Reductive Diselenide-Selenoester Ligation in Batch at Dilution

Having established an optimized protocol for reductive diselenide-selenoester ligation in flow at high dilution, the inventors investigated whether reductive diselenide-selenoester ligation in batch could be carried out. Surprisingly, the inventors found that reductive diselenide-selenoester ligation in batch at high dilutions proceeded in the presence of an additive.

Two solutions were prepared, one containing (H-US-PGYS-NH$_2$)$_2$ S14 (SEQ ID NO: 26; 5 mM, 0.1 mL; 0.5 mM, 0.1 mL; or 0.05 mM, 1.0 mL; with respects to the dimer), TCEP (30 mM), and DPDS (20 mM) in ligation buffer (6 M Gdn·HCl, 0.2 M BIS-TRIS, pH 5.2), and the other containing 2 equiv. Ac-LYRANV-SePh S15 (SEQ ID NO: 27; 20 mM, 0.1 mL; 2 mM, 0.1 mL; or 0.2 mM, 1.0 mL), TCEP (30 mM), and DPDS (20 mM) in ligation buffer (6 M Gdn·HCl, 0.2 M BIS-TRIS, pH 5.2). These solutions were combined and incubated at 37° C. Ligation time-courses for reaction mixtures containing final concentrations of 5 mM or 0.5 mM (H-USPGYS-NH$_2$)$_2$ (SEQ ID NO: 26) monomer were obtained via quenching reaction aliquots of 5 μL with an equal volume of 7 vol. % N$_2$H$_4$·H$_2$O in Milli-Q water. After 10 minutes these solutions were diluted with 20 μL of 1.5% % TFA in Milli-Q water and analyzed by UPLC. For reaction mixtures containing 0.05 mM (H-USPGYS-NH$_2$)$_2$ (SEQ ID NO: 26) monomer, 100 UL aliquots were quenched with 10 μL of 30 vol. % N$_2$H$_4$.H$_2$O in Milli-Q water then diluted with 11 μL of 30 vol. % TFA in Milli-Q water after 10 minutes and subsequently analysed by analytical HPLC coupled with an FLR detector. Conversion estimates were based on the relative peak areas of the starting material (H-USPGYS-NH$_2$)$_2$ S14 (SEQ ID NO: 26) and the desired ligation product (Ac-LYRANVUSPGYS-NH$_2$)$_2$ (SEQ ID NO: 29) at λ=280 nm.

(H-USPGYS-NH$_2$)$_2$ (S14, SEQ ID NO: 26)

Peptide S14 was synthesized using the outlined procedure for Fmoc-strategy SPPS on Rink amide resin. The peptide was cleaved from resin and deprotected under acidic conditions according to general procedures. Purification via preparative reverse-phase HPLC (0 to 20% B over 40 min, 0.1% TFA) followed by lyophilization afforded peptide S14 as a white solid (78 mg, 61% yield). UPLC: Rt 3.79 min (0 to 40% B over 5 min, 0.1% TFA, λ=214 nm); Calculated Mass [M+H]$^+$: 1317.4, [M+2H]$^{2+}$: 659.2. Mass Found (ESI$^+$): 1317.3 [M+H]$^+$, 659.3 [M+2H]$^{2+}$. (ESI-MS data was collected over the entire gradient and wash cycle of the UPLC-MS).

Ac-LYRANV-SePh (S15, SEQ ID NO: 27)

The fully sidechain protected peptide S15 was synthesized using the outlined procedure for Fmoc-strategy SPPS on 2-CTC resin. The protected peptide was cleaved from resin, selenoesterified and deprotected according to general procedures. Purification via preparative reverse-phase HPLC (0 to 40% B over 40 min, 0.1% TFA) followed by lyophilization afforded peptide S15 as a white solid (428 mg, 77% yield). UPLC: Rt 4.71 min (0 to 60% B over 5 min, 0.1% TFA, $\lambda$=214 nm); Calculated Mass [M+H]$^+$: 917.4. Mass Found (ESI$^+$): 917.4 [M+H]$^+$. (ESI-MS data was collected over the entire gradient and wash cycle of the UPLC-MS).

Ac-LYRANF-SePh (S16, SEQ ID NO: 28)

The fully sidechain protected peptide S16 was synthesized using the outlined procedure for Fmoc-strategy SPPS on 2-CTC resin. The protected peptide was cleaved from resin, selenoesterified and deprotected according to general procedures.

Purification via preparative reverse-phase HPLC (0 to 40% B over 40 min, 0.1% TFA) followed by lyophilization afforded peptide S16 as a white solid (13.2 mg, 37% yield). UPLC: Rt 4.52 min (0 to 60% B over 5 min, 0.1% TFA, $\lambda$=214 nm); Calculated Mass [M+H]$^+$: 965.4. Mass Found (ESI$^+$): 965.3 [M+H]$^+$. (ESI-MS data was collected over the entire gradient and wash cycle of the UPLC-MS).

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

REFERENCES

1. Hay, M.; Thomas, D. W.; Craighead, J. L.; Economides, C.; Rosenthanl, J. Nat. Biotechnol. 2014, 32, 40.
2. Fosgerau, K; Hoffman, T. Drug Discov. Today 2015, 20, 122.
3. Usmani, S. S.; Bedi, G.; Samuel, J. S.; Singh, S.; Kalra, S.; Kumar, P.; Ahuja, A. A.; Sharma, M.; Gautam, A.; Raghava, G. P. PloS One 2017, 12, e0181748.
4. Merrifield, R. B. J. Am. Chem. Soc. 1963, 85, 2149.
5. Kent, S. B. Ann. Rev. Biochem. 1988, 57, 957.
6. Dawson, P. E.; Muir, T. W.; Clark-Lewis, I.; Kent, S. B. Science 1994, 266, 776.
7. Kent, S. B. H. Chem Soc. Rev. 2009, 38, 338.
8. Johnson, E. C. B.; Kent, S. B. H. J. Am. Chem. Soc. 2006, 128, 6640.
9. Thompson, R. E.; Liu, X.; Alonso-Garcia, N.; Pereira, P. J. B.; Jolliffe, K. A.; Payne, R. J. J. Am. Chem. Soc. 2014, 136, 8161.
10. Yan, L. Z.; Dawson, P. E. J. Am. Chem. Soc. 2001, 123, 526.
11. Wan, Q.; Danishefsky, S. J. Angew. Chem. Int. Ed. 2007, 46, 9248.
12. Jin, K.; Li, T.; Chow, H. Y.; Liu, H.; Li, X. Angew Chem. Int. Ed. 2017, 56, 14607.
13. Dawson, P. E. Isr. J. Chem. 2011, 51, 862.

14. Kulkarni, S. S.; Sayers, J.; Premdjee, B.; Payne, R. *J. Nat. Rev. Chem.* 2018, 2, 112.

15. Malins, L. R.; Payne, R. *J. Aust. J. Chem.* 2015, 68, 521.

16. Malins, L. R.; Payne, R. *J. Curr. Opin. Chem. Biol.* 2014, 22, 70.

17. Malins, L. R.; Payne, R. *J. Top. Curr. Chem.* 2015, 362, 27.

18. Bondalapiti, S; Jbara, M.; Brik, A. *Nat. Chem.* 2016, 8, 407.

19. Huang, Y. C.; Chen, C. C.; Gao, S; Wang, Y. H.; Xiao, H.; Wang, F.; Tian, C. L.; Li, Y. M. *Chem. Eur. J.* 2016, 22, 7623.

20. Sayers, J.; Thompson, R. E.; Perry, K. J.; Malins, L. R.; Payne, R. *J. Org. Lett.* 2015, 17, 4902.

21. Thompson, R. E.; Chan, B. Radom, L.; Jolliffe, K. A.; Payne, R. *J. Angew. Chem. Int. Ed.* 2013, 52, 9723.

22. Zheng, J. S.; Tang, S.; Qi, Y.-K.; Wang, Z.-P.; Liu, L. *Nat. Protoc.* 2013, 8, 2483-2495.

23. Sakamoto, K.; Tsuda, S.; Mochizuki, M.; Nohara, Y.; Nishio, H.; Yoshiya, T. *Chem. Eur. J.* 2016, 22, 17940.

24. Hoffmann, F. W.; Ess, R. J.; Simmons, T. C.; Hanzel, R. S. *J. Am. Chem. Soc.* 1956, 78, 6414.

The invention claimed is:

1. A method of preparing a polypeptide n a continuous flow reaction comprising the step of reacting:

(i) an ester, with (ii) a molecule comprising a terminal amino acid selected from the group consisting of cysteine, cystine, an amino acid comprising a thiol, an amino acid comprising a disulfide, selenocysteine, selenocystine, an amino acid comprising a selenol, and an amino acid comprising a diselenide;

wherein the ester is a thioester or selenoester; and wherein the ester reacts with the cysteine, cystine, amino acid comprising a thiol, amino acid comprising a disulfide, selenocysteine, selenocystine, amino acid comprising a selenol, or amino acid comprising a diselenide, of the terminal amino acid of the molecule in a continuous flow reaction, thereby preparing a polypeptide compound in a continuous flow reaction;

wherein the polypeptide is defined by formula (I):

the ester is defined by formula (II):

the molecule comprising a terminal amino acid selected from the group consisting of cysteine, an amino acid comprising a thiol, selenocysteine, and an amino acid comprising a selenol is defined by formula (III):

$$H_2N \overset{AA_{lig}}{\diagdown} \underset{O}{\overset{(AA)_n}{\diagup}} C_{term} \qquad \text{III}$$

the molecule comprising a terminal amino acid selected from the group consisting of cystine, an amino acid comprising a disulfide, selenocystine and an amino acid comprising a diselenide is defined by formula (IV):

$$\text{IV}$$

$$H_2N \diagdown \underset{AA_{lig}}{\overset{O}{\diagup}} \underset{(AA)_n}{\diagdown} C_{term}$$
$$H_2N \diagdown \underset{AA_{lig}}{\overset{\diagup}{\diagdown}} \underset{(AA)_n}{\overset{O}{\diagdown}} C_{term}$$

wherein:

N$_{term}$ is the N-terminus of the polypeptide;

C$_{term}$ is the C-terminus of the polypeptide;

AA is an amino acid;

n is an integer;

(AA)$_n$ represents a polypeptide comprising n number of amino acid monomers;

DG is a displaceable group selected from a thiolate and a selenoate; and $$\overset{AA_{lig}}{\diagdown}$$

is a portion of an amino acid residue excluding the alpha-amine and alpha-carboxylate of the amino acid residue;

wherein the portion of the amino acid residue comprises a thiol, disulfide, selenol or diselenide at the ligation site such that the amino acid residue is selected from the group consisting of cysteine, cystine, an amino acid comprising a thiol, an amino acid comprising a disulfide, selenocysteine, selenocystine, an amino acid comprising a selenol, and an amino acid comprising a diselenide.

2. The method according to claim 1, wherein the reaction is conducted in the presence of a thiol additive or a selenol additive thereby transforming the ester into a reactive ester.

3. The method according to claim 2, wherein the ester is selected from the group consisting of ethyl 3-mercaptopropionate thioester, reduced L-glutathione (GSH) thioester, dithiothreitol (DTT) thioester, mercaptopropionic acid-leucine thioester, tertbutylthiol thioester, mercaptopropanoyl glycine thioester, selenoacetamide selenoester, selenopropionic acid-isoleucine selenoester, and (9-fluorenylmethyl) selenoester.

4. The method according to claim 2, wherein:

the ester is a thioester;

the thiol additive is selected from the group consisting of trifluoroethanethiol, 4-mercaptophenyl acetic acid, mercaptoethylsulfonate, methylthioglycolate, thiophenol, and benzylmercaptan; and the selenol additive is an aryl selenol.

5. The method according to claim 2, wherein the ester is a selenoester and the selenol additive is an aryl selenol.

6. The method according to claim 4, wherein the aryl selenol is selected from the group consisting of phenylselenol and 4-selenophenyl acetic acid.

7. The method according to claim 1, wherein the ester is a reactive ester capable of reacting with the terminal amino acid in the molecule in the absence of a thiol additive or selenol additive.

8. The method according to claim 7, wherein the reactive ester is selected from the group consisting of trifluoroethyl thioester, 4-mercaptophenyl acetic acid thioester, mercaptoethylsulfonate thioester, methylthioglycolate thioester, thiophenyl thioester, benzylmercaptan thioester, phenylselenoester, and 4-selenophenyl acetic acid selenoester.

9. The method according to claim 7, wherein the reaction is conducted in the absence of a thiol additive or selenol additive.

10. The method according to claim 1, wherein the reaction is conducted in a solvent that includes an aqueous solution and/or the reaction is conducted in an aqueous solution.

11. The method according to claim 1, wherein the reaction is conducted in the presence of a first nucleophilic agent thereby accelerating the rate of the reaction.

12. The method according to claim 11, wherein the first nucleophilic agent comprises an imidazole.

13. The method according to claim 12, wherein the first nucleophilic agent is selected from the group consisting of 2-methylimidazole, imidazole, and combinations thereof.

14. The method according to claim 1, wherein a second nucleophilic agent is added to thiolyze, aminolyze, hydrolyze or hydrazinolyze product ester formed by the amide containing compound reacting with the ester.

15. The method according to claim 14, wherein the second nucleophilic agent is selected from the group consisting of reduced glutathione (GSH), dithiothreitol (DTT), cysteine, an imidazole, an amine, hydroxide ion, hydrazine, and combinations thereof.

16. The method according to claim 14, wherein the second nucleophilic agent is added after completion of the reaction.

17. The method according to claim 1, additionally comprising the step of desulfurizing or deselenizing the amide containing compound in a continuous flow reaction.

18. The method of claim 17, comprising the step of desulfurizing an amide containing compound comprising a thiol group or disulfide group in a continuous flow reaction.

19. The method of claim 17, comprising deselenizing an amide containing compound comprising a selenol group or diselenide group in a continuous flow reaction.

20. The method according to claim 17, wherein the desulfurization or deselenization comprises exposing the compound to UV irradiation in the presence of a phosphine source.

21. The method of claim 20, comprising desulfurizing an amide containing compound comprising a thiol group or disulfide group, wherein the desulfurization comprises exposing the compound to UV irradiation in the presence of a phosphine source.

22. The method of claim 20, comprising deselenizing an amide containing compound comprising a selenol group or diselenide group, wherein the deselenization comprises exposing the compound to UV irradiation in the presence of a phosphine source.

23. The method according to claim 20, wherein the phosphine source is tris-(2-carboxyethyl)phosphine (TCEP).

24. The method according to claim 20, further comprising a hydrogen atom source.

25. The method according to claim 24, wherein the hydrogen atom source is selected from the group consisting of reduced L-glutathione (GSH), dithiothreitol (DTT), tert-butylthiol, cysteine, and combinations thereof.

26. The method according to claim 17, wherein the method is conducted in the absence of a chemical radical initiator.

27. The method according to claim 1, wherein the molecule comprising a terminal amino acid is selected from the group consisting of cysteine, cystine, selenocysteine, and selenocystine.

* * * * *

SEQUENCE LISTING

```
<160> NUMBER OF SEQ ID NOS: 38

<210> SEQ ID NO 1
<211> LENGTH: 6
<212> TYPE: PRT
<213> ORGANISM: Artificial Sequence
<220> FEATURE:
<223> OTHER INFORMATION: Model peptide 1

<400> SEQUENCE: 1

Cys Ser Pro Gly Tyr Ser
1               5

<210> SEQ ID NO 2
<211> LENGTH: 6
<212> TYPE: PRT
<213> ORGANISM: Artificial Sequence
<220> FEATURE:
<223> OTHER INFORMATION: Model peptide thioester 2 with acetylated amino
      terminus and thioester carboxyl terminus

<400> SEQUENCE: 2

Leu Tyr Arg Ala Asn Ala
1               5

<210> SEQ ID NO 3
<211> LENGTH: 6
<212> TYPE: PRT
<213> ORGANISM: Artificial Sequence
<220> FEATURE:
<223> OTHER INFORMATION: Model peptide thioester 3 with acetylated amino
      terminus and thioester carboxyl terminus

<400> SEQUENCE: 3

Leu Tyr Arg Ala Asn Val
1               5

<210> SEQ ID NO 4
<211> LENGTH: 6
<212> TYPE: PRT
<213> ORGANISM: Artificial Sequence
<220> FEATURE:
<223> OTHER INFORMATION: Model peptide thioester 4 with acetylated amino
      terminus and trifluoroethyl thioester carboxyl terminus

<400> SEQUENCE: 4

Leu Tyr Arg Ala Asn Ala
1               5

<210> SEQ ID NO 5
<211> LENGTH: 6
<212> TYPE: PRT
<213> ORGANISM: Artificial Sequence
<220> FEATURE:
<223> OTHER INFORMATION: Model peptide thioester 5 with acetylated amino
``` terminus and trifluoroethyl thioester carboxyl terminus

<400> SEQUENCE: 5

Leu Tyr Arg Ala Asn Val
1               5

<210> SEQ ID NO 6
<211> LENGTH: 12
<212> TYPE: PRT
<213> ORGANISM: Artificial Sequence
<220> FEATURE:
<223> OTHER INFORMATION: Peptide 6 ligation product of 1 and 4 with
      acetylated amino terminus

<400> SEQUENCE: 6

Leu Tyr Arg Ala Asn Ala Cys Ser Pro Gly Tyr Ser
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Peptide 7 ligation product of 1 and 5 with
      acetylated amino terminus

<400> SEQUENCE: 7

Leu Tyr Arg Ala Asn Val Cys Ser Pro Gly Tyr Ser
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Peptide 8

<400> SEQUENCE: 8

Ala Ser Pro Gly Tyr Ser
1               5

<210> SEQ ID NO 9
<211> LENGTH: 12
<212> TYPE: PRT
<213> ORGANISM: Artificial Sequence
<220> FEATURE:
<223> OTHER INFORMATION: Peptide 9 with acetylated amino terminus

<400> SEQUENCE: 9

Leu Tyr Arg Ala Asn Ala Ala Ser Pro Gly Tyr Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Peptide 10 with acetylated amino terminus

<400> SEQUENCE: 10

Leu Tyr Arg Ala Asn Val Ala Ser Pro Gly Tyr Ser
1               5                   10

<210> SEQ ID NO 11
<211> LENGTH: 18
<212> TYPE: PRT
<213> ORGANISM: Artificial Sequence -continued

```
<220> FEATURE:
<223> OTHER INFORMATION: Peptide 11 enfuvirtide 1-18 with acetylated
      amino terminus and trifluoroethyl thioester carboxyl terminus

<400> SEQUENCE: 11

Tyr Thr Ser Leu Ile His Ser Leu Ile Glu Glu Ser Gln Asn Gln Gln
1               5                   10                  15

Glu Leu

<210> SEQ ID NO 12
<211> LENGTH: 18
<212> TYPE: PRT
<213> ORGANISM: Artificial Sequence
<220> FEATURE:
<223> OTHER INFORMATION: Peptide 12 enfuvirtide 19-36

<400> SEQUENCE: 12

Cys Glu Gln Glu Leu Leu Glu Leu Asp Lys Trp Ala Ser Leu Trp Asn
1               5                   10                  15

Trp Phe

<210> SEQ ID NO 13
<211> LENGTH: 36
<212> TYPE: PRT
<213> ORGANISM: Artificial Sequence
<220> FEATURE:
<223> OTHER INFORMATION: Peptide 13 enfuvirtide full

<400> SEQUENCE: 13

Tyr Thr Ser Leu Ile His Ser Leu Ile Glu Glu Ser Gln Asn Gln Gln
1               5                   10                  15

Glu Leu Cys Glu Gln Glu Leu Leu Glu Leu Asp Lys Trp Ala Ser Leu
            20                  25                  30

Trp Asn Trp Phe
        35

<210> SEQ ID NO 14
<211> LENGTH: 18
<212> TYPE: PRT
<213> ORGANISM: Artificial Sequence
<220> FEATURE:
<223> OTHER INFORMATION: Peptide 14 somatorelin 1-18 with trifluoroethyl
      thioester on carboxyl terminus

<400> SEQUENCE: 14

Tyr Ala Asp Ala Ile Phe Thr Asn Ser Tyr Arg Lys Val Leu Gly Gln
1               5                   10                  15

Leu Ser

<210> SEQ ID NO 15
<211> LENGTH: 26
<212> TYPE: PRT
<213> ORGANISM: Artificial Sequence
<220> FEATURE:
<223> OTHER INFORMATION: Peptide 15 somatorelin 19-44

<400> SEQUENCE: 15

Cys Arg Lys Leu Leu Gln Asp Ile Met Ser Arg Gln Gln Gly Glu Ser
1               5                   10                  15

Asn Gln Glu Arg Gly Ala Arg Ala Arg Leu
            20                  25

<210> SEQ ID NO 16
```

```
<211> LENGTH: 18
<212> TYPE: PRT
<213> ORGANISM: Artificial Sequence
<220> FEATURE:
<223> OTHER INFORMATION: Peptide S3 branched at residue 6 with
      acetylated amino termini

<400> SEQUENCE: 16

Leu Tyr Arg Ala Asn Ala Leu Tyr Arg Ala Asn Ala Cys Ser Pro Gly
1               5                   10                  15

Tyr Ser

<210> SEQ ID NO 17
<211> LENGTH: 18
<212> TYPE: PRT
<213> ORGANISM: Artificial Sequence
<220> FEATURE:
<223> OTHER INFORMATION: Peptide S4 branched at residue 6 with
      acetylated amino termini

<400> SEQUENCE: 17

Leu Tyr Arg Ala Asn Val Leu Tyr Arg Ala Asn Val Cys Ser Pro Gly
1               5                   10                  15

Tyr Ser

<210> SEQ ID NO 18
<211> LENGTH: 6
<212> TYPE: PRT
<213> ORGANISM: Artificial Sequence
<220> FEATURE:
<223> OTHER INFORMATION: Peptide S6

<400> SEQUENCE: 18

Cys Ser Pro Met Tyr Ser
1               5

<210> SEQ ID NO 19
<211> LENGTH: 6
<212> TYPE: PRT
<213> ORGANISM: Artificial Sequence
<220> FEATURE:
<223> OTHER INFORMATION: Peptide S7

<400> SEQUENCE: 19

Ala Ser Pro Met Tyr Ser
1               5

<210> SEQ ID NO 20
<211> LENGTH: 6
<212> TYPE: PRT
<213> ORGANISM: Artificial Sequence
<220> FEATURE:
<223> OTHER INFORMATION: Peptide S8 with acetamidomethyl group on
      residue 3
<220> FEATURE:
<221> NAME/KEY: MOD_RES
<222> LOCATION: (3)..(3)
<223> OTHER INFORMATION: Residue modified with an acetamidomethyl group

<400> SEQUENCE: 20

Cys Ser Pro Cys Tyr Ser
1               5

<210> SEQ ID NO 21
<211> LENGTH: 6
<212> TYPE: PRT
<213> ORGANISM: Artificial Sequence
```

```
<220> FEATURE:
<223> OTHER INFORMATION: Peptide S9 with acetamidomethyl group on Cys
      residue
<220> FEATURE:
<221> NAME/KEY: MOD_RES
<222> LOCATION: (4)..(4)
<223> OTHER INFORMATION: Residue modified with an acetamidomethyl group

<400> SEQUENCE: 21

Ala Ser Pro Cys Tyr Ser
1               5

<210> SEQ ID NO 22
<211> LENGTH: 6
<212> TYPE: PRT
<213> ORGANISM: Artificial Sequence
<220> FEATURE:
<223> OTHER INFORMATION: Peptide S10 with L-pencillamine residue on
      amino terminus residue
<220> FEATURE:
<221> NAME/KEY: MOD_RES
<222> LOCATION: (1)..(1)
<223> OTHER INFORMATION: L-penicillamine

<400> SEQUENCE: 22

Xaa Ser Pro Gly Tyr Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Peptide S11

<400> SEQUENCE: 23

Val Ser Pro Gly Tyr Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Peptide S12 with beta-SH substitution on
      carboxyl terminus residue
<220> FEATURE:
<221> NAME/KEY: MOD_RES
<222> LOCATION: (6)..(6)
<223> OTHER INFORMATION: Residue modified with beta-SH substitution

<400> SEQUENCE: 24

Asp Ser Pro Gly Tyr Ser
1               5

<210> SEQ ID NO 25
<211> LENGTH: 6
<212> TYPE: PRT
<213> ORGANISM: Artificial Sequence
<220> FEATURE:
<223> OTHER INFORMATION: Peptide S13

<400> SEQUENCE: 25

Asp Ser Pro Gly Tyr Ser
1               5

<210> SEQ ID NO 26
<211> LENGTH: 6
<212> TYPE: PRT
```

-continued

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Selenocysteine

<400> SEQUENCE: 26

Xaa Ser Pro Gly Tyr Ser
1               5

<210> SEQ ID NO 27
<211> LENGTH: 6
<212> TYPE: PRT
<213> ORGANISM: Artificial Sequence
<220> FEATURE:
<223> OTHER INFORMATION: Peptide S15 with acetylated amino terminus and
      phenyl selenoester carboxyl terminus

<400> SEQUENCE: 27

Leu Tyr Arg Ala Asn Val
1               5

<210> SEQ ID NO 28
<211> LENGTH: 6
<212> TYPE: PRT
<213> ORGANISM: Artificial Sequence
<220> FEATURE:
<223> OTHER INFORMATION: Peptide S16 with acetylated amino terminus and
      phenyl selenoester carboxyl terminus

<400> SEQUENCE: 28

Leu Tyr Arg Ala Asn Phe
1               5

<210> SEQ ID NO 29
<211> LENGTH: 18
<212> TYPE: PRT
<213> ORGANISM: Artificial Sequence
<220> FEATURE:
<223> OTHER INFORMATION: Ligation produce of S14 and S15 branched at
      residue 6 with acetylated amino terminus
<220> FEATURE:
<221> NAME/KEY: MOD_RES
<222> LOCATION: (7)..(7)
<223> OTHER INFORMATION: Selenocysteine
<220> FEATURE:
<221> NAME/KEY: MOD_RES
<222> LOCATION: (13)..(13)
<223> OTHER INFORMATION: Selenocysteine

<400> SEQUENCE: 29

Leu Tyr Arg Ala Asn Val Xaa Ser Pro Gly Tyr Ser Xaa Ser Pro Gly
1               5                   10                  15

Tyr Ser

<210> SEQ ID NO 30
<211> LENGTH: 12
<212> TYPE: PRT
<213> ORGANISM: Artificial Sequence
<220> FEATURE:
<223> OTHER INFORMATION: Ligation product of S14 and S16 following
      deselenization with acetylated amino terminus
<220> FEATURE:
<221> NAME/KEY: MOD_RES
<222> LOCATION: (7)..(7)
<223> OTHER INFORMATION: Xaa can be any naturally occurring amino acid
```

```
<400> SEQUENCE: 30

Leu Tyr Arg Ala Asn Phe Xaa Ser Pro Gly Tyr Ser
1               5                   10

<210> SEQ ID NO 31
<211> LENGTH: 44
<212> TYPE: PRT
<213> ORGANISM: Artificial Sequence
<220> FEATURE:
<223> OTHER INFORMATION: Peptide 16 somatorelin full

<400> SEQUENCE: 31

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 32
<211> LENGTH: 12
<212> TYPE: PRT
<213> ORGANISM: Artificial Sequence
<220> FEATURE:
<223> OTHER INFORMATION: Peptide S14
<220> FEATURE:
<221> NAME/KEY: MOD_RES
<222> LOCATION: (6)..(7)
<223> OTHER INFORMATION: Xaa can be any naturally occurring amino acid

<400> SEQUENCE: 32

Ser Tyr Gly Pro Ser Xaa Xaa Ser Pro Gly Tyr Ser
1               5                   10

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Tyr Arg Ala Asn Ala
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Tyr Arg Ala Asn Ala
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35
```

-continued

```
Leu Tyr Arg Ala Asn Val
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Tyr Arg Ala Asn Ala
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Tyr Arg Ala Asn Val
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Tyr Arg Ala Asn Val
1               5
```